(12) United States Patent
Nicholas et al.

(10) Patent No.: US 11,549,112 B1
(45) Date of Patent: Jan. 10, 2023

(54) RNAI AGENTS FOR INHIBITING EXPRESSION OF XANTHINE DEHYDROGENASE (XDH), PHARMACEUTICAL COMPOSITIONS THEREOF, AND METHODS OF USE

(71) Applicant: Arrowhead Pharmaceuticals, Inc., Pasadena, CA (US)

(72) Inventors: Anthony Nicholas, Oregon, WI (US); Tao Pei, Middleton, WI (US); Zhao Xu, Brookfield, WI (US); Daniel Braas, Madison, WI (US); Zhi-Ming Ding, Waunakee, WI (US)

(73) Assignee: ARROWHEAD PHARMACEUTICALS, INC., Pasadena, CA (US)

( * ) Notice: Subject to any disclaimer, the term of this patent is extended or adjusted under 35 U.S.C. 154(b) by 0 days.

(21) Appl. No.: 17/748,779

(22) Filed: May 19, 2022

Related U.S. Application Data

(60) Provisional application No. 63/323,430, filed on Mar. 24, 2022, provisional application No. 63/213,097, filed on Jun. 21, 2021.

(51) Int. Cl.
*C12N 15/113* (2010.01)

(52) U.S. Cl.
CPC ...... *C12N 15/1137* (2013.01); *C12N 2310/14* (2013.01); *C12N 2310/3515* (2013.01)

(58) Field of Classification Search
None
See application file for complete search history.

(56) References Cited

U.S. PATENT DOCUMENTS

| | | | |
|---|---|---|---|
| 5,885,968 | A | 3/1999 | Biessen et al. |
| 5,998,203 | A | 12/1999 | Matulic-Adamic et al. |
| 2008/0113351 | A1 | 5/2008 | Naito et al. |
| 2012/0052487 | A9 | 3/2012 | Khvorova et al. |

FOREIGN PATENT DOCUMENTS

| | | |
|---|---|---|
| WO | WO-0053722 A2 | 9/2000 |
| WO | WO-2008022309 A2 | 2/2008 |
| WO | WO-2011104169 A1 | 9/2011 |
| WO | WO-2012083185 A2 | 6/2012 |
| WO | WO-2013032829 A1 | 3/2013 |
| WO | WO-2013158141 A1 | 10/2013 |
| WO | WO-2017019660 A1 | 2/2017 |
| WO | WO-2017156012 A1 | 9/2017 |
| WO | WO-2018044350 A1 | 3/2018 |
| WO | WO-2020238766 A1 | 12/2020 |
| WO | WO-2021257782 A1 | 12/2021 |
| WO | WO-2022223557 A1 | 10/2022 |

OTHER PUBLICATIONS

Baenziger et al. Galactose and N-acetylgalactosamine-specific endocytosis of glycopeptides by isolated rat hepatocytes. Cell 22:611-620 (1980).
Biessen et al. Synthesis of cluster galactosides with high affinity for the hepatic asialoglycoprotein receptor. J Med Chem 38:1538-1546 (1995).
Connolly et al. Binding and endocytosis of cluster glycosides by rabbit hepatocytes. Evidence for a short-circuit pathway that does not lead to degradation. J. Biol. Chem. 257:939-945 (1982).
Co-pending U.S. Appl. No. 17/748,767, inventors Nicholas; Anthony et al., filed May 19, 2022.
Czauderna et al. Structural variations and stabilising modifications of synthetic siRNAs in mammalian cells. Nucleic Acids Res. 31(11):2705-16 (2003).
Iobst et al. Selective sugar binding to the carbohydrate recognition domains of the rat hepatic and macrophage asialoglycoprotein receptors. J Biol Chem 271:6686-6693 (1996).

*Primary Examiner* — Brian Whiteman
(74) *Attorney, Agent, or Firm* — Wilson Sonsini Goodrich & Rosati

(57) ABSTRACT

The present disclosure relates to RNAi agents, e.g., double stranded RNAi agents, able to inhibit xanthine dehydrogenase (XDH) gene expression. Also disclosed are pharmaceutical compositions that include XDH RNAi agents and methods of use thereof. The XDH RNAi agents disclosed herein may be conjugated to targeting ligands to facilitate the delivery to cells, including to hepatocytes. Delivery of the XDH RNAi agents in vivo provides for inhibition of XDH gene expression. The RNAi agents can be used in methods of treatment of diseases, disorders, or symptoms mediated in part by XDH gene expression, such as gout and hyperuricemia.

14 Claims, No Drawings
Specification includes a Sequence Listing.

US 11,549,112 B1

SEQUENCE LISTING

<160> NUMBER OF SEQ ID NOS: 1688

<210> SEQ ID NO 1
<211> LENGTH: 5715
<212> TYPE: DNA
<213> ORGANISM: Artificial sequence
<220> FEATURE:
<223> OTHER INFORMATION: Homo sapiens xanthine dehydrogenase (XDH), mRNA
      transcript (NM_000379.4)

<400> SEQUENCE: 1

| | | | | | |
|---|---|---|---|---|---|
| acagagcagt | gataactacc | tgccagtgtc | tcttaggagt | gaggtacctg | gagttcgggg | 60 |
| accccaacct | gtgacaatga | cagcagacaa | attggttttc | tttgtgaatg | cagaaaggt | 120 |
| ggtggagaaa | aatgcagatc | cagagacaac | ccttttggcc | tacctgagaa | gaaagttggg | 180 |
| gctgagtgga | accaagctcg | gctgtggaga | gggggctgc | ggggcttgca | cagtgatgct | 240 |
| ctccaagtat | gatcgtctgc | agaacaagat | cgtccacttt | tctgccaatg | cctgcctggc | 300 |
| ccccatctgc | tccttgcacc | atgttgcagt | gacaactgtg | gaaggaatag | aagcaccaa | 360 |
| gacgaggctg | catcctgtgc | aggagagaat | tgccaaaagc | cacggctccc | agtgcgggtt | 420 |
| ctgcaccct | ggcatcgtca | tgagtatgta | cacactgctc | cggaatcagc | ccgagcccac | 480 |
| catggaggag | attgagaatg | ccttccaagg | aaatctgtgc | cgctgcacag | gctacagacc | 540 |
| catcctccag | ggcttccgga | cctttgccag | ggatggtgga | tgctgtggag | gagatgggaa | 600 |
| taatccaaat | tgctgcatga | accagaagaa | agaccactca | gtcagcctct | cgccatcttt | 660 |
| attcaaacca | gaggagttca | cgcccctgga | tccaacccag | gagcccattt | ttccccaga | 720 |
| gttgctgagg | ctgaaagaca | ctcctcggaa | gcagctgcga | tttgaagggg | agcgtgtgac | 780 |
| gtggatacag | gcctcaaccc | tcaaggagct | gctggacctc | aaggctcagc | accctgacgc | 840 |
| caagctggtc | gtggggaaca | cggagattgg | cattgagatg | aagttcaaga | atatgctgtt | 900 |
| tcctatgatt | gtctgcccag | cctggatccc | tgagctgaat | cggtagaac | atggacccga | 960 |
| cggtatctcc | tttggagctg | cttgcccct | gagcattgtg | gaaaaaccc | tggtggatgc | 1020 |
| tgttgctaag | cttcctgccc | aaaagacaga | ggtgttcaga | ggggtcctgg | agcagctgcg | 1080 |
| ctggtttgct | gggaagcaag | tcaagtctgt | ggcgtccgtt | ggagggaaca | tcatcactgc | 1140 |
| cagccccatc | tccgacctca | ccccgtgtt | catggccagt | ggggcaagc | tgacacttgt | 1200 |
| gtccagaggc | accaggagaa | ctgtccagat | ggaccacacc | ttcttccctg | gctacagaaa | 1260 |
| gaccctgctg | agcccggagg | agatactgct | ctccatagag | atccctaca | gcagggaggg | 1320 |
| ggagtatttc | tcagcattca | gcaggcctc | ccggagagaa | gatgacattg | ccaaggtaac | 1380 |
| cagtggcatg | agagttttat | tcaagccagg | aaccacagag | gtacaggagc | tggccctttg | 1440 |
| ctatggtgga | atggccaaca | gaaccatctc | agccctcaag | accactcaga | ggcagctttc | 1500 |
| caagctctgg | aaggaggagc | tgctgcagga | cgtgtgtgca | ggactggcag | aggagctgca | 1560 |
| tctgcctccc | gatgcccctg | gtggcatggt | ggacttccgg | tgcaccctca | ccctcagctt | 1620 |
| cttcttcaag | ttctacctga | cagtccttca | gaagctgggc | caagagaacc | tggaagacaa | 1680 |
| gtgtggtaaa | ctggaccca | ctttcgccag | tgcaacttta | ctgtttcaga | agacccccc | 1740 |
| agccgatgtc | cagctcttcc | aagaggtgcc | caagggtcag | tctgaggagg | acatggtggg | 1800 |
| ccggccctg | ccccacctgg | cagcggacat | gcaggcctct | ggtgaggccg | tgtactgtga | 1860 |
| cgacattcct | cgctacgaga | atgagctgtc | tctccggctg | gtcaccagca | cccgggccca | 1920 |
| cgccaagatc | aagtccatag | atacatcaga | agctaagaag | gttccagggt | ttgtttgttt | 1980 |

```
catttccgct gatgatgttc ctgggagtaa cataactgga atttgtaatg atgagacagt    2040
ctttgcgaag gataaggtta cttgtgttgg gcatatcatt ggtgctgtgg ttgctgacac    2100
cccggaacac acacagagag ctgcccaagg ggtgaaaatc acctatgaag aactaccagc    2160
cattatcaca attgaggatg ctataaagaa caactccttt tatggacctg agctgaagat    2220
cgagaaaggg gacctaaaga aggggttttc cgaagcagat aatgttgtgt caggggagat    2280
atacatcggt ggccaagagc acttctacct ggagactcac tgcaccattg ctgttccaaa    2340
aggcgaggca ggggagatgg agctctttgt gtctacacag aacaccatga agacccagag    2400
ctttgttgca aaaatgttgg gggttccagc aaaccggatt gtggttcgag tgaagagaat    2460
gggaggaggc tttggaggca aggagacccg gagcactgtg gtgtccacgg cagtggccct    2520
ggctgcatat aagaccggcc gccctgtgcg atgcatgctg accgtgatg aggacatgct    2580 gataactggt ggcagacatc ccttcctggc cagatacaag gttggcttca tgaagactgg    2640
gacagttgtg gctcttgagg tggaccactt cagcaatgtg gggaacaccc aggatctctc    2700
tcagagtatt atgaacgag ctttattcca catggacaac tgctataaaa tccccaacat    2760
ccggggcact gggcggctgt gcaaaaccaa ccttccctcc aacacggcct tccggggctt    2820 tgggggccc caggggatgc tcattgccga gtgctggatg agtgaagttg cagtgacctg    2880
tgggatgcct gcagaggagg tgcggagaaa aaacctgtac aaagaagggg acctgacaca    2940
cttcaaccag aagcttgagg gtttcacctt gcccagatgc tgggaagaat gcctagcaag    3000
ctctcagtat catgctcgga agagtgaggt tgacaagttc aacaaggaga attgttggaa    3060
aaagagagga ttgtgcataa tcccaccaa gtttggaata agctttacag ttcctttctc    3120
gaatcaggca ggagccctac ttcatgtgta cacagatggc tctgtgctgc tgacccacgg    3180
ggggactgag atgggccaag gccttcatac caaaatggtc caggtggcca gtagagctct    3240
gaaaatcccc acctctaaga tttatatcag cgagacaagc actaacactg tgcccaacac    3300
ctctcccacg gctgcctctg tcagcgctga cctcaatgga caggccgtct atgcggcttg    3360
tcagaccatc ttgaaaaggc tggaacccta caagaagaag aatcccagtg ctcctgggga    3420
agactgggtc acagctgcct acatggacac agtgagcttg tctgccactg gttttatag    3480 aacacccaat ctgggctaca gctttgagac taactcaggg aacccccttcc actacttcag    3540 ctatggggtg gcttgctctg aagtagaaat cgactgccta acaggagatc ataagaacct    3600
ccgcacagat attgtcatgg atgttggctc cagtctaaac cctgccattg atattggaca    3660
ggtggaaggg gcatttgtcc agggccttgg cctcttcacc ctagaggagc tacactattc    3720 cccccgagggg agcctgcaca cccgtggccc tagcacctac aagatcccgg catttggcag    3780
catccccatt gagttcaggg tgtccctgct ccgcgactgc cccaacaaga aggccatcta    3840
tgcatcgaag gctgttggag agccgcccct cttcctggct gcttctatct tctttgccat    3900
caaagatgcc atccgtgcag ctcgagctca gcacacaggt aataacgtga aggaactctt    3960
ccggctagac agccctgcca ccccggagaa gatccgcaat gcctgcgtgg acaagttcac    4020
caccctgtgt gtcactggtg tcccagaaaa ctgcaaaccc tggtctgtga ggtctaaag    4080 agagagtcct cagcagagtc ttcttgtgct gcctttgggc ttccatggag caggaggaac    4140
ataccacaga acatggatct attaaagtca cagaatgaca gacctgtgat tgtcaagat    4200 gggatttgga agacaagtga atgcaatgga agattttgat caaaaatgta atttgtaaac    4260
acaatgataa gcaaattcaa aactgttatg cctaaatggt gaatatgcaa ttaggatcat    4320
tttctgtctg ttttaatcat gtatctggaa tagggtcggg aagggtttgt gctattcccc    4380
```

-continued

```
acttactgga cagcctgtat aacctcaagt tctgatggtg tctgtccttt gaagaggatt    4440
cccacaaacc tctagaagct taaaccgaag ttactttaaa tcgtgtgcct tcctgtgaaa    4500
gcctggcctt caaaccaatg aacagcaaag cataaccttg aatctatact caaattttgc    4560
aatgaggcag tggggtaagg ttaaatcctc taaccatctt tgaatcattg gaaagaataa    4620
agaatgaaac aaattcaagg ttaattggat ctgattttgt gaagctgcat aaagcaagat    4680
tactctataa tacaaaaatc caaccaactc aattattgag cacgtacaat gttctagatt    4740
tctttccctt cctctttgaa gagaatattt gtattccaaa tactctttga gtatttacaa    4800 aaagattat gtttaatctt tacatttgaa gccaaagtaa tttccaccta gaaatgatgc      4860
tatcagtcct ggcatggtgg ctcacccta taatcccagc actttgggag gctaaggcag      4920
gagaattgct tgagcccagc agtttgagac cagcctgggc aacatagaga gctcctgtct    4980
ttaaaaaaaa ttttttttaat tagttggtct tgatagtgca tgcctgtagt cccaactact    5040
tgaaaggctg aggtggagag atcatttgag ctcaggaggt tgaggctgca gtgagctatg    5100
attgcgccac tgcactcctg cctgagcgac tgagcaagat cttgtctctg aagaaaaaaa    5160
aagaaataaa aatgctgcta tcaaaatcaa gcccaaccag aggtagaaga gccaagaagc    5220
ctgggttctc atcctagctc tgtctcttct gtctctatct ttgtgatctt ggactgtcaa    5280
ttccccttcc tgtgatccat tttactgcaa acataagggt tgcagtaaag ggttgtctca    5340
cgtcttctgc tttaaaagcc tataaatata tgacctgaaa actccagtta cataaaggat    5400
ctgcagctat ctaaggcttg gttttcttac tgtcatatga tacctgggtc taatgaactc    5460
tgctgagatc acctcaagtt tctgcggttg gtaaagagaa caagggaaga acaaacatcc    5520
cttttattgc tccaaatggt gatttaatcc ctacatggtg ctgggtggac aatgtgtcac    5580
tgtcacatgc cttcactgta taaatccaac cttctgccag agagaatctg tggttctggc    5640
catggaggga ggatagtgga aatgatatag ttggactggt gcttgatgtc actaataaat    5700
gaaactgtca gctgg                                                    5715
```

<210> SEQ ID NO 2
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 2
ucagcuucuu cuucaaguu                                                 19

<210> SEQ ID NO 3
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 3
agcuucuucu ucaaguucu                                                 19

<210> SEQ ID NO 4
<211> LENGTH: 19
<212> TYPE: RNA
<213> ORGANISM: Artificial sequence
<220> FEATURE:

<223> OTHER INFORMATION: XDH 19-mer gene transcript (mRNA) target
      sequence

<400> SEQUENCE: 4
uucuucuuca aguucuacc                                                    19

<210> SEQ ID NO 5
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 5
gggugaaaau caccuauga                                                    19

<210> SEQ ID NO 6
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 6
gugaaaauca ccuaugaag                                                    19

<210> SEQ ID NO 7
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 7
ugaaaaucac cuaugaaga                                                    19

<210> SEQ ID NO 8
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 8
gaaaaucacc uaugaagaa                                                    19

<210> SEQ ID NO 9
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 9
accagccauu aucacaauu                                                    19

<210> SEQ ID NO 10
<211> LENGTH: 19
<212> TYPE: RNA
<213> ORGANISM: Artificial sequence
<220> FEATURE:
<223> OTHER INFORMATION: XDH 19-mer gene transcript (mRNA) target -continued sequence

<400> SEQUENCE: 10
agaacaacuc cuuuuaugg                                            19

<210> SEQ ID NO 11
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 11
gaacaacucc uuuuaugga                                            19

<210> SEQ ID NO 12
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 12
gacaagcacu aacacugug                                            19

<210> SEQ ID NO 13
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 13
gucaugagua uguacacac                                            19

<210> SEQ ID NO 14
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 14
gacaugcuga uaacuggug                                            19

<210> SEQ ID NO 15
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 15
auacaagguu ggcuucaug                                            19

<210> SEQ ID NO 16
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

```
<400> SEQUENCE: 16
aagguuggcu ucaugaaga                                            19

<210> SEQ ID NO 17
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 17
agguuggcuu caugaagac                                            19

<210> SEQ ID NO 18
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 18
guuggcuuca ugaagacug                                            19

<210> SEQ ID NO 19
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 19
gagaauuguu ggaaaaaga                                            19

<210> SEQ ID NO 20
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 20
ggcuugcucu gaaguagaa                                            19

<210> SEQ ID NO 21
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 21
uugcucugaa guagaaauc                                            19

<210> SEQ ID NO 22
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence
```

```
<400> SEQUENCE: 22
cugccauuga uauuggaca                                              19

<210> SEQ ID NO 23
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 23
agaucgucca cuuucugc                                               19

<210> SEQ ID NO 24
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 24
ccgaagcaga uaauguugu                                              19

<210> SEQ ID NO 25
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 25
cucucucaga guauuaugg                                              19

<210> SEQ ID NO 26
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 26
caccaaguuu ggaauaagc                                              19

<210> SEQ ID NO 27
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 27
gcauaaagca agauuacuc                                              19

<210> SEQ ID NO 28
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 28
```

```
caauguucua gauuucuuu                                        19

<210> SEQ ID NO 29
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 29
ugcuggauga gugaaguug                                        19

<210> SEQ ID NO 30
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 30
gcuggaugag ugaaguugc                                        19

<210> SEQ ID NO 31
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 31
cuggaugagu gaaguugca                                        19

<210> SEQ ID NO 32
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 32
ugcucuccaa guaugaucg                                        19

<210> SEQ ID NO 33
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 33
gaucgucugc agaacaaga                                        19

<210> SEQ ID NO 34
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 34
```
cgucugcaga acaagaucg                                        19

<210> SEQ ID NO 35
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 35
cgccagugca acuuuacug                                        19

<210> SEQ ID NO 36
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 36
gauaagguua cuuguguug                                        19

<210> SEQ ID NO 37
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 37
cagccauuau cacaauuga                                        19

<210> SEQ ID NO 38
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 38
agcucucagu aucaugcuc                                        19

<210> SEQ ID NO 39
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 39
agagugaggu ugacaaguu                                        19

<210> SEQ ID NO 40
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 40
gagugagguu gacaaguuc                                        19

```
<210> SEQ ID NO 41
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 41
ucaacaagga gaauuguug                                                       19

<210> SEQ ID NO 42
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 42
aacauaccac agaacaugg                                                       19

<210> SEQ ID NO 43
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 43
acauggaucu auuaaaguc                                                       19

<210> SEQ ID NO 44
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 44
cauggaucua uuaaaguca                                                       19

<210> SEQ ID NO 45
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 45
ccuaaauggu gaauaugca                                                       19

<210> SEQ ID NO 46
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 46
accucuagaa gcuuaaacc                                                       19
```

<210> SEQ ID NO 47
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 47
ccuucaaacc aaugaacag                                               19

<210> SEQ ID NO 48
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 48
aaugaacagc aaagcauaa                                               19

<210> SEQ ID NO 49
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 49
ugaacagcaa agcauaacc                                               19

<210> SEQ ID NO 50
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 50
gaacagcaaa gcauaaccu                                               19

<210> SEQ ID NO 51
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 51
acagcaaagc auaaccuug                                               19

<210> SEQ ID NO 52
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 52
aaagcauaac cuugaaucu                                               19

```
<210> SEQ ID NO 53
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 53
aaccaacuca auuauugag                                                     19

<210> SEQ ID NO 54
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 54
uccugugauc cauuuuacu                                                     19

<210> SEQ ID NO 55
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 55
uuuucuuacu gucauauga                                                     19

<210> SEQ ID NO 56
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 56
ggagaaaaau gcagaucca                                                     19

<210> SEQ ID NO 57
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 57
cagagacaac ccuuuuggc                                                     19

<210> SEQ ID NO 58
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 58
cuccaaguau gaucgucug                                                     19

<210> SEQ ID NO 59
```

```
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 59
aacuguggaa ggaauagga                                                    19

<210> SEQ ID NO 60
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 60
gcaucgucau gaguaugua                                                    19

<210> SEQ ID NO 61
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 61
cuuccaagga aaucugugc                                                    19

<210> SEQ ID NO 62
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 62
ggcauugaga ugaaguuca                                                    19

<210> SEQ ID NO 63
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 63
ugaaguucaa gaauaugcu                                                    19

<210> SEQ ID NO 64
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 64
aauaugcugu uuccuauga                                                    19

<210> SEQ ID NO 65
<211> LENGTH: 19
```

```
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 65
ugcucuccau agagauccc                                                  19

<210> SEQ ID NO 66
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 66
guauuucuca gcauucaag                                                  19

<210> SEQ ID NO 67
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 67
ccaagaucaa guccauaga                                                  19

<210> SEQ ID NO 68
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 68
caggguuugu uuguuucau                                                  19

<210> SEQ ID NO 69
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 69
caccuaugaa gaacuacca                                                  19

<210> SEQ ID NO 70
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 70
gaacuaccag ccauuauca                                                  19

<210> SEQ ID NO 71
<211> LENGTH: 19
<212> TYPE: RNA
```

```
<213> ORGANISM: Artificial sequence
<220> FEATURE:
<223> OTHER INFORMATION: XDH 19-mer gene transcript (mRNA) target
      sequence

<400> SEQUENCE: 71
gccauuauca caauugagg                                              19

<210> SEQ ID NO 72
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 72
agcugaagau cgagaaagg                                              19

<210> SEQ ID NO 73
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 73
gcaccauugc uguuccaaa                                              19

<210> SEQ ID NO 74
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 74
ggagcucuuu gugucuaca                                              19

<210> SEQ ID NO 75
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 75
cucuuugugu cuacacaga                                              19

<210> SEQ ID NO 76
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 76
cucucagagu auuauggaa                                              19

<210> SEQ ID NO 77
<211> LENGTH: 19
<212> TYPE: RNA
<213> ORGANISM: Artificial sequence
```

```
<220> FEATURE:
<223> OTHER INFORMATION: XDH 19-mer gene transcript (mRNA) target
      sequence

<400> SEQUENCE: 77
agaguauuau ggaacgagc                                              19

<210> SEQ ID NO 78
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 78
aggguuuguu uguuucauu                                              19

<210> SEQ ID NO 79
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 79
ggguuuguuu guuucauuu                                              19

<210> SEQ ID NO 80
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 80
guuuguuugu uucauuucc                                              19

<210> SEQ ID NO 81
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 81
ucuccaagua ugaucgucu                                              19

<210> SEQ ID NO 82
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 82
aggagauuga gaaugccuu                                              19

<210> SEQ ID NO 83
<211> LENGTH: 19
<212> TYPE: RNA
<213> ORGANISM: Artificial sequence
<220> FEATURE:
```

```
<223> OTHER INFORMATION: XDH 19-mer gene transcript (mRNA) target
      sequence

<400> SEQUENCE: 83
agaaugccuu ccaaggaaa                                                   19

<210> SEQ ID NO 84
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 84
ugccuuccaa ggaaaucug                                                   19

<210> SEQ ID NO 85
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 85
agaauaugcu guuuccuau                                                   19

<210> SEQ ID NO 86
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 86
uuggagggaa caucaucac                                                   19

<210> SEQ ID NO 87
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 87
gcuucuucuu caaguucua                                                   19

<210> SEQ ID NO 88
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 88
guugggcaua ucauuggug                                                   19

<210> SEQ ID NO 89
<211> LENGTH: 19
<212> TYPE: RNA
<213> ORGANISM: Artificial sequence
<220> FEATURE:
<223> OTHER INFORMATION: XDH 19-mer gene transcript (mRNA) target
```

-continued

```
      sequence

<400> SEQUENCE: 89
ucuacacaga acaccauga                                                19

<210> SEQ ID NO 90
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 90
cacccaggau cucucucag                                                19

<210> SEQ ID NO 91
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 91
caagcucuca guaucaugc                                                19

<210> SEQ ID NO 92
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 92
ggaagaguga gguugacaa                                                19

<210> SEQ ID NO 93
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 93
caaggagaau uguuggaaa                                                19

<210> SEQ ID NO 94
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 94
agcuuugaga cuaacucag                                                19

<210> SEQ ID NO 95
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence
```

-continued

```
<400> SEQUENCE: 95
uccgcacaga uauugucau                                              19

<210> SEQ ID NO 96
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 96
cgcacagaua uugucaugg                                              19

<210> SEQ ID NO 97
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 97
cugcuucuau cuucuuugc                                              19

<210> SEQ ID NO 98
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 98
cacacaggua auaacguga                                              19

<210> SEQ ID NO 99
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 99
uguauaaccu caaguucug                                              19

<210> SEQ ID NO 100
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 100
ccaaugaaca gcaaagcau                                              19

<210> SEQ ID NO 101
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence
```

```
<400> SEQUENCE: 101
uaaccuugaa ucuauacuc                                                 19

<210> SEQ ID NO 102
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 102
cauaaagcaa gauuacucu                                                 19

<210> SEQ ID NO 103
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 103
caccuagaaa ugaugcuau                                                 19

<210> SEQ ID NO 104
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 104
agcucugucu cuucugucu                                                 19

<210> SEQ ID NO 105
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 105
aaggcuuggu uuucuuacu                                                 19

<210> SEQ ID NO 106
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 106
gugaugcucu ccaaguaug                                                 19

<210> SEQ ID NO 107
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 107
```
caaguaugau cgucugcag                                           19

<210> SEQ ID NO 108
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 108
gcaugagagu uuuauucaa                                           19

<210> SEQ ID NO 109
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 109
caagaucguc cacuuuucu                                           19

<210> SEQ ID NO 110
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 110
cauguugcag ugacaacug                                           19

<210> SEQ ID NO 111
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 111
ugacaacugu ggaaggaau                                           19

<210> SEQ ID NO 112
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 112
ggaggagauu gagaaugcc                                           19

<210> SEQ ID NO 113
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 113
cacggagauu ggcauugag                                                    19

<210> SEQ ID NO 114
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 114
agaugaaguu caagaauau                                                    19

<210> SEQ ID NO 115
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 115
gagauacugc ucuccauag                                                    19

<210> SEQ ID NO 116
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 116
ggaguauuuc ucagcauuc                                                    19

<210> SEQ ID NO 117
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 117
gaguauuucu cagcauuca                                                    19

<210> SEQ ID NO 118
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 118
ggagagaaga ugacauugc                                                    19

<210> SEQ ID NO 119
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 119
uaacauaacu ggaauuugu                                                    19

```
<210> SEQ ID NO 120
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 120
agccauuauc acaauugag                                              19

<210> SEQ ID NO 121
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 121 gcuuguugc aaaaauguu                                               19

<210> SEQ ID NO 122
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 122
uuuguugcaa aaauguugg                                              19

<210> SEQ ID NO 123
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 123
gauguggugu cgagugaag                                              19

<210> SEQ ID NO 124
<211> LENGTH: 19
<212> TYPE: RNA
<213> ORGANISM: Artificial sequence
<220> FEATURE:
<223> OTHER INFORMATION: XDH 19-mer gene transcript (mRNA) target
      sequence

<400> SEQUENCE: 124
gauugagaau gccuuccaa                                              19

<210> SEQ ID NO 125
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 125
aacuugaaga agaagcuga                                              19
```

```
<210> SEQ ID NO 126
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 126
uacuugaaga agaagcuga                                                  19

<210> SEQ ID NO 127
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase any nucleobase

<400> SEQUENCE: 127
nacuugaaga agaagcuga                                                  19

<210> SEQ ID NO 128
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase any nucleobase

<400> SEQUENCE: 128
nacuugaaga agaagcugn                                                  19

<210> SEQ ID NO 129
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 129
agaacuugaa gaagaagcu                                                  19

<210> SEQ ID NO 130
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 130
ugaacuugaa gaagaagcu                                                  19

<210> SEQ ID NO 131
<211> LENGTH: 19
<212> TYPE: RNA
<213> ORGANISM: Artificial sequence
<220> FEATURE:
```

```
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 131
ngaacuugaa gaagaagcu                                                    19

<210> SEQ ID NO 132
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 132
ngaacuugaa gaagaagcn                                                    19

<210> SEQ ID NO 133
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 133
uguagaacuu gaagaagaa                                                    19

<210> SEQ ID NO 134
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 134
nguagaacuu gaagaagaa                                                    19

<210> SEQ ID NO 135
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 135
nguagaacuu gaagaagan                                                    19

<210> SEQ ID NO 136
<211> LENGTH: 19
<212> TYPE: RNA
```

```
<213> ORGANISM: Artificial sequence
<220> FEATURE:
<223> OTHER INFORMATION: RNAi agent antisense strand 19-mer core base
      sequence

<400> SEQUENCE: 136
ucauagguga uuuucaccc                                                    19

<210> SEQ ID NO 137
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 137
ncauagguga uuuucaccc                                                    19

<210> SEQ ID NO 138
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 138
ncauagguga uuuucaccn                                                    19

<210> SEQ ID NO 139
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 139
uuucauaggu gauuuucac                                                    19

<210> SEQ ID NO 140
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 140
nuucauaggu gauuuucac                                                    19

<210> SEQ ID NO 141
<211> LENGTH: 19
<212> TYPE: RNA
<213> ORGANISM: Artificial sequence
<220> FEATURE:
```

```
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 141
nuucauaggu gauuuucan                                                      19

<210> SEQ ID NO 142
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 142
ucuucauagg ugauuuuca                                                      19

<210> SEQ ID NO 143
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 143
ncuucauagg ugauuuuca                                                      19

<210> SEQ ID NO 144
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 144
ncuucauagg ugauuuucn                                                      19

<210> SEQ ID NO 145
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 145
uucuucauag gugauuuuc                                                      19

<210> SEQ ID NO 146
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
```

```
<220> FEATURE:
<221> NAME/KEY: modified_base
<222> LOCATION: 1
<223> OTHER INFORMATION: n = any nucleobase

<400> SEQUENCE: 146
nucuucauag gugauuuuc                                                      19

<210> SEQ ID NO 147
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 147
nucuucauag gugauuuun                                                      19

<210> SEQ ID NO 148
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 148
aauugugaua auggcuggu                                                      19

<210> SEQ ID NO 149
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 149
uauugugaua auggcuggu                                                      19

<210> SEQ ID NO 150
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 150
nauugugaua auggcuggu                                                      19

<210> SEQ ID NO 151
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
```

```
<222> LOCATION: 1, 19
<223> OTHER INFORMATION: n = any nucleobase

<400> SEQUENCE: 151
nauugugaua auggcuggn                                                    19

<210> SEQ ID NO 152
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 152
ucauaaaagg aguuguucu                                                    19

<210> SEQ ID NO 153
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 153
ncauaaaagg aguuguucu                                                    19

<210> SEQ ID NO 154
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 154
ncauaaaagg aguuguucn                                                    19

<210> SEQ ID NO 155
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 155
uccauaaaag gaguuguuc                                                    19

<210> SEQ ID NO 156
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase
```

<400> SEQUENCE: 156
nccauaaaag gaguuguuc                                                       19

<210> SEQ ID NO 157
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 157
nccauaaaag gaguuguun                                                       19

<210> SEQ ID NO 158
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 158
uacaguguua gugcuuguc                                                       19

<210> SEQ ID NO 159
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 159
nacaguguua gugcuuguc                                                       19

<210> SEQ ID NO 160
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 160
nacaguguua gugcuugun                                                       19

<210> SEQ ID NO 161
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 161
uuguguacau acucaugac                                          19

<210> SEQ ID NO 162
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 162
nuguguacau acucaugac                                          19

<210> SEQ ID NO 163
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 163
nuguguacau acucaugan                                          19

<210> SEQ ID NO 164
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 164
uaccaguuau cagcauguc                                          19

<210> SEQ ID NO 165
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 165
naccaguuau cagcauguc                                          19

<210> SEQ ID NO 166
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

```
<400> SEQUENCE: 166
naccaguuau cagcaugun                                              19

<210> SEQ ID NO 167
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 167
uaccaguuau cagcauguc                                              19

<210> SEQ ID NO 168
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 168
naccaguuau cagcauguc                                              19

<210> SEQ ID NO 169
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 169
naccaguuau cagcaugun                                              19

<210> SEQ ID NO 170
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 170
uaugaagcca accuuguau                                              19

<210> SEQ ID NO 171
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 171
```
naugaagcca accuuguau                                                    19

<210> SEQ ID NO 172
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 172
naugaagcca accuuguan                                                    19

<210> SEQ ID NO 173
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 173
ucuucaugaa gccaaccuu                                                    19

<210> SEQ ID NO 174
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 174
ncuucaugaa gccaaccuu                                                    19

<210> SEQ ID NO 175
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 175
ncuucaugaa gccaaccun                                                    19

<210> SEQ ID NO 176
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 176
uucuucauga agccaaccu                                                    19

-continued

<210> SEQ ID NO 177
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 177
nucuucauga agccaaccu                                                    19

<210> SEQ ID NO 178
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 178
nucuucauga agccaaccn                                                    19

<210> SEQ ID NO 179
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 179
uagucuucau gaagccaac                                                    19

<210> SEQ ID NO 180
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 180
nagucuucau gaagccaac                                                    19

<210> SEQ ID NO 181
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 181
nagucuucau gaagccaan    19

<210> SEQ ID NO 182
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 182
ucuuuuucca acaauucuc    19

<210> SEQ ID NO 183
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 183
ncuuuuucca acaauucuc    19

<210> SEQ ID NO 184
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 184
ncuuuuucca acaauucun    19

<210> SEQ ID NO 185
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 185
uucuacuuca gagcaagcc    19

<210> SEQ ID NO 186
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 186
nucuacuuca gagcaagcc    19

```
<210> SEQ ID NO 187
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 187
nucuacuuca gagcaagcn                                                    19

<210> SEQ ID NO 188
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 188
uauuucuacu ucagagcaa                                                    19

<210> SEQ ID NO 189
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 189
nauuucuacu ucagagcaa                                                    19

<210> SEQ ID NO 190
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 190
nauuucuacu ucagagcan                                                    19

<210> SEQ ID NO 191
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 191
uguccaauau caauggcag                                                    19
```

```
<210> SEQ ID NO 192
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 192
nguccaauau caauggcag                                                    19

<210> SEQ ID NO 193
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 193
nguccaauau caauggcan                                                    19

<210> SEQ ID NO 194
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 194
ucagaaaagu ggacgaucu                                                    19

<210> SEQ ID NO 195
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 195
ncagaaaagu ggacgaucu                                                    19

<210> SEQ ID NO 196
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 196
ncagaaaagu ggacgaucn                                                    19
```

-continued

<210> SEQ ID NO 197
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 197
acaacauuau cugcuucgg                                                      19

<210> SEQ ID NO 198
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 198
ucaacauuau cugcuucgg                                                      19

<210> SEQ ID NO 199
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 199
ncaacauuau cugcuucgg                                                      19

<210> SEQ ID NO 200
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 200
ncaacauuau cugcuucgn                                                      19

<210> SEQ ID NO 201
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 201
ucauaauacu cugagagag                                                      19

<210> SEQ ID NO 202
<211> LENGTH: 19
<212> TYPE: RNA
<213> ORGANISM: Artificial sequence

```
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 202
ncauaauacu cugagagag                                                      19

<210> SEQ ID NO 203
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 203
ncauaauacu cugagagan                                                      19

<210> SEQ ID NO 204
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 204
ucuuauucca aacuuggug                                                      19

<210> SEQ ID NO 205
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 205
ncuuauucca aacuuggug                                                      19

<210> SEQ ID NO 206
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 206
ncuuauucca aacuuggun                                                      19

<210> SEQ ID NO 207
<211> LENGTH: 19
```

```
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 207
uaguaaucuu gcuuuaugc                                                   19

<210> SEQ ID NO 208
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 208
naguaaucuu gcuuuaugc                                                   19

<210> SEQ ID NO 209
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 209
naguaaucuu gcuuuaugn                                                   19

<210> SEQ ID NO 210
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 210
aaagaaaucu agaacauug                                                   19

<210> SEQ ID NO 211
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 211
uaagaaaucu agaacauug                                                   19

<210> SEQ ID NO 212
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
```

```
<221> NAME/KEY: modified_base
<222> LOCATION: 1
<223> OTHER INFORMATION: n = any nucleobase

<400> SEQUENCE: 212
naagaaaucu agaacauug                                                   19

<210> SEQ ID NO 213
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 213
naagaaaucu agaacauun                                                   19

<210> SEQ ID NO 214
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 214
uaacuucacu cauccagca                                                   19

<210> SEQ ID NO 215
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 215
naacuucacu cauccagca                                                   19

<210> SEQ ID NO 216
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 216
naacuucacu cauccagcn                                                   19

<210> SEQ ID NO 217
<211> LENGTH: 19
<212> TYPE: RNA
<213> ORGANISM: Artificial sequence
<220> FEATURE:
<223> OTHER INFORMATION: RNAi agent antisense strand 19-mer core base
``` sequence

<400> SEQUENCE: 217
ucaacuucac ucauccagc                                              19

<210> SEQ ID NO 218
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 218
ncaacuucac ucauccagc                                              19

<210> SEQ ID NO 219
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 219
ncaacuucac ucauccagn                                              19

<210> SEQ ID NO 220
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 220
ugcaacuuca cucauccag                                              19

<210> SEQ ID NO 221
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 221
ngcaacuuca cucauccag                                              19

<210> SEQ ID NO 222
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:

```
<221> NAME/KEY: modified_base
<222> LOCATION: 1, 19
<223> OTHER INFORMATION: n = any nucleobase

<400> SEQUENCE: 222
ngcaacuuca cucauccan                                                        19

<210> SEQ ID NO 223
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 223
ugaucauacu uggagagca                                                        19

<210> SEQ ID NO 224
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 224
ngaucauacu uggagagca                                                        19

<210> SEQ ID NO 225
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 225
ngaucauacu uggagagcn                                                        19

<210> SEQ ID NO 226
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 226
ucuuguucug cagacgauc                                                        19

<210> SEQ ID NO 227
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
```

```
<223> OTHER INFORMATION: n = any nucleobase

<400> SEQUENCE: 227
ncuuguucug cagacgauc                                              19

<210> SEQ ID NO 228
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 228
ncuuguucug cagacgauc                                              19

<210> SEQ ID NO 229
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 229
ugaucuuguu cugcagacg                                              19

<210> SEQ ID NO 230
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 230
ngaucuuguu cugcagacg                                              19

<210> SEQ ID NO 231
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 231
ngaucuuguu cugcagacn                                              19

<210> SEQ ID NO 232
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
```

```
<400> SEQUENCE: 232
uaguaaaguu gcacuggcg                                                19

<210> SEQ ID NO 233
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 233
naguaaaguu gcacuggcg                                                19

<210> SEQ ID NO 234
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 234
naguaaaguu gcacuggcn                                                19

<210> SEQ ID NO 235
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 235
uaacacaagu aaccuuauc                                                19

<210> SEQ ID NO 236
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 236
naacacaagu aaccuuauc                                                19

<210> SEQ ID NO 237
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
```

<223> OTHER INFORMATION: n = any nucleobase

<400> SEQUENCE: 237
naacacaagu aaccuuaun                                                    19

<210> SEQ ID NO 238
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 238
ucaauuguga uaauggcug                                                    19

<210> SEQ ID NO 239
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 239
ncaauuguga uaauggcug                                                    19

<210> SEQ ID NO 240
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 240
ncaauuguga uaauggcun                                                    19

<210> SEQ ID NO 241
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 241
uagcaugaua cugagagcu                                                    19

<210> SEQ ID NO 242
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

```
<400> SEQUENCE: 242
nagcaugaua cugagagcu                                               19

<210> SEQ ID NO 243
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 243
nagcaugaua cugagagcn                                               19

<210> SEQ ID NO 244
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 244
aacuugucaa ccucacucu                                               19

<210> SEQ ID NO 245
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 245
uacuugucaa ccucacucu                                               19

<210> SEQ ID NO 246
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 246
nacuugucaa ccucacucu                                               19

<210> SEQ ID NO 247
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 247
```
nacuugucaa ccucacucn    19

<210> SEQ ID NO 248
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 248
uaacuuguca accucacuc    19

<210> SEQ ID NO 249
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 249
naacuuguca accucacuc    19

<210> SEQ ID NO 250
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 250
naacuuguca accucacun    19

<210> SEQ ID NO 251
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 251
uaacaauucu ccuuguuga    19

<210> SEQ ID NO 252
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 252
naacaauucu ccuuguuga    19

<210> SEQ ID NO 253
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 253
naacaauucu ccuuguugn                                                    19

<210> SEQ ID NO 254
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 254
ucauguucug ugguauguu                                                    19

<210> SEQ ID NO 255
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 255
ncauguucug ugguauguu                                                    19

<210> SEQ ID NO 256
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 256
ncauguucug ugguaugun                                                    19

<210> SEQ ID NO 257
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 257
uacuuuaaua gauccaugu                                                    19

<210> SEQ ID NO 258

-continued

```
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 258
nacuuuaaua gauccaugu                                                    19

<210> SEQ ID NO 259
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 259
nacuuuaaua gauccaugn                                                    19

<210> SEQ ID NO 260
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 260
ugacuuuaau agauccaug                                                    19

<210> SEQ ID NO 261
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 261
ngacuuuaau agauccaug                                                    19

<210> SEQ ID NO 262
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 262
ngacuuuaau agauccaun                                                    19
```

<210> SEQ ID NO 263
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 263
ugcauauuca ccauuuagg                                                19

<210> SEQ ID NO 264
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 264
ngcauauuca ccauuuagg                                                19

<210> SEQ ID NO 265
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 265
ngcauauuca ccauuuagn                                                19

<210> SEQ ID NO 266
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 266
uguuuaagcu ucuagaggu                                                19

<210> SEQ ID NO 267
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 267
nguuuaagcu ucuagaggu                                                19

<210> SEQ ID NO 268

-continued

```
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 268
nguuuaagcu ucuagaggn                                                    19

<210> SEQ ID NO 269
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 269
uuguucauug guugaagg                                                     19

<210> SEQ ID NO 270
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 270
nuguucauug guugaagg                                                     19

<210> SEQ ID NO 271
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 271
nuguucauug guugaagn                                                     19

<210> SEQ ID NO 272
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 272
uuaugcuuug cuguucauu                                                    19

<210> SEQ ID NO 273
<211> LENGTH: 19
<212> TYPE: RNA
```

```
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 273
nuaugcuuug cguucauu                                                   19

<210> SEQ ID NO 274
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 274
nuaugcuuug cguucaun                                                   19

<210> SEQ ID NO 275
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 275
uguuaugcuu ugcuguuca                                                  19

<210> SEQ ID NO 276
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 276
nguuaugcuu ugcuguuca                                                  19

<210> SEQ ID NO 277
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 277
nguuaugcuu ugcuguucn                                                  19

<210> SEQ ID NO 278
```

```
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 278
agguuaugcu uugcuguuc                                                19

<210> SEQ ID NO 279
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 279
ugguuaugcu uugcuguuc                                                19

<210> SEQ ID NO 280
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 280
ngguuaugcu uugcuguuc                                                19

<210> SEQ ID NO 281
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 281
ngguuaugcu uugcuguun                                                19

<210> SEQ ID NO 282
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 282
uaagguuaug cuuugcugu                                                19

<210> SEQ ID NO 283
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
```

```
<220> FEATURE:
<221> NAME/KEY: modified_base
<222> LOCATION: 1
<223> OTHER INFORMATION: n = any nucleobase

<400> SEQUENCE: 283
naagguuaug cuuugcugu                                            19

<210> SEQ ID NO 284
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 284
naagguuaug cuuugcugn                                            19

<210> SEQ ID NO 285
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 285
agauucaagg uuaugcuuu                                            19

<210> SEQ ID NO 286
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 286
ugauucaagg uuaugcuuu                                            19

<210> SEQ ID NO 287
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 287
ngauucaagg uuaugcuuu                                            19

<210> SEQ ID NO 288
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
```

```
<222> LOCATION: 1, 19
<223> OTHER INFORMATION: n = any nucleobase

<400> SEQUENCE: 288
ngauucaagg uuaugcuun                                                19

<210> SEQ ID NO 289
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 289
uucaauaauu gaguugguu                                                19

<210> SEQ ID NO 290
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 290
nucaauaauu gaguugguu                                                19

<210> SEQ ID NO 291
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 291
nucaauaauu gaguuggun                                                19

<210> SEQ ID NO 292
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 292
aguaaaaugg aucacagga                                                19

<210> SEQ ID NO 293
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 293
uguaaaaugg aucacagga                                                19
```

<210> SEQ ID NO 294
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 294
nguaaaaugg aucacagga                                              19

<210> SEQ ID NO 295
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 295
nguaaaaugg aucacaggn                                              19

<210> SEQ ID NO 296
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 296
ucauaugaca guaagaaaa                                              19

<210> SEQ ID NO 297
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 297
ncauaugaca guaagaaaa                                              19

<210> SEQ ID NO 298
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 298
ncauaugaca guaagaaan                                          19

<210> SEQ ID NO 299
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 299
uggaucugca uuuuucucc                                          19

<210> SEQ ID NO 300
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 300
nggaucugca uuuuucucc                                          19

<210> SEQ ID NO 301
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 301
nggaucugca uuuuucucn                                          19

<210> SEQ ID NO 302
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 302
uccaaaaggg uugucucug                                          19

<210> SEQ ID NO 303
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 303
nccaaaaggg uugucucug                                          19

<210> SEQ ID NO 304
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 304
nccaaaaggg uugucucun                                                  19

<210> SEQ ID NO 305
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 305
uagacgauca uacuuggag                                                  19

<210> SEQ ID NO 306
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 306
nagacgauca uacuuggag                                                  19

<210> SEQ ID NO 307
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 307
nagacgauca uacuuggan                                                  19

<210> SEQ ID NO 308
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 308
uccuauuccu uccacaguu                                                  19

```
<210> SEQ ID NO 309
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 309
nccuauuccu uccacaguu                                                    19

<210> SEQ ID NO 310
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 310
nccuauuccu uccacagun                                                    19

<210> SEQ ID NO 311
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 311
uacauacuca ugacgaugc                                                    19

<210> SEQ ID NO 312
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 312
nacauacuca ugacgaugc                                                    19

<210> SEQ ID NO 313
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 313
nacauacuca ugacgaugn                                                    19
```

```
<210> SEQ ID NO 314
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 314
ucacagauuu ccuuggaag                                                    19

<210> SEQ ID NO 315
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 315
ncacagauuu ccuuggaag                                                    19

<210> SEQ ID NO 316
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 316
ncacagauuu ccuuggaan                                                    19

<210> SEQ ID NO 317
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 317
ugaacuucau cucaaugcc                                                    19

<210> SEQ ID NO 318
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 318
ngaacuucau cucaaugcc                                                    19
```

```
<210> SEQ ID NO 319
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 319
ngaacuucau cucaaugcn                                              19

<210> SEQ ID NO 320
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 320
agcauauucu ugaacuuca                                              19

<210> SEQ ID NO 321
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 321
ugcauauucu ugaacuuca                                              19

<210> SEQ ID NO 322
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 322
ngcauauucu ugaacuuca                                              19

<210> SEQ ID NO 323
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 323
ngcauauucu ugaacuucn                                              19

<210> SEQ ID NO 324
<211> LENGTH: 19
```

```
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 324
ucauaggaaa cagcauauu                                                    19

<210> SEQ ID NO 325
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 325
ncauaggaaa cagcauauu                                                    19

<210> SEQ ID NO 326
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 326
ncauaggaaa cagcauaun                                                    19

<210> SEQ ID NO 327
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 327
uggaucucua uggagagca                                                    19

<210> SEQ ID NO 328
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 328
nggaucucua uggagagca                                                    19

<210> SEQ ID NO 329
<211> LENGTH: 19
<212> TYPE: RNA
<213> ORGANISM: Artificial sequence
```

```
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 329
nggaucucua uggagagcn                                                   19

<210> SEQ ID NO 330
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 330
uuugaaugcu gagaaauac                                                   19

<210> SEQ ID NO 331
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 331
nuugaaugcu gagaaauac                                                   19

<210> SEQ ID NO 332
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 332
nuugaaugcu gagaaauan                                                   19

<210> SEQ ID NO 333
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 333
ucuauggacu ugaucuugg                                                   19

<210> SEQ ID NO 334
<211> LENGTH: 19
<212> TYPE: RNA
<213> ORGANISM: Artificial sequence
<220> FEATURE:
<223> OTHER INFORMATION: RNAi agent antisense strand 19-mer core base
```

```
        sequence
<220> FEATURE:
<221> NAME/KEY: modified_base
<222> LOCATION: 1
<223> OTHER INFORMATION: n = any nucleobase

<400> SEQUENCE: 334
ncuauggacu ugaucuugg                                                  19

<210> SEQ ID NO 335
<211> LENGTH: 19
<212> TYPE: RNA
<213> ORGANISM: Artificial sequence
<220> FEATURE:
<223> OTHER INFORMATION: RNAi agent antisense strand 19-mer core base
        sequence
<220> FEATURE:
<221> NAME/KEY: modified_base
<222> LOCATION: 1, 19
<223> OTHER INFORMATION: n = any nucleobase

<400> SEQUENCE: 335
ncuauggacu ugaucuugn                                                  19

<210> SEQ ID NO 336
<211> LENGTH: 19
<212> TYPE: RNA
<213> ORGANISM: Artificial sequence
<220> FEATURE:
<223> OTHER INFORMATION: RNAi agent antisense strand 19-mer core base
        sequence

<400> SEQUENCE: 336
augaaacaaa caaacccug                                                  19

<210> SEQ ID NO 337
<211> LENGTH: 19
<212> TYPE: RNA
<213> ORGANISM: Artificial sequence
<220> FEATURE:
<223> OTHER INFORMATION: RNAi agent antisense strand 19-mer core base
        sequence

<400> SEQUENCE: 337
uugaaacaaa caaacccug                                                  19

<210> SEQ ID NO 338
<211> LENGTH: 19
<212> TYPE: RNA
<213> ORGANISM: Artificial sequence
<220> FEATURE:
<223> OTHER INFORMATION: RNAi agent antisense strand 19-mer core base
        sequence
<220> FEATURE:
<221> NAME/KEY: modified_base
<222> LOCATION: 1
<223> OTHER INFORMATION: n = any nucleobase

<400> SEQUENCE: 338
nugaaacaaa caaacccug                                                  19

<210> SEQ ID NO 339
<211> LENGTH: 19
<212> TYPE: RNA
<213> ORGANISM: Artificial sequence
<220> FEATURE:
<223> OTHER INFORMATION: RNAi agent antisense strand 19-mer core base
        sequence
<220> FEATURE:
```

```
<221> NAME/KEY: modified_base
<222> LOCATION: 1, 19
<223> OTHER INFORMATION: n = any nucleobase

<400> SEQUENCE: 339
nugaaacaaa caaacccun                                                  19

<210> SEQ ID NO 340
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 340
ugguaguucu ucauaggug                                                  19

<210> SEQ ID NO 341
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 341
ngguaguucu ucauaggug                                                  19

<210> SEQ ID NO 342
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 342
ngguaguucu ucauaggun                                                  19

<210> SEQ ID NO 343
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 343
ugauaauggc ugguaguuc                                                  19

<210> SEQ ID NO 344
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
```

```
<223> OTHER INFORMATION: n = any nucleobase

<400> SEQUENCE: 344
ngauaauggc ugguaguuc                                              19

<210> SEQ ID NO 345
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 345
ngauaauggc ugguaguun                                              19

<210> SEQ ID NO 346
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 346
ucucaauugu gauaauggc                                              19

<210> SEQ ID NO 347
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 347
ncucaauugu gauaauggc                                              19

<210> SEQ ID NO 348
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 348
ncucaauugu gauaauggn                                              19

<210> SEQ ID NO 349
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
```

-continued

```
<400> SEQUENCE: 349 ucuucucga ucuucagcu                                               19

<210> SEQ ID NO 350
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 350 ncuucucga ucuucagcu                                               19

<210> SEQ ID NO 351
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 351 ncuucucga ucuucagcn                                               19

<210> SEQ ID NO 352
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 352
uuuggaacag caauggugc                                              19

<210> SEQ ID NO 353
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 353
nuuggaacag caauggugc                                              19

<210> SEQ ID NO 354
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
```

```
<223> OTHER INFORMATION: n = any nucleobase

<400> SEQUENCE: 354
nuuggaacag caauggugn                                                   19

<210> SEQ ID NO 355
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 355
uguagacaca aagagcucc                                                   19

<210> SEQ ID NO 356
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 356
nguagacaca aagagcucc                                                   19

<210> SEQ ID NO 357
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 357
nguagacaca aagagcucn                                                   19

<210> SEQ ID NO 358
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 358
ucuguguaga cacaaagag                                                   19

<210> SEQ ID NO 359
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase
```

```
<400> SEQUENCE: 359
ncuguguaga cacaaagag                                              19

<210> SEQ ID NO 360
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 360
ncuguguaga cacaaagan                                              19

<210> SEQ ID NO 361
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 361
uuccauaaua cucugagag                                              19

<210> SEQ ID NO 362
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 362
nuccauaaua cucugagag                                              19

<210> SEQ ID NO 363
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 363
nuccauaaua cucugagan                                              19

<210> SEQ ID NO 364
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 364
```
ucucguucca uaauacucu         19

<210> SEQ ID NO 365
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 365
ncucguucca uaauacucu         19

<210> SEQ ID NO 366
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 366
ncucguucca uaauacucn         19

<210> SEQ ID NO 367
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 367
aaugaaacaa acaaacccu         19

<210> SEQ ID NO 368
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 368
uaugaaacaa acaaacccu         19

<210> SEQ ID NO 369
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 369
naugaaacaa acaaacccu         19

<210> SEQ ID NO 370
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 370
naugaaacaa acaaacccn                                                    19

<210> SEQ ID NO 371
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 371
aaaugaaaca aacaaaccc                                                    19

<210> SEQ ID NO 372
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 372
uaaugaaaca aacaaaccc                                                    19

<210> SEQ ID NO 373
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 373
naaugaaaca aacaaaccc                                                    19

<210> SEQ ID NO 374
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 374
naaugaaaca aacaaaccn                                                    19

<210> SEQ ID NO 375

```
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 375
ugaaaugaaa caaacaaac                                                      19

<210> SEQ ID NO 376
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 376
ngaaaugaaa caaacaaac                                                      19

<210> SEQ ID NO 377
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 377
ngaaaugaaa caaacaaan                                                      19

<210> SEQ ID NO 378
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 378
agacgaucau acuuggaga                                                      19

<210> SEQ ID NO 379
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 379
ugacgaucau acuuggaga                                                      19

<210> SEQ ID NO 380
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
```

```
<220> FEATURE:
<221> NAME/KEY: modified_base
<222> LOCATION: 1
<223> OTHER INFORMATION: n = any nucleobase

<400> SEQUENCE: 380
ngacgaucau acuuggaga                                                  19

<210> SEQ ID NO 381
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 381
ngacgaucau acuuggagn                                                  19

<210> SEQ ID NO 382
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 382
aaggcauucu caaucuccu                                                  19

<210> SEQ ID NO 383
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 383
uaggcauucu caaucuccu                                                  19

<210> SEQ ID NO 384
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 384
naggcauucu caaucuccu                                                  19

<210> SEQ ID NO 385
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
```

<222> LOCATION: 1, 19
<223> OTHER INFORMATION: n = any nucleobase

<400> SEQUENCE: 385
naggcauucu caaucuccn                                                    19

<210> SEQ ID NO 386
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 386
uuuccuugga aggcauucu                                                    19

<210> SEQ ID NO 387
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 387
nuuccuugga aggcauucu                                                    19

<210> SEQ ID NO 388
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 388
nuuccuugga aggcauucn                                                    19

<210> SEQ ID NO 389
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 389
uagauuuccu uggaaggca                                                    19

<210> SEQ ID NO 390
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 390
nagauuuccu uggaaggca                                           19

<210> SEQ ID NO 391
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 391
nagauuuccu uggaaggcn                                           19

<210> SEQ ID NO 392
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 392
auaggaaaca gcauauucu                                           19

<210> SEQ ID NO 393
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 393
uuaggaaaca gcauauucu                                           19

<210> SEQ ID NO 394
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 394
nuaggaaaca gcauauucu                                           19

<210> SEQ ID NO 395
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 395
nuaggaaaca gcauauucn                                                19

<210> SEQ ID NO 396
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 396
uugaugaugu ucccuccaa                                                19

<210> SEQ ID NO 397
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 397
nugaugaugu ucccuccaa                                                19

<210> SEQ ID NO 398
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 398
nugaugaugu ucccuccan                                                19

<210> SEQ ID NO 399
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 399
uagaacuuga agaagaagc                                                19

<210> SEQ ID NO 400
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 400
nagaacuuga agaagaagc                                                19

<210> SEQ ID NO 401
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 401
nagaacuuga agaagaagn                                              19

<210> SEQ ID NO 402
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 402
uaccaaugau augcccaac                                              19

<210> SEQ ID NO 403
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 403
naccaaugau augcccaac                                              19

<210> SEQ ID NO 404
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 404
naccaaugau augcccaan                                              19

<210> SEQ ID NO 405
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 405
ucaugguguu cuguguaga                                              19

```
<210> SEQ ID NO 406
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 406
ncaugguguu cuguguaga                                                19

<210> SEQ ID NO 407
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 407
ncaugguguu cuguguagn                                                19

<210> SEQ ID NO 408
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 408
uugagagaga uccugggug                                                19

<210> SEQ ID NO 409
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 409
nugagagaga uccugggug                                                19

<210> SEQ ID NO 410
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 410
nugagagaga uccugggun                                                19
```

<210> SEQ ID NO 411
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 411
ucaugauacu gagagcuug                                                19

<210> SEQ ID NO 412
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 412
ncaugauacu gagagcuug                                                19

<210> SEQ ID NO 413
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 413
ncaugauacu gagagcuun                                                19

<210> SEQ ID NO 414
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 414
uugucaaccu cacucuucc                                                19

<210> SEQ ID NO 415
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 415
nugucaaccu cacucuucc                                                19

```
<210> SEQ ID NO 416
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 416
nugucaaccu cacucuucn                                                    19

<210> SEQ ID NO 417
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 417
uuuccaacaa uucuccuug                                                    19

<210> SEQ ID NO 418
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 418
nuuccaacaa uucuccuug                                                    19

<210> SEQ ID NO 419
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 419
nuuccaacaa uucuccuun                                                    19

<210> SEQ ID NO 420
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 420
uugaguuagu cucaaagcu                                                    19

<210> SEQ ID NO 421
<211> LENGTH: 19
```

```
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 421
nugaguuagu cucaaagcu                                                    19

<210> SEQ ID NO 422
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 422
nugaguuagu cucaaagcn                                                    19

<210> SEQ ID NO 423
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 423
augacaauau cugugcgga                                                    19

<210> SEQ ID NO 424
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 424
uugacaauau cugugcgga                                                    19

<210> SEQ ID NO 425
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 425
nugacaauau cugugcgga                                                    19

<210> SEQ ID NO 426
<211> LENGTH: 19
<212> TYPE: RNA
<213> ORGANISM: Artificial sequence
```

```
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 426
nugacaauau cugugcggn                                              19

<210> SEQ ID NO 427
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 427
ucaugacaau aucugugcg                                              19

<210> SEQ ID NO 428
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 428
ncaugacaau aucugugcg                                              19

<210> SEQ ID NO 429
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 429
ncaugacaau aucugugcn                                              19

<210> SEQ ID NO 430
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 430
ucaaagaaga uagaagcag                                              19

<210> SEQ ID NO 431
<211> LENGTH: 19
<212> TYPE: RNA
<213> ORGANISM: Artificial sequence
<220> FEATURE:
<223> OTHER INFORMATION: RNAi agent antisense strand 19-mer core base
```

```
            sequence
<220> FEATURE:
<221> NAME/KEY: modified_base
<222> LOCATION: 1
<223> OTHER INFORMATION: n = any nucleobase

<400> SEQUENCE: 431
ncaaagaaga uagaagcag                                           19

<210> SEQ ID NO 432
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 432
ncaaagaaga uagaagcan                                           19

<210> SEQ ID NO 433
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 433
ucacguuauu accugugug                                           19

<210> SEQ ID NO 434
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 434
ncacguuauu accugugug                                           19

<210> SEQ ID NO 435
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 435
ncacguuauu accugugun                                           19

<210> SEQ ID NO 436
<211> LENGTH: 19
<212> TYPE: RNA
<213> ORGANISM: Artificial sequence
```

```
<220> FEATURE:
<223> OTHER INFORMATION: RNAi agent antisense strand 19-mer core base
      sequence

<400> SEQUENCE: 436
uagaacuuga gguuauaca                                                      19

<210> SEQ ID NO 437
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 437
nagaacuuga gguuauaca                                                      19

<210> SEQ ID NO 438
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 438
nagaacuuga gguuauacn                                                      19

<210> SEQ ID NO 439
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 439
augcuuugcu guucauugg                                                      19

<210> SEQ ID NO 440
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 440
uugcuuugcu guucauugg                                                      19

<210> SEQ ID NO 441
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
```

```
<223> OTHER INFORMATION: n = any nucleobase

<400> SEQUENCE: 441
nugcuuugcu guucauugg                                                    19

<210> SEQ ID NO 442
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 442
nugcuuugcu guucauugn                                                    19

<210> SEQ ID NO 443
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 443
uaguauagau ucaagguua                                                    19

<210> SEQ ID NO 444
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 444
naguauagau ucaagguua                                                    19

<210> SEQ ID NO 445
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 445
naguauagau ucaagguun                                                    19

<210> SEQ ID NO 446
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
```

```
<400> SEQUENCE: 446
agaguaaucu ugcuuuaug                                               19

<210> SEQ ID NO 447
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 447
ugaguaaucu ugcuuuaug                                               19

<210> SEQ ID NO 448
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 448
ngaguaaucu ugcuuuaug                                               19

<210> SEQ ID NO 449
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 449
ngaguaaucu ugcuuuaun                                               19

<210> SEQ ID NO 450
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 450
auagcaucau uucuaggug                                               19

<210> SEQ ID NO 451
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 451
uuagcaucau uucuaggug                                               19

<210> SEQ ID NO 452
```

```
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 452
nuagcaucau uucuaggug                                                   19

<210> SEQ ID NO 453
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 453
nuagcaucau uucuaggun                                                   19

<210> SEQ ID NO 454
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 454
agacagaaga gacagagcu                                                   19

<210> SEQ ID NO 455
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 455
ugacagaaga gacagagcu                                                   19

<210> SEQ ID NO 456
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 456
ngacagaaga gacagagcu                                                   19

<210> SEQ ID NO 457
<211> LENGTH: 19
<212> TYPE: DNA
```

```
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 457
ngacagaaga gacagagcn                                                  19

<210> SEQ ID NO 458
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 458
aguaagaaaa ccaagccuu                                                  19

<210> SEQ ID NO 459
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 459
uguaagaaaa ccaagccuu                                                  19

<210> SEQ ID NO 460
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 460
nguaagaaaa ccaagccuu                                                  19

<210> SEQ ID NO 461
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 461
nguaagaaaa ccaagccun                                                  19

<210> SEQ ID NO 462
<211> LENGTH: 19
<212> TYPE: RNA
<213> ORGANISM: Artificial sequence
<220> FEATURE:
```

```
<223> OTHER INFORMATION: RNAi agent antisense strand 19-mer core base
      sequence

<400> SEQUENCE: 462
aguaagaaaa ccaagccuu                                                  19

<210> SEQ ID NO 463
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 463
uguaagaaaa ccaagccuu                                                  19

<210> SEQ ID NO 464
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 464
nguaagaaaa ccaagccuu                                                  19

<210> SEQ ID NO 465
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 465
nguaagaaaa ccaagccun                                                  19

<210> SEQ ID NO 466
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 466
uauacuugga gagcaucac                                                  19

<210> SEQ ID NO 467
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase
```

-continued

<400> SEQUENCE: 467
nauacuugga gagcaucac                                                      19

<210> SEQ ID NO 468
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 468
nauacuugga gagcaucan                                                      19

<210> SEQ ID NO 469
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 469
uugcagacga ucauacuug                                                      19

<210> SEQ ID NO 470
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 470
nugcagacga ucauacuug                                                      19

<210> SEQ ID NO 471
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 471
nugcagacga ucauacuun                                                      19

<210> SEQ ID NO 472
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 472
uugaauaaaa cucucaugc                                              19

<210> SEQ ID NO 473
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 473
nugaauaaaa cucucaugc                                              19

<210> SEQ ID NO 474
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 474
nugaauaaaa cucucaugn                                              19

<210> SEQ ID NO 475
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 475
uugaauaaaa cucucaugc                                              19

<210> SEQ ID NO 476
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 476
nugaauaaaa cucucaugc                                              19

<210> SEQ ID NO 477
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 477
nugaauaaaa cucucaugn                                                 19

<210> SEQ ID NO 478
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 478
agaaaagugg acgaucuug                                                 19

<210> SEQ ID NO 479
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 479
ugaaaagugg acgaucuug                                                 19

<210> SEQ ID NO 480
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 480
ngaaaagugg acgaucuug                                                 19

<210> SEQ ID NO 481
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 481
ngaaaagugg acgaucuun                                                 19

<210> SEQ ID NO 482
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 482
uaguugucac ugcaacaug                                                 19

```
<210> SEQ ID NO 483
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 483
naguugucac ugcaacaug                                                   19

<210> SEQ ID NO 484
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 484
naguugucac ugcaacaun                                                   19

<210> SEQ ID NO 485
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 485
auuccuucca caguuguca                                                   19

<210> SEQ ID NO 486
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 486
uuuccuucca caguuguca                                                   19

<210> SEQ ID NO 487
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 487
nuuccuucca caguuguca                                                   19

<210> SEQ ID NO 488
<211> LENGTH: 19
```

```
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 488
nuuccuucca caguugucn                                                    19

<210> SEQ ID NO 489
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 489
ugcauucuca aucuccucc                                                    19

<210> SEQ ID NO 490
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 490
ngcauucuca aucuccucc                                                    19

<210> SEQ ID NO 491
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 491
ngcauucuca aucuccucn                                                    19

<210> SEQ ID NO 492
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 492
uucaaugcca aucuccgug                                                    19

<210> SEQ ID NO 493
<211> LENGTH: 19
<212> TYPE: RNA
<213> ORGANISM: Artificial sequence
```

```
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 493
nucaaugcca aucccgug                                                       19

<210> SEQ ID NO 494
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 494
nucaaugcca aucccgun                                                       19

<210> SEQ ID NO 495
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 495
auauucuuga acuucaucu                                                      19

<210> SEQ ID NO 496
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 496
uuauucuuga acuucaucu                                                      19

<210> SEQ ID NO 497
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 497
nuauucuuga acuucaucu                                                      19

<210> SEQ ID NO 498
<211> LENGTH: 19
<212> TYPE: RNA
<213> ORGANISM: Artificial sequence
<220> FEATURE:
<223> OTHER INFORMATION: RNAi agent antisense strand 19-mer core base
```

```
              sequence
<220> FEATURE:
<221> NAME/KEY: modified_base
<222> LOCATION: 1, 19
<223> OTHER INFORMATION: n = any nucleobase

<400> SEQUENCE: 498
nuauucuuga acuucaucn                                                19

<210> SEQ ID NO 499
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 499
auauucuuga acuucaucu                                                19

<210> SEQ ID NO 500
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 500
uuauucuuga acuucaucu                                                19

<210> SEQ ID NO 501
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 501
nuauucuuga acuucaucu                                                19

<210> SEQ ID NO 502
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 502
nuauucuuga acuucaucn                                                19

<210> SEQ ID NO 503
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
```

```
<400> SEQUENCE: 503
uuauggagag caguaucuc                                                      19

<210> SEQ ID NO 504
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 504
nuauggagag caguaucuc                                                      19

<210> SEQ ID NO 505
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 505
nuauggagag caguaucun                                                      19

<210> SEQ ID NO 506
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 506
uaaugcugag aaauacucc                                                      19

<210> SEQ ID NO 507
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 507
naaugcugag aaauacucc                                                      19

<210> SEQ ID NO 508
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
```

```
<223> OTHER INFORMATION: n = any nucleobase

<400> SEQUENCE: 508
naaugcugag aaauacucn                                                    19

<210> SEQ ID NO 509
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 509
ugaaugcuga gaaauacuc                                                    19

<210> SEQ ID NO 510
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 510
ngaaugcuga gaaauacuc                                                    19

<210> SEQ ID NO 511
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 511
ngaaugcuga gaaauacun                                                    19

<210> SEQ ID NO 512
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 512
ucaaugucau cuucucucc                                                    19

<210> SEQ ID NO 513
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase
```

```
<400> SEQUENCE: 513
ncaaugucau cuucucucc                                                      19

<210> SEQ ID NO 514
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 514
ncaaugucau cuucucucn                                                      19

<210> SEQ ID NO 515
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 515
acaaauucca guuauguua                                                      19

<210> SEQ ID NO 516
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 516
ucaaauucca guuauguua                                                      19

<210> SEQ ID NO 517
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 517
ncaaauucca guuauguua                                                      19

<210> SEQ ID NO 518
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 518
```
ncaaauucca guuauguun					19

<210> SEQ ID NO 519
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 519
uucaauugug auaauggcu					19

<210> SEQ ID NO 520
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 520
nucaauugug auaauggcu					19

<210> SEQ ID NO 521
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 521
nucaauugug auaauggcn					19

<210> SEQ ID NO 522
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 522
aacauuuuug caacaaagc					19

<210> SEQ ID NO 523
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 523
uacauuuuug caacaaagc					19

<210> SEQ ID NO 524
<211> LENGTH: 19
<212> TYPE: RNA

```
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 524 nacauuuug caacaaagc                                                    19

<210> SEQ ID NO 525
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 525 nacauuuug caacaaagn                                                    19

<210> SEQ ID NO 526
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 526
ucaacauuuu ugcaacaaa                                                   19

<210> SEQ ID NO 527
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 527
ncaacauuuu ugcaacaaa                                                   19

<210> SEQ ID NO 528
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 528
ncaacauuuu ugcaacaan                                                   19

<210> SEQ ID NO 529
```

```
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 529
uuucacucga accacaauc                                                    19

<210> SEQ ID NO 530
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 530
nuucacucga accacaauc                                                    19

<210> SEQ ID NO 531
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 531
nuucacucga accacaaun                                                    19

<210> SEQ ID NO 532
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 532
uuggaaggca uucucaauc                                                    19

<210> SEQ ID NO 533
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 533
nuggaaggca uucucaauc                                                    19

<210> SEQ ID NO 534
<211> LENGTH: 19
<212> TYPE: RNA
```

```
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 534
nuggaaggca uucucaaun                                                   19

<210> SEQ ID NO 535
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 535
ucagcuucuu cuucaaguu                                                   19

<210> SEQ ID NO 536
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 536
ucagcuucuu cuucaagua                                                   19

<210> SEQ ID NO 537
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 537
ucagcuucuu cuucaagun                                                   19

<210> SEQ ID NO 538
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 538
ncagcuucuu cuucaagun                                                   19

<210> SEQ ID NO 539
<211> LENGTH: 19
<212> TYPE: RNA
<213> ORGANISM: Artificial sequence
<220> FEATURE:
```

```
<223> OTHER INFORMATION: RNAi agent sense strand 19-mer core base
      sequence

<400> SEQUENCE: 539
agcuucuucu ucaaguucu                                                    19

<210> SEQ ID NO 540
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 540
agcuucuucu ucaaguuca                                                    19

<210> SEQ ID NO 541
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 541
agcuucuucu ucaaguucn                                                    19

<210> SEQ ID NO 542
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 542
ngcuucuucu ucaaguucn                                                    19

<210> SEQ ID NO 543
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 543
uucuucuuca aguucuaca                                                    19

<210> SEQ ID NO 544
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase
```

-continued

<400> SEQUENCE: 544
uucuucuuca aguucuacn                                            19

<210> SEQ ID NO 545
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 545
nucuucuuca aguucuacn                                            19

<210> SEQ ID NO 546
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 546
gggugaaaau caccauga                                             19

<210> SEQ ID NO 547
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 547
gggugaaaau caccaugn                                             19

<210> SEQ ID NO 548
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 548
nggugaaaau caccaugn                                             19

<210> SEQ ID NO 549
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 549
gugaaaauca ccaugaaa                                             19

<210> SEQ ID NO 550
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 550
gugaaaauca ccaugaan                                             19

<210> SEQ ID NO 551
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 551
nugaaaauca ccaugaan                                             19

<210> SEQ ID NO 552
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 552
ugaaaaucac cuaugaaga                                            19

<210> SEQ ID NO 553
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 553
ugaaaaucac cuaugaagn                                            19

<210> SEQ ID NO 554
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase -continued

<400> SEQUENCE: 554
ngaaaaucac cuaugaagn                                          19

<210> SEQ ID NO 555
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 555
gaaaaucacc uaugaagaa                                          19

<210> SEQ ID NO 556
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 556
gaaaaucacc uaugaagan                                          19

<210> SEQ ID NO 557
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 557
naaaaucacc uaugaagan                                          19

<210> SEQ ID NO 558
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 558
accagccauu aucacaauu                                          19

<210> SEQ ID NO 559
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 559
accagccauu aucacaaua                                          19

```
<210> SEQ ID NO 560
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 560
accagccauu aucacaaun                                              19

<210> SEQ ID NO 561
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 561
nccagccauu aucacaaun                                              19

<210> SEQ ID NO 562
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 562
agaacaacuc cuuuuauga                                              19

<210> SEQ ID NO 563
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 563
agaacaacuc cuuuuaugn                                              19

<210> SEQ ID NO 564
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 564
ngaacaacuc cuuuuaugn                                              19
```

```
<210> SEQ ID NO 565
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 565
gaacaacucc uuuuaugga                                                    19

<210> SEQ ID NO 566
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 566
gaacaacucc uuuuauggn                                                    19

<210> SEQ ID NO 567
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 567
naacaacucc uuuuauggn                                                    19

<210> SEQ ID NO 568
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 568
gacaagcacu aacacugua                                                    19

<210> SEQ ID NO 569
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 569
gacaagcacu aacacugun                                                    19
```

```
<210> SEQ ID NO 570
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 570
nacaagcacu aacacugun                                                    19

<210> SEQ ID NO 571
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 571
gucaugagua uguacacaa                                                    19

<210> SEQ ID NO 572
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 572
gucaugagua uguacacan                                                    19

<210> SEQ ID NO 573
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 573
nucaugagua uguacacan                                                    19

<210> SEQ ID NO 574
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 17
<223> OTHER INFORMATION: n = inosine (hypoxanthine)

<400> SEQUENCE: 574
gacaugcuga uaacugnua                                                    19
```

```
<210> SEQ ID NO 575
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 17
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 575
gacaugcuga uaacugnun                                              19

<210> SEQ ID NO 576
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 17
<223> OTHER INFORMATION: n = inosine (hypoxanthine)

<400> SEQUENCE: 576
nacaugcuga uaacugnun                                              19

<210> SEQ ID NO 577
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 577
gacaugcuga uaacuggua                                              19

<210> SEQ ID NO 578
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 578
gacaugcuga uaacuggua                                              19

<210> SEQ ID NO 579
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 579
```

```
gacaugcuga uaacuggua                                              19

<210> SEQ ID NO 580
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 580
auacaagguu ggcuucaua                                              19

<210> SEQ ID NO 581
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 581
auacaagguu ggcuucaun                                              19

<210> SEQ ID NO 582
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 582
nuacaagguu ggcuucaun                                              19

<210> SEQ ID NO 583
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 583
aagguuggcu ucaugaaga                                              19

<210> SEQ ID NO 584
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 584
aagguuggcu ucaugaagn                                              19
```

<210> SEQ ID NO 585
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 585
nagguuggcu ucaugaagn                                                      19

<210> SEQ ID NO 586
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 586
agguuggcuu caugaagaa                                                      19

<210> SEQ ID NO 587
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 587
agguuggcuu caugaagan                                                      19

<210> SEQ ID NO 588
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 588
ngguuggcuu caugaagan                                                      19

<210> SEQ ID NO 589
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 589
guuggcuuca ugaagacua                                                      19

```
<210> SEQ ID NO 590
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 590
guuggcuuca ugaagacun                                              19

<210> SEQ ID NO 591
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 591
nuuggcuuca ugaagacun                                              19

<210> SEQ ID NO 592
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 592
gagaauuguu ggaaaaaga                                              19

<210> SEQ ID NO 593
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 593
gagaauuguu ggaaaaagn                                              19

<210> SEQ ID NO 594
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 594
nagaauuguu ggaaaaagn                                              19
```

<210> SEQ ID NO 595
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 595
ggcuugcucu gaaguagaa                                                19

<210> SEQ ID NO 596
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 596
ggcuugcucu gaaguagan                                                19

<210> SEQ ID NO 597
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 597
ngcuugcucu gaaguagan                                                19

<210> SEQ ID NO 598
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 598
uugcucugaa guagaaaua                                                19

<210> SEQ ID NO 599
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 599
uugcucugaa guagaaaun                                                19

```
<210> SEQ ID NO 600
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 600
nugcucugaa guagaaaun                                                19

<210> SEQ ID NO 601
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)

<400> SEQUENCE: 601
cugccauuga uauungaca                                                19

<210> SEQ ID NO 602
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 602
cugccauuga uauungacn                                                19

<210> SEQ ID NO 603
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = inosine (hypoxanthine)

<400> SEQUENCE: 603
nugccauuga uauungacn                                                19

<210> SEQ ID NO 604
<211> LENGTH: 19
<212> TYPE: RNA
```

```
<213> ORGANISM: Artificial sequence
<220> FEATURE:
<223> OTHER INFORMATION: RNAi agent sense strand 19-mer core base
      sequence

<400> SEQUENCE: 604
agaucgucca cuuuucuga                                                    19

<210> SEQ ID NO 605
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 605
agaucgucca cuuuucugn                                                    19

<210> SEQ ID NO 606
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 606
ngaucgucca cuuuucugn                                                    19

<210> SEQ ID NO 607
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 607
ccgaagcaga uaauguugu                                                    19

<210> SEQ ID NO 608
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 608
ccgaagcaga uaauguugu                                                    19

<210> SEQ ID NO 609
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
```

-continued

<222> LOCATION: 19
<223> OTHER INFORMATION: n = any nucleobase

<400> SEQUENCE: 609
ccgaagcaga uaauguugn                                                19

<210> SEQ ID NO 610
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 610
ncgaagcaga uaauguugn                                                19

<210> SEQ ID NO 611
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 611
cucucucaga guauuauga                                                19

<210> SEQ ID NO 612
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 612
cucucucaga guauuaugn                                                19

<210> SEQ ID NO 613
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 613
nucucucaga guauuaugn                                                19

<210> SEQ ID NO 614
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 614
caccaaguuu ggaauaaga                                        19

<210> SEQ ID NO 615
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 615
caccaaguuu ggaauaagn                                        19

<210> SEQ ID NO 616
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 616
naccaaguuu ggaauaagn                                        19

<210> SEQ ID NO 617
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 617
gcauaaagca agauuacua                                        19

<210> SEQ ID NO 618
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 618
gcauaaagca agauuacun                                        19

<210> SEQ ID NO 619
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base

```
<222> LOCATION: 1, 19
<223> OTHER INFORMATION: n = any nucleobase

<400> SEQUENCE: 619
ncauaaagca agauuacun                                                        19

<210> SEQ ID NO 620
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 620
caauguucua gauucuuu                                                         19

<210> SEQ ID NO 621
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 621
caauguucua gauucuua                                                         19

<210> SEQ ID NO 622
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 622
caauguucua gauucuun                                                         19

<210> SEQ ID NO 623
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 623
naauguucua gauucuun                                                         19

<210> SEQ ID NO 624
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 624
ugcuggauga gugaaguua                                                        19
```

<210> SEQ ID NO 625
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 625
ugcuggauga gugaaguun                                            19

<210> SEQ ID NO 626
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 626
ngcuggauga gugaaguun                                            19

<210> SEQ ID NO 627
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 4
<223> OTHER INFORMATION: n = inosine (hypoxanthine)

<400> SEQUENCE: 627
gcungaugag ugaaguuga                                            19

<210> SEQ ID NO 628
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 4
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 628
gcungaugag ugaaguugn                                            19

<210> SEQ ID NO 629
<211> LENGTH: 19
<212> TYPE: RNA
<213> ORGANISM: Artificial sequence
<220> FEATURE:

```
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 4
<223> OTHER INFORMATION: n = inosine (hypoxanthine)

<400> SEQUENCE: 629
ncungaugag ugaaguugn                                                   19

<210> SEQ ID NO 630
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 17
<223> OTHER INFORMATION: n = inosine (hypoxanthine)

<400> SEQUENCE: 630
cuggaugagu gaaguunca                                                   19

<210> SEQ ID NO 631
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 17
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 631
cuggaugagu gaaguuncn                                                   19

<210> SEQ ID NO 632
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 17
<223> OTHER INFORMATION: n = inosine (hypoxanthine)

<400> SEQUENCE: 632
nuggaugagu gaaguuncn                                                   19

<210> SEQ ID NO 633
<211> LENGTH: 19
<212> TYPE: RNA
<213> ORGANISM: Artificial sequence
```

<220> FEATURE:
<223> OTHER INFORMATION: RNAi agent sense strand 19-mer core base
      sequence

<400> SEQUENCE: 633
ugcucuccaa guaugauca                                                  19

<210> SEQ ID NO 634
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 634
ugcucuccaa guaugaucn                                                  19

<210> SEQ ID NO 635
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 635
ngcucuccaa guaugaucn                                                  19

<210> SEQ ID NO 636
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 636
gaucgucugc agaacaaga                                                  19

<210> SEQ ID NO 637
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 637
gaucgucugc agaacaagn                                                  19

<210> SEQ ID NO 638
<211> LENGTH: 19
<212> TYPE: RNA
<213> ORGANISM: Artificial sequence
<220> FEATURE:
<223> OTHER INFORMATION: RNAi agent sense strand 19-mer core base -continued

```
      sequence
<220> FEATURE:
<221> NAME/KEY: modified_base
<222> LOCATION: 19
<223> OTHER INFORMATION: n = any nucleobase

<400> SEQUENCE: 638
gaucgucugc agaacaagn                                                  19

<210> SEQ ID NO 639
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 639
cgucugcaga acaagauca                                                  19

<210> SEQ ID NO 640
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 640
cgucugcaga acaagaucn                                                  19

<210> SEQ ID NO 641
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 641
ngucugcaga acaagaucn                                                  19

<210> SEQ ID NO 642
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 642
cgccagugca acuuuacua                                                  19

<210> SEQ ID NO 643
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
```

<221> NAME/KEY: modified_base
<222> LOCATION: 19
<223> OTHER INFORMATION: n = any nucleobase

<400> SEQUENCE: 643
cgccagugca acuuuacun                                                19

<210> SEQ ID NO 644
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 644
ngccagugca acuuuacun                                                19

<210> SEQ ID NO 645
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 645
gauaagguua cuuguguua                                                19

<210> SEQ ID NO 646
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 646
gauaagguua cuuguguun                                                19

<210> SEQ ID NO 647
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 647
nauaagguua cuuguguun                                                19

<210> SEQ ID NO 648
<211> LENGTH: 19
<212> TYPE: RNA
<213> ORGANISM: Artificial sequence
<220> FEATURE:
<223> OTHER INFORMATION: RNAi agent sense strand 19-mer core base -continued sequence

<400> SEQUENCE: 648
cagccauuau cacaauuga                                                    19

<210> SEQ ID NO 649
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 649
cagccauuau cacaauugn                                                    19

<210> SEQ ID NO 650
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 650
nagccauuau cacaauugn                                                    19

<210> SEQ ID NO 651
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 651
agcucucagu aucaugcua                                                    19

<210> SEQ ID NO 652
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 652
agcucucagu aucaugcun                                                    19

<210> SEQ ID NO 653
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:

```
<221> NAME/KEY: modified_base
<222> LOCATION: 1, 19
<223> OTHER INFORMATION: n = any nucleobase

<400> SEQUENCE: 653
ngcucucagu aucaugcun                                                19

<210> SEQ ID NO 654
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 654
agagugaggu ugacaaguu                                                19

<210> SEQ ID NO 655
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 655
agagugaggu ugacaagua                                                19

<210> SEQ ID NO 656
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 656
agagugaggu ugacaagun                                                19

<210> SEQ ID NO 657
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 657
ngagugaggu ugacaagun                                                19

<210> SEQ ID NO 658
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 658
```
gagugagguu gacaaguua                                                    19

<210> SEQ ID NO 659
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 659
gagugagguu gacaaguun                                                    19

<210> SEQ ID NO 660
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 660
nagugagguu gacaaguun                                                    19

<210> SEQ ID NO 661
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 661
ucaacaagga gaauuguua                                                    19

<210> SEQ ID NO 662
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 662
ucaacaagga gaauuguun                                                    19

<210> SEQ ID NO 663
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

```
<400> SEQUENCE: 663
ncaacaagga gaauuguun                                              19

<210> SEQ ID NO 664
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 664
aacauaccac agaacauga                                              19

<210> SEQ ID NO 665
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 665
aacauaccac agaacaugn                                              19

<210> SEQ ID NO 666
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 666
nacauaccac agaacaugn                                              19

<210> SEQ ID NO 667
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 667
acauggaucu auuaaagua                                              19

<210> SEQ ID NO 668
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 668
```
acauggaucu auuaaagun                                                19

<210> SEQ ID NO 669
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 669
ncauggaucu auuaaagun                                                19

<210> SEQ ID NO 670
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 670
cauggaucua uuaaaguca                                                19

<210> SEQ ID NO 671
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 671
cauggaucua uuaaagucn                                                19

<210> SEQ ID NO 672
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 672
nauggaucua uuaaagucn                                                19

<210> SEQ ID NO 673
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 673
ccuaaauggu gaauaugca                                                19

<210> SEQ ID NO 674
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 674
ccuaaauggu gaauaugcn                                                19

<210> SEQ ID NO 675
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 675
ncuaaauggu gaauaugcn                                                19

<210> SEQ ID NO 676
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 676
accucuagaa gcuuaaaca                                                19

<210> SEQ ID NO 677
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 677
accucuagaa gcuuaaacn                                                19

<210> SEQ ID NO 678
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 678
nccucuagaa gcuuaaacn                                              19

<210> SEQ ID NO 679
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 679
ccuucaaacc aaugaacaa                                              19

<210> SEQ ID NO 680
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 680
ccuucaaacc aaugaacan                                              19

<210> SEQ ID NO 681
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 681
ncuucaaacc aaugaacan                                              19

<210> SEQ ID NO 682
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 682
aaugaacagc aaagcauaa                                              19

<210> SEQ ID NO 683
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 683
aaugaacagc aaagcaun                                               19

-continued

<210> SEQ ID NO 684
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 684
naugaacagc aaagcauan                                                19

<210> SEQ ID NO 685
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 685
ugaacagcaa agcauaaca                                                19

<210> SEQ ID NO 686
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 686
ugaacagcaa agcauaacn                                                19

<210> SEQ ID NO 687
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 687
ngaacagcaa agcauaacn                                                19

<210> SEQ ID NO 688
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 688
gaacagcaaa gcauaaccu                                                19

<210> SEQ ID NO 689

```
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 689
gaacagcaaa gcauaacca                                                  19

<210> SEQ ID NO 690
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 690
gaacagcaaa gcauaaccn                                                  19

<210> SEQ ID NO 691
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 691
naacagcaaa gcauaaccn                                                  19

<210> SEQ ID NO 692
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 692
acagcaaagc auaaccuua                                                  19

<210> SEQ ID NO 693
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 693
acagcaaagc auaaccuun                                                  19

<210> SEQ ID NO 694
<211> LENGTH: 19
<212> TYPE: RNA
```

```
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 694
ncagcaaagc auaaccuun                                                   19

<210> SEQ ID NO 695
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 695
aaagcauaac cuugaaucu                                                   19

<210> SEQ ID NO 696
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 696
aaagcauaac cuugaauca                                                   19

<210> SEQ ID NO 697
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 697
aaagcauaac cuugaaucn                                                   19

<210> SEQ ID NO 698
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 698
naagcauaac cuugaaucn                                                   19

<210> SEQ ID NO 699
<211> LENGTH: 19
<212> TYPE: RNA
<213> ORGANISM: Artificial sequence
<220> FEATURE:
```

```
<223> OTHER INFORMATION: RNAi agent sense strand 19-mer core base
      sequence

<400> SEQUENCE: 699
aaccaacuca auuauugaa                                                    19

<210> SEQ ID NO 700
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 700
aaccaacuca auuauugan                                                    19

<210> SEQ ID NO 701
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 701
naccaacuca auuauugan                                                    19

<210> SEQ ID NO 702
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 702
uccugugauc cauuuuacu                                                    19

<210> SEQ ID NO 703
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 703
uccugugauc cauuuuaca                                                    19

<210> SEQ ID NO 704
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase
```

```
<400> SEQUENCE: 704
uccugugauc cauuuuacn                                              19

<210> SEQ ID NO 705
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 705
nccugugauc cauuuuacn                                              19

<210> SEQ ID NO 706
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 706
uuuucuuacu gucauauga                                              19

<210> SEQ ID NO 707
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 707
uuuucuuacu gucauaugn                                              19

<210> SEQ ID NO 708
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 708
nuuucuuacu gucauaugn                                              19

<210> SEQ ID NO 709
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
```

<222> LOCATION: 14
<223> OTHER INFORMATION: n = inosine (hypoxanthine)

<400> SEQUENCE: 709
ggagaaaaau gcanaucca                                               19

<210> SEQ ID NO 710
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 14
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 710
ggagaaaaau gcanauccn                                               19

<210> SEQ ID NO 711
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = inosine (hypoxanthine)

<400> SEQUENCE: 711
ngagaaaaau gcanauccn                                               19

<210> SEQ ID NO 712
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 712
cagagacaac ucuuugga                                                19

<210> SEQ ID NO 713
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 713
cagagacaac ucuuuggn                                                19

<210> SEQ ID NO 714
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 714
nagagacaac ucuuuuggn                                                19

<210> SEQ ID NO 715
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)

<400> SEQUENCE: 715
cuccaaguau gaucnucua                                                19

<210> SEQ ID NO 716
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 716
cuccaaguau gaucnucun                                                19

<210> SEQ ID NO 717
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = inosine (hypoxanthine)

<400> SEQUENCE: 717
nuccaaguau gaucnucun                                                19

<210> SEQ ID NO 718
<211> LENGTH: 19

```
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 718 aacguggaa ggaauagga                                                    19

<210> SEQ ID NO 719
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 719 aacguggaa ggaauaggn                                                    19

<210> SEQ ID NO 720
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 720 nacguggaa ggaauaggn                                                    19

<210> SEQ ID NO 721
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 721
gcaucgucau gaguaugua                                                   19

<210> SEQ ID NO 722
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 722
gcaucgucau gaguaugun                                                   19

<210> SEQ ID NO 723
<211> LENGTH: 19
<212> TYPE: RNA
<213> ORGANISM: Artificial sequence
```

```
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 723
ncaucgucau gaguaugun                                                   19

<210> SEQ ID NO 724
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = inosine (hypoxanthine)

<400> SEQUENCE: 724
cuuccaagga aaucuguna                                                   19

<210> SEQ ID NO 725
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 725
cuuccaagga aaucugunn                                                   19

<210> SEQ ID NO 726
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = inosine (hypoxanthine)

<400> SEQUENCE: 726
nuuccaagga aaucugunn                                                   19

<210> SEQ ID NO 727
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
```

```
<400> SEQUENCE: 727
ggcauugaga ugaaguuca                                              19

<210> SEQ ID NO 728
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 728
ggcauugaga ugaaguucn                                              19

<210> SEQ ID NO 729
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 729
ngcauugaga ugaaguucn                                              19

<210> SEQ ID NO 730
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 730
ugaaguucaa gaauaugcu                                              19

<210> SEQ ID NO 731
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 731
ugaaguucaa gaauaugca                                              19

<210> SEQ ID NO 732
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 732
```
ugaaguucaa gaauaugcn        19

<210> SEQ ID NO 733
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 733
ngaaguucaa gaauaugcn        19

<210> SEQ ID NO 734
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 734
aauaugcugu uuccauga         19

<210> SEQ ID NO 735
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 735
aauaugcugu uuccaugn         19

<210> SEQ ID NO 736
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 736
nauaugcugu uuccaugn         19

<210> SEQ ID NO 737
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 14
<223> OTHER INFORMATION: n = inosine (hypoxanthine)

<400> SEQUENCE: 737
ugcucuccau aganaucca                                                19

<210> SEQ ID NO 738
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 14
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 738
ugcucuccau aganauccn                                                19

<210> SEQ ID NO 739
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = inosine (hypoxanthine)

<400> SEQUENCE: 739
ngcucuccau aganauccn                                                19

<210> SEQ ID NO 740
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 740
guauuucuca gcauucaaa                                                19

<210> SEQ ID NO 741
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 741
guauuucuca gcauucaan                                                19

<210> SEQ ID NO 742

```
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 742
nuauuucuca gcauucaan                                                    19

<210> SEQ ID NO 743
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 743
ccaagaucaa guccauaga                                                    19

<210> SEQ ID NO 744
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 744
ccaagaucaa guccauagn                                                    19

<210> SEQ ID NO 745
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 745
ncaagaucaa guccauagn                                                    19

<210> SEQ ID NO 746
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 746
caggguuugu uuguuucau                                                    19

<210> SEQ ID NO 747
<211> LENGTH: 19
<212> TYPE: RNA
```

```
<213> ORGANISM: Artificial sequence
<220> FEATURE:
<223> OTHER INFORMATION: RNAi agent sense strand 19-mer core base
      sequence

<400> SEQUENCE: 747
caggguuugu uuguuucaa                                                   19

<210> SEQ ID NO 748
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 748
caggguuugu uuguuucan                                                   19

<210> SEQ ID NO 749
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 749
naggguuugu uuguuucan                                                   19

<210> SEQ ID NO 750
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 750
caccuaugaa gaacuacca                                                   19

<210> SEQ ID NO 751
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 751
caccuaugaa gaacuaccn                                                   19

<210> SEQ ID NO 752
<211> LENGTH: 19
<212> TYPE: RNA
<213> ORGANISM: Artificial sequence
<220> FEATURE:
```

```
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 752
naccuaugaa gaacuaccn                                                      19

<210> SEQ ID NO 753
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 753
gaacuaccag ccauuauca                                                      19

<210> SEQ ID NO 754
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 754
gaacuaccag ccauuaucn                                                      19

<210> SEQ ID NO 755
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 755
naacuaccag ccauuaucn                                                      19

<210> SEQ ID NO 756
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 756
gccauuauca caauugaga                                                      19

<210> SEQ ID NO 757
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
```

```
<220> FEATURE:
<221> NAME/KEY: modified_base
<222> LOCATION: 19
<223> OTHER INFORMATION: n = any nucleobase

<400> SEQUENCE: 757
gccauuauca caauugagn                                                  19

<210> SEQ ID NO 758
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 758
nccauuauca caauugagn                                                  19

<210> SEQ ID NO 759
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 759
agcugaagau cgagaaaga                                                  19

<210> SEQ ID NO 760
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 760
agcugaagau cgagaaagn                                                  19

<210> SEQ ID NO 761
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 761
ngcugaagau cgagaaagn                                                  19

<210> SEQ ID NO 762
<211> LENGTH: 19
<212> TYPE: RNA
<213> ORGANISM: Artificial sequence
<220> FEATURE:
```

```
<223> OTHER INFORMATION: RNAi agent sense strand 19-mer core base
      sequence

<400> SEQUENCE: 762
gcaccauugc uguuccaaa                                                    19

<210> SEQ ID NO 763
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 763
gcaccauugc uguuccaan                                                    19

<210> SEQ ID NO 764
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 764
ncaccauugc uguuccaan                                                    19

<210> SEQ ID NO 765
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 765
ggagcucuuu guguuuaca                                                    19

<210> SEQ ID NO 766
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 766
ggagcucuuu guguuuacn                                                    19

<210> SEQ ID NO 767
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
```

<220> FEATURE:
<221> NAME/KEY: modified_base
<222> LOCATION: 1, 19
<223> OTHER INFORMATION: n = any nucleobase

<400> SEQUENCE: 767
ngagcucuuu guguuuacn                                                19

<210> SEQ ID NO 768
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = inosine (hypoxanthine)

<400> SEQUENCE: 768
cucuuugugu cuacacana                                                19

<210> SEQ ID NO 769
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 769
cucuuugugu cuacacann                                                19

<210> SEQ ID NO 770
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = inosine (hypoxanthine)

<400> SEQUENCE: 770
nucuuugugu cuacacann                                                19

<210> SEQ ID NO 771
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 771

-continued cucucagagu auuauggaa					19

<210> SEQ ID NO 772
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 772
cucucagagu auuauggan					19

<210> SEQ ID NO 773
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 773
nucucagagu auuauggan					19

<210> SEQ ID NO 774
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = inosine (hypoxanthine)

<400> SEQUENCE: 774
agaguauuau ggaacgana					19

<210> SEQ ID NO 775
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 775
agaguauuau ggaacgann					19

<210> SEQ ID NO 776
<211> LENGTH: 19
<212> TYPE: RNA
<213> ORGANISM: Artificial sequence

```
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = inosine (hypoxanthine)

<400> SEQUENCE: 776
ngaguauuau ggaacgann                                               19

<210> SEQ ID NO 777
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 777
aggguuuguu uguuucauu                                               19

<210> SEQ ID NO 778
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 778
aggguuuguu uguuucaua                                               19

<210> SEQ ID NO 779
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 779
aggguuuguu uguuucaun                                               19

<210> SEQ ID NO 780
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 780
nggguuuguu uguuucaun                                               19

<210> SEQ ID NO 781
<211> LENGTH: 19
```

```
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 781
ggguuuguuu guuucauuu                                                   19

<210> SEQ ID NO 782
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 782
ggguuuguuu guuucauua                                                   19

<210> SEQ ID NO 783
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 783
ggguuuguuu guuucauun                                                   19

<210> SEQ ID NO 784
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 784
ngguuuguuu guuucauun                                                   19

<210> SEQ ID NO 785
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 785
guuuguuugu uucauuuca                                                   19

<210> SEQ ID NO 786
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
```

<221> NAME/KEY: modified_base
<222> LOCATION: 19
<223> OTHER INFORMATION: n = any nucleobase

<400> SEQUENCE: 786
guuuguuugu uucauuucn			19

<210> SEQ ID NO 787
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 787
nuuuguuugu uucauuucn			19

<210> SEQ ID NO 788
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 16
<223> OTHER INFORMATION: n = inosine (hypoxanthine)

<400> SEQUENCE: 788
ucuccaagua ugaucnucu			19

<210> SEQ ID NO 789
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 16
<223> OTHER INFORMATION: n = inosine (hypoxanthine)

<400> SEQUENCE: 789
ucuccaagua ugaucnuca			19

<210> SEQ ID NO 790
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 16
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 790
ucuccaagua ugaucnucn			19

<210> SEQ ID NO 791
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 16
<223> OTHER INFORMATION: n = inosine (hypoxanthine)

<400> SEQUENCE: 791
ncuccaagua ugaucnucn                                              19

<210> SEQ ID NO 792
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)

<400> SEQUENCE: 792
aggagauuga gaaunccuu                                              19

<210> SEQ ID NO 793
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)

<400> SEQUENCE: 793
aggagauuga gaaunccua                                              19

<210> SEQ ID NO 794
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 794
aggagauuga gaaunccun                                              19

<210> SEQ ID NO 795

```
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 1, 19
<223> OTHER INFORMATION: n = any nucleobase

<400> SEQUENCE: 795
nggagauuga gaaunccun                                                  19

<210> SEQ ID NO 796
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 796
agaaugccuu ccaaggaaa                                                  19

<210> SEQ ID NO 797
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 797
agaaugccuu ccaaggaan                                                  19

<210> SEQ ID NO 798
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 798
ngaaugccuu ccaaggaan                                                  19

<210> SEQ ID NO 799
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 799
ugccuuccaa ggaaaucua                                                  19
```

```
<210> SEQ ID NO 800
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 800
ugccuuccaa ggaaaucun                                              19

<210> SEQ ID NO 801
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 801
ngccuuccaa ggaaaucun                                              19

<210> SEQ ID NO 802
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 802
agaauaugcu guuccuau                                               19

<210> SEQ ID NO 803
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 803
agaauaugcu guuccuaa                                               19

<210> SEQ ID NO 804
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 804
agaauaugcu guuccuan                                               19

<210> SEQ ID NO 805
```

```
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 805
ngaauaugcu guuccuan                                                       19

<210> SEQ ID NO 806
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 806
uuggagggaa caucaucaa                                                      19

<210> SEQ ID NO 807
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 807
uuggagggaa caucaucan                                                      19

<210> SEQ ID NO 808
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 808
nuggagggaa caucaucan                                                      19

<210> SEQ ID NO 809
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 809
gcuucuucuu caaguucua                                                      19

<210> SEQ ID NO 810
<211> LENGTH: 19
<212> TYPE: RNA
```

-continued

<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 810
gcuucuucuu caaguucun                                              19

<210> SEQ ID NO 811
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 811
ncuucuucuu caaguucun                                              19

<210> SEQ ID NO 812
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 812
guugggcaua ucauuggua                                              19

<210> SEQ ID NO 813
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 813
guugggcaua ucauuggun                                              19

<210> SEQ ID NO 814
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 814
nuugggcaua ucauuggun                                              19

<210> SEQ ID NO 815

```
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 815
ucuacacaga acaccauga                                                    19

<210> SEQ ID NO 816
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 816
ucuacacaga acaccaugn                                                    19

<210> SEQ ID NO 817
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 817
ncuacacaga acaccaugn                                                    19

<210> SEQ ID NO 818
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 818
cacccaggau cucuuucaa                                                    19

<210> SEQ ID NO 819
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 819
cacccaggau cucuuucan                                                    19

<210> SEQ ID NO 820
<211> LENGTH: 19
<212> TYPE: RNA
```

```
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 820
nacccaggau cucuuucan                                               19

<210> SEQ ID NO 821
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 821
caagcucuca guaucauga                                               19

<210> SEQ ID NO 822
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 822
caagcucuca guaucaugn                                               19

<210> SEQ ID NO 823
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 823
naagcucuca guaucaugn                                               19

<210> SEQ ID NO 824
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 824
ggaagaguga gguugacaa                                               19

<210> SEQ ID NO 825
<211> LENGTH: 19
<212> TYPE: RNA
<213> ORGANISM: Artificial sequence
<220> FEATURE:
```

```
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 825
ggaagaguga gguugacan                                                      19

<210> SEQ ID NO 826
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 826
ngaagaguga gguugacan                                                      19

<210> SEQ ID NO 827
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 827
caaggagaau uguuggaaa                                                      19

<210> SEQ ID NO 828
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 828
caaggagaau uguuggaan                                                      19

<210> SEQ ID NO 829
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 829
naaggagaau uguuggaan                                                      19

<210> SEQ ID NO 830
<211> LENGTH: 19
<212> TYPE: RNA
```

```
<213> ORGANISM: Artificial sequence
<220> FEATURE:
<223> OTHER INFORMATION: RNAi agent sense strand 19-mer core base
      sequence

<400> SEQUENCE: 830
agcuuugaga cuaacucaa                                                  19

<210> SEQ ID NO 831
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 831
agcuuugaga cuaacucan                                                  19

<210> SEQ ID NO 832
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 832
ngcuuugaga cuaacucan                                                  19

<210> SEQ ID NO 833
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 833
uccgcacaga uauugucau                                                  19

<210> SEQ ID NO 834
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 834
uccgcacaga uauugucaa                                                  19

<210> SEQ ID NO 835
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
```

```
<222> LOCATION: 19
<223> OTHER INFORMATION: n = any nucleobase

<400> SEQUENCE: 835
uccgcacaga uauugucan                                                  19

<210> SEQ ID NO 836
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 836
nccgcacaga uauugucan                                                  19

<210> SEQ ID NO 837
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 837
cgcacagaua uugucauga                                                  19

<210> SEQ ID NO 838
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 838
cgcacagaua uugucaugn                                                  19

<210> SEQ ID NO 839
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 839
ngcacagaua uugucaugn                                                  19

<210> SEQ ID NO 840
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
```

```
<400> SEQUENCE: 840
cugcuucuau cuucuuuga                                                   19

<210> SEQ ID NO 841
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 841
cugcuucuau cuucuuugn                                                   19

<210> SEQ ID NO 842
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 842
nugcuucuau cuucuuugn                                                   19

<210> SEQ ID NO 843
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = inosine (hypoxanthine)

<400> SEQUENCE: 843
cacacaggua auaacguna                                                   19

<210> SEQ ID NO 844
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 844
cacacaggua auaacgunn                                                   19

<210> SEQ ID NO 845
```

```
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = inosine (hypoxanthine)

<400> SEQUENCE: 845
nacacaggua auaacgunn                                                  19

<210> SEQ ID NO 846
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 846
uguauaaccu caaguucua                                                  19

<210> SEQ ID NO 847
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 847
uguauaaccu caaguucun                                                  19

<210> SEQ ID NO 848
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 848
nguauaaccu caaguucun                                                  19

<210> SEQ ID NO 849
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 849
ccaaugaaca gcaaagcau                                                  19
```

<210> SEQ ID NO 850
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 850
ccaaugaaca gcaaagcaa                                                 19

<210> SEQ ID NO 851
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 851
ccaaugaaca gcaaagcan                                                 19

<210> SEQ ID NO 852
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 852
ncaaugaaca gcaaagcan                                                 19

<210> SEQ ID NO 853
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 853
uaaccuugaa ucuauacua                                                 19

<210> SEQ ID NO 854
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 854
uaaccuugaa ucuauacun                                                 19

<210> SEQ ID NO 855

-continued

```
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 855
naaccuugaa ucuauacun                                                    19

<210> SEQ ID NO 856
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 856
cauaaagcaa gauuacucu                                                    19

<210> SEQ ID NO 857
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 857
cauaaagcaa gauuacuca                                                    19

<210> SEQ ID NO 858
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 858
cauaaagcaa gauuacucn                                                    19

<210> SEQ ID NO 859
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 859
nauaaagcaa gauuacucn                                                    19

<210> SEQ ID NO 860
<211> LENGTH: 19
<212> TYPE: RNA
```

```
<213> ORGANISM: Artificial sequence
<220> FEATURE:
<223> OTHER INFORMATION: RNAi agent sense strand 19-mer core base
      sequence

<400> SEQUENCE: 860
caccuagaaa ugaugcuau                                                      19

<210> SEQ ID NO 861
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 861
caccuagaaa ugaugcuaa                                                      19

<210> SEQ ID NO 862
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 862
caccuagaaa ugaugcuan                                                      19

<210> SEQ ID NO 863
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 863
naccuagaaa ugaugcuan                                                      19

<210> SEQ ID NO 864
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 16
<223> OTHER INFORMATION: n = inosine (hypoxanthine)

<400> SEQUENCE: 864
agcucugucu cuucunucu                                                      19

<210> SEQ ID NO 865
<211> LENGTH: 19
<212> TYPE: RNA
<213> ORGANISM: Artificial sequence
<220> FEATURE:
```

<223> OTHER INFORMATION: RNAi agent sense strand 19-mer core base
      sequence
<220> FEATURE:
<221> NAME/KEY: modified_base
<222> LOCATION: 16
<223> OTHER INFORMATION: n = inosine (hypoxanthine)

<400> SEQUENCE: 865
agcucugucu cuucunuca                                            19

<210> SEQ ID NO 866
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 16
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 866
agcucugucu cuucunucn                                            19

<210> SEQ ID NO 867
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 16
<223> OTHER INFORMATION: n = inosine (hypoxanthine)

<400> SEQUENCE: 867
ngcucugucu cuucunucn                                            19

<210> SEQ ID NO 868
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = 2-aminoadenine nucleotide

<400> SEQUENCE: 868
naggcuuggu uuucuuacu                                            19

<210> SEQ ID NO 869
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:

```
<221> NAME/KEY: modified_base
<222> LOCATION: 1
<223> OTHER INFORMATION: n = 2-aminoadenine nucleotide

<400> SEQUENCE: 869
naggcuuggu uuucuuaca                                                    19

<210> SEQ ID NO 870
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = 2-aminoadenine nucleotide
<220> FEATURE:
<221> NAME/KEY: modified_base
<222> LOCATION: 19
<223> OTHER INFORMATION: n = any nucleobase

<400> SEQUENCE: 870
naggcuuggu uuucuuacn                                                    19

<210> SEQ ID NO 871
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 871
naggcuuggu uuucuuacn                                                    19

<210> SEQ ID NO 872
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 872
aaggcuuggu uuucuuacu                                                    19

<210> SEQ ID NO 873
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 873
aaggcuuggu uuucuuaca                                                    19

<210> SEQ ID NO 874
<211> LENGTH: 19
<212> TYPE: RNA
<213> ORGANISM: Artificial sequence
<220> FEATURE:
<223> OTHER INFORMATION: RNAi agent sense strand 19-mer core base
```

```
            sequence
<220> FEATURE:
<221> NAME/KEY: modified_base
<222> LOCATION: 19
<223> OTHER INFORMATION: n = any nucleobase

<400> SEQUENCE: 874
aaggcuuggu uuucuuacn                                                    19

<210> SEQ ID NO 875
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 875
naggcuuggu uuucuuacn                                                    19

<210> SEQ ID NO 876
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 876
gugaugcucu ccaaguaua                                                    19

<210> SEQ ID NO 877
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 877
gugaugcucu ccaaguaun                                                    19

<210> SEQ ID NO 878
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 878
nugaugcucu ccaaguaun                                                    19

<210> SEQ ID NO 879
<211> LENGTH: 19
<212> TYPE: RNA
<213> ORGANISM: Artificial sequence
```

```
<220> FEATURE:
<221> NAME/KEY: modified_base
<222> LOCATION: 16
<223> OTHER INFORMATION: n = inosine (hypoxanthine)
<220> FEATURE:
<223> OTHER INFORMATION: RNAi agent sense strand 19-mer core base
      sequence

<400> SEQUENCE: 879
caaguaugau cgucuncaa                                                      19

<210> SEQ ID NO 880
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 16
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 880
caaguaugau cgucuncan                                                      19

<210> SEQ ID NO 881
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 16
<223> OTHER INFORMATION: n = inosine (hypoxanthine)

<400> SEQUENCE: 881
naaguaugau cgucuncan                                                      19

<210> SEQ ID NO 882
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 882
gcaugagagu uuuauucaa                                                      19

<210> SEQ ID NO 883
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase
```

<400> SEQUENCE: 883
gcaugagagu uuuauucan                                           19

<210> SEQ ID NO 884
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 884
ncaugagagu uuuauucan                                           19

<210> SEQ ID NO 885
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 14
<223> OTHER INFORMATION: n = 2-aminoadenine nucleotide

<400> SEQUENCE: 885
gcaugagagu uuunuucaa                                           19

<210> SEQ ID NO 886
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 14
<223> OTHER INFORMATION: n = 2-aminoadenine nucleotide
<220> FEATURE:
<221> NAME/KEY: modified_base
<222> LOCATION: 19
<223> OTHER INFORMATION: n = any nucleobase

<400> SEQUENCE: 886
gcaugagagu uuunuu can                                          19

<210> SEQ ID NO 887
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = 2-aminoadenine nucleotide

<400> SEQUENCE: 887
ncaugagagu uuunuucan                                           19

<210> SEQ ID NO 888
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 888
caagaucguc cacuuuucu                                                   19

<210> SEQ ID NO 889
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 889
caagaucguc cacuuuucu                                                   19

<210> SEQ ID NO 890
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 890
caagaucguc cacuuuucn                                                   19

<210> SEQ ID NO 891
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 891
naagaucguc cacuuuucn                                                   19

<210> SEQ ID NO 892
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 892
cauguugcag ugacaacua                                                   19

<210> SEQ ID NO 893
<211> LENGTH: 19
<212> TYPE: RNA
<213> ORGANISM: Artificial sequence

```
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 893
cauguugcag ugacaacun                                                   19

<210> SEQ ID NO 894
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 894
nauguugcag ugacaacun                                                   19

<210> SEQ ID NO 895
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 895
ugacaacugu ggaaggaau                                                   19

<210> SEQ ID NO 896
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 896
ugacaacugu ggaaggaaa                                                   19

<210> SEQ ID NO 897
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 897
ugacaacugu ggaaggaan                                                   19

<210> SEQ ID NO 898
<211> LENGTH: 19
<212> TYPE: RNA
<213> ORGANISM: Artificial sequence
<220> FEATURE:
<223> OTHER INFORMATION: RNAi agent sense strand 19-mer core base
``` sequence
<220> FEATURE:
<221> NAME/KEY: modified_base
<222> LOCATION: 1, 19
<223> OTHER INFORMATION: n = any nucleobase

<400> SEQUENCE: 898
ngacaacugu ggaaggaan                                                  19

<210> SEQ ID NO 899
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 899
ggaggagauu gagaaugca                                                  19

<210> SEQ ID NO 900
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 900
ggaggagauu gagaaugcn                                                  19

<210> SEQ ID NO 901
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 901
ngaggagauu gagaaugcn                                                  19

<210> SEQ ID NO 902
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 902
cacggagauu ggcauugaa                                                  19

<210> SEQ ID NO 903
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:

```
<221> NAME/KEY: modified_base
<222> LOCATION: 19
<223> OTHER INFORMATION: n = any nucleobase

<400> SEQUENCE: 903
cacggagauu ggcauugan                                                       19

<210> SEQ ID NO 904
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 904
nacggagauu ggcauugan                                                       19

<210> SEQ ID NO 905
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = 2-aminoadenine nucleotide

<400> SEQUENCE: 905
agaugaaguu caagaaunu                                                       19

<210> SEQ ID NO 906
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = 2-aminoadenine nucleotide

<400> SEQUENCE: 906
agaugaaguu caagaauna                                                       19

<210> SEQ ID NO 907
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = 2-aminoadenine nucleotide
<220> FEATURE:
<221> NAME/KEY: modified_base
<222> LOCATION: 19
<223> OTHER INFORMATION: n = any nucleobase

<400> SEQUENCE: 907
agaugaaguu caagaaunn                                                       19
```

<210> SEQ ID NO 908
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = 2-aminoadenine nucleotide

<400> SEQUENCE: 908
ngaugaaguu caagaaunn                                                19

<210> SEQ ID NO 909
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 909
agaugaaguu caagaauau                                                19

<210> SEQ ID NO 910
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 910
agaugaaguu caagaauaa                                                19

<210> SEQ ID NO 911
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 911
agaugaaguu caagaauan                                                19

<210> SEQ ID NO 912
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 912
ngaugaaguu caagaauan                                                19

<210> SEQ ID NO 913
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 913
gagauacugc ucuccauaa                                                19

<210> SEQ ID NO 914
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 914
gagauacugc ucuccauan                                                19

<210> SEQ ID NO 915
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 915
nagauacugc ucuccauan                                                19

<210> SEQ ID NO 916
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 916
ggaguauuuc ucagcauua                                                19

<210> SEQ ID NO 917
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 917
ggaguauuuc ucagcauun                                                19

<210> SEQ ID NO 918
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 918
ngaguauuuc ucagcauun                                                  19

<210> SEQ ID NO 919
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 919
gaguauuucu cagcauuca                                                  19

<210> SEQ ID NO 920
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 920
gaguauuucu cagcauucn                                                  19

<210> SEQ ID NO 921
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 921
naguauuucu cagcauucn                                                  19

<210> SEQ ID NO 922
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 922
ggagagaaga ugacauuga                                                  19

```
<210> SEQ ID NO 923
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 923
ggagagaaga ugacauugn                                                  19

<210> SEQ ID NO 924
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 924
ngagagaaga ugacauugn                                                  19

<210> SEQ ID NO 925
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 925
uaacauaacu ggaauuugu                                                  19

<210> SEQ ID NO 926
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 926
uaacauaacu ggaauuuga                                                  19

<210> SEQ ID NO 927
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 927
uaacauaacu ggaauuugn                                                  19

<210> SEQ ID NO 928
<211> LENGTH: 19
```

```
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 928
naacauaacu ggaauuugn                                                    19

<210> SEQ ID NO 929
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 929
agccauuauc acaauugaa                                                    19

<210> SEQ ID NO 930
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 930
agccauuauc acaauugan                                                    19

<210> SEQ ID NO 931
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 931
ngccauuauc acaauugan                                                    19

<210> SEQ ID NO 932
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 932
gcuuuguugc aaaaauguu                                                    19

<210> SEQ ID NO 933
<211> LENGTH: 19
<212> TYPE: RNA
<213> ORGANISM: Artificial sequence
```

```
<220> FEATURE:
<223> OTHER INFORMATION: RNAi agent sense strand 19-mer core base
      sequence

<400> SEQUENCE: 933 gcuuguugc aaaaugua                                                  19

<210> SEQ ID NO 934
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 934 gcuuguugc aaaaugun                                                  19

<210> SEQ ID NO 935
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 935 ncuuguugc aaaaugun                                                  19

<210> SEQ ID NO 936
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 936
uuuguugcaa aauguuga                                                 19

<210> SEQ ID NO 937
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 937
uuuguugcaa aauguugn                                                 19

<210> SEQ ID NO 938
<211> LENGTH: 19
<212> TYPE: RNA
<213> ORGANISM: Artificial sequence
<220> FEATURE:
<223> OTHER INFORMATION: RNAi agent sense strand 19-mer core base
``` sequence
<220> FEATURE:
<221> NAME/KEY: modified_base
<222> LOCATION: 1, 19
<223> OTHER INFORMATION: n = any nucleobase

<400> SEQUENCE: 938
nuuguugcaa aaauguugn                                                      19

<210> SEQ ID NO 939
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 939
gauugugguu cgagugaaa                                                      19

<210> SEQ ID NO 940
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 940
gauugugguu cgagugaan                                                      19

<210> SEQ ID NO 941
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 941
nauugugguu cgagugaan                                                      19

<210> SEQ ID NO 942
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 942
gauugagaau gccuuccaa                                                      19

<210> SEQ ID NO 943
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:

```
<221> NAME/KEY: modified_base
<222> LOCATION: 19
<223> OTHER INFORMATION: n = any nucleobase

<400> SEQUENCE: 943
gauugagaau gccuuccan                                              19

<210> SEQ ID NO 944
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 944
nauugagaau gccuuccan                                              19

<210> SEQ ID NO 945
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 945
uuggaaggca uucucaaucu c                                           21

<210> SEQ ID NO 946
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 946
uuggaaggca uucucaaucu c                                           21

<210> SEQ ID NO 947
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 947
aacuugaaga agaagcugag g                                           21

<210> SEQ ID NO 948
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 948
agaacuugaa gaagaagcug c                                           21

<210> SEQ ID NO 949
<211> LENGTH: 21
<212> TYPE: RNA
<213> ORGANISM: Artificial sequence
<220> FEATURE:
```

<210> SEQ ID NO 950
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 949
uguagaacuu gaagaagaag c                                              21

<210> SEQ ID NO 950
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 950
ucauagguga uuuucacccc u                                              21

<210> SEQ ID NO 951
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 951
uuucauaggu gauuuucacc c                                              21

<210> SEQ ID NO 952
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 952
ucuucauagg ugauuuucac c                                              21

<210> SEQ ID NO 953
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 953
uucuucauag gugauuuuca c                                              21

<210> SEQ ID NO 954
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 954
aauugugaua auggcuggua g                                              21

<210> SEQ ID NO 955
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 955
ucauaaaagg aguuguucuu c                                              21

```
<210> SEQ ID NO 956
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 956
uccauaaaag gaguuguucu c                                              21

<210> SEQ ID NO 957
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 957
uacaguguua gugcuugucu c                                              21

<210> SEQ ID NO 958
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 958
uuguguacau acucaugacg a                                              21

<210> SEQ ID NO 959
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 959
uaccaguuau cagcaugucc u                                              21

<210> SEQ ID NO 960
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 960
uaugaagcca accuuguauc c                                              21

<210> SEQ ID NO 961
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 961
ucuucaugaa gccaaccuug c                                              21

<210> SEQ ID NO 962
<211> LENGTH: 21
<212> TYPE: RNA
<213> ORGANISM: Artificial sequence
<220> FEATURE:
<223> OTHER INFORMATION: RNAi agent antisense strand modified sequence
```

```
<400> SEQUENCE: 962
uucuucauga agccaaccuu g                                              21

<210> SEQ ID NO 963
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 963
uagucuucau gaagccaacc u                                              21

<210> SEQ ID NO 964
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 964
ucuuuuucca acaauucucc u                                              21

<210> SEQ ID NO 965
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 965
uucuacuuca gagcaagcca c                                              21

<210> SEQ ID NO 966
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 966
uauuucuacu ucagagcaag c                                              21

<210> SEQ ID NO 967
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 967
uguccaauau caauggcagg g                                              21

<210> SEQ ID NO 968
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 968
ucagaaaagu ggacgaucuu g                                              21

<210> SEQ ID NO 969
<211> LENGTH: 21
```

-continued

```
<212> TYPE: RNA
<213> ORGANISM: Artificial sequence
<220> FEATURE:
<223> OTHER INFORMATION: RNAi agent antisense strand modified sequence

<400> SEQUENCE: 969
acaacauuau cugcuucgga c                                              21

<210> SEQ ID NO 970
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 970
ucauaauacu cugagagaga c                                              21

<210> SEQ ID NO 971
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 971
ucuuauucca aacuuggugg g                                              21

<210> SEQ ID NO 972
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 972
uaguaaucuu gcuuuaugca g                                              21

<210> SEQ ID NO 973
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 973
aaagaaaucu agaacauugu c                                              21

<210> SEQ ID NO 974
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 974
ucagaaaagu ggacgaucuu g                                              21

<210> SEQ ID NO 975
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 975
```
acaacauuau cugcuucgga c        21

<210> SEQ ID NO 976
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 976
ucauaauacu cugagagaga c        21

<210> SEQ ID NO 977
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 977
aaagaaaucu agaacauuuu c        21

<210> SEQ ID NO 978
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 978
ucagaaaagu ggacgaucuu g        21

<210> SEQ ID NO 979
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 979
ucauaauacu cugagagaga c        21

<210> SEQ ID NO 980
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 980
ucuuauucca aacuuggugg g        21

<210> SEQ ID NO 981
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 981
uaguaaucuu gcuuuaugca g        21

<210> SEQ ID NO 982
<211> LENGTH: 21
<212> TYPE: RNA
<213> ORGANISM: Artificial sequence -continued
<220> FEATURE:
<223> OTHER INFORMATION: RNAi agent antisense strand modified sequence

<400> SEQUENCE: 982
uaacuucacu cauccagcac u					21

<210> SEQ ID NO 983
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 983
ucaacuucac ucauccagca c					21

<210> SEQ ID NO 984
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 984
ugcaacuuca cucauccagc a					21

<210> SEQ ID NO 985
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 985
ugaucauacu uggagagcau c					21

<210> SEQ ID NO 986
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 986
ucuuguucug cagacgauca c					21

<210> SEQ ID NO 987
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 987
ugaucuuguu cugcagacga c					21

<210> SEQ ID NO 988
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 988
uaguaaaguu gcacuggcga c					21

```
<210> SEQ ID NO 989
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 989
uaacacaagu aaccuuaucc u                                              21

<210> SEQ ID NO 990
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 990
ucaauuguga uaauggcugg u                                              21

<210> SEQ ID NO 991
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 991
uagcaugaua cugagagcuu g                                              21

<210> SEQ ID NO 992
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 992
aacuugucaa ccucacucuu c                                              21

<210> SEQ ID NO 993
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 993
uaacuuguca accucacucu c                                              21

<210> SEQ ID NO 994
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 994
uaacaauucu ccuuguugaa c                                              21

<210> SEQ ID NO 995
<211> LENGTH: 21
<212> TYPE: RNA
<213> ORGANISM: Artificial sequence
<220> FEATURE:
<223> OTHER INFORMATION: RNAi agent antisense strand modified sequence
```

-continued

```
<400> SEQUENCE: 995
ucauguucug ugguauguuc c                                              21

<210> SEQ ID NO 996
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 996
uacuuuaaua gauccauguu c                                              21

<210> SEQ ID NO 997
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 997
ugacuuuaau agauccaugu c                                              21

<210> SEQ ID NO 998
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 998
ugcauauuca ccauuuaggc a                                              21

<210> SEQ ID NO 999
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 999
uguuuaagcu ucuagagguu c                                              21

<210> SEQ ID NO 1000
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1000
uuguucauug guuugaaggc c                                              21

<210> SEQ ID NO 1001
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1001
uuaugcuuug cuguucauug g                                              21

<210> SEQ ID NO 1002
```

```
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1002
uguuaugcuu ugcuguucau c                                              21

<210> SEQ ID NO 1003
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1003
agguuaugcu uugcuguuca c                                              21

<210> SEQ ID NO 1004
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1004
uaagguuaug cuuugcuguu c                                              21

<210> SEQ ID NO 1005
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1005
agauucaagg uuaugcuuug c                                              21

<210> SEQ ID NO 1006
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1006
uucaauaauu gaguugguug g                                              21

<210> SEQ ID NO 1007
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1007
aguaaaaugg aucacaggaa g                                              21

<210> SEQ ID NO 1008
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1008
```
ucauaugaca guaagaaaac c                                                21

<210> SEQ ID NO 1009
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1009
uuggaaggca uucucgaucu c                                                21

<210> SEQ ID NO 1010
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1010
ucaucauuga aaaugccagu c                                                21

<210> SEQ ID NO 1011
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1011
aaagacaguu ucaucauuga c                                                21

<210> SEQ ID NO 1012
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1012
aacacaagua accucauccu c                                                21

<210> SEQ ID NO 1013
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1013
agacaacauu gucagcuuca g                                                21

<210> SEQ ID NO 1014
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1014
ucaacaucuu ugcaauaaag c                                                21

<210> SEQ ID NO 1015
<211> LENGTH: 21
<212> TYPE: RNA

```
<213> ORGANISM: Artificial sequence
<220> FEATURE:
<223> OTHER INFORMATION: RNAi agent antisense strand modified sequence

<400> SEQUENCE: 1015
agauuagucu uacaaauccu c                                                21

<210> SEQ ID NO 1016
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1016
ucuuauucca aacuuagucg g                                                21

<210> SEQ ID NO 1017
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1017
ucagaaaaga aagugugaag c                                                21

<210> SEQ ID NO 1018
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1018
uagaguuugu cucaaagcug c                                                21

<210> SEQ ID NO 1019
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1019
uuguuaagca gucaauuucu c                                                21

<210> SEQ ID NO 1020
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1020
uuggaaaucu ggauacuacg g                                                21

<210> SEQ ID NO 1021
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1021
ucuugaaaau gccauccugc u                                                21
```

<210> SEQ ID NO 1022
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1022
augauuugga ucacaauugu c                                              21

<210> SEQ ID NO 1023
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1023
uagaauuacu caaaacugcc a                                              21

<210> SEQ ID NO 1024
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1024
ugaucaaaaa uggacucaga c                                              21

<210> SEQ ID NO 1025
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1025
uaagaaagca ugcagaucua g                                              21

<210> SEQ ID NO 1026
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1026
ucagauauaa gcucucugaa g                                              21

<210> SEQ ID NO 1027
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1027
uaugaagcca accuuguauc c                                              21

<210> SEQ ID NO 1028
<211> LENGTH: 21
<212> TYPE: RNA
<213> ORGANISM: Artificial sequence
<220> FEATURE:

<223> OTHER INFORMATION: RNAi agent antisense strand modified sequence

<400> SEQUENCE: 1028
uaugaagcca accuuguauc c					21

<210> SEQ ID NO 1029
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1029
uaugaagcca accuuguauc c					21

<210> SEQ ID NO 1030
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1030
uaugaaguca accuuguauc c					21

<210> SEQ ID NO 1031
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1031
uaugaagcua accuuguauc c					21

<210> SEQ ID NO 1032
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1032
uaugaagcca accuuguauc c					21

<210> SEQ ID NO 1033
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1033
ucuucaugaa gccaaccuug c					21

<210> SEQ ID NO 1034
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1034
ucuucaugaa gccaaccuug c					21

```
<210> SEQ ID NO 1035
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1035
ucuucaugaa gccaaccuug c                                              21

<210> SEQ ID NO 1036
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1036
uggaucugca uuuucucca c                                               21

<210> SEQ ID NO 1037
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1037 uccaaaggg uugucucugg a                                               21

<210> SEQ ID NO 1038
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1038
uagacgauca uacuuggaga g                                              21

<210> SEQ ID NO 1039
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1039 uccuauccu uccacaguug c                                               21

<210> SEQ ID NO 1040
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1040
uacauacuca ugacgaugcc a                                              21

<210> SEQ ID NO 1041
<211> LENGTH: 21
<212> TYPE: RNA
<213> ORGANISM: Artificial sequence
<220> FEATURE:
<223> OTHER INFORMATION: RNAi agent antisense strand modified sequence
```

<400> SEQUENCE: 1041
ucacagauuu ccuuggaagg c                                              21

<210> SEQ ID NO 1042
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1042
ugaacuucau cucaaugcca c                                              21

<210> SEQ ID NO 1043
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1043
agcauauucu ugaacuucau c                                              21

<210> SEQ ID NO 1044
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1044
ucauaggaaa cagcauauuc c                                              21

<210> SEQ ID NO 1045
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1045
uggaucucua uggagagcag c                                              21

<210> SEQ ID NO 1046
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1046
uuugaaugcu gagaaauacu c                                              21

<210> SEQ ID NO 1047
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1047
ucuauggacu ugaucuuggc g                                              21

<210> SEQ ID NO 1048
<211> LENGTH: 21

-continued

<212> TYPE: RNA
<213> ORGANISM: Artificial sequence
<220> FEATURE:
<223> OTHER INFORMATION: RNAi agent antisense strand modified sequence

<400> SEQUENCE: 1048
augaaacaaa caaacccugg a                                              21

<210> SEQ ID NO 1049
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1049
ugguaguucu ucauagguga c                                              21

<210> SEQ ID NO 1050
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1050
ugauaauggc ugguaguucu c                                              21

<210> SEQ ID NO 1051
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1051
ucucaauugu gauaauggcu g 21

<210> SEQ ID NO 1052
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1052
ucuuucucga ucuucagcuc a 21

<210> SEQ ID NO 1053
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1053
uuuggaacag caauggugca g 21

<210> SEQ ID NO 1054
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1054

```
uguagacaca aagagcucca c                                              21
```

<210> SEQ ID NO 1055
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1055

```
ucuguguaga cacaaagagc u                                              21
```

<210> SEQ ID NO 1056
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1056

```
uuccauaaua cucugagaga g                                              21
```

<210> SEQ ID NO 1057
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1057

```
ucucguucca uaauacucug c                                              21
```

<210> SEQ ID NO 1058
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1058

```
uugaaacaaa caaacccugg a                                              21
```

<210> SEQ ID NO 1059
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1059

```
uuccauaaua cucugagaga g                                              21
```

<210> SEQ ID NO 1060
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1060

```
aaugaaacaa acaaacccug g                                              21
```

<210> SEQ ID NO 1061
<211> LENGTH: 21
<212> TYPE: RNA
<213> ORGANISM: Artificial sequence

```
<220> FEATURE:
<223> OTHER INFORMATION: RNAi agent antisense strand modified sequence

<400> SEQUENCE: 1061
aaaugaaaca aacaaacccu g                                              21

<210> SEQ ID NO 1062
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1062
ugaaaugaaa caaacaaacc c                                              21

<210> SEQ ID NO 1063
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1063
uugaaacaaa caaacccugg a                                              21

<210> SEQ ID NO 1064
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1064
uugaaacaaa caaacccugg a                                              21

<210> SEQ ID NO 1065
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1065
uugaaacaaa caaacccugg a                                              21

<210> SEQ ID NO 1066
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1066
uugaaacaaa caaacccugg a                                              21

<210> SEQ ID NO 1067
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1067
agacgaucau acuuggagag c                                              21
```

```
<210> SEQ ID NO 1068
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1068
aaggcauucu caaucccuc c                                          21

<210> SEQ ID NO 1069
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1069
uuuccuugga aggcauucuc g                                         21

<210> SEQ ID NO 1070
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1070
uagauuuccu uggaaggcau c                                         21

<210> SEQ ID NO 1071
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1071
auaggaaaca gcauauucuu g                                         21

<210> SEQ ID NO 1072
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1072
uugaugaugu ucccuccaac g                                         21

<210> SEQ ID NO 1073
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1073
uagaacuuga agaagaagcu g                                         21

<210> SEQ ID NO 1074
<211> LENGTH: 21
<212> TYPE: RNA
<213> ORGANISM: Artificial sequence
<220> FEATURE:
<223> OTHER INFORMATION: RNAi agent antisense strand modified sequence
```

-continued

<400> SEQUENCE: 1074
uaccaaugau augcccaaca c                                              21

<210> SEQ ID NO 1075
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1075
ucauguguuu cuguguagac g                                              21

<210> SEQ ID NO 1076
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1076
uugagagaga uccugggugu c                                              21

<210> SEQ ID NO 1077
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1077
ucaugauacu gagagcuugc u                                              21

<210> SEQ ID NO 1078
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1078
uugucaaccu cacucuuccg a                                              21

<210> SEQ ID NO 1079
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1079
uuuccaacaa uucuccuugu c                                              21

<210> SEQ ID NO 1080
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1080
uugaguuagu cucaaagcug c                                              21

<210> SEQ ID NO 1081

-continued

```
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1081
augacaauau cugugcggag g                                               21

<210> SEQ ID NO 1082
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1082
ucaugacaau aucugugcgg a                                               21

<210> SEQ ID NO 1083
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1083
ucaaagaaga uagaagcagc c                                               21

<210> SEQ ID NO 1084
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1084
ucacguuauu accugugugc u                                               21

<210> SEQ ID NO 1085
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1085
uagaacuuga gguuauacag g                                               21

<210> SEQ ID NO 1086
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1086
augcuuugcu guucauuggu c                                               21

<210> SEQ ID NO 1087
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1087
```
uaguauagau ucaagguuau g                                              21

<210> SEQ ID NO 1088
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1088
agaguaaucu ugcuuuaugc c                                              21

<210> SEQ ID NO 1089
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1089
auagcaucau uucuaggugg a                                              21

<210> SEQ ID NO 1090
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1090
agacagaaga gacagagcua g                                              21

<210> SEQ ID NO 1091
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1091
aguaagaaaa ccaagccuua g                                              21

<210> SEQ ID NO 1092
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1092
uuccauaaua cucugagaga g                                              21

<210> SEQ ID NO 1093
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1093
uuccauaaua cucugagaga g                                              21

<210> SEQ ID NO 1094
<211> LENGTH: 21
<212> TYPE: RNA

```
<213> ORGANISM: Artificial sequence
<220> FEATURE:
<223> OTHER INFORMATION: RNAi agent antisense strand modified sequence

<400> SEQUENCE: 1094
uuccauaaua cucugagaga g                                              21

<210> SEQ ID NO 1095
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1095
uuccauaaua cucugagaga g                                              21

<210> SEQ ID NO 1096
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1096
uuccauaaua cucugagaga g                                              21

<210> SEQ ID NO 1097
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1097
uauacuugga gagcaucacu g                                              21

<210> SEQ ID NO 1098
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1098
uugcagacga ucauacuugg c                                              21

<210> SEQ ID NO 1099
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1099
uugaauaaaa cucucaugcc a                                              21

<210> SEQ ID NO 1100
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1100
uugaauaaaa cucucaugcc a                                              21
```

<210> SEQ ID NO 1101
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1101
uacuugaaga agaagcugag g                                              21

<210> SEQ ID NO 1102
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1102
uacuugaaga agaagcugag g                                              21

<210> SEQ ID NO 1103
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1103
uacuugaaga agaagcugag g                                              21

<210> SEQ ID NO 1104
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1104
uacuugaaga agaagcugag g                                              21

<210> SEQ ID NO 1105
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1105
uacuugaaga agaagcugag g                                              21

<210> SEQ ID NO 1106
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1106
uacuugaaga agaagcugag g                                              21

<210> SEQ ID NO 1107
<211> LENGTH: 21
<212> TYPE: RNA
<213> ORGANISM: Artificial sequence
<220> FEATURE:

```
<223> OTHER INFORMATION: RNAi agent antisense strand modified sequence

<400> SEQUENCE: 1107
uacuugaaga agaagcugag g                                              21

<210> SEQ ID NO 1108
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1108
uuugaaugcu gagaaauacu c                                              21

<210> SEQ ID NO 1109
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1109
uuugaaugcu gagaaauacu c                                              21

<210> SEQ ID NO 1110
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1110
uuugaaugcu gagaaauacu c                                              21

<210> SEQ ID NO 1111
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1111
uuugaaugcu gagaaauacu c                                              21

<210> SEQ ID NO 1112
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1112
uuugaaugcu gagaaauacu c                                              21

<210> SEQ ID NO 1113
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1113
agaaaagugg acgaucuugu c                                              21
```

```
<210> SEQ ID NO 1114
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1114
uaguugucac ugcaacaugg u                                               21

<210> SEQ ID NO 1115
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1115
auuccuucca caguugucac c                                               21

<210> SEQ ID NO 1116
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1116
ugcauucuca aucuccucca c                                               21

<210> SEQ ID NO 1117
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1117
uucaaugcca aucuccgugu c                                               21

<210> SEQ ID NO 1118
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1118
auauucuuga acuucaucuc g                                               21

<210> SEQ ID NO 1119
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1119
uuauggagag caguaucucc u                                               21

<210> SEQ ID NO 1120
<211> LENGTH: 21
<212> TYPE: RNA
<213> ORGANISM: Artificial sequence
<220> FEATURE:
<223> OTHER INFORMATION: RNAi agent antisense strand modified sequence
```

<400> SEQUENCE: 1120
uaaugcugag aaauacuccc c                                              21

<210> SEQ ID NO 1121
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1121
ugaaugcuga gaaauacucc c                                              21

<210> SEQ ID NO 1122
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1122
ucaaugucau cuucucuccg g                                              21

<210> SEQ ID NO 1123
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1123
acaaauucca guuauguuac c                                              21

<210> SEQ ID NO 1124
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1124
uucaauugug auaauggcug g                                              21

<210> SEQ ID NO 1125
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1125
aacauuuuug caacaaagcu c                                              21

<210> SEQ ID NO 1126
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1126
ucaacauuuu ugcaacaaag c                                              21

<210> SEQ ID NO 1127
<211> LENGTH: 21

```
<212> TYPE: RNA
<213> ORGANISM: Artificial sequence
<220> FEATURE:
<223> OTHER INFORMATION: RNAi agent antisense strand modified sequence

<400> SEQUENCE: 1127
uuucacucga accacaaucc g                                              21

<210> SEQ ID NO 1128
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1128
ucuuauucca aacuuggugg g                                              21

<210> SEQ ID NO 1129
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1129
ucuuauucca aacuuggugg g                                              21

<210> SEQ ID NO 1130
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1130
ucuuauucca aacuuggugg g                                              21

<210> SEQ ID NO 1131
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1131
ugcauauuca ccauuuaggc a                                              21

<210> SEQ ID NO 1132
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1132
ugcauauuca ccauuuaggc a                                              21

<210> SEQ ID NO 1133
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1133
```
ugcauauuca ccauuuaggc a          21

<210> SEQ ID NO 1134
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1134
ugcauauuca ccauuuaggc a          21

<210> SEQ ID NO 1135
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1135
ugcauauuca ccauuuaggc a          21

<210> SEQ ID NO 1136
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1136
ugcauauuca ccauuuaggc a          21

<210> SEQ ID NO 1137
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1137
augaaacaaa caaacccugg a          21

<210> SEQ ID NO 1138
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1138
augaaacaaa caaacccugg a          21

<210> SEQ ID NO 1139
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1139
augaaacaaa caaacccugg a          21

<210> SEQ ID NO 1140
<211> LENGTH: 21
<212> TYPE: RNA
<213> ORGANISM: Artificial sequence

```
<220> FEATURE:
<223> OTHER INFORMATION: RNAi agent antisense strand modified sequence

<400> SEQUENCE: 1140
augaaacaaa caaacccugg a                                              21

<210> SEQ ID NO 1141
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1141
augaaacaaa caaacccugg a                                              21

<210> SEQ ID NO 1142
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1142
augaaacaaa caaacccugg a                                              21

<210> SEQ ID NO 1143
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1143
augaaacaaa caaacccugg a                                              21

<210> SEQ ID NO 1144
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1144
augaaacaaa caaacccugg a                                              21

<210> SEQ ID NO 1145
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1145
uuccauaaua cucugagaga g                                              21

<210> SEQ ID NO 1146
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1146
uuccauaaua cucugagaga g                                              21
```

<210> SEQ ID NO 1147
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1147
uuccauaaua cucugagaga c        21

<210> SEQ ID NO 1148
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1148
uuccauaaua cucugagagg g        21

<210> SEQ ID NO 1149
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1149
uuccauaaua cucugagagg c        21

<210> SEQ ID NO 1150
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1150
uuccauaaua cucugagagg u        21

<210> SEQ ID NO 1151
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1151
uuccauaaua cucugagagg a        21

<210> SEQ ID NO 1152
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1152
uuccauaaua cucugagaga g        21

<210> SEQ ID NO 1153
<211> LENGTH: 21
<212> TYPE: RNA
<213> ORGANISM: Artificial sequence
<220> FEATURE:
<223> OTHER INFORMATION: RNAi agent antisense strand modified sequence

```
<400> SEQUENCE: 1153
ugcauauuca ccauuuaggc a                                              21

<210> SEQ ID NO 1154
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1154
ugcauauuca ccauuuaggc a                                              21

<210> SEQ ID NO 1155
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1155
ugcauauuca ccauuuaggc a                                              21

<210> SEQ ID NO 1156
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1156
ugcauauuca ccauuuaggc a                                              21

<210> SEQ ID NO 1157
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1157
ugcauauuca ccauuuaggc a                                              21

<210> SEQ ID NO 1158
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1158
ugcauauuca ccauuuaggc a                                              21

<210> SEQ ID NO 1159
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1159
ugcauauuca ccauuuaggc a                                              21

<210> SEQ ID NO 1160
```

```
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1160
ugcauauuca ccauuuaggc a                                              21

<210> SEQ ID NO 1161
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1161
augacaauau cugugcggag g                                              21

<210> SEQ ID NO 1162
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1162
augacaauau cugugcggag g                                              21

<210> SEQ ID NO 1163
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1163
augacaauau cugugcggag g                                              21

<210> SEQ ID NO 1164
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1164
uugacaauau cugugcggag g                                              21

<210> SEQ ID NO 1165
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1165
augacaauau cugugcggag g                                              21

<210> SEQ ID NO 1166
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1166
```
augacaauau cugugcggag g                                      21

<210> SEQ ID NO 1167
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1167
augacaauau cugugcggag g                                      21

<210> SEQ ID NO 1168
<211> LENGTH: 20
<212> TYPE: RNA
<213> ORGANISM: Artificial sequence
<220> FEATURE:
<223> OTHER INFORMATION: RNAi agent antisense strand modified sequence

<400> SEQUENCE: 1168
augacaauau cugugcggag                                        20

<210> SEQ ID NO 1169
<211> LENGTH: 19
<212> TYPE: RNA
<213> ORGANISM: Artificial sequence
<220> FEATURE:
<223> OTHER INFORMATION: RNAi agent antisense strand modified sequence

<400> SEQUENCE: 1169
augacaauau cugugcgga                                         19

<210> SEQ ID NO 1170
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1170
uuccauaaua cucugagaga g                                      21

<210> SEQ ID NO 1171
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1171
uuccauaaua cucugagaga c                                      21

<210> SEQ ID NO 1172
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1172
uugaaacaaa caaacccugg a                                      21

<210> SEQ ID NO 1173
<211> LENGTH: 21
<212> TYPE: RNA

```
<213> ORGANISM: Artificial sequence
<220> FEATURE:
<223> OTHER INFORMATION: RNAi agent antisense strand modified sequence

<400> SEQUENCE: 1173
augaaacaaa caaacccugg a                                              21

<210> SEQ ID NO 1174
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1174
augaaacaaa caaacccugg a                                              21

<210> SEQ ID NO 1175
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1175
gagauugaga augccuucca a                                              21

<210> SEQ ID NO 1176
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1176
gagauugaga augccuucca a                                              21

<210> SEQ ID NO 1177
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1177
ccucagcuuc uucuucaagu u                                              21

<210> SEQ ID NO 1178
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1178
gcagcuucuu cuucaaguuc u                                              21

<210> SEQ ID NO 1179
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1179
gcuucuucuu caaguucuac a                                              21
```

<210> SEQ ID NO 1180
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1180
aggggugaaa aucaccuaug a        21

<210> SEQ ID NO 1181
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1181
gggugaaaau caccuaugaa a        21

<210> SEQ ID NO 1182
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1182
ggugaaaauc accuaugaag a        21

<210> SEQ ID NO 1183
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1183
gugaaaauca ccuaugaaga a        21

<210> SEQ ID NO 1184
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1184
cuaccagcca uuaucacaau u        21

<210> SEQ ID NO 1185
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1185
gaagaacaac uccuuuuaug a        21

<210> SEQ ID NO 1186
<211> LENGTH: 21
<212> TYPE: RNA
<213> ORGANISM: Artificial sequence
<220> FEATURE:

<223> OTHER INFORMATION: RNAi agent sense strand modified sequence

<400> SEQUENCE: 1186
gagaacaacu ccuuuuaugg a                                              21

<210> SEQ ID NO 1187
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1187
gagacaagca cuaacacugu a                                              21

<210> SEQ ID NO 1188
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1188
ucgucaugag uauguacaca a                                              21

<210> SEQ ID NO 1189
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 1189
aggacaugcu gauaacugnu a                                              21

<210> SEQ ID NO 1190
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1190
ggauacaagg uuggcuucau a                                              21

<210> SEQ ID NO 1191
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1191
gcaagguugg cuucaugaag a                                              21

<210> SEQ ID NO 1192
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1192
caagguuggc uucaugaaga a                                              21

<210> SEQ ID NO 1193
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1193
agguuggcuu caugaagacu a                                              21

<210> SEQ ID NO 1194
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1194
aggagaauug uuggaaaaag a                                              21

<210> SEQ ID NO 1195
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1195
guggcuugcu cugaaguaga a                                              21

<210> SEQ ID NO 1196
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1196
gcuugcucug aaguagaaau a                                              21

<210> SEQ ID NO 1197
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1197
cccugccauu gauauungac a                                              21

<210> SEQ ID NO 1198
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1198
caagaucguc cacuuuucug a                                              21

<210> SEQ ID NO 1199
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1199
guccgaagca gauaauguug u          21

<210> SEQ ID NO 1200
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1200
gucucucuca gaguauuaug a          21

<210> SEQ ID NO 1201
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1201
cccaccaagu uuggaauaag a          21

<210> SEQ ID NO 1202
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1202
cugcauaaag caagauuacu a          21

<210> SEQ ID NO 1203
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1203
gacaauguuc uagauuucuu u          21

<210> SEQ ID NO 1204
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1204
caagaucguc cacuuuucug a          21

<210> SEQ ID NO 1205
<211> LENGTH: 21
<212> TYPE: RNA
<213> ORGANISM: Artificial sequence
<220> FEATURE:
<223> OTHER INFORMATION: RNAi agent sense strand modified sequence

```
<400> SEQUENCE: 1205
gucucucuca gaguauuaug a                                              21

<210> SEQ ID NO 1206
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1206
gaaaauguuc uagauuucuu u                                              21

<210> SEQ ID NO 1207
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1207
agugcuggau gagugaaguu a                                              21

<210> SEQ ID NO 1208
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 6
<223> OTHER INFORMATION: n = 2'-O-methylinosine-3'-phosphate

<400> SEQUENCE: 1208
gugcungaug agugaaguug a                                              21

<210> SEQ ID NO 1209
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 1209
ugcuggauga gugaaguunc a                                              21

<210> SEQ ID NO 1210
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1210
gaugcucucc aaguaugauc a                                              21

<210> SEQ ID NO 1211
<211> LENGTH: 21
<212> TYPE: RNA
<213> ORGANISM: Artificial sequence
<220> FEATURE:
```

<223> OTHER INFORMATION: RNAi agent sense strand modified sequence

<400> SEQUENCE: 1211
gugaucgucu gcagaacaag a                                              21

<210> SEQ ID NO 1212
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1212
gucgucugca gaacaagauc a                                              21

<210> SEQ ID NO 1213
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1213
gucgccagug caacuuuacu a                                              21

<210> SEQ ID NO 1214
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1214
aggauaaggu uacuuguguu a                                              21

<210> SEQ ID NO 1215
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1215
accagccauu aucacaauug a                                              21

<210> SEQ ID NO 1216
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1216
caagcucuca guaucaugcu a                                              21

<210> SEQ ID NO 1217
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1217
gaagagugag guugacaagu u                                              21

<210> SEQ ID NO 1218
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1218
gagagugagg uugacaaguu a                                              21

<210> SEQ ID NO 1219
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1219
guucaacaag gagaauuguu a                                              21

<210> SEQ ID NO 1220
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1220
ggaacauacc acagaacaug a                                              21

<210> SEQ ID NO 1221
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1221
gaacauggau cuauuaaagu a                                              21

<210> SEQ ID NO 1222
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1222
gacauggauc uauuaaaguc a                                              21

<210> SEQ ID NO 1223
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1223
ugccuaaaug gugaauaugc a                                              21

<210> SEQ ID NO 1224
<211> LENGTH: 21
<212> TYPE: RNA
<213> ORGANISM: Artificial sequence
<220> FEATURE:
<223> OTHER INFORMATION: RNAi agent sense strand modified sequence

```
<400> SEQUENCE: 1224
gaaccucuag aagcuuaaac a                                              21

<210> SEQ ID NO 1225
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1225
ggccuucaaa ccaaugaaca a                                              21

<210> SEQ ID NO 1226
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1226
ccaaugaaca gcaaagcaua a                                              21

<210> SEQ ID NO 1227
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1227
gaugaacagc aaagcauaac a                                              21

<210> SEQ ID NO 1228
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1228
gugaacagca aagcauaacc u                                              21

<210> SEQ ID NO 1229
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1229
gaacagcaaa gcauaaccuu a                                              21

<210> SEQ ID NO 1230
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1230
gcaaagcaua accuugaauc u                                              21

<210> SEQ ID NO 1231
<211> LENGTH: 21
```

```
<212> TYPE: RNA
<213> ORGANISM: Artificial sequence
<220> FEATURE:
<223> OTHER INFORMATION: RNAi agent sense strand modified sequence

<400> SEQUENCE: 1231
ccaaccaacu caauuauuga a                                              21

<210> SEQ ID NO 1232
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1232
cuuccuguga uccauuuuac u                                              21

<210> SEQ ID NO 1233
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1233
gguuuucuua cugucauaug a                                              21

<210> SEQ ID NO 1234
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1234
gagaucgaga augccuucca a                                              21

<210> SEQ ID NO 1235
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1235
gacuggcauu uucaaugaug a                                              21

<210> SEQ ID NO 1236
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1236
gucaaugaug aaacugucuu u                                              21

<210> SEQ ID NO 1237
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1237
```

```
gaggaugagg uuacuugugu u                                              21
```

<210> SEQ ID NO 1238
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1238

```
cugaagcuga caauguuguc u                                              21
```

<210> SEQ ID NO 1239
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1239

```
gcuuuauugc aaagauguug a                                              21
```

<210> SEQ ID NO 1240
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1240

```
gaggauuugu aagacuaauc u                                              21
```

<210> SEQ ID NO 1241
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1241

```
ccgacuaagu uuggaauaag a                                              21
```

<210> SEQ ID NO 1242
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1242

```
gcuucacacu uucuuuucug a                                              21
```

<210> SEQ ID NO 1243
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1243

```
gcagcuuuga gacaaacucu a                                              21
```

<210> SEQ ID NO 1244
<211> LENGTH: 21
<212> TYPE: RNA
<213> ORGANISM: Artificial sequence

```
<220> FEATURE:
<223> OTHER INFORMATION: RNAi agent sense strand modified sequence

<400> SEQUENCE: 1244
gagaaauuga cugcuuaaca a                                              21

<210> SEQ ID NO 1245
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1245
ccguaguauc cagauuucca a                                              21

<210> SEQ ID NO 1246
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1246
agcaggaugg cauuuucaag a                                              21

<210> SEQ ID NO 1247
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1247
gacaauugug auccaaauca u                                              21

<210> SEQ ID NO 1248
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1248
uggcaguuuu gaguaauucu a                                              21

<210> SEQ ID NO 1249
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1249
gucugagucc auuuuugauc a                                              21

<210> SEQ ID NO 1250
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1250
cuagaucugc augcuuucuu a                                              21
```

<210> SEQ ID NO 1251
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1251
cuucagagag cuuauaucug a                                              21

<210> SEQ ID NO 1252
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1252
ggauacaagg uuggcuucau a                                              21

<210> SEQ ID NO 1253
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methylinosine-3'-phosphate

<400> SEQUENCE: 1253
ggauacaagg uugncuucau a                                              21

<210> SEQ ID NO 1254
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-O-methylinosine-3'-phosphate

<400> SEQUENCE: 1254
ggauacaagg uungcuucau a                                              21

<210> SEQ ID NO 1255
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1255
ggauacaagg uugguuucau a                                              21

<210> SEQ ID NO 1256
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1256
ggauacaagg uuggcuucau a                                              21

<210> SEQ ID NO 1257
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1257
ggauacaagg uuggcuucau a                                            21

<210> SEQ ID NO 1258
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1258
gcaagguugg cuucaugaag a                                            21

<210> SEQ ID NO 1259
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1259
guggagaaaa augcanaucc a                                            21

<210> SEQ ID NO 1260
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1260
uccagagaca acucuuuugg a                                            21

<210> SEQ ID NO 1261
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1261
cucuccaagu augaucnucu a                                            21

<210> SEQ ID NO 1262
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1262
gcaacugugg aaggaauagg a                           21

<210> SEQ ID NO 1263
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1263
uggcaucguc augaguaugu a                           21

<210> SEQ ID NO 1264
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1264
gccuuccaag gaaaucugun a                           21

<210> SEQ ID NO 1265
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1265
guggcauuga gaugaaguuc a                           21

<210> SEQ ID NO 1266
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate

<400> SEQUENCE: 1266
gnugaaguuc aagaauaugc u                           21

<210> SEQ ID NO 1267
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1267
ggaauaugcu guuuccuaug a                           21

<210> SEQ ID NO 1268
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1268
gcugcucucc auaganaucc a        21

<210> SEQ ID NO 1269
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1269
gaguauuucu cagcauucaa a        21

<210> SEQ ID NO 1270
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1270
cgccaagauc aaguccauag a        21

<210> SEQ ID NO 1271
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1271
uccaggguuu guuuguuuca u        21

<210> SEQ ID NO 1272
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1272
gucaccuaug aagaacuacc a        21

<210> SEQ ID NO 1273
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1273
gagaacuacc agccauuauc a        21

<210> SEQ ID NO 1274
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1274
cagccauuau cacaauugag a        21

<210> SEQ ID NO 1275
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1275
ugagcugaag aucgagaaag a                                              21

<210> SEQ ID NO 1276
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1276
cugcaccauu gcuguuccaa a                                              21

<210> SEQ ID NO 1277
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1277
guggagcucu uuguguuuac a                                              21

<210> SEQ ID NO 1278
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1278
agcucuuugu gucuacacan a                                              21

<210> SEQ ID NO 1279
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1279
cucucucaga guauuaugga a                                              21

<210> SEQ ID NO 1280
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1280
gcagaguauu auggaacgan a                                              21

```
<210> SEQ ID NO 1281
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1281
uccaggguuu guuuguuuca a                                               21

<210> SEQ ID NO 1282
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1282
ccaggguuug uuuguuucau u                                               21

<210> SEQ ID NO 1283
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1283 cagggut ugu uguuucauu u                                               21

<210> SEQ ID NO 1284
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1284
ggguuuguuu guuucauuuc a                                               21

<210> SEQ ID NO 1285
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1285
uccaggguuu guuuguuuca a                                               21

<210> SEQ ID NO 1286
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1286
uccaggguuu guuuguuuca a                                               21

<210> SEQ ID NO 1287
<211> LENGTH: 21
<212> TYPE: RNA
<213> ORGANISM: Artificial sequence
<220> FEATURE:
```

```
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1287
gcucuccaag uaugaucnuc u                                              21

<210> SEQ ID NO 1288
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1288
ggaggagauu gagaanuccu u                                              21

<210> SEQ ID NO 1289
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1289
cgagaaugcc uuccaaggaa a                                              21

<210> SEQ ID NO 1290
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1290
gaugccuucc aaggaaaucu a                                              21

<210> SEQ ID NO 1291
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate

<400> SEQUENCE: 1291
cnagaauaug cuguuuccua u                                              21

<210> SEQ ID NO 1292
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1292
cguuggaggg aacaucauca a                                              21
```

```
<210> SEQ ID NO 1293
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1293 cagcucuuc uucaaguucu a                                              21

<210> SEQ ID NO 1294
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1294
guguugggca uaucauuggu a                                             21

<210> SEQ ID NO 1295
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1295
cgucuacaca gaacaccaug a                                             21

<210> SEQ ID NO 1296
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1296
gacacccagg aucucuuuca a                                             21

<210> SEQ ID NO 1297
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1297
agcaagcucu caguaucaug a                                             21

<210> SEQ ID NO 1298
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1298
ucggaagagu gagguugaca a                                             21

<210> SEQ ID NO 1299
<211> LENGTH: 21
<212> TYPE: RNA
<213> ORGANISM: Artificial sequence
<220> FEATURE:
<223> OTHER INFORMATION: RNAi agent sense strand modified sequence
```

```
<400> SEQUENCE: 1299
gacaaggaga auuguuggaa a                                               21

<210> SEQ ID NO 1300
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1300
gcagcuuuga gacuaacuca a                                               21

<210> SEQ ID NO 1301
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1301
ccuccgcaca gauauuguca u                                               21

<210> SEQ ID NO 1302
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1302
uccgcacaga uauugucaug a                                               21

<210> SEQ ID NO 1303
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1303
ggcugcuucu aucuucuuug a                                               21

<210> SEQ ID NO 1304
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1304
agcacacagg uaauaacgun a                                               21

<210> SEQ ID NO 1305
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1305
ccuguauaac cucaaguucu a                                               21
```

```
<210> SEQ ID NO 1306
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1306
gaccaaugaa cagcaaagca u                                                 21

<210> SEQ ID NO 1307
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate

<400> SEQUENCE: 1307
cnuaaccuug aaucuauacu a                                                 21

<210> SEQ ID NO 1308
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1308
ggcauaaagc aagauuacuc u                                                 21

<210> SEQ ID NO 1309
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1309
uccaccuaga aaugaugcua u                                                 21

<210> SEQ ID NO 1310
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1310
cuagcucugu cucuucunuc u                                                 21

<210> SEQ ID NO 1311
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 3
```

<223> OTHER INFORMATION: n = 2'-O-methyl-2-aminoadenosine-3'-phosphate

<400> SEQUENCE: 1311
cunaggcuug guuucuuac u            21

<210> SEQ ID NO 1312
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1312
cucucucaga guauuaugga a            21

<210> SEQ ID NO 1313
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1313
cucucucaga guauuaugga a            21

<210> SEQ ID NO 1314
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1314
cagugaugcu cuccaaguau a            21

<210> SEQ ID NO 1315
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1315
gccaaguaug aucgucunca a            21

<210> SEQ ID NO 1316
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1316
uggcaugaga guuuuauuca a            21

<210> SEQ ID NO 1317
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base

```
<222> LOCATION: 16
<223> OTHER INFORMATION: n = 2'-O-methyl-2-aminoadenosine-3'-phosphate

<400> SEQUENCE: 1317
uggcaugaga guuuunuuca a                                              21

<210> SEQ ID NO 1318
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1318
ccucagcuuc uucuucaagu a                                              21

<210> SEQ ID NO 1319
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1319
ccucagcuuc uucuuuaagu a                                              21

<210> SEQ ID NO 1320
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1320
ccucagcuuc uucuucaagu a                                              21

<210> SEQ ID NO 1321
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1321
ccucagcuuc uucuucaagu a                                              21

<210> SEQ ID NO 1322
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1322
gaguauuucu cagcauucaa a                                              21

<210> SEQ ID NO 1323
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1323
gacaagaucg uccacuuuuc u                                              21
```

<210> SEQ ID NO 1324
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1324
accauguugc agugacaacu a                                           21

<210> SEQ ID NO 1325
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1325
ggugacaacu guggaaggaa u                                           21

<210> SEQ ID NO 1326
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1326
guggaggaga uugagaaugc a                                           21

<210> SEQ ID NO 1327
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1327
gacacggaga uuggcauuga a                                           21

<210> SEQ ID NO 1328
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methyl-2-aminoadenosine-3'-phosphate

<400> SEQUENCE: 1328
cgagaugaag uucaagaaun u                                           21

<210> SEQ ID NO 1329
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1329
aggagauacu gcucuccaua a                                           21

<210> SEQ ID NO 1330
<211> LENGTH: 21

```
<212> TYPE: RNA
<213> ORGANISM: Artificial sequence
<220> FEATURE:
<223> OTHER INFORMATION: RNAi agent sense strand modified sequence

<400> SEQUENCE: 1330
ggggaguauu ucucagcauu a                                              21

<210> SEQ ID NO 1331
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1331
gggaguauuu cucagcauuc a                                              21

<210> SEQ ID NO 1332
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1332
ccggagagaa gaugacauug a                                              21

<210> SEQ ID NO 1333
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1333
gguaacauaa cuggaauuug u                                              21

<210> SEQ ID NO 1334
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1334
ccagccauua ucacaauuga a                                              21

<210> SEQ ID NO 1335
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1335
gagcuuuguu gcaaaaaugu u                                              21

<210> SEQ ID NO 1336
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1336
```
gcuuguuugc aaaaauguug a                                              21

<210> SEQ ID NO 1337
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1337
cggauugugg uucgagugaa a                                              21

<210> SEQ ID NO 1338
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1338
cccaccaagu uuggaauaag a                                              21

<210> SEQ ID NO 1339
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1339
cccaccaagu uuggaauaag a                                              21

<210> SEQ ID NO 1340
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1340
ugccuaaaug gugaauaugc a                                              21

<210> SEQ ID NO 1341
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1341
ugccuaaaug gugaauaugc a                                              21

<210> SEQ ID NO 1342
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1342
uccaggguuu guuuguuuca u                                              21

<210> SEQ ID NO 1343
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1343
gucucucaga guauuaugga a 21

<210> SEQ ID NO 1344
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1344
cccucucaga guauuaugga a 21

<210> SEQ ID NO 1345
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1345
gccucucaga guauuaugga a 21

<210> SEQ ID NO 1346
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1346
accucucaga guauuaugga a 21

<210> SEQ ID NO 1347
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1347
uccucucaga guauuaugga a 21

<210> SEQ ID NO 1348
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1348
ccuccgcaca gauauuguca u 21

<210> SEQ ID NO 1349
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1349
ccuccgcaca gauauuguca a 21

<210> SEQ ID NO 1350
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 1350
cuccgcacag auauugucau                                              20

<210> SEQ ID NO 1351
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 1351
uccgcacaga uauugucau                                               19

<210> SEQ ID NO 1352
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1352
uuggaaggca uucucaaucu c                                            21

<210> SEQ ID NO 1353
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1353
aacuugaaga agaagcugag g                                            21

<210> SEQ ID NO 1354
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1354
agaacuugaa gaagaagcug c                                            21

<210> SEQ ID NO 1355
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1355
uguagaacuu gaagaagaag c                                            21

<210> SEQ ID NO 1356
<211> LENGTH: 21

```
<212> TYPE: RNA
<213> ORGANISM: Artificial sequence
<220> FEATURE:
<223> OTHER INFORMATION: RNAi agent antisense strand underlying base
      sequence

<400> SEQUENCE: 1356
ucauagguga uuuucacccc u                                              21

<210> SEQ ID NO 1357
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1357
uuucauaggu gauuuucacc c                                              21

<210> SEQ ID NO 1358
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1358
ucuucauagg ugauuuucac c                                              21

<210> SEQ ID NO 1359
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1359
uucuucauag gugauuuuca c                                              21

<210> SEQ ID NO 1360
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1360
aauugugaua auggcuggua g                                              21

<210> SEQ ID NO 1361
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1361
ucauaaaagg aguuguucuu c                                              21

<210> SEQ ID NO 1362
<211> LENGTH: 21
<212> TYPE: RNA
```

<213> ORGANISM: Artificial sequence
<220> FEATURE:
<223> OTHER INFORMATION: RNAi agent antisense strand underlying base
      sequence

<400> SEQUENCE: 1362
uccauaaaag gaguuguucu c                                              21

<210> SEQ ID NO 1363
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1363
uacaguguua gugcuugucu c                                              21

<210> SEQ ID NO 1364
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1364
uuguguacau acucaugacg a                                              21

<210> SEQ ID NO 1365
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1365
uaccaguuau cagcaugucc u                                              21

<210> SEQ ID NO 1366
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1366
uaugaagcca accuuguauc c                                              21

<210> SEQ ID NO 1367
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1367
ucuucaugaa gccaaccuug c                                              21

<210> SEQ ID NO 1368
<211> LENGTH: 21
<212> TYPE: RNA
<213> ORGANISM: Artificial sequence

```
<220> FEATURE:
<223> OTHER INFORMATION: RNAi agent antisense strand underlying base
      sequence

<400> SEQUENCE: 1368
uucuucauga agccaaccuu g                                              21

<210> SEQ ID NO 1369
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1369
uagucuucau gaagccaacc u                                              21

<210> SEQ ID NO 1370
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1370
ucuuuuucca acaauucucc u                                              21

<210> SEQ ID NO 1371
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1371
uucuacuuca gagcaagcca c                                              21

<210> SEQ ID NO 1372
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1372
uauuucuacu ucagagcaag c                                              21

<210> SEQ ID NO 1373
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1373
uguccaauau caauggcagg g                                              21

<210> SEQ ID NO 1374
<211> LENGTH: 21
<212> TYPE: RNA
<213> ORGANISM: Artificial sequence
<220> FEATURE:
```

```
<223> OTHER INFORMATION: RNAi agent antisense strand underlying base
      sequence

<400> SEQUENCE: 1374
ucagaaaagu ggacgaucuu g                                              21

<210> SEQ ID NO 1375
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1375
acaacauuau cugcuucgga c                                              21

<210> SEQ ID NO 1376
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1376
ucauaauacu cugagagaga c                                              21

<210> SEQ ID NO 1377
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1377
ucuuauucca aacuuggugg g                                              21

<210> SEQ ID NO 1378
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1378
uaguaaucuu gcuuuaugca g                                              21

<210> SEQ ID NO 1379
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1379
aaagaaaucu agaacauugu c                                              21

<210> SEQ ID NO 1380
<211> LENGTH: 21
<212> TYPE: RNA
<213> ORGANISM: Artificial sequence
<220> FEATURE:
<223> OTHER INFORMATION: RNAi agent antisense strand underlying base
```

-continued

<400> SEQUENCE: 1380
aaagaaaucu agaacauuuu c                                              21

<210> SEQ ID NO 1381
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1381
uaacuucacu cauccagcac u                                              21

<210> SEQ ID NO 1382
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1382
ucaacuucac ucauccagca c                                              21

<210> SEQ ID NO 1383
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1383
ugcaacuuca cucauccagc a                                              21

<210> SEQ ID NO 1384
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1384
ugaucauacu uggagagcau c                                              21

<210> SEQ ID NO 1385
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1385
ucuuguucug cagacgauca c                                              21

<210> SEQ ID NO 1386
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1386
ugaucuuguu cugcagacga c					21

<210> SEQ ID NO 1387
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1387
uaguaaaguu gcacuggcga c					21

<210> SEQ ID NO 1388
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1388
uaacacaagu aaccuuaucc u					21

<210> SEQ ID NO 1389
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1389
ucaauuguga uaauggcugg u					21

<210> SEQ ID NO 1390
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1390
uagcaugaua cugagagcuu g					21

<210> SEQ ID NO 1391
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1391
aacuugucaa ccucacucuu c					21

<210> SEQ ID NO 1392
<211> LENGTH: 21
<212> TYPE: RNA
<213> ORGANISM: Artificial sequence
<220> FEATURE:
<223> OTHER INFORMATION: RNAi agent antisense strand underlying base
      sequence

```
<400> SEQUENCE: 1392
uaacuuguca accucacucu c                                              21

<210> SEQ ID NO 1393
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1393
uaacaauucu ccuuguugaa c                                              21

<210> SEQ ID NO 1394
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1394
ucauguucug ugguauguuc c                                              21

<210> SEQ ID NO 1395
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1395
uacuuuaaua gauccauguu c                                              21

<210> SEQ ID NO 1396
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1396
ugacuuuaau agauccaugu c                                              21

<210> SEQ ID NO 1397
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1397
ugcauauuca ccauuuaggc a                                              21

<210> SEQ ID NO 1398
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1398
```
uguuuaagcu ucuagagguu c    21

<210> SEQ ID NO 1399
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1399
uuguucauug guuugaaggc c    21

<210> SEQ ID NO 1400
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1400
uuaugcuuug cuguucauug g    21

<210> SEQ ID NO 1401
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1401
uguuaugcuu ugcuguucau c    21

<210> SEQ ID NO 1402
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1402
agguuaugcu uugcuguuca c    21

<210> SEQ ID NO 1403
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1403
uaagguuaug cuuugcuguu c    21

<210> SEQ ID NO 1404
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1404
agauucaagg uuaugcuuug c                    21

<210> SEQ ID NO 1405
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1405
uucaauaauu gaguugguug g                    21

<210> SEQ ID NO 1406
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1406
aguaaaaugg aucacaggaa g                    21

<210> SEQ ID NO 1407
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1407
ucauaugaca guaagaaaac c                    21

<210> SEQ ID NO 1408
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1408
uuggaaggca uucucgaucu c                    21

<210> SEQ ID NO 1409
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1409
ucaucauuga aaaugccagu c                    21

<210> SEQ ID NO 1410
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1410
aaagacaguu ucaucauuga c                    21

<210> SEQ ID NO 1411
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1411
aacacaagua accucauccu c                                              21

<210> SEQ ID NO 1412
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1412
agacaacauu gucagcuuca g                                              21

<210> SEQ ID NO 1413
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1413
ucaacaucuu ugcaauaaag c                                              21

<210> SEQ ID NO 1414
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1414
agauuagucu uacaaauccu c                                              21

<210> SEQ ID NO 1415
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1415
ucuuauucca aacuuagucg g                                              21

<210> SEQ ID NO 1416
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1416
ucagaaaaga aagugugaag c                                              21

```
<210> SEQ ID NO 1417
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1417
uagaguuugu cucaaagcug c                                                   21

<210> SEQ ID NO 1418
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1418
uuguuaagca gucaauuucu c                                                   21

<210> SEQ ID NO 1419
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1419
uuggaaaucu ggauacuacg g                                                   21

<210> SEQ ID NO 1420
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1420
ucuugaaaau gccauccugc u                                                   21

<210> SEQ ID NO 1421
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1421
augauuugga ucacaauugu c                                                   21

<210> SEQ ID NO 1422
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1422
uagaauuacu caaaacugcc a                                                   21
```

```
<210> SEQ ID NO 1423
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1423
ugaucaaaaa uggacucaga c                                              21

<210> SEQ ID NO 1424
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1424
uaagaaagca ugcagaucua g                                              21

<210> SEQ ID NO 1425
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1425
ucagauauaa gcucucugaa g                                              21

<210> SEQ ID NO 1426
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1426
uaugaaguca accuuguauc c                                              21

<210> SEQ ID NO 1427
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1427
uaugaagcua accuuguauc c                                              21

<210> SEQ ID NO 1428
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1428
uggaucugca uuuuucucca c                                              21

<210> SEQ ID NO 1429
```

```
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1429
uccaaaaggg uugucucugg a                                            21

<210> SEQ ID NO 1430
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1430
uagacgauca uacuuggaga g                                            21

<210> SEQ ID NO 1431
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1431
uccuauuccu uccacaguug c                                            21

<210> SEQ ID NO 1432
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1432
uacauacuca ugacgaugcc a                                            21

<210> SEQ ID NO 1433
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1433
ucacagauuu ccuuggaagg c                                            21

<210> SEQ ID NO 1434
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1434
ugaacuucau cucaaugcca c                                            21

<210> SEQ ID NO 1435
<211> LENGTH: 21
```

```
<212> TYPE: RNA
<213> ORGANISM: Artificial sequence
<220> FEATURE:
<223> OTHER INFORMATION: RNAi agent antisense strand underlying base
      sequence

<400> SEQUENCE: 1435
agcauauucu ugaacuucau c                                              21

<210> SEQ ID NO 1436
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1436
ucauaggaaa cagcauauuc c                                              21

<210> SEQ ID NO 1437
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1437
uggaucucua uggagagcag c                                              21

<210> SEQ ID NO 1438
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1438
uuugaaugcu gagaaauacu c                                              21

<210> SEQ ID NO 1439
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1439
ucuauggacu ugaucuuggc g                                              21

<210> SEQ ID NO 1440
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1440
augaaacaaa caaacccugg a                                              21

<210> SEQ ID NO 1441
<211> LENGTH: 21
<212> TYPE: RNA
```

```
<213> ORGANISM: Artificial sequence
<220> FEATURE:
<223> OTHER INFORMATION: RNAi agent antisense strand underlying base
      sequence

<400> SEQUENCE: 1441
ugguaguucu ucauagguga c                                               21

<210> SEQ ID NO 1442
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1442
ugauaauggc ugguaguucu c                                               21

<210> SEQ ID NO 1443
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1443
ucucaauugu gauaauggcu g                                               21

<210> SEQ ID NO 1444
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1444
ucuuucucga ucuucagcuc a                                               21

<210> SEQ ID NO 1445
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1445
uuuggaacag caauggugca g                                               21

<210> SEQ ID NO 1446
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1446
uguagacaca aagagcucca c                                               21

<210> SEQ ID NO 1447
<211> LENGTH: 21
<212> TYPE: RNA
<213> ORGANISM: Artificial sequence
```

```
<220> FEATURE:
<223> OTHER INFORMATION: RNAi agent antisense strand underlying base
      sequence

<400> SEQUENCE: 1447
ucuguguaga cacaaagagc u                                              21

<210> SEQ ID NO 1448
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1448
uuccauaaua cucugagaga g                                              21

<210> SEQ ID NO 1449
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1449
ucucguucca uaauacucug c                                              21

<210> SEQ ID NO 1450
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1450
uugaaacaaa caaacccugg a                                              21

<210> SEQ ID NO 1451
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1451
aaugaaacaa acaaacccug g                                              21

<210> SEQ ID NO 1452
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1452
aaaugaaaca aacaaacccu g                                              21

<210> SEQ ID NO 1453
<211> LENGTH: 21
<212> TYPE: RNA
<213> ORGANISM: Artificial sequence
<220> FEATURE:
```

<223> OTHER INFORMATION: RNAi agent antisense strand underlying base
      sequence

<400> SEQUENCE: 1453
ugaaaugaaa caaacaaacc c                                               21

<210> SEQ ID NO 1454
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1454
agacgaucau acuuggagag c                                               21

<210> SEQ ID NO 1455
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1455
aaggcauucu caaucccuc c                                                21

<210> SEQ ID NO 1456
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1456
uuuccuugga aggcauucuc g                                               21

<210> SEQ ID NO 1457
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1457
uagauuuccu uggaaggcau c                                               21

<210> SEQ ID NO 1458
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1458
auaggaaaca gcauauucuu g                                               21

<210> SEQ ID NO 1459
<211> LENGTH: 21
<212> TYPE: RNA
<213> ORGANISM: Artificial sequence
<220> FEATURE:
<223> OTHER INFORMATION: RNAi agent antisense strand underlying base -continued sequence

<400> SEQUENCE: 1459
uugaugaugu ucccuccaac g                                          21

<210> SEQ ID NO 1460
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1460
uagaacuuga agaagaagcu g                                          21

<210> SEQ ID NO 1461
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1461
uaccaaugau augcccaaca c                                          21

<210> SEQ ID NO 1462
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1462 ucauggguguu cuguguagac g                                         21

<210> SEQ ID NO 1463
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1463
uugagagaga uccugggugu c                                          21

<210> SEQ ID NO 1464
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1464
ucaugauacu gagagcuugc u                                          21

<210> SEQ ID NO 1465
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1465
uugucaaccu cacucuuccg a                                              21

<210> SEQ ID NO 1466
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1466 uuccaacaa uucuccuugu c                                               21

<210> SEQ ID NO 1467
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1467
uugaguuagu cucaaagcug c                                              21

<210> SEQ ID NO 1468
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1468
augacaauau cugugcggag g                                              21

<210> SEQ ID NO 1469
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1469
ucaugacaau aucugugcgg a                                              21

<210> SEQ ID NO 1470
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1470
ucaaagaaga uagaagcagc c                                              21

<210> SEQ ID NO 1471
<211> LENGTH: 21
<212> TYPE: RNA
<213> ORGANISM: Artificial sequence
<220> FEATURE:
<223> OTHER INFORMATION: RNAi agent antisense strand underlying base
      sequence

```
<400> SEQUENCE: 1471
ucacguuauu accugugugc u                                              21

<210> SEQ ID NO 1472
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1472
uagaacuuga gguuauacag g                                              21

<210> SEQ ID NO 1473
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1473
augcuuugcu guucauuggu c                                              21

<210> SEQ ID NO 1474
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1474
uaguauagau ucaagguuau g                                              21

<210> SEQ ID NO 1475
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1475
agaguaaucu ugcuuuaugc c                                              21

<210> SEQ ID NO 1476
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1476
auagcaucau uucuaggugg a                                              21

<210> SEQ ID NO 1477
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1477
```
agacagaaga gacagagcua g                                          21

<210> SEQ ID NO 1478
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1478
aguaagaaaa ccaagccuua g                                          21

<210> SEQ ID NO 1479
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1479
uauacuugga gagcaucacu g                                          21

<210> SEQ ID NO 1480
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1480
uugcagacga ucauacuugg c                                          21

<210> SEQ ID NO 1481
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1481
uugaauaaaa cucucaugcc a                                          21

<210> SEQ ID NO 1482
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1482
uacuugaaga agaagcugag g                                          21

<210> SEQ ID NO 1483
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1483
agaaaagugg acgaucuugu c					21

<210> SEQ ID NO 1484
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1484
uaguugucac ugcaacaugg u					21

<210> SEQ ID NO 1485
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1485
auuccuucca caguugucac c					21

<210> SEQ ID NO 1486
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1486
ugcauucuca aucccucca c					21

<210> SEQ ID NO 1487
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1487
uucaaugcca aucuccgugu c					21

<210> SEQ ID NO 1488
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1488
auauucuuga acuucaucuc g					21

<210> SEQ ID NO 1489
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1489
uuauggagag caguaucucc u					21

<210> SEQ ID NO 1490
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1490
uaaugcugag aaauacuccc c                                               21

<210> SEQ ID NO 1491
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1491
ugaaugcuga gaaauacucc c                                               21

<210> SEQ ID NO 1492
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1492
ucaaugucau cuucucuccg g                                               21

<210> SEQ ID NO 1493
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1493
acaaauucca guuauguuac c                                               21

<210> SEQ ID NO 1494
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1494
uucaauugug auaauggcug g                                               21

<210> SEQ ID NO 1495
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1495
aacauuuuug caacaaagcu c                                               21

```
<210> SEQ ID NO 1496
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1496
ucaacauuuu ugcaacaaag c                                              21

<210> SEQ ID NO 1497
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1497
uuucacucga accacaaucc g                                              21

<210> SEQ ID NO 1498
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1498
uuccauaaua cucugagaga c                                              21

<210> SEQ ID NO 1499
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1499
uuccauaaua cucugagagg g                                              21

<210> SEQ ID NO 1500
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1500
uuccauaaua cucugagagg c                                              21

<210> SEQ ID NO 1501
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1501
uuccauaaua cucugagagg u                                              21
```

```
<210> SEQ ID NO 1502
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1502
uuccauaaua cucugagagg a                                              21

<210> SEQ ID NO 1503
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1503
uugacaauau cugugcggag g                                              21

<210> SEQ ID NO 1504
<211> LENGTH: 20
<212> TYPE: RNA
<213> ORGANISM: Artificial sequence
<220> FEATURE:
<223> OTHER INFORMATION: RNAi agent antisense strand underlying base
      sequence

<400> SEQUENCE: 1504
augacaauau cugugcggag                                                20

<210> SEQ ID NO 1505
<211> LENGTH: 19
<212> TYPE: RNA
<213> ORGANISM: Artificial sequence
<220> FEATURE:
<223> OTHER INFORMATION: RNAi agent antisense strand underlying base
      sequence

<400> SEQUENCE: 1505
augacaauau cugugcgga                                                 19

<210> SEQ ID NO 1506
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1506
gagauugaga augccuucca a                                              21

<210> SEQ ID NO 1507
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1507
ccucagcuuc uucuucaagu u                                              21

<210> SEQ ID NO 1508
```

```
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1508
gcagcuucuu cuucaaguuc u                                             21

<210> SEQ ID NO 1509
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1509
gcuucuucuu caaguucuac a                                             21

<210> SEQ ID NO 1510
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1510
aggggugaaa aucaccuaug a                                             21

<210> SEQ ID NO 1511
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1511
gggugaaaau caccuaugaa a                                             21

<210> SEQ ID NO 1512
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1512
ggugaaaauc accuaugaag a                                             21

<210> SEQ ID NO 1513
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1513
gugaaaauca ccuaugaaga a                                             21

<210> SEQ ID NO 1514
<211> LENGTH: 21
```

```
<212> TYPE: RNA
<213> ORGANISM: Artificial sequence
<220> FEATURE:
<223> OTHER INFORMATION: RNAi agent sense strand underlying base
      sequence

<400> SEQUENCE: 1514
cuaccagcca uuaucacaau u                                              21

<210> SEQ ID NO 1515
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1515
gaagaacaac uccuuuuaug a                                              21

<210> SEQ ID NO 1516
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1516
gagaacaacu ccuuuuaugg a                                              21

<210> SEQ ID NO 1517
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1517
gagacaagca cuaacacugu a                                              21

<210> SEQ ID NO 1518
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1518
ucgucaugag uauguacaca a                                              21

<210> SEQ ID NO 1519
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = inosine (hypoxanthine)

<400> SEQUENCE: 1519
aggacaugcu gauaacugnu a                                              21
```

<210> SEQ ID NO 1520
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1520 ggaucaagg uuggcuucau a                                               21

<210> SEQ ID NO 1521
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1521
gcaagguugg cuucaugaag a                                              21

<210> SEQ ID NO 1522
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1522
caagguuggc uucaugaaga a                                              21

<210> SEQ ID NO 1523
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1523
agguuggcuu caugaagacu a                                              21

<210> SEQ ID NO 1524
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1524
aggagaauug uuggaaaaag a                                              21

<210> SEQ ID NO 1525
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1525
guggcuugcu cugaaguaga a                                              21

```
<210> SEQ ID NO 1526
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1526
gcuugcucug aaguagaaau a                                                 21

<210> SEQ ID NO 1527
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = inosine (hypoxanthine)

<400> SEQUENCE: 1527
cccugccauu gauauungac a                                                 21

<210> SEQ ID NO 1528
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1528
caagaucguc cacuuuucug a                                                 21

<210> SEQ ID NO 1529
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1529
guccgaagca gauaauguug u                                                 21

<210> SEQ ID NO 1530
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1530
gucucucuca gaguauuaug a                                                 21

<210> SEQ ID NO 1531
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1531
```

-continued cccaccaagu uuggaauaag a                     21

<210> SEQ ID NO 1532
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1532
cugcauaaag caagauuacu a                     21

<210> SEQ ID NO 1533
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1533
gacaauguuc uagauuucuu u                     21

<210> SEQ ID NO 1534
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1534
gaaaauguuc uagauuucuu u                     21

<210> SEQ ID NO 1535
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1535
agugcuggau gagugaaguu a                     21

<210> SEQ ID NO 1536
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 6
<223> OTHER INFORMATION: n = inosine (hypoxanthine)

<400> SEQUENCE: 1536
gugcungaug agugaaguug a                     21

<210> SEQ ID NO 1537
<211> LENGTH: 21
<212> TYPE: RNA
<213> ORGANISM: Artificial sequence
<220> FEATURE:
<223> OTHER INFORMATION: RNAi agent sense strand underlying base
      sequence

```
<220> FEATURE:
<221> NAME/KEY: modified_base
<222> LOCATION: 19
<223> OTHER INFORMATION: n = inosine (hypoxanthine)

<400> SEQUENCE: 1537
ugcuggauga gugaaguunc a                                              21

<210> SEQ ID NO 1538
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1538
gaugcucucc aaguaugauc a                                              21

<210> SEQ ID NO 1539
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1539
gugaucgucu gcagaacaag a                                              21

<210> SEQ ID NO 1540
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1540
gucgucugca gaacaagauc a                                              21

<210> SEQ ID NO 1541
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1541
gucgccagug caacuuuacu a                                              21

<210> SEQ ID NO 1542
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1542
aggauaaggu uacuuguguu a                                              21

<210> SEQ ID NO 1543
<211> LENGTH: 21
<212> TYPE: RNA
<213> ORGANISM: Artificial sequence
```

```
<220> FEATURE:
<223> OTHER INFORMATION: RNAi agent sense strand underlying base
      sequence

<400> SEQUENCE: 1543
accagccauu aucacaauug a                                              21

<210> SEQ ID NO 1544
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1544
caagcucuca guaucaugcu a                                              21

<210> SEQ ID NO 1545
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1545
gaagagugag guugacaagu u                                              21

<210> SEQ ID NO 1546
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1546
gagagugagg uugacaaguu a                                              21

<210> SEQ ID NO 1547
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1547
guucaacaag gagaauuguu a                                              21

<210> SEQ ID NO 1548
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1548
ggaacauacc acagaacaug a                                              21

<210> SEQ ID NO 1549
<211> LENGTH: 21
<212> TYPE: RNA
<213> ORGANISM: Artificial sequence
<220> FEATURE:
```

```
<223> OTHER INFORMATION: RNAi agent sense strand underlying base
      sequence

<400> SEQUENCE: 1549
gaacauggau cuauuaaagu a                                              21

<210> SEQ ID NO 1550
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1550
gacauggauc uauuaaaguc a                                              21

<210> SEQ ID NO 1551
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1551
ugccuaaaug gugaauaugc a                                              21

<210> SEQ ID NO 1552
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1552
gaaccucuag aagcuuaaac a                                              21

<210> SEQ ID NO 1553
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1553
ggccuucaaa ccaaugaaca a                                              21

<210> SEQ ID NO 1554
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1554
ccaaugaaca gcaaagcaua a                                              21

<210> SEQ ID NO 1555
<211> LENGTH: 21
<212> TYPE: RNA
<213> ORGANISM: Artificial sequence
<220> FEATURE:
<223> OTHER INFORMATION: RNAi agent sense strand underlying base
```

-continued

```
    sequence

<400> SEQUENCE: 1555
gaugaacagc aaagcauaac a                                              21

<210> SEQ ID NO 1556
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1556
gugaacagca aagcauaacc u                                              21

<210> SEQ ID NO 1557
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1557
gaacagcaaa gcauaaccuu a                                              21

<210> SEQ ID NO 1558
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1558
gcaaagcaua accuugaauc u                                              21

<210> SEQ ID NO 1559
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1559
ccaaccaacu caauuauuga a                                              21

<210> SEQ ID NO 1560
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1560
cuuccuguga uccauuuuac u                                              21

<210> SEQ ID NO 1561
<211> LENGTH: 21
<212> TYPE: RNA
<213> ORGANISM: Artificial sequence
<220> FEATURE:
<223> OTHER INFORMATION: RNAi agent sense strand underlying base
      sequence
```

```
<400> SEQUENCE: 1561
gguuuucuua cugucauaug a                                                21

<210> SEQ ID NO 1562
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1562
gagaucgaga augccuucca a                                                21

<210> SEQ ID NO 1563
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1563
gacuggcauu uucaaugaug a                                                21

<210> SEQ ID NO 1564
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1564
gucaaugaug aaacugucuu u                                                21

<210> SEQ ID NO 1565
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1565
gaggaugagg uuacuugugu u                                                21

<210> SEQ ID NO 1566
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1566
cugaagcuga caauguuguc u                                                21

<210> SEQ ID NO 1567
<211> LENGTH: 21
<212> TYPE: RNA
<213> ORGANISM: Artificial sequence
<220> FEATURE:
<223> OTHER INFORMATION: RNAi agent sense strand underlying base
      sequence
```

```
<400> SEQUENCE: 1567
gcuuuauugc aaagauguug a                                         21

<210> SEQ ID NO 1568
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1568
gaggauuugu aagacuaauc u                                         21

<210> SEQ ID NO 1569
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1569
ccgacuaagu uuggaauaag a                                         21

<210> SEQ ID NO 1570
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1570
gcuucacacu uucuuuucug a                                         21

<210> SEQ ID NO 1571
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1571
gcagcuuuga gacaaacucu a                                         21

<210> SEQ ID NO 1572
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1572
gagaaauuga cugcuuaaca a                                         21

<210> SEQ ID NO 1573
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1573
```
ccguaguauc cagauuucca a                                              21

<210> SEQ ID NO 1574
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1574
agcaggaugg cauuuucaag a                                              21

<210> SEQ ID NO 1575
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1575
gacaauugug auccaaauca u                                              21

<210> SEQ ID NO 1576
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1576
uggcaguuuu gaguaauucu a                                              21

<210> SEQ ID NO 1577
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1577
gucugagucc auuuuugauc a                                              21

<210> SEQ ID NO 1578
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1578
cuagaucugc augcuuucuu a                                              21

<210> SEQ ID NO 1579
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1579
cuucagagag cuuauaucug a				21

<210> SEQ ID NO 1580
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 14
<223> OTHER INFORMATION: n = inosine (hypoxanthine)

<400> SEQUENCE: 1580
ggauacaagg uugncuucau a				21

<210> SEQ ID NO 1581
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 13
<223> OTHER INFORMATION: n = inosine (hypoxanthine)

<400> SEQUENCE: 1581
ggauacaagg uungcuucau a				21

<210> SEQ ID NO 1582
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1582
ggauacaagg uugguuucau a				21

<210> SEQ ID NO 1583
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16
<223> OTHER INFORMATION: n = inosine (hypoxanthine)

<400> SEQUENCE: 1583
guggagaaaa augcanaucc a				21

<210> SEQ ID NO 1584
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1584
uccagagaca acucuuuugg a				21

<210> SEQ ID NO 1585
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = inosine (hypoxanthine)

<400> SEQUENCE: 1585
cucuccaagu augaucnucu a                                              21

<210> SEQ ID NO 1586
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1586
gcaacugugg aaggaauagg a                                              21

<210> SEQ ID NO 1587
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1587
uggcaucguc augaguaugu a                                              21

<210> SEQ ID NO 1588
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = inosine (hypoxanthine)

<400> SEQUENCE: 1588
gccuuccaag gaaaucugun a                                              21

<210> SEQ ID NO 1589
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1589
guggcauuga gaugaaguuc a                                              21

<210> SEQ ID NO 1590
<211> LENGTH: 21
<212> TYPE: RNA
<213> ORGANISM: Artificial sequence
<220> FEATURE:

```
<223> OTHER INFORMATION: RNAi agent sense strand underlying base
      sequence
<220> FEATURE:
<221> NAME/KEY: modified_base
<222> LOCATION: 2
<223> OTHER INFORMATION: n = 2-aminoadenosine (2-aminoadenine)

<400> SEQUENCE: 1590
gnugaaguuc aagaauaugc u                                              21

<210> SEQ ID NO 1591
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1591
ggaauaugcu guuccuaug a                                               21

<210> SEQ ID NO 1592
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16
<223> OTHER INFORMATION: n = inosine (hypoxanthine)

<400> SEQUENCE: 1592
gcugcucucc auaganaucc a                                              21

<210> SEQ ID NO 1593
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1593
gaguauuucu cagcauucaa a                                              21

<210> SEQ ID NO 1594
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1594
cgccaagauc aaguccauag a                                              21

<210> SEQ ID NO 1595
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1595
uccaggguuu guuuguuuca u                                              21
```

<210> SEQ ID NO 1596
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1596
gucaccuaug aagaacuacc a                                              21

<210> SEQ ID NO 1597
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1597
gagaacuacc agccauuauc a                                              21

<210> SEQ ID NO 1598
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1598
cagccauuau cacaauugag a                                              21

<210> SEQ ID NO 1599
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1599
ugagcugaag aucgagaaag a                                              21

<210> SEQ ID NO 1600
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1600
cugcaccauu gcuguuccaa a                                              21

<210> SEQ ID NO 1601
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1601
guggagcucu uuguguuuac a                                              21

<210> SEQ ID NO 1602
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = inosine (hypoxanthine)

<400> SEQUENCE: 1602
agcucuuugu gucuacacan a                                              21

<210> SEQ ID NO 1603
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1603
cucucucaga guauuaugga a                                              21

<210> SEQ ID NO 1604
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = inosine (hypoxanthine)

<400> SEQUENCE: 1604
gcagaguauu auggaacgan a                                              21

<210> SEQ ID NO 1605
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1605
uccaggguuu guuuguuuca a                                              21

<210> SEQ ID NO 1606
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1606
ccaggguuug uuuguuucau u                                              21

<210> SEQ ID NO 1607
<211> LENGTH: 21
<212> TYPE: RNA
<213> ORGANISM: Artificial sequence
<220> FEATURE:

```
<223> OTHER INFORMATION: RNAi agent sense strand underlying base
      sequence

<400> SEQUENCE: 1607 cagggquuugu uuguuucauu u                                             21

<210> SEQ ID NO 1608
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1608
ggguuuguuu guuucauuuc a                                              21

<210> SEQ ID NO 1609
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 18
<223> OTHER INFORMATION: n = inosine (hypoxanthine)

<400> SEQUENCE: 1609
gcucuccaag uaugaucnuc u                                              21

<210> SEQ ID NO 1610
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = inosine (hypoxanthine)

<400> SEQUENCE: 1610
ggaggagauu gagaaunccu u                                              21

<210> SEQ ID NO 1611
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1611
cgagaaugcc uuccaaggaa a                                              21

<210> SEQ ID NO 1612
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1612
gaugccuucc aaggaaaucu a                                              21
```

<210> SEQ ID NO 1613
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 2
<223> OTHER INFORMATION: n = 2-aminoadenosine (2-aminoadenine)

<400> SEQUENCE: 1613
cnagaauaug cuguuuccua u                                       21

<210> SEQ ID NO 1614
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1614
cguuggaggg aacaucauca a                                       21

<210> SEQ ID NO 1615
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1615
cagcuucuuc uucaaguucu a                                       21

<210> SEQ ID NO 1616
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1616
guguugggca uaucauuggu a                                       21

<210> SEQ ID NO 1617
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1617
cgucuacaca gaacaccaug a                                       21

<210> SEQ ID NO 1618
<211> LENGTH: 21
<212> TYPE: RNA
<213> ORGANISM: Artificial sequence
<220> FEATURE:
<223> OTHER INFORMATION: RNAi agent sense strand underlying base
      sequence -continued

```
<400> SEQUENCE: 1618
gacacccagg aucucuuuca a                                              21

<210> SEQ ID NO 1619
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1619
agcaagcucu caguaucaug a                                              21

<210> SEQ ID NO 1620
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1620
ucggaagagu gagguugaca a                                              21

<210> SEQ ID NO 1621
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1621
gacaaggaga auguuggaa a                                               21

<210> SEQ ID NO 1622
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1622
gcagcuuuga gacuaacuca a                                              21

<210> SEQ ID NO 1623
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1623
ccuccgcaca gauauuguca u                                              21

<210> SEQ ID NO 1624
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1624
```

-continued uccgcacaga uauugucaug a                                              21

<210> SEQ ID NO 1625
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1625
ggcugcuucu aucuucuuug a                                              21

<210> SEQ ID NO 1626
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = inosine (hypoxanthine)

<400> SEQUENCE: 1626
agcacacagg uauaacgun a                                               21

<210> SEQ ID NO 1627
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1627
ccuguauaac cucaaguucu a                                              21

<210> SEQ ID NO 1628
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1628
gaccaaugaa cagcaaagca u                                              21

<210> SEQ ID NO 1629
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 2
<223> OTHER INFORMATION: n = 2-aminoadenosine (2-aminoadenine)

<400> SEQUENCE: 1629
cnuaaccuug aaucuauacu a                                              21

<210> SEQ ID NO 1630
<211> LENGTH: 21

```
<212> TYPE: RNA
<213> ORGANISM: Artificial sequence
<220> FEATURE:
<223> OTHER INFORMATION: RNAi agent sense strand underlying base
      sequence

<400> SEQUENCE: 1630
ggcauaaagc aagauuacuc u                                             21

<210> SEQ ID NO 1631
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1631
uccaccuaga aaugaugcua u                                             21

<210> SEQ ID NO 1632
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 18
<223> OTHER INFORMATION: n = inosine (hypoxanthine)

<400> SEQUENCE: 1632
cuagcucugu cucuucunuc u                                             21

<210> SEQ ID NO 1633
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 3
<223> OTHER INFORMATION: n = 2-aminoadenosine (2-aminoadenine)

<400> SEQUENCE: 1633
cunaggcuug guuucuuac u                                              21

<210> SEQ ID NO 1634
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1634
cagugaugcu cuccaaguau a                                             21

<210> SEQ ID NO 1635
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
```

-continued

<221> NAME/KEY: modified_base
<222> LOCATION: 18
<223> OTHER INFORMATION: n = inosine (hypoxanthine)

<400> SEQUENCE: 1635
gccaaguaug aucgucunca a                                              21

<210> SEQ ID NO 1636
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1636
uggcaugaga guuuuauuca a                                              21

<210> SEQ ID NO 1637
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16
<223> OTHER INFORMATION: n = 2-aminoadenosine (2-aminoadenine)

<400> SEQUENCE: 1637
uggcaugaga guuuunuuca a                                              21

<210> SEQ ID NO 1638
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1638
ccucagcuuc uucuucaagu a                                              21

<210> SEQ ID NO 1639
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1639
ccucagcuuc uucuuuaagu a                                              21

<210> SEQ ID NO 1640
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1640
gacaagaucg uccacuuuuc u                                              21

<210> SEQ ID NO 1641

```
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1641
accauguugc agugacaacu a                                              21

<210> SEQ ID NO 1642
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1642
ggugacaacu guggaaggaa u                                              21

<210> SEQ ID NO 1643
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1643
guggaggaga uugagaaugc a                                              21

<210> SEQ ID NO 1644
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1644
gacacggaga uuggcauuga a                                              21

<210> SEQ ID NO 1645
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = 2-aminoadenosine (2-aminoadenine)

<400> SEQUENCE: 1645
cgagaugaag uucaagaaun u                                              21

<210> SEQ ID NO 1646
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1646
aggagauacu gcucuccaua a                                              21
```

<210> SEQ ID NO 1647
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1647
ggggaguauu ucucagcauu a                                              21

<210> SEQ ID NO 1648
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1648
gggaguauuu cucagcauuc a                                              21

<210> SEQ ID NO 1649
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1649
ccggagagaa gaugacauug a                                              21

<210> SEQ ID NO 1650
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1650
gguaacauaa cuggaauuug u                                              21

<210> SEQ ID NO 1651
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1651
ccagccauua ucacaauuga a                                              21

<210> SEQ ID NO 1652
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1652
gagcuuuguu gcaaaaaugu u                                              21

<210> SEQ ID NO 1653
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1653 gcuuguugc aaaaauguug a                                              21

<210> SEQ ID NO 1654
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1654
cggauugugg uucgagugaa a                                             21

<210> SEQ ID NO 1655
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1655
gucucucaga guauuaugga a                                             21

<210> SEQ ID NO 1656
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1656
cccucucaga guauuaugga a                                             21

<210> SEQ ID NO 1657
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1657
gccucucaga guauuaugga a                                             21

<210> SEQ ID NO 1658
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1658
accucucaga guauuaugga a                                             21

```
<210> SEQ ID NO 1659
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1659
uccucucaga guauuaugga a                                              21

<210> SEQ ID NO 1660
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1660
ccuccgcaca gauauuguca a                                              21

<210> SEQ ID NO 1661
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 1661
cuccgcacag auauugucau                                                20

<210> SEQ ID NO 1662
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 1662
uccgcacaga uauugucau                                                 19

<210> SEQ ID NO 1663
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1663
cucucucaga guauuaugga a                                              21

<210> SEQ ID NO 1664
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1664
ccuccgcaca gauauuguca u                                              21

<210> SEQ ID NO 1665
<211> LENGTH: 21
<212> TYPE: RNA
```

-continued

<213> ORGANISM: Artificial sequence
<220> FEATURE:
<223> OTHER INFORMATION: RNAi agent sense strand modified sequence

<400> SEQUENCE: 1665
ugccuaaaug gugaauaugc a                                              21

<210> SEQ ID NO 1666
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1666
uccaggguuu guuuguuuca u                                              21

<210> SEQ ID NO 1667
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1667
gcucuccaag uaugaucnuc u                                              21

<210> SEQ ID NO 1668
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1668
gaguauuucu cagcauucaa a                                              21

<210> SEQ ID NO 1669
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1669
gacaaggaga auuguuggaa a                                              21

<210> SEQ ID NO 1670
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1670
ucggaagagu gagguugaca a                                              21

<210> SEQ ID NO 1671
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1671
agcaagcucu caguaucaug a                                             21

<210> SEQ ID NO 1672
<211> LENGTH: 23
<212> TYPE: RNA
<213> ORGANISM: Artificial sequence
<220> FEATURE:
<223> OTHER INFORMATION: RNAi agent antisense strand modified sequence

<400> SEQUENCE: 1672
acucguucca uaauacucug aga                                           23

<210> SEQ ID NO 1673
<211> LENGTH: 23
<212> TYPE: RNA
<213> ORGANISM: Artificial sequence
<220> FEATURE:
<223> OTHER INFORMATION: RNAi agent antisense strand modified sequence

<400> SEQUENCE: 1673
auccauaaua cucugagaga gau                                           23

<210> SEQ ID NO 1674
<211> LENGTH: 23
<212> TYPE: RNA
<213> ORGANISM: Artificial sequence
<220> FEATURE:
<223> OTHER INFORMATION: RNAi agent antisense strand underlying base
      sequence

<400> SEQUENCE: 1674
acucguucca uaauacucug aga                                           23

<210> SEQ ID NO 1675
<211> LENGTH: 23
<212> TYPE: RNA
<213> ORGANISM: Artificial sequence
<220> FEATURE:
<223> OTHER INFORMATION: RNAi agent antisense strand underlying base
      sequence

<400> SEQUENCE: 1675
auccauaaua cucugagaga gau                                           23

<210> SEQ ID NO 1676
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1676
ucagaguauu auggaacgag u                                             21

<210> SEQ ID NO 1677
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1677
cucucucaga guauuaugga u                                             21

<210> SEQ ID NO 1678
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1678
ucagaguauu auggaacgag u                                             21

<210> SEQ ID NO 1679
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1679
cucucucaga guauuaugga u                                             21

<210> SEQ ID NO 1680
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1680
cucucucaga guauuaugga a                                             21

<210> SEQ ID NO 1681
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1681
ccuccgcaca gauauuguca u                                             21

<210> SEQ ID NO 1682
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1682
ugccuaaaug gugaauaugc a                                             21

<210> SEQ ID NO 1683
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1683
uccaggguuu guuuguuuca u                                             21

<210> SEQ ID NO 1684
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1684
gcucuccaag uaugaucnuc u                                      21

<210> SEQ ID NO 1685
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1685
gaguauuucu cagcauucaa a                                      21

<210> SEQ ID NO 1686
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1686
gacaaggaga auuguuggaa a                                      21

<210> SEQ ID NO 1687
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1687
ucggaagagu gagguugaca a                                      21

<210> SEQ ID NO 1688
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1688
agcaagcucu caguaucaug a                                      21

RNAI AGENTS FOR INHIBITING EXPRESSION OF XANTHINE DEHYDROGENASE (XDH), PHARMACEUTICAL COMPOSITIONS THEREOF, AND METHODS OF USE

CROSS REFERENCE TO RELATED APPLICATIONS

This application claims priority from U.S. Provisional Patent Application Ser. No. 63/213,097, filed on Jun. 21, 2021, and U.S. Provisional Patent Application Ser. No. 63/323,430, filed on Mar. 24, 2022, the contents of each of which are incorporated herein by reference in their entirety.

SEQUENCE LISTING

This application contains a Sequence Listing which has been submitted in ASCII format and is hereby incorporated by reference in its entirety. The ASCII copy is named 58651_713_202SL.txt and is 411 kb in size.

FIELD OF THE INVENTION

The present disclosure relates to RNA interference (RNAi) agents, e.g., double stranded RNAi agents, for inhibition Xanthine Dehydrogenase (XDH; alternatively referred to as XO, XOR, xanthine dehydrogenase/oxidase, xanthine oxidoreductase, or XAN1), pharmaceutical compositions that include XDH RNAi agents, and methods of use thereof.

BACKGROUND

Gout is a progressive inflammatory arthritis caused by hyperuricemia (elevated serum uric acid levels) and deposition of monosodium urate crystals in joints and tendons. Gout is estimated to affect 0.6% of the world population with a substantially higher prevalence in certain geographical regions and ethnic groups. Gout patients without receiving a urate-lowering therapy suffer from recurrent episodes of gout flare (inflammation response) and ultimately can develop advanced gout, which is characterized by chronic joint pain and activity limitation.

Xanthine dehydrogenase is a molybdenum-containing hydroxylase that catalyzes the production of uric acid from xanthine. XDH is highly expressed in liver and gastrointestinal tract. Hepatocyte-specific ablation of XDH or global inhibition of XDH activity reverses hyperuricemia phenotype in animal models.

Small molecule inhibitors of XDH have been widely used for urate-lowering therapies. However, a large population of gout patients are intolerant of or refractory to these therapies, and some serious side effects include increased risk of death. There remains an unmet need for novel XDH inhibitors, such as XDH RNAi agents, to reduce hepatic XDH levels and treat hyperuricemia and gout.

SUMMARY

Disclosed herein are RNAi agents for inhibiting expression of an XDH gene, comprising an antisense strand comprising at least 17 contiguous nucleotides differing by 0 or 1 nucleotide from any one of the sequences of Table 2, Table 3, or Table 5C; and a sense strand comprising a nucleotide sequence that is at least partially complementary to the antisense strand.

In some aspects, the antisense strand comprises nucleotides 2-18 of any one of the sequences of Table 2, Table 3, or Table 5C.

In some aspects, the sense strand comprises a nucleotide sequence of at least 15 contiguous nucleotides differing by 0 or 1 nucleotide from 15 contiguous nucleotides of any one of the sense strand sequences of Table 2 or Table 4, and wherein the sense strand has a region of at least 85% complementarity over the 15 contiguous nucleotides to the antisense strand.

In some aspects, at least one nucleotide of the RNAi agent is a modified nucleotide or includes a modified internucleoside linkage.

According to some aspects, all or substantially all of the nucleotides of the sense and/or antisense strand of the RNAi agent are modified nucleotides.

In some aspects, the modified nucleotide is selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate containing nucleotide, cyclopropyl phosphonate containing nucleotide, and 3'-O-methyl nucleotide.

In certain aspects, the all or substantially all of the modified nucleotides are 2'-O-methyl nucleotides, 2'-fluoro nucleotides, or combinations thereof.

In some aspects, the antisense strand consists of, consists essentially of, or comprises the nucleotide sequence of any one of the modified antisense strand sequences of Table 3.

In some aspects, the sense strand consists of, consists essentially of, or comprises the nucleotide sequence of any of the modified sense strand sequences of Table 4.

In some aspects, the antisense strand comprises the nucleotide sequence of any one of the modified sequences of Table 3 and the sense strand comprises the nucleotide sequence of any one of the modified sequences of Table 4.

In certain aspects, the RNAi agents are linked to a targeting ligand. In some aspects, the targeting ligand comprises N-acetyl-galactosamine. In certain aspects, the targeting ligand comprises the structure of (NAG37) or (NAG37)s. In certain aspects, the targeting ligand is linked to the sense strand. In some aspects, the targeting ligand is linked to the 5' terminal end of the sense strand.

In some aspects, the sense strand is between 15 and 30 nucleotides in length, and the antisense strand is between 18 and 30 nucleotides in length. In other aspects, the sense strand and the antisense strand are each between 18 and 27 nucleotides in length. In other aspects, the sense strand and the antisense strand are each between 18 and 24 nucleotides in length. In still other aspects, sense strand and the antisense strand are each 21 nucleotides in length.

In some aspects, the RNAi agents have two blunt ends.

In some aspects, the sense strand comprises one or two terminal caps. In other aspects, the sense strand comprises one or two inverted abasic residues.

In some aspects, the RNAi agents are comprised of a sense strand and an antisense strand that form a duplex sequence of any one of the duplex structures shown in Table 5A, 5B or 5C.

In some aspects, the sense strand further includes inverted abasic residues at the 3' terminal end of the nucleotide sequence, at the 5' end of the nucleotide sequence, or at both.

In some aspects, the sense strand of the RNAi agents is linked to a targeting ligand. In some aspects, the targeting ligand has affinity for the asialoglycoprotein receptor. In some aspects, the targeting ligand comprises N-acetyl-galactosamine.

In further aspects, the targeting ligand comprises:

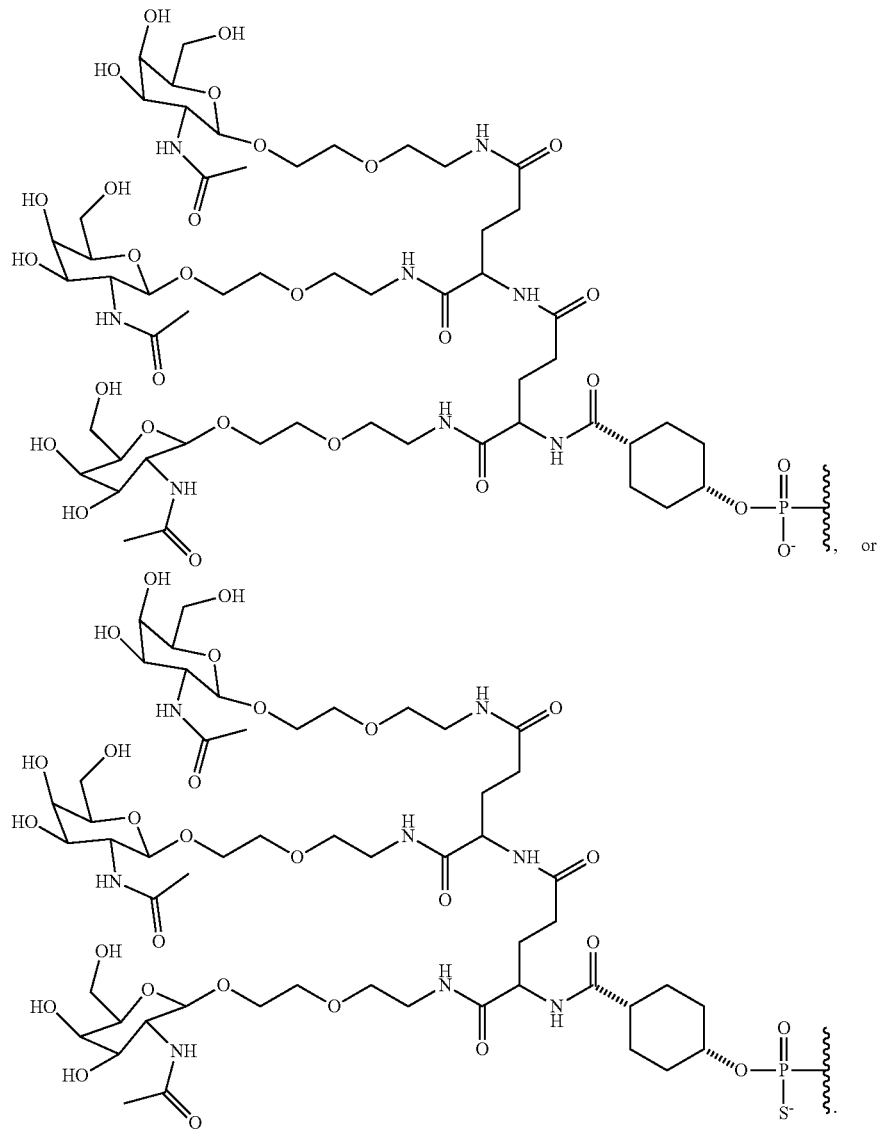

Also disclosed herein are compositions comprising the disclosed RNAi agents, wherein the compositions further comprise a pharmaceutically acceptable excipient.

Also provided herein are methods for inhibiting expression of an XDH gene in a cell, the methods comprising introducing into a cell an effective amount of the disclosed RNAi agents or the disclosed compositions.

In some aspects, the cell is within a subject. In some aspects, the subject is a human subject.

In some aspects, the XDH gene expression is inhibited by at least about 30%. In some aspects, the XDH gene expression is inhibited by at least about 50% in the cytoplasm of hepatocytes.

Further provided herein are methods of treating an XDH-related disease, disorder, or symptom, the methods comprising administering to a human subject in need thereof a therapeutically effective amount of the disclosed compositions.

In some aspects, the disease is gout.

In some aspects, the symptom is hyperuricemia.

In some aspects, the RNAi agents are administered at a dose of about 0.05 mg/kg to about 5.0 mg/kg of body weight of the human subject.

In other aspects, the RNAi agent is administered in two or more doses.

Also provided herein are usages of the disclosed RNAi agents or the disclosed compositions, for the treatment of a disease, disorder, or symptom that is mediated at least in part by XDH gene expression.

In some aspects, the disease is gout.

In some aspects, the symptom is hyperuricemia.

Further provided herein are usages of the disclosed RNAi agents or the disclosed compositions, for the preparation of a pharmaceutical compositions for treating a disease, disorder, or symptom that is mediated at least in part by XDH gene expression.

In some aspects, the RNAi agent is administered at a dose of about 0.05 mg/kg to about 5.0 mg/kg of body weight of the human subject.

DETAILED DESCRIPTION

The disclosed RNAi agents, compositions thereof, and methods of use may be understood more readily by reference to the following detailed description, which form a part of this disclosure. It is to be understood that the disclosure is not limited to what is specifically described and/or shown herein, and that the terminology used herein is for the purpose of describing particular embodiments by way of example only and is not intended to be limiting.

It is to be appreciated that while certain features of the disclosures included herein are, for clarity, described herein in the context of separate embodiments, they may also be provided in combination in a single embodiment. Conversely, various features of the disclosed methods that are, for brevity, described in the context of a single embodiment, may also be provided separately or in any subcombination.

Definitions

As used herein, an "RNAi agent" means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target gene in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e. XDH mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature. A nucleic acid molecule can comprise unmodified and/or modified nucleotides. A nucleotide sequence can comprise unmodified and/or modified nucleotides.

As used herein, a "base," "nucleotide base," or "nucleobase," is a heterocyclic pyrimidine or purine compound that is a component of a nucleotide, and includes the primary purine bases adenine and guanine, and the primary pyrimidine bases cytosine, thymine, and uracil. A nucleobase may further be modified to include, without limitation, universal bases, hydrophobic bases, promiscuous bases, size-expanded bases, and fluorinated bases. (See, e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, the term "nucleotide" has the same meaning as commonly understood in the art. Thus, the term "nucleotide" as used herein, refers to a glycoside comprising a sugar moiety, a base moiety and a covalently linked group (linkage group), such as a phosphate or phosphorothioate internucleoside linkage group, and covers both naturally occurring nucleotides, such as DNA or RNA, and non-naturally occurring nucleotides comprising modified sugar and/or base moieties, which are also referred to as nucleotide analogs herein. Herein, a single nucleotide can be referred to as a monomer or unit.

As used herein, and unless otherwise indicated, the term "complementary," when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or otherwise suitable in vivo or in vitro conditions) and form a duplex or double helical structure under certain standard conditions with an oligonucleotide that includes the second nucleotide sequence. The person of ordinary skill in the art would be able to select the set of conditions most appropriate for a hybridization test. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "partially complementary" means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "substantially complementary" means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms "complementary," "fully complementary," "partially complementary," and "substantially complementary" are used with respect to the nucleobase or nucleotide matching between the sense strand and the antisense strand of an RNAi agent, or between the antisense strand of an RNAi agent and a sequence of an MUC5AC mRNA.

As used herein, the term "substantially identical" or "substantial identity," as applied to a nucleic acid sequence means the nucleotide sequence (or a portion of a nucleotide sequence) has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The subject matter disclosed herein encompass nucleotide sequences substantially identical to those disclosed herein.

As used herein, the terms "individual", "patient" and "subject", are used interchangeably to refer to a member of any animal species including, but not limited to, birds, humans and other primates, and other mammals including commercially relevant mammals or animal models such as mice, rats, monkeys, cattle, pigs, horses, sheep, cats, and dogs. Preferably, the subject is a human.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the prevention, management, prophylactic treatment, and/or inhibition or reduction of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means delivering the RNAi agent to the cell in a manner that enables the RNAi agent to have the expected biological activity, e.g., sequence-specific inhibition of gene expression.

Unless stated otherwise, use of the symbol as used herein means that any group or groups may be linked thereto that is in accordance with the scope of the subject matters described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art. Correspondingly, compounds described herein with labile protons or basic atoms should also be understood to represent salt forms of the corresponding compound. Compounds described herein may be in a free acid, free base, or salt form. Pharmaceutically acceptable salts of the compounds described herein should be understood to be within the scope of the invention.

As used herein, the term "linked" or "conjugated" when referring to the connection between two compounds or molecules means that two compounds or molecules are joined by a covalent bond. Unless stated, the terms "linked" and "conjugated" as used herein may refer to the connection between a first compound and a second compound either with or without any intervening atoms or groups of atoms.

As used herein, the term "including" is used to herein mean, and is used interchangeably with, the phrase "including but not limited to." The term "or" is used herein to mean, and is used interchangeably with, the term "and/or," unless the context clearly indicates otherwise.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Where a value is explicitly recited, it is to be understood that values which are about the same quantity or amount as the recited value are also within the scope of the disclosure. Where a combination is disclosed, each sub-combination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

The term "about" or "approximately" as used herein when referring to a measurable value such as a parameter, an amount, a temporal duration, and the like, is meant to encompass variations of +/−20% or less, +/−10% or less, +/−5% or less, or +/−1% or less of and from the specified value, insofar such variations are appropriate to perform in the present disclosure. It is to be understood that the value to which the modifier "about" or "approximately" refers is itself. For example, "about 4" includes 4.

Other objects, features, aspects, and advantages of the invention will be apparent from the following detailed description, accompanying figures, and from the claims.

DETAILED DESCRIPTION

RNAi Agents

Described herein are RNAi agents for inhibiting expression of an XDH gene. Each XDH RNAi agent comprises a sense strand and an antisense strand. The sense strand can be 15 to 49 nucleotides in length. The antisense strand can be 18 to 49 nucleotides in length. The sense and antisense strands can be either the same length or they can be different lengths. In some aspects, the sense and antisense strands are each independently 18 to 27 nucleotides in length. In some aspects, both the sense and antisense strands are each 21-26 nucleotides in length. In some aspects, the sense and antisense strands are each 21-24 nucleotides in length. In some aspects, the sense and antisense strands are each independently 19-21 nucleotides in length. In some aspects, the sense strand is about 19 nucleotides in length while the antisense strand is about 21 nucleotides in length. In some aspects, the sense strand is about 21 nucleotides in length while the antisense strand is about 23 nucleotides in length. In some aspects, a sense strand is 23 nucleotides in length and an antisense strand is 21 nucleotides in length. In some aspects, both the sense and antisense strands are each 21 nucleotides in length. In some aspects, the RNAi agent antisense strands are each 18, 19, 20, 21, 22, 23, 24, 25, 26, 27, 28, 29, or 30 nucleotides in length. In some embodiments, the RNAi agent sense strands are each 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides in length. The sense and antisense strands are annealed to form a duplex, and in some aspects, a double-stranded RNAi agent has a duplex length of about 15, 16, 17, 18, 19, 20, 21, 22, 23 or 24 nucleotides.

Examples of nucleotide sequences used in forming XDH RNAi agents are provided in Tables 2, 3, 4, and 5C. Examples of RNAi agent duplexes, that include the sense strand and antisense strand sequences in Tables 2, 3, 4 and 5C, are shown in Tables 5A, 5B and 5C.

In some aspects, the region of perfect, substantial, or partial complementarity between the sense strand and the antisense strand is 15-26 (e.g., 15, 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly, substantially, or partially complementary).

A sense strand of the XDH RNAi agents described herein includes at least 15 consecutive nucleotides that have at least 85% identity to a core stretch sequence (also referred to herein as a "core stretch" or "core sequence") of the same number of nucleotides in an XDH mRNA. In some aspects, a sense strand core stretch sequence is 100% (perfectly) complementary or at least about 85% (substantially) complementary to a core stretch sequence in the antisense strand, and thus the sense strand core stretch sequence is typically perfectly identical or at least about 85% identical to a nucleotide sequence of the same length (sometimes referred to, e.g., as a target sequence) present in the XDH mRNA target. In some aspects, this sense strand core stretch is 15, 16, 17, 18, 19, 20, 21, 22, or 23 nucleotides in length. In some aspects, this sense strand core stretch is 17 nucleotides in length. In some aspects, this sense strand core stretch is 19 nucleotides in length.

An antisense strand of an XDH RNAi agent described herein includes at least 15 consecutive nucleotides that have at least 85% complementarity to a core stretch of the same number of nucleotides in an XDH mRNA and to a core stretch of the same number of nucleotides in the corresponding sense strand. In some aspects, an antisense strand core stretch is 100% (perfectly) complementary or at least about 85% (substantially) complementary to a nucleotide sequence (e.g., target sequence) of the same length present in the XDH mRNA target. In some aspects, this antisense strand core stretch is 15, 16, 17, 18, 19, 20, 21, 22, or 23 nucleotides in length. In some aspects, this antisense strand core stretch is 19 nucleotides in length. In some aspects, this antisense strand core stretch is 17 nucleotides in length. A sense strand core stretch sequence can be the same length as a corresponding antisense core sequence or it can be a different length.

The XDH RNAi agent sense and antisense strands anneal to form a duplex. A sense strand and an antisense strand of an XDH RNAi agent can be partially, substantially, or fully complementary to each other. Within the complementary duplex region, the sense strand core stretch sequence is at least 85% complementary or 100% complementary to the antisense core stretch sequence. In some aspects, the sense strand core stretch sequence contains a sequence of at least 15, at least 16, at least 17, at least 18, at least 19, at least 20, at least 21, at least 22, at least 23, at least 24, or at least 25 nucleotides that is at least 85% or 100% complementary to a corresponding 15, 16, 17, 18, 19, 20, 21, 22, 23, 24, or 25 nucleotide sequence of the antisense strand core stretch sequence (i.e., the sense and antisense core stretch sequences of an XDH RNAi agent have a region of at least 15, at least 16, at least 17, at least 18, at least 19, at least 20, at least 21, at least 22, at least 23, at least 24, or at least 25 nucleotides that is at least 85% base paired or 100% base paired.)

In some aspects, the antisense strand of an XDH RNAi agent disclosed herein differs by 0, 1, 2, or 3 nucleotides from any of the antisense strand sequences in Table 2, Table 3, or Table 5C. In some aspects, the sense strand of an XDH RNAi agent disclosed herein differs by 0, 1, 2, or 3 nucleotides from any of the sense strand sequences in Table 2, Table 4, or Table 5C.

In some aspects, the sense strand and/or the antisense strand can optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in the XDH mRNA. The sense strand additional nucleotides, if present, may or may not be identical to the corresponding sequence in the XDH mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some aspects, both the sense strand and the antisense strand of an RNAi agent contain 3' and 5' extensions. In some aspects, one or more of the 3' extension nucleotides of one strand base pairs with one or more 5' extension nucleotides of the other strand. In other aspects, one or more of 3' extension nucleotides of one strand do not base pair with one or more 5' extension nucleotides of the other strand. In some aspects, an XDH RNAi agent has an antisense strand having a 3' extension and a sense strand having a 5' extension. In some aspects, the extension nucleotide(s) are unpaired and form an overhang. As used herein, an "overhang" refers to a stretch of one or more unpaired nucleotides located at a terminal end of either the sense strand or the antisense strand that does not form part of the hybridized or duplexed portion of an RNAi agent disclosed herein.

In some aspects, an XDH RNAi agent comprises an antisense strand having a 3' extension of 1, 2, 3, 4, 5, or 6 nucleotides in length. In other aspects, an XDH RNAi agent comprises an antisense strand having a 3' extension of 1, 2, or 3 nucleotides in length. In some aspects, one or more of the antisense strand extension nucleotides comprise nucleotides that are complementary to the corresponding XDH mRNA sequence. In some aspects, one or more of the antisense strand extension nucleotides comprise nucleotides that are not complementary to the corresponding XDH mRNA sequence.

In some aspects, an XDH RNAi agent comprises a sense strand having a 3' extension of 1, 2, 3, 4, or 5 nucleotides in length. In some aspects, one or more of the sense strand extension nucleotides comprises adenosine, uracil, or thymidine nucleotides, AT dinucleotide, or nucleotides that correspond to or are the identical to nucleotides in the XDH mRNA sequence. In some aspects, the 3' sense strand extension includes or consists of one of the following sequences, but is not limited to: T, UT, TT, UU, UUT, TTT, or TTTT (each listed 5' to 3').

A sense strand can have a 3' extension and/or a 5' extension. In some aspects, an XDH RNAi agent comprises a sense strand having a 5' extension of 1, 2, 3, 4, 5, or 6 nucleotides in length. In some aspects, one or more of the sense strand extension nucleotides comprise nucleotides that correspond to or are identical to nucleotides in the XDH mRNA sequence.

Examples of sequences used in forming XDH RNAi agents are provided in Tables 2, 3, 4, and 5C. In some aspects, an XDH RNAi agent antisense strand includes a sequence of any of the sequences in Tables 2, 3, or 5C. In certain aspects, an XDH RNAi agent antisense strand comprises or consists of any one of the modified sequences in Table 3. In some aspects, an XDH RNAi agent antisense strand includes the sequence of nucleotides (from 5' end→3' end) at positions 1-17, 2-15, 2-17, 1-18, 2-18, 1-19, 2-19, 1-20, 2-20, 1-21, or 2-21, of any of the sequences in Tables 2, 3, or 5C. In some aspects, an XDH RNAi agent sense strand includes the sequence of any of the sequences in Tables 2, 4, or 5C. In some aspects, an XDH RNAi agent sense strand includes the sequence of nucleotides (from 5' end→3' end) at positions 1-18, 1-19, 1-20, 1-21, 2-19, 2-20, 2-21, 3-20, 3-21, or 4-21 of any of the sequences in Tables 2, 4, or 5C. In certain aspects, an XDH RNAi agent sense strand comprises or consists of a modified sequence of any one of the modified sequences in Table 4.

In some aspects, the sense and antisense strands of the RNAi agents described herein contain the same number of nucleotides. In some aspects, the sense and antisense strands of the RNAi agents described herein contain different numbers of nucleotides. In some aspects, the sense strand 5' end and the antisense strand 3' end of an RNAi agent form a blunt end. In some aspects, the sense strand 3' end and the antisense strand 5' end of an RNAi agent form a blunt end. In some aspects, both ends of an RNAi agent form blunt ends. In some aspects, neither end of an RNAi agent is blunt-ended. As used herein a "blunt end" refers to an end of a double stranded RNAi agent in which the terminal nucleotides of the two annealed strands are complementary (form a complementary base-pair).

In some aspects, the sense strand 5' end and the antisense strand 3' end of an RNAi agent form a frayed end. In some aspects, the sense strand 3' end and the antisense strand 5' end of an RNAi agent form a frayed end. In some aspects, both ends of an RNAi agent form a frayed end. In some aspects, neither end of an RNAi agent is a frayed end. As used herein a frayed end refers to an end of a double stranded RNAi agent in which the terminal nucleotides of the two annealed strands from a pair (i.e., do not form an overhang) but are not complementary (i.e. form a non-complementary pair). In some aspects, one or more unpaired nucleotides at the end of one strand of a double stranded RNAi agent form an overhang. The unpaired nucleotides may be on the sense strand or the antisense strand, creating either 3' or 5' overhangs. In some aspects, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends. Typically, when present, overhangs are located at the 3' terminal ends of the sense strand, the antisense strand, or both the sense strand and the antisense strand.

The XDH RNAi agents disclosed herein may also be comprised of one or more modified nucleotides. In some aspects, substantially all of the nucleotides of the sense strand and substantially all of the nucleotides of the antisense strand of the XDH RNAi agent are modified nucleotides. The XDH RNAi agents disclosed herein may further be comprised of one or more modified internucleoside linkages, e.g., one or more phosphorothioate linkages. In some aspects, an XDH RNAi agent contains one or more modified nucleotides and one or more modified internucleoside linkages. In some aspects, a 2'-modified nucleotide is combined with modified internucleoside linkage.

In some aspects, an XDH RNAi agent is prepared or provided as a salt, mixed salt, or a free-acid. In some aspects, an XDH RNAi agent is prepared as a pharmaceutically acceptable salt. In some aspects, an XDH RNAi agent is prepared as a pharmaceutically acceptable sodium salt. Such forms that are well known in the art are within the scope of the inventions disclosed herein.

Modified Nucleotides

Modified nucleotides, when used in various oligonucleotide constructs, can preserve activity of the compound in cells while at the same time increasing the serum stability of these compounds, and can also minimize the possibility of activating interferon activity in humans upon administering of the oligonucleotide construct.

In some aspects, an XDH RNAi agent contains one or more modified nucleotides. As used herein, a "modified nucleotide" is a nucleotide other than a ribonucleotide (2'-hydroxyl nucleotide). In some aspects, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides can include, but are not limited to, deoxyribonucleotides, nucleotide mimics, abasic nucleotides, 2'-modified nucleotides, inverted nucleotides, modified nucleobase-comprising nucleotides, bridged nucleotides, peptide nucleic acids (PNAs), 2',3'-seco nucleotide mimics (unlocked nucleobase analogues), locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides. 2'-modified nucleotides (i.e., a nucleotide with a group other than a hydroxyl group at the 2' position of the five-membered sugar ring) include, but are not limited to, 2'-O-methyl nucleotides, 2'-fluoro nucleotides (also referred to herein as 2'-deoxy-2'-fluoro nucleotides), 2'-deoxy nucleotides, 2'-methoxyethyl (2'-O-2-methoxyethyl) nucleotides (also referred to as 2'-MOE), 2'-amino nucleotides, and 2'-alkyl nucleotides. It is not necessary for all positions in a given compound to be uniformly modified. Conversely, more than one modification can be incorporated in a single XDH RNAi agent or even in a single nucleotide thereof. The XDH RNAi agent sense strands and antisense strands can be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some aspects, the 5' and/or 3' end of the antisense strand can include abasic residues (Ab), which can also be referred to as an "abasic site" or "abasic nucleotide." An abasic residue (Ab) is a nucleotide or nucleoside that lacks a nucleobase at the 1' position of the sugar moiety. In some aspects, an abasic residue can be placed internally in a nucleotide sequence. In some aspects, Ab or AbAb can be added to the 3' end of the antisense strand. In some aspects, the 5' end of the sense strand can include one or more additional abasic residues (e.g., (Ab) or (AbAb)). In some aspects, UUAb, UAb, or Ab are added to the 3' end of the sense strand. In some aspects, an abasic (deoxyribose) residue can be replaced with a ribitol (abasic ribose) residue.

In some aspects, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being unmodified ribonucleotides. As used herein, an antisense sense strand wherein substantially all of the nucleotides present are modified nucleotides is an antisense strand having two or fewer (i.e., 0, 1, or 2) nucleotides in the sense strand being unmodified ribonucleotides. In some aspects, one or more nucleotides of an RNAi agent is an unmodified ribonucleotide. Chemical structures for certain modified nucleotides are set forth in Table 6 herein.

Modified Internucleoside Linkages

In some aspects, one or more nucleotides of an XDH RNAi agent are linked by non-standard linkages or backbones (i.e., modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some aspects, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some aspects, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some aspects, a sense strand of an XDH RNAi agent can contain 1, 2, 3, 4, 5, or 6 phosphorothioate linkages, an antisense strand of an XDH RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some aspects, a sense strand of an XDH RNAi agent can contain 1, 2, 3, or 4 phosphorothioate linkages, an antisense strand of an XDH RNAi agent can contain 1, 2, 3, or 4 phosphorothioate linkages, or both the sense strand and the antisense strand independently can contain 1, 2, 3, or 4 phosphorothioate linkages.

In some aspects, an XDH RNAi agent sense strand contains at least two phosphorothioate internucleoside linkages. In some aspects, the phosphorothioate internucleoside linkages are between the nucleotides at positions 1-3 from the 3' end of the sense strand. In some aspects, one phosphorothioate internucleoside linkage is at the 5' end of the sense strand nucleotide sequence, and another phosphorothioate linkage is at the 3' end of the sense strand nucleotide sequence. In some aspects, two phosphorothioate internucleoside linkages are located at the 5' end of the sense strand, and another phosphorothioate linkage is at the 3' end of the sense strand. In some aspects, the sense strand does not include any phosphorothioate internucleoside linkages between the nucleotides, but contains one, two, or three phosphorothioate linkages between the terminal nucleotides on both the 5' and 3' ends and the optionally present inverted abasic residue terminal caps. In some aspects, the targeting ligand is linked to the sense strand via a phosphorothioate linkage.

In some aspects, an XDH RNAi agent antisense strand contains four phosphorothioate internucleoside linkages. In some aspects, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some aspects, three phosphorothioate internucleoside linkages are located between positions 1-4 from the 5' end of the antisense strand, and a fourth phosphorothioate internucleoside linkage is located between positions 20-21 from the 5' end of the antisense strand. In some aspects, an XDH RNAi agent contains at least three or four phosphorothioate internucleoside linkages in the antisense strand.

Capping Residues or Moieties

In some aspects, the sense strand may include one or more capping residues or moieties, sometimes referred to in the art as a "cap," a "terminal cap," or a "capping residue." As used herein, a "capping residue" is a non-nucleotide compound or other moiety that can be incorporated at one or more termini of a nucleotide sequence of an RNAi agent disclosed herein. A capping residue can provide the RNAi agent, in some instances, with certain beneficial properties, such as, for example, protection against exonuclease degradation. In some aspects, inverted abasic residues (invAb) (also referred to in the art as "inverted abasic sites") are added as capping residues. (See, e.g., F. Czaudema, Nucleic Acids Res., 2003, 31(11), 2705-16; U.S. Pat. No. 5,998,203). Capping residues are generally known in the art, and include, for example, inverted abasic residues as well as carbon chains such as a terminal $C_3H_7$ (propyl), $C_6H_{13}$ (hexyl), or $C_{12}H_{25}$ (dodecyl) groups. In some aspects, a capping residue is present at either the 5' terminal end, the 3' terminal end, or both the 5' and 3' terminal ends of the sense strand. In some aspects, the 5' end and/or the 3' end of the sense strand may include more than one inverted abasic deoxyribose moiety as a capping residue.

In some aspects, one or more inverted abasic residues (invAb) are added to the 3' end of the sense strand. In some aspects, one or more inverted abasic residues (invAb) are added to the 5' end of the sense strand. In some aspects, one or more inverted abasic residues or inverted abasic sites are inserted between the targeting ligand and the nucleotide sequence of the sense strand of the RNAi agent. In some aspects, the inclusion of one or more inverted abasic residues or inverted abasic sites at or near the terminal end or terminal ends of the sense strand of an RNAi agent allows for enhanced activity or other desired properties of an RNAi agent.

In some aspects, one or more inverted abasic residues (invAb) are added to the 5' end of the sense strand. In some aspects, one or more inverted abasic residues can be inserted between the targeting ligand and the nucleotide sequence of the sense strand of the RNAi agent. The inverted abasic residues may be linked via phosphate, phosphorothioate (e.g., shown herein as (invAb)s), or other linkages. In some aspects, the inclusion of one or more inverted abasic residues at or near the terminal end or terminal ends of the sense strand of an RNAi agent may allow for enhanced activity or other desired properties of an RNAi agent. In some aspects, an inverted abasic (deoxyribose) residue can be replaced with an inverted ribitol (abasic ribose) residue. In some aspects, the 3' end of the antisense strand core stretch sequence, or the 3' end of the antisense strand sequence, may include an inverted abasic residue. The chemical structures for inverted abasic deoxyribose residues are shown in Table 6 below.

XDH RNAi Agents

The XDH RNAi agents disclosed herein are designed to target specific positions on an XDH gene (e.g., SEQ ID NO:1).

```
NM_000379.4 Homo sapiens xanthine dehydrogenase (XDH),
mRNA transcript (SEQ ID NO: 1):
    1 acagagcagt gataactacc tgccagtgtc tcttaggagt gaggtacctg gagttcgggg 61 accccaacct gtgacaatga cagcagacaa attggttttc tttgtgaatg gcagaaaggt 121 ggtggagaaa aatgcagatc cagagacaac ccittiggcc tacctgagaa gaaagttggg 181 gctgagtgga accaagctcg gctgtggaga gggggctgc ggggcttgca cagtgatgct 241 ctccaagtat gatcgtctgc agaacaagat cgtccacttt tctgccaatg cctgcctggc 301 ccccatctgc tccttgcacc atgttgcagt gacaactgtg gaaggaatag gaagcaccaa 361 gacgaggctg catcctgtgc aggagagaat tgccaaaagc cacggctccc agtgcgggtt 421 ctgcacccct ggcatcgtca tgagtatgta cacactgctc cggaatcagc ccgagcccac 481 catggaggag attgagaatg ccttccaagg aaatctgtgc cgctgcacag gctacagacc 541 catcctccag ggcttccgga cctttgccag ggatggtgga tgctgtggag gagatgggaa 601 taatccaaat tgctgcatga accagaagaa agaccactca gtcagcctct cgccatcttt 661 attcaaacca gaggagttca cgcccctgga tccaacccag gagcccattt ttcccccaga 721 gttgctgagg ctgaaagaca ctcctcggaa gcagctgcga tttgaagggg agcgtgtgac 781 gtggatacag gcctcaaccc tcaaggagct gctggacctc aaggctcagc accctgacgc
```

-continued

```
 841 caagctggtc gtggggaaca cggagattgg cattgagatg aagttcaaga atatgctgtt
 901 tcctatgatt gtctgcccag cctggatccc tgagctgaat tcggtagaac atggacccga
 961 cggtatctcc tttggagctg cttgccccct gagcattgtg aaaaaaccc tggtggatgc
1021 tgttgctaag cttcctgccc aaaagacaga ggtgttcaga ggggtcctgg agcagctgcg
1081 ctggtttgct gggaagcaag tcaagtctgt ggcgtccgtt ggagggaaca tcatcactgc
1141 cagccccatc tccgacctca accccgtgtt catggccagt ggggccaagc tgacacttgt
1201 gtccagaggc accaggagaa ctgtccagat ggaccacacc ttcttccctg ctacagaaa
1261 gaccctgctg agcccggagg agatactgct ctccatagag atcccctaca gcagggaggg
1321 ggagtatttc tcagcattca agcaggcctc ccggagagaa gatgacattg ccaaggtaac
1381 cagtggcatg agagattat tcaagccagg aaccacagag gtacaggagc tggccctttg
1441 ctatggtgga atggccaaca gaaccatctc agccctcaag accactcaga ggcagctttc
1501 caagctctgg aaggaggagc tgctgcagga cgtgtgtgca ggactggcag aggagctgca
1561 tctgcctccc gatgccctg gtggcatggt ggacttccgg tgcaccctca ccctcagctt
1621 cttcttcaag ttctacctga cagtccttca gaagctgggc caagagaacc tggaagacaa
1681 gtgtggtaaa ctggaccca ctttcgccag tgcaacttta ctgtttcaga agacccccc
1741 agccgatgtc cagctcttcc aagaggtgcc caagggtcag tctgaggagg acatggtggg
1801 ccggcccctg ccccacctgg cagcggacat gcaggcctct ggtgaggccg tgtactgtga
1861 cgacattcct cgctacgaga atgagctgtc tctccggctg gtcaccagca cccgggccca
1921 cgccaagatc aagtccatag atacatcaga agctaagaag gttccagggt ttgtttgttt
1981 catttccgct gatgatgttc ctgggagtaa cataactgga atttgtaatg atgagacagt
2041 ctttgcgaag gataaggtta cttgtgttgg gcatatcatt ggtgctgtgg ttgctgacac
2101 cccggaacac acacagagag ctgcccaagg ggtgaaaatc acctatgaag aactaccagc
2161 cattatcaca attgaggatg ctataaagaa caactccttt tatggacctg agctgaagat
2221 cgagaaaggg gacctaaaga aggggatc cgaagcagat aatgttgtgt caggggagat
2281 atacatcggt ggccaagagc acttctacct ggagactcac tgcaccattg ctgttccaaa
2341 aggcgaggca ggggagatgg agctctttgt gtctacacag aacaccatga agacccagag
2401 ctttgttgca aaaatgttgg gggttccagc aaaccggatt gtggttcgag tgaagagaat
2461 gggaggaggc tttggaggca aggagacccg gagcactgtg gtgtccacgg cagtggccct
2521 ggctgcatat aagaccggcc gccctgtgcg atgcatgctg accgtgatg aggacatgct
2581 gataactggt ggcagacatc ccttcctggc cagatacaag gttggcttca tgaagactgg
2641 gacagttgtg gctcttgagg tggaccactt cagcaatgtg gggaacaccc aggatctctc
2701 tcagagtatt atggaacgag ctttattcca catggacaac tgctataaaa tccccaacat
2761 ccggggcact gggcggctgt gcaaaaccaa ccttccctcc aacacggcct tccggggctt
2821 tggggggccc cagggatgc tcattgccga gtgctggatg agtgaagttg cagtgacctg
2881 tgggatgcct gcagaggagg tgcggagaaa aaacctgtac aaagaagggg acctgacaca
2941 cttcaaccag aagcttgagg gtttcacctt gcccagatgc tgggaagaat gcctagcaag
3001 ctctcagtat catgctcgga agagtgaggt tgacaagttc aacaaggaga attgttggaa
3061 aaagagagga ttgtgcataa ttcccaccaa gtttggaata agctttacag ttccatict
3121 gaatcaggca ggagccctac ttcatgtgta cacagatggc tctgtgctgc tgacccacgg
3181 ggggactgag atgggccaag gccttcatac caaaatggtc caggtggcca gtagagctct
```

-continued

```
3241 gaaaatccce acctctaaga tttatatcag cgagacaagc actaacactg tgcccaacac 3301 ctctcccacg gctgcctctg tcagcgctga cctcaatgga caggccgtct atgcggcttg 3361 tcagaccatc ttgaaaaggc tggaacccta caagaagaag aatcccagtg gctcctggga 3421 agactgggtc acagctgcct acatggacac agtgagcttg tctgccactg ggttttatag 3481 aacacccaat ctgggctaca gctttgagac taactcaggg aaccccttcc actacttcag 3541 ctatggggtg gcttgctctg aagtagaaat cgactgccta acaggagatc ataagaacct 3601 ccgcacagat attgtcatgg atgttggctc cagtctaaac cctgccattg atattggaca 3661 ggtggaaggg gcatttgtcc agggccttgg cctcttcacc ctagaggagc tacactattc 3721 ccccgagggg agcctgcaca cccgtggccc tagcacctac aagatcccgc catttggcag 3781 catccccatt gagttcaggg tgtccctgct ccgcgactgc cccaacaaga aggccatcta 3841 tgcatcgaag gctgttggag agccgcccct cttcctggct gcttctatct tctttgccat 3901 caaagatgcc atccgtgcag ctcgagctca gcacacaggt aataacgtga aggaactctt 3961 ccggctagac agccctgcca ccccggagaa gatccgcaat gcctgcgtgg acaagttcac 4021 caccctgtgt gtcactggtg tcccagaaaa ctgcaaaccc tggtctgtga gggtctaaag 4081 agagagtcct cagcagagtc ttcttgtgct gcctttgggc ttccatggag caggaggaac 4141 ataccacaga acatggatct attaaagtca cagaatgaca gacctgtgat ttgtcaagat 4201 gggatttgga agacaagtga atgcaatgga agattagat caaaaatgta atttgtaaac 4261 acaatgataa gcaaattcaa aactgttatg cctaaatggt gaatatgcaa ttaggatcat 4321 tttctgtctg ttttaatcat gtatctggaa tagggtcggg aagggtttgt gctattcccc 4381 acttactgga cagcctgtat aacctcaagt tctgatggtg tctgtcctt gaagaggatt 4441 cccacaaacc tctagaagct taaaccgaag ttactttaaa tcgtgtgcct tcctgtgaaa 4501 gcctggcctt caaaccaatg aacagcaaag cataaccttg aatctatact caaattagc 4561 aatgaggcag tggggtaagg ttaaatcctc taaccatctt tgaatcattg gaaagaataa 4621 agaatgaaac aaattcaagg ttaattggat ctgattagt gaagctgcat aaagcaagat 4681 tactctataa tacaaaaatc caaccaactc aattattgag cacgtacaat gttctagatt 4741 tctttcccctt cctctttgaa gagaatattt gtattccaaa tactctttga gtatttacaa 4801 aaaagattat gtttaatctt tacatttgaa gccaaagtaa tttccaccta gaaatgatgc 4861 tatcagtcct ggcatggtgg ctcacccta taatcccagc actttgggag gctaaggcag 4921 gagaattgct tgagcccagc agtttgagac cagcctgggc aacatagaga gctcctgtct 4981 ttaaaaaaaa ttlattaat tagttggtct tgatagtgca tgcctgtagt cccaactact 5041 tgaaaggctg aggtggagag atcatttgag ctcaggaggt tgaggctgca gtgagctatg 5101 attgcgccac tgcactcctg cctgagcgac tgagcaagat cttgtctctg aagaaaaaaa 5161 aagaaataaa aatgctgcta tcaaaatcaa gcccaaccag aggtagaaga gccaagaagc 5221 ctgggttctc atcctagctc tgtctcttct gtctctatct ttgtgatctt ggactgtcaa 5281 ttccccttcc tgtgatccat tttactgcaa acataagggt tgcagtaaag ggttgtctca 5341 cgtcttctgc tttaaaagcc tataaatata tgacctgaaa actccagtta cataaaggat 5401 ctgcagctat ctaaggcttg gttttcttac tgtcatatga tacctgggtc taatgaactc 5461 tgctgagatc acctcaagtt tctgcggttg gtaaagagaa caagggaaga acaaacatcc 5521 callattgc tccaaatggt gatttaatcc ctacatggtg ctgggtggac aatgtgtcac
```

```
5581 tgtcacatgc cttcactgta taaatccaac cttctgccag agagaatctg tggttctggc 5641 catggaggga ggatagtgga aatgatatag ttggactggt gcttgatgtc actaataaat 5701 gaaactgtca gctgg
```

As defined herein, an antisense strand sequence is designed to target an XDH gene at a given position on the gene when the 5' terminal nucleobase of the antisense strand is aligned with a position that is 21 nucleotides downstream (towards the 3' end) from the position on the gene when base pairing to the gene. For example, as illustrated in Tables 1 and 2 herein, an antisense strand sequence designed to target an XDH gene at position 1322 requires that when base pairing to the gene, the 5' terminal nucleobase of the antisense strand is aligned with position 1342 of the XDH gene.

As provided herein, an XDH RNAi agent does not require that the nucleobase at position 1 (5'→3') of the antisense strand be complementary to the gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. For example, for an XDH RNAi agent disclosed herein that is designed to target position 1322 of an XDH gene, the 5' terminal nucleobase of the antisense strand of the of the XDH RNAi agent is aligned with position 1342 of the gene; however, the 5' terminal nucleobase of the antisense strand may be, but is not required to be, complementary to position 1342 of an XDH gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. As shown by, among other things, the various examples disclosed herein, the specific site of binding of the gene by the antisense strand of the XDH RNAi agent (e.g., whether the XDH RNAi agent is designed to target an XDH gene at position 238, at position 1322, at position 1963, at position 2696, at position 2995, at position 3041, at position 3016, at position 3598, at position 4289, at position 2612, or at some other position) is important to the level of inhibition achieved by the XDH RNAi agent.

In some aspects, the XDH RNAi agents disclosed herein target an XDH gene at or near the positions of the XDH gene sequence shown in Table 1. In some aspects, the antisense strand of an XDH RNAi agent disclosed herein includes a core stretch sequence that is fully, substantially, or at least partially complementary to a target XDH 19-mer sequence disclosed in Table 1.

TABLE 1

| SEQ ID No. | XDH 19-mer Target Sequences (5' → 3') | Corresponding Positions of Sequence on SEQ ID NO: 1 | Targeted Gene Position (as referred to herein) |
|---|---|---|---|
| 2 | UCAGCUUCUUCUUCAAGUU | 1614-1632 | 1612 |
| 3 | AGCUUCUUCUUCAAGUUCU | 1616-1634 | 1614 |
| 4 | UUCUUCUUCAAGUUCUACC | 1619-1637 | 1617 |
| 5 | GGGUGAAAAUCACCUAUGA | 2130-2148 | 2128 |
| 6 | GUGAAAAUCACCUAUGAAG | 2132-2150 | 2130 |
| 7 | UGAAAAUCACCUAUGAAGA | 2133-2151 | 2131 |
| 8 | GAAAAUCACCUAUGAAGAA | 2134-2152 | 2132 |
| 9 | ACCAGCCAUUAUCACAAUU | 2155-2173 | 2153 |
| 10 | AGAACAACUCCUUUUAUGG | 2187-2205 | 2185 |
| 11 | GAACAACUCCUUUUAUGGA | 2188-2206 | 2186 |
| 12 | GACAAGCACUAACACUGUG | 3274-3292 | 3272 |
| 13 | GUCAUGAGUAUGUACACAC | 437-455 | 435 |
| 14 | GACAUGCUGAUAACUGGUG | 2573-2591 | 2571 |
| 15 | AUACAAGGUUGGCUUCAUG | 2614-2632 | 2612 |
| 16 | AAGGUUGGCUUCAUGAAGA | 2618-2636 | 2616 |
| 17 | AGGUUGGCUUCAUGAAGAC | 2619-2637 | 2617 |
| 18 | GUUGGCUUCAUGAAGACUG | 2621-2639 | 2619 |

XDH 19-mer mRNA Target Sequences (taken from *homo sapiens* xanthine dehydrogenase (XDH), mRNA, GenBank NM_000379.4 (SEQ ID NO: 1))

TABLE 1-continued

XDH 19-mer mRNA Target Sequences (taken from *homo sapiens* xanthine dehydrogenase (XDH), mRNA, GenBank NM_000379.4 (SEQ ID NO: 1))

| SEQ ID No. | XDH 19-mer Target Sequences (5' → 3') | Corresponding Positions of Sequence on SEQ ID NO: 1 | Targeted Gene Position (as referred to herein) |
|---|---|---|---|
| 19 | GAGAAUUGUUGGAAAAAGA | 3047-3065 | 3045 |
| 20 | GGCUUGCUCUGAAGUAGAA | 3550-3568 | 3548 |
| 21 | UUGCUCUGAAGUAGAAAUC | 3553-3571 | 3551 |
| 22 | CUGCCAUUGAUAUUGGACA | 3642-3660 | 3640 |
| 23 | AGAUCGUCCACUUUUCUGC | 267-285 | 265 |
| 24 | CCGAAGCAGAUAAUGUUGU | 2250-2268 | 2248 |
| 25 | CUCUCUCAGAGUAUUAUGG | 2696-2714 | 2694 |
| 26 | CACCAAGUUUGGAAUAAGC | 3085-3103 | 3083 |
| 27 | GCAUAAAGCAAGAUUACUC | 4667-4685 | 4665 |
| 28 | CAAUGUUCUAGAUUUCUUU | 4727-4745 | 4725 |
| 29 | UGCUGGAUGAGUGAAGUUG | 2852-2870 | 2850 |
| 30 | GCUGGAUGAGUGAAGUUGC | 2853-2871 | 2851 |
| 31 | CUGGAUGAGUGAAGUUGCA | 2854-2872 | 2852 |
| 32 | UGCUCUCCAAGUAUGAUCG | 237-255 | 235 |
| 33 | GAUCGUCUGCAGAACAAGA | 251-269 | 249 |
| 34 | CGUCUGCAGAACAAGAUCG | 254-272 | 252 |
| 35 | CGCCAGUGCAACUUUACUG | 1705-1723 | 1703 |
| 36 | GAUAAGGUUACUUGUGUUG | 2051-2069 | 2049 |
| 37 | CAGCCAUUAUCACAAUUGA | 2157-2175 | 2155 |
| 38 | AGCUCUCAGUAUCAUGCUC | 2999-3017 | 2997 |
| 39 | AGAGUGAGGUUGACAAGUU | 3021-3038 | 3019 |
| 40 | GAGUGAGGUUGACAAGUUC | 3022-3040 | 3020 |
| 41 | UCAACAAGGAGAAUUGUUG | 3039-3057 | 3037 |
| 42 | AACAUACCACAGAACAUGG | 4138-4156 | 4136 |
| 43 | ACAUGGAUCUAUUAAAGUC | 4151-4169 | 4149 |
| 44 | CAUGGAUCUAUUAAAGUCA | 4152-4170 | 4150 |
| 45 | CCUAAAUGGUGAAUAUGCA | 4291-4309 | 4289 |
| 46 | ACCUCUAGAAGCUUAAACC | 4448-4466 | 4446 |
| 47 | CCUUCAAACCAAUGAACAG | 4507-4525 | 4505 |
| 48 | AAUGAACAGCAAAGCAUAA | 4517-4535 | 4515 |
| 49 | UGAACAGCAAAGCAUAACC | 4519-4537 | 4517 |
| 50 | GAACAGCAAAGCAUAACCU | 4520-4538 | 4518 |
| 51 | ACAGCAAAGCAUAACCUUG | 4522-4540 | 4520 |
| 52 | AAAGCAUAACCUUGAAUCU | 4527-4545 | 4525 |
| 53 | AACCAACUCAAUUAUUGAG | 4702-4720 | 4700 |
| 54 | UCCUGUGAUCCAUUUUACU | 5288-5306 | 5286 |
| 55 | UUUUCUUACUGUCAUAUGA | 5422-5440 | 5420 |

TABLE 1-continued

XDH 19-mer mRNA Target Sequences (taken from *homo sapiens* xanthine dehydrogenase (XDH), mRNA, GenBank NM_000379.4 (SEQ ID NO: 1))

| SEQ ID No. | XDH 19-mer Target Sequences (5' → 3') | Corresponding Positions of Sequence on SEQ ID NO: 1 | Targeted Gene Position (as referred to herein) |
|---|---|---|---|
| 56 | GGAGAAAAAUGCAGAUCCA | 124-142 | 122 |
| 57 | CAGAGACAACCCUUUUGGC | 141-159 | 139 |
| 58 | CUCCAAGUAUGAUCGUCUG | 241-259 | 239 |
| 59 | AACUGUGGAAGGAAUAGGA | 334-352 | 332 |
| 60 | GCAUCGUCAUGAGUAUGUA | 432-450 | 430 |
| 61 | CUUCCAAGGAAAUCUGUGC | 502-520 | 500 |
| 62 | GGCAUUGAGAUGAAGUUCA | 869-887 | 867 |
| 63 | UGAAGUUCAAGAAUAUGCU | 879-897 | 877 |
| 64 | AAUAUGCUGUUUCCUAUGA | 890-908 | 888 |
| 65 | UGCUCUCCAUAGAGAUCCC | 1287-1305 | 1285 |
| 66 | GUAUUUCUCAGCAUUCAAG | 1324-1342 | 1322 |
| 67 | CCAAGAUCAAGUCCAUAGA | 1923-1941 | 1921 |
| 68 | CAGGGUUUGUUUGUUUCAU | 1965-1983 | 1963 |
| 69 | CACCUAUGAAGAACUACCA | 2140-2158 | 2138 |
| 70 | GAACUACCAGCCAUUAUCA | 2150-2168 | 2148 |
| 71 | GCCAUUAUCACAAUUGAGG | 2159-2177 | 2157 |
| 72 | AGCUGAAGAUCGAGAAAGG | 2211-2229 | 2209 |
| 73 | GCACCAUUGCUGUUCCAAA | 2322-2340 | 2320 |
| 74 | GGAGCUCUUUGUGUCUACA | 2359-2377 | 2357 |
| 75 | CUCUUUGUGUCUACACAGA | 2363-2381 | 2361 |
| 76 | CUCUCAGAGUAUUAUGGAA | 2698-2716 | 2696 |
| 77 | AGAGUAUUAUGGAACGAGC | 2703-2721 | 2701 |
| 78 | AGGGUUUGUUUGUUUCAUU | 1966-1984 | 1964 |
| 79 | GGGUUUGUUUGUUUCAUUU | 1967-1985 | 1965 |
| 80 | GUUUGUUUGUUUCAUUUCC | 1969-1987 | 1967 |
| 81 | UCUCCAAGUAUGAUCGUCU | 240-258 | 238 |
| 82 | AGGAGAUUGAGAAUGCCUU | 486-504 | 484 |
| 83 | AGAAUGCCUUCCAAGGAAA | 495-513 | 493 |
| 84 | UGCCUUCCAAGGAAAUCUG | 499-517 | 497 |
| 85 | AGAAUAUGCUGUUUCCUAU | 888-906 | 886 |
| 86 | UUGGAGGGAACAUCAUCAC | 1119-1137 | 1117 |
| 87 | GCUUCUUCUUCAAGUUCUA | 1617-1635 | 1615 |
| 88 | GUUGGGCAUAUCAUUGGUG | 2066-2084 | 2064 |
| 89 | UCUACACAGAACACCAUGA | 2372-2390 | 2370 |
| 90 | CACCCAGGAUCUCUCUCAG | 2686-2704 | 2684 |
| 91 | CAAGCUCUCAGUAUCAUGC | 2997-3015 | 2995 |

TABLE 1-continued

XDH 19-mer mRNA Target Sequences (taken from homo sapiens xanthine dehydrogenase (XDH), mRNA, GenBank NM_000379.4 (SEQ ID NO: 1))

| SEQ ID No. | XDH 19-mer Target Sequences (5' → 3') | Corresponding Positions of Sequence on SEQ ID NO: 1 | Targeted Gene Position (as referred to herein) |
|---|---|---|---|
| 92 | GGAAGAGUGAGGUUGACAA | 3018-3036 | 3016 |
| 93 | CAAGGAGAAUUGUUGGAAA | 3043-3061 | 3041 |
| 94 | AGCUUUGAGACUAACUCAG | 3500-3518 | 3498 |
| 95 | UCCGCACAGAUAUUGUCAU | 3600-3618 | 3598 |
| 96 | CGCACAGAUAUUGUCAUGG | 3602-3620 | 3600 |
| 97 | CUGCUUCUAUCUUCUUUGC | 3879-3897 | 3877 |
| 98 | CACACAGGUAAUAACGUGA | 3932-3950 | 3930 |
| 99 | UGUAUAACCUCAAGUUCUG | 4396-4414 | 4394 |
| 100 | CCAAUGAACAGCAAAGCAU | 4515-4533 | 4513 |
| 101 | UAACCUUGAAUCUAUACUC | 4533-4551 | 4531 |
| 102 | CAUAAAGCAAGAUUACUCU | 4668-4686 | 4666 |
| 103 | CACCUAGAAAUGAUGCUAU | 4845-4863 | 4843 |
| 104 | AGCUCUGUCUCUUCUGUCU | 5236-5254 | 5234 |
| 105 | AAGGCUUGGUUUUCUUACU | 5413-5431 | 5411 |
| 106 | GUGAUGCUCUCCAAGUAUG | 233-251 | 231 |
| 107 | CAAGUAUGAUCGUCUGCAG | 244-262 | 242 |
| 108 | GCAUGAGAGUUUUAUUCAA | 1386-1404 | 1384 |
| 109 | CAAGAUCGUCCACUUUUCU | 265-283 | 263 |
| 110 | CAUGUUGCAGUGACAACUG | 320-338 | 318 |
| 111 | UGACAACUGUGGAAGGAAU | 330-348 | 328 |
| 112 | GGAGGAGAUUGAGAAUGCC | 484-502 | 482 |
| 113 | CACGGAGAUUGGCAUUGAG | 859-877 | 857 |
| 114 | AGAUGAAGUUCAAGAAUAU | 876-894 | 874 |
| 115 | GAGAUACUGCUCUCCAUAG | 1280-1298 | 1278 |
| 116 | GGAGUAUUUCUCAGCAUUC | 1321-1339 | 1319 |
| 117 | GAGUAUUUCUCAGCAUUCA | 1322-1340 | 1320 |
| 118 | GGAGAGAAGAUGACAUUGC | 1353-1371 | 1351 |
| 119 | UAACAUAACUGGAAUUUGU | 2008-2026 | 2006 |
| 120 | AGCCAUUAUCACAAUUGAG | 2158-2176 | 2156 |
| 121 | GCUUUGUUGCAAAAAUGUU | 2400-2418 | 2398 |
| 122 | UUUGUUGCAAAAAUGUUGG | 2402-2420 | 2400 |
| 123 | GAUUGUGGUUCGAGUGAAG | 2437-2455 | 2435 |
| 124 | GAUUGAGAAUGCCUUCCAA | 490-508 | 488 |

In some aspects, an XDH RNAi agent includes an antisense strand wherein position 19 of the antisense strand (5'→3') is capable of forming a base pair with position 1 of a 19-mer target sequence disclosed in Table 1. In some aspects, an XDH RNAi agent includes an antisense strand wherein position 1 of the antisense strand (5'→3') is capable of forming a base pair with position 19 of the 19-mer target sequence disclosed in Table 1.

In some aspects, an XDH RNAi agent includes an antisense strand wherein position 2 of the antisense strand (5'→3') is capable of forming a base pair with position 18 of the 19-mer target sequence disclosed in Table 1. In some aspects, an XDH RNAi agent includes an antisense strand wherein positions 2 through 18 of the antisense strand (5'→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to the XDH gene, or can be non-complementary to the XDH gene. In some aspects, the nucleotide at position 1 of the antisense strand (from 5' end→3' end) is a U, A, or dT. In some aspects, the nucleotide at position 1 of the antisense strand (from 5' end→3' end) forms an A:U or U:A base pair with the sense strand.

In some aspects, an XDH RNAi agent antisense strand comprises the sequence of nucleotides (from 5' end→3' end) at positions 2-18, 2-19, 2-20, or 2-21 of any of the antisense strand sequences in Table 2, Table 3, or Table 5C. In some aspects, an XDH RNAi sense strand comprises the sequence of nucleotides (from 5' end→3' end) at positions 3-21, 2-21, 1-21, 3-20, 2-20, 1-20, 3-19, 2-19, 1-19, 3-18, 2-18, or 1-18 of any of the sense strand sequences in Table 2, Table 4, or Table 5C.

In some aspects, an XDH RNAi agent antisense strand comprises the sequence of nucleotides (from 5' end→3' end) at positions 2-18, 2-19, 2-20, or 2-21 of any of the antisense strand sequences of Table 2, Table 3, or Table 5C. In some aspects, an XDH RNAi sense strand comprises the sequence of nucleotides (from 5' end→3' end) at positions 3-21, 2-21, 1-21, 3-20, 2-20, 1-20, 3-19, 2-19, 1-19, 3-18, 2-18, or 1-18 of any of the sense strand sequences of Table 2, Table 4, or Table 5C.

In some aspects, an XDH RNAi agent is comprised of (i) an antisense strand comprising the sequence of nucleotides (from 5' end→3' end) at positions 2-18 or 2-19 of any of the antisense strand sequences in Table 2 or Table 3, and (ii) a sense strand comprising the sequence of nucleotides (from 5' end→3' end) at positions 3-21, 2-21, 1-21, 3-20, 2-20, 1-20, 3-19, 2-19, 1-19, 3-18, 2-18, or 1-18 of any of the sense strand sequences in Table 2 or Table 4.

In some aspects, the XDH RNAi agents include core 19-mer nucleotide sequences shown in the following Table 2.

TABLE 2

XDH RNAi Agent Antisense Strand and Sense Strand Core Stretch Base Sequences

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 125 | AACUUGAAGAAGAAGCUGA | 535 | UCAGCUUCUUCUUCAAGUU | 1614-1632 | 1612 |
| 126 | UACUUGAAGAAGAAGCUGA | 536 | UCAGCUUCUUCUUCAAGUA | 1614-1632 | 1612 |
| 127 | NACUUGAAGAAGAAGCUGA | 537 | UCAGCUUCUUCUUCAAGUN | 1614-1632 | 1612 |
| 128 | NACUUGAAGAAGAAGCUGN | 538 | NCAGCUUCUUCUUCAAGUN | 1614-1632 | 1612 |
| 129 | AGAACUUGAAGAAGAAGCU | 539 | AGCUUCUUCUUCAAGUUCU | 1616-1634 | 1614 |
| 130 | UGAACUUGAAGAAGAAGCU | 540 | AGCUUCUUCUUCAAGUUCA | 1616-1634 | 1614 |
| 131 | NGAACUUGAAGAAGAAGCU | 541 | AGCUUCUUCUUCAAGUUCN | 1616-1634 | 1614 |
| 132 | NGAACUUGAAGAAGAAGCN | 542 | NGCUUCUUCUUCAAGUUCN | 1616-1634 | 1614 |
| 133 | UGUAGAACUUGAAGAAGAA | 543 | UUCUUCUUCAAGUUCUACA | 1619-1637 | 1617 |
| 134 | NGUAGAACUUGAAGAAGAA | 544 | UUCUUCUUCAAGUUCUACN | 1619-1637 | 1617 |
| 135 | NGUAGAACUUGAAGAAGAN | 545 | NUCUUCUUCAAGUUCUACN | 1619-1637 | 1617 |
| 136 | UCAUAGGUGAUUUUCACCC | 546 | GGGUGAAAAUCACCUAUGA | 2130-2148 | 2128 |
| 137 | NCAUAGGUGAUUUUCACCC | 547 | GGGUGAAAAUCACCUAUGN | 2130-2148 | 2128 |
| 138 | NCAUAGGUGAUUUUCACCN | 548 | NGGUGAAAAUCACCUAUGN | 2130-2148 | 2128 |
| 139 | UUUCAUAGGUGAUUUUCAC | 549 | GUGAAAAUCACCUAUGAAA | 2132-2150 | 2130 |
| 140 | NUUCAUAGGUGAUUUUCAC | 550 | GUGAAAAUCACCUAUGAAN | 2132-2150 | 2130 |
| 141 | NUUCAUAGGUGAUUUUCAN | 551 | NUGAAAAUCACCUAUGAAN | 2132-2150 | 2130 |
| 142 | UCUUCAUAGGUGAUUUUCA | 552 | UGAAAAUCACCUAUGAAGA | 2133-2151 | 2131 |
| 143 | NCUUCAUAGGUGAUUUUCA | 553 | UGAAAAUCACCUAUGAAGN | 2133-2151 | 2131 |
| 144 | NCUUCAUAGGUGAUUUUCN | 554 | NGAAAAUCACCUAUGAAGN | 2133-2151 | 2131 |
| 145 | UUCUUCAUAGGUGAUUUUC | 555 | GAAAAUCACCUAUGAAGAA | 2134-2152 | 2132 |

TABLE 2-continued

XDH RNAi Agent Antisense Strand and Sense Strand Core Stretch Base Sequences

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 146 | NUCUUCAUAGGUGAUUUUC | 556 | GAAAAUCACCUAUGAAGAN | 2134-2152 | 2132 |
| 147 | NUCUUCAUAGGUGAUUUUN | 557 | NAAAAUCACCUAUGAAGAN | 2134-2152 | 2132 |
| 148 | AAUUGUGAUAAUGGCUGGU | 558 | ACCAGCCAUUAUCACAAUU | 2155-2173 | 2153 |
| 149 | UAUUGUGAUAAUGGCUGGU | 559 | ACCAGCCAUUAUCACAAUA | 2155-2173 | 2153 |
| 150 | NAUUGUGAUAAUGGCUGGU | 560 | ACCAGCCAUUAUCACAAUN | 2155-2173 | 2153 |
| 151 | NAUUGUGAUAAUGGCUGGN | 561 | NCCAGCCAUUAUCACAAUN | 2155-2173 | 2153 |
| 152 | UCAUAAAAGGAGUUGUUCU | 562 | AGAACAACUCCUUUUAUGA | 2187-2205 | 2185 |
| 153 | NCAUAAAAGGAGUUGUUCU | 563 | AGAACAACUCCUUUUAUGN | 2187-2205 | 2185 |
| 154 | NCAUAAAAGGAGUUGUUCN | 564 | NGAACAACUCCUUUUAUGN | 2187-2205 | 2185 |
| 155 | UCCAUAAAAGGAGUUGUUC | 565 | GAACAACUCCUUUUAUGGA | 2188-2206 | 2186 |
| 156 | NCCAUAAAAGGAGUUGUUC | 566 | GAACAACUCCUUUUAUGGN | 2188-2206 | 2186 |
| 157 | NCCAUAAAAGGAGUUGUUN | 567 | NAACAACUCCUUUUAUGGN | 2188-2206 | 2186 |
| 158 | UACAGUGUUAGUGCUUGUC | 568 | GACAAGCACUAACACUGUA | 3274-3292 | 3272 |
| 159 | NACAGUGUUAGUGCUUGUC | 569 | GACAAGCACUAACACUGUN | 3274-3292 | 3272 |
| 160 | NACAGUGUUAGUGCUUGUN | 570 | NACAAGCACUAACACUGUN | 3274-3292 | 3272 |
| 161 | UUGUGUACAUACUCAUGAC | 571 | GUCAUGAGUAUGUACACAA | 437-455 | 435 |
| 162 | NUGUGUACAUACUCAUGAC | 572 | GUCAUGAGUAUGUACACAN | 437-455 | 435 |
| 163 | NUGUGUACAUACUCAUGAN | 573 | NUCAUGAGUAUGUACACAN | 437-455 | 435 |
| 164 | UACCAGUUAUCAGCAUGUC | 574 | GACAUGCUGAUAACUGIUA | 2573-2591 | 2571 |
| 165 | NACCAGUUAUCAGCAUGUC | 575 | GACAUGCUGAUAACUGIUN | 2573-2591 | 2571 |
| 166 | NACCAGUUAUCAGCAUGUN | 576 | NACAUGCUGAUAACUGIUN | 2573-2591 | 2571 |
| 167 | UACCAGUUAUCAGCAUGUC | 577 | GACAUGCUGAUAACUGGUA | 2573-2591 | 2571 |
| 168 | NACCAGUUAUCAGCAUGUC | 578 | GACAUGCUGAUAACUGGUA | 2573-2591 | 2571 |
| 169 | NACCAGUUAUCAGCAUGUN | 579 | GACAUGCUGAUAACUGGUA | 2573-2591 | 2571 |
| 170 | UAUGAAGCCAACCUUGUAU | 580 | AUACAAGGUUGGCUUCAUA | 2614-2632 | 2612 |
| 171 | NAUGAAGCCAACCUUGUAU | 581 | AUACAAGGUUGGCUUCAUN | 2614-2632 | 2612 |
| 172 | NAUGAAGCCAACCUUGUAN | 582 | NUACAAGGUUGGCUUCAUN | 2614-2632 | 2612 |
| 173 | UCUUCAUGAAGCCAACCUU | 583 | AAGGUUGGCUUCAUGAAGA | 2618-2636 | 2616 |
| 174 | NCUUCAUGAAGCCAACCUU | 584 | AAGGUUGGCUUCAUGAAGN | 2618-2636 | 2616 |
| 175 | NCUUCAUGAAGCCAACCUN | 585 | NAGGUUGGCUUCAUGAAGN | 2618-2636 | 2616 |
| 176 | UUCUUCAUGAAGCCAACCU | 586 | AGGUUGGCUUCAUGAAGAA | 2619-2637 | 2617 |
| 177 | NUCUUCAUGAAGCCAACCU | 587 | AGGUUGGCUUCAUGAAGAN | 2619-2637 | 2617 |
| 178 | NUCUUCAUGAAGCCAACCN | 588 | NGGUUGGCUUCAUGAAGAN | 2619-2637 | 2617 |
| 179 | UAGUCUUCAUGAAGCCAAC | 589 | GUUGGCUUCAUGAAGACUA | 2621-2639 | 2619 |
| 180 | NAGUCUUCAUGAAGCCAAC | 590 | GUUGGCUUCAUGAAGACUN | 2621-2639 | 2619 |

TABLE 2-continued

XDH RNAi Agent Antisense Strand and Sense Strand Core Stretch Base Sequences

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 181 | NAGUCUUCAUGAAGCCAAN | 591 | NUUGGCUUCAUGAAGACUN | 2621-2639 | 2619 |
| 182 | UCUUUUUCCAACAAUUCUC | 592 | GAGAAUUGUUGGAAAAAGA | 3047-3065 | 3045 |
| 183 | NCUUUUUCCAACAAUUCUC | 593 | GAGAAUUGUUGGAAAAAGN | 3047-3065 | 3045 |
| 184 | NCUUUUUCCAACAAUUCUN | 594 | NAGAAUUGUUGGAAAAAGN | 3047-3065 | 3045 |
| 185 | UUCUACUUCAGAGCAAGCC | 595 | GGCUUGCUCUGAAGUAGAA | 3550-3568 | 3548 |
| 186 | NUCUACUUCAGAGCAAGCC | 596 | GGCUUGCUCUGAAGUAGAN | 3550-3568 | 3548 |
| 187 | NUCUACUUCAGAGCAAGCN | 597 | NGCUUGCUCUGAAGUAGAN | 3550-3568 | 3548 |
| 188 | UAUUUCUACUUCAGAGCAA | 598 | UUGCUCUGAAGUAGAAAUA | 3553-3571 | 3551 |
| 189 | NAUUUCUACUUCAGAGCAA | 599 | UUGCUCUGAAGUAGAAAUN | 3553-3571 | 3551 |
| 190 | NAUUUCUACUUCAGAGCAN | 600 | NUGCUCUGAAGUAGAAAUN | 3553-3571 | 3551 |
| 191 | UGUCCAAUAUCAAUGGCAG | 601 | CUGCCAUUGAUAUUIGACA | 3642-3660 | 3640 |
| 192 | NGUCCAAUAUCAAUGGCAG | 602 | CUGCCAUUGAUAUUIGACN | 3642-3660 | 3640 |
| 193 | NGUCCAAUAUCAAUGGCAN | 603 | NUGCCAUUGAUAUUIGACN | 3642-3660 | 3640 |
| 194 | UCAGAAAAGUGGACGAUCU | 604 | AGAUCGUCCACUUUUCUGA | 267-285 | 265 |
| 195 | NCAGAAAAGUGGACGAUCU | 605 | AGAUCGUCCACUUUUCUGN | 267-285 | 265 |
| 196 | NCAGAAAAGUGGACGAUCN | 606 | NGAUCGUCCACUUUUCUGN | 267-285 | 265 |
| 197 | ACAACAUUAUCUGCUUCGG | 607 | CCGAAGCAGAUAAUGUUGU | 2250-2268 | 2248 |
| 198 | UCAACAUUAUCUGCUUCGG | 608 | CCGAAGCAGAUAAUGUUGU | 2250-2268 | 2248 |
| 199 | NCAACAUUAUCUGCUUCGG | 609 | CCGAAGCAGAUAAUGUUGN | 2250-2268 | 2248 |
| 200 | NCAACAUUAUCUGCUUCGN | 610 | NCGAAGCAGAUAAUGUUGN | 2250-2268 | 2248 |
| 201 | UCAUAAUACUCUGAGAGAG | 611 | CUCUCUCAGAGUAUUAUGA | 2696-2714 | 2694 |
| 202 | NCAUAAUACUCUGAGAGAG | 612 | CUCUCUCAGAGUAUUAUGN | 2696-2714 | 2694 |
| 203 | NCAUAAUACUCUGAGAGAN | 613 | NUCUCUCAGAGUAUUAUGN | 2696-2714 | 2694 |
| 204 | UCUUAUUCCAAACUUGGUG | 614 | CACCAAGUUUGGAAUAAGA | 3085-3103 | 3083 |
| 205 | NCUUAUUCCAAACUUGGUG | 615 | CACCAAGUUUGGAAUAAGN | 3085-3103 | 3083 |
| 206 | NCUUAUUCCAAACUUGGUN | 616 | NACCAAGUUUGGAAUAAGN | 3085-3103 | 3083 |
| 207 | UAGUAAUCUUGCUUUAUGC | 617 | GCAUAAAGCAAGAUUACUA | 4667-4685 | 4665 |
| 208 | NAGUAAUCUUGCUUUAUGC | 618 | GCAUAAAGCAAGAUUACUN | 4667-4685 | 4665 |
| 209 | NAGUAAUCUUGCUUUAUGN | 619 | NCAUAAAGCAAGAUUACUN | 4667-4685 | 4665 |
| 210 | AAAGAAAUCUAGAACAUUG | 620 | CAAUGUUCUAGAUUUCUUU | 4727-4745 | 4725 |
| 211 | UAAGAAAUCUAGAACAUUG | 621 | CAAUGUUCUAGAUUUCUUA | 4727-4745 | 4725 |
| 212 | NAAGAAAUCUAGAACAUUG | 622 | CAAUGUUCUAGAUUUCUUN | 4727-4745 | 4725 |
| 213 | NAAGAAAUCUAGAACAUUN | 623 | NAAUGUUCUAGAUUUCUUN | 4727-4745 | 4725 |
| 214 | UAACUUCACUCAUCCAGCA | 624 | UGCUGGAUGAGUGAAGUUA | 2852-2870 | 2850 |
| 215 | NAACUUCACUCAUCCAGCA | 625 | UGCUGGAUGAGUGAAGUUN | 2852-2870 | 2850 |

TABLE 2-continued

XDH RNAi Agent Antisense Strand and Sense Strand Core Stretch Base Sequences

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 216 | NAACUUCACUCAUCCAGCN | 626 | NGCUGGAUGAGUGAAGUUN | 2852-2870 | 2850 |
| 217 | UCAACUUCACUCAUCCAGC | 627 | GCUIGAUGAGUGAAGUUGA | 2853-2871 | 2851 |
| 218 | NCAACUUCACUCAUCCAGC | 628 | GCUIGAUGAGUGAAGUUGN | 2853-2871 | 2851 |
| 219 | NCAACUUCACUCAUCCAGN | 629 | NCUIGAUGAGUGAAGUUGN | 2853-2871 | 2851 |
| 220 | UGCAACUUCACUCAUCCAG | 630 | CUGGAUGAGUGAAGUUICA | 2854-2872 | 2852 |
| 221 | NGCAACUUCACUCAUCCAG | 631 | CUGGAUGAGUGAAGUUICN | 2854-2872 | 2852 |
| 222 | NGCAACUUCACUCAUCCAN | 632 | NUGGAUGAGUGAAGUUICN | 2854-2872 | 2852 |
| 223 | UGAUCAUACUUGGAGAGCA | 633 | UGCUCUCCAAGUAUGAUCA | 237-255 | 235 |
| 224 | NGAUCAUACUUGGAGAGCA | 634 | UGCUCUCCAAGUAUGAUCN | 237-255 | 235 |
| 225 | NGAUCAUACUUGGAGAGCN | 635 | NGCUCUCCAAGUAUGAUCN | 237-255 | 235 |
| 226 | UCUUGUUCUGCAGACGAUC | 636 | GAUCGUCUGCAGAACAAGA | 251-269 | 249 |
| 227 | NCUUGUUCUGCAGACGAUC | 637 | GAUCGUCUGCAGAACAAGN | 251-269 | 249 |
| 228 | NCUUGUUCUGCAGACGAUC | 638 | GAUCGUCUGCAGAACAAGN | 251-269 | 249 |
| 229 | UGAUCUUGUUCUGCAGACG | 639 | CGUCUGCAGAACAAGAUCA | 254-272 | 252 |
| 230 | NGAUCUUGUUCUGCAGACG | 640 | CGUCUGCAGAACAAGAUCN | 254-272 | 252 |
| 231 | NGAUCUUGUUCUGCAGACN | 641 | NGUCUGCAGAACAAGAUCN | 254-272 | 252 |
| 232 | UAGUAAAGUUGCACUGGCG | 642 | CGCCAGUGCAACUUUACUA | 1705-1723 | 1703 |
| 233 | NAGUAAAGUUGCACUGGCG | 643 | CGCCAGUGCAACUUUACUN | 1705-1723 | 1703 |
| 234 | NAGUAAAGUUGCACUGGCN | 644 | NGCCAGUGCAACUUUACUN | 1705-1723 | 1703 |
| 235 | UAACACAAGUAACCUUAUC | 645 | GAUAAGGUUACUUGUGUUA | 2051-2069 | 2049 |
| 236 | NAACACAAGUAACCUUAUC | 646 | GAUAAGGUUACUUGUGUUN | 2051-2069 | 2049 |
| 237 | NAACACAAGUAACCUUAUN | 647 | NAUAAGGUUACUUGUGUUN | 2051-2069 | 2049 |
| 238 | UCAAUUGUGAUAAUGGCUG | 648 | CAGCCAUUAUCACAAUUGA | 2157-2175 | 2155 |
| 239 | NCAAUUGUGAUAAUGGCUG | 649 | CAGCCAUUAUCACAAUUGN | 2157-2175 | 2155 |
| 240 | NCAAUUGUGAUAAUGGCUN | 650 | NAGCCAUUAUCACAAUUGN | 2157-2175 | 2155 |
| 241 | UAGCAUGAUACUGAGAGCU | 651 | AGCUCUCAGUAUCAUGCUA | 2999-3017 | 2997 |
| 242 | NAGCAUGAUACUGAGAGCU | 652 | AGCUCUCAGUAUCAUGCUN | 2999-3017 | 2997 |
| 243 | NAGCAUGAUACUGAGAGCN | 653 | NGCUCUCAGUAUCAUGCUN | 2999-3017 | 2997 |
| 244 | AACUUGUCAACCUCACUCU | 654 | AGAGUGAGGUUGACAAGUU | 3021-3039 | 3019 |
| 245 | UACUUGUCAACCUCACUCU | 655 | AGAGUGAGGUUGACAAGUA | 3021-3039 | 3019 |
| 246 | NACUUGUCAACCUCACUCU | 656 | AGAGUGAGGUUGACAAGUN | 3021-3039 | 3019 |
| 247 | NACUUGUCAACCUCACUCN | 657 | NGAGUGAGGUUGACAAGUN | 3021-3039 | 3019 |
| 248 | UAACUUGUCAACCUCACUC | 658 | GAGUGAGGUUGACAAGUUA | 3022-3040 | 3020 |
| 249 | NAACUUGUCAACCUCACUC | 659 | GAGUGAGGUUGACAAGUUN | 3022-3040 | 3020 |
| 250 | NAACUUGUCAACCUCACUN | 660 | NAGUGAGGUUGACAAGUUN | 3022-3040 | 3020 |

TABLE 2-continued

XDH RNAi Agent Antisense Strand and Sense Strand Core Stretch Base Sequences

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 251 | UAACAAUUCUCCUUGUUGA | 661 | UCAACAAGGAGAAUUGUUA | 3039-3057 | 3037 |
| 252 | NAACAAUUCUCCUUGUUGA | 662 | UCAACAAGGAGAAUUGUUN | 3039-3057 | 3037 |
| 253 | NAACAAUUCUCCUUGUUGN | 663 | NCAACAAGGAGAAUUGUUN | 3039-3057 | 3037 |
| 254 | UCAUGUUCUGUGGUAUGUU | 664 | AACAUACCACAGAACAUGA | 4138-4156 | 4136 |
| 255 | NCAUGUUCUGUGGUAUGUU | 665 | AACAUACCACAGAACAUGN | 4138-4156 | 4136 |
| 256 | NCAUGUUCUGUGGUAUGUN | 666 | NACAUACCACAGAACAUGN | 4138-4156 | 4136 |
| 257 | UACUUUAAUAGAUCCAUGU | 667 | ACAUGGAUCUAUUAAAGUA | 4151-4169 | 4149 |
| 258 | NACUUUAAUAGAUCCAUGU | 668 | ACAUGGAUCUAUUAAAGUN | 4151-4169 | 4149 |
| 259 | NACUUUAAUAGAUCCAUGN | 669 | NCAUGGAUCUAUUAAAGUN | 4151-4169 | 4149 |
| 260 | UGACUUUAAUAGAUCCAUG | 670 | CAUGGAUCUAUUAAAGUCA | 4152-4170 | 4150 |
| 261 | NGACUUUAAUAGAUCCAUG | 671 | CAUGGAUCUAUUAAAGUCN | 4152-4170 | 4150 |
| 262 | NGACUUUAAUAGAUCCAUN | 672 | NAUGGAUCUAUUAAAGUCN | 4152-4170 | 4150 |
| 263 | UGCAUAUUCACCAUUUAGG | 673 | CCUAAAUGGUGAAUAUGCA | 4291-4309 | 4289 |
| 264 | NGCAUAUUCACCAUUUAGG | 674 | CCUAAAUGGUGAAUAUGCN | 4291-4309 | 4289 |
| 265 | NGCAUAUUCACCAUUUAGN | 675 | NCUAAAUGGUGAAUAUGCN | 4291-4309 | 4289 |
| 266 | UGUUUAAGCUUCUAGAGGU | 676 | ACCUCUAGAAGCUUAAACA | 4448-4466 | 4446 |
| 267 | NGUUUAAGCUUCUAGAGGU | 677 | ACCUCUAGAAGCUUAAACN | 4448-4466 | 4446 |
| 268 | NGUUUAAGCUUCUAGAGGN | 678 | NCCUCUAGAAGCUUAAACN | 4448-4466 | 4446 |
| 269 | UUGUUCAUUGGUUUGAAGG | 679 | CCUUCAAACCAAUGAACAA | 4507-4525 | 4505 |
| 270 | NUGUUCAUUGGUUUGAAGG | 680 | CCUUCAAACCAAUGAACAN | 4507-4525 | 4505 |
| 271 | NUGUUCAUUGGUUUGAAGN | 681 | NCUUCAAACCAAUGAACAN | 4507-4525 | 4505 |
| 272 | UUAUGCUUUGCUGUUCAUU | 682 | AAUGAACAGCAAAGCAUAA | 4517-4535 | 4515 |
| 273 | NUAUGCUUUGCUGUUCAUU | 683 | AAUGAACAGCAAAGCAUAN | 4517-4535 | 4515 |
| 274 | NUAUGCUUUGCUGUUCAUN | 684 | NAUGAACAGCAAAGCAUAN | 4517-4535 | 4515 |
| 275 | UGUUAUGCUUUGCUGUUCA | 685 | UGAACAGCAAAGCAUAACA | 4519-4537 | 4517 |
| 276 | NGUUAUGCUUUGCUGUUCA | 686 | UGAACAGCAAAGCAUAACN | 4519-4537 | 4517 |
| 277 | NGUUAUGCUUUGCUGUUCN | 687 | NGAACAGCAAAGCAUAACN | 4519-4537 | 4517 |
| 278 | AGGUUAUGCUUUGCUGUUC | 688 | GAACAGCAAAGCAUAACCU | 4520-4538 | 4518 |
| 279 | UGGUUAUGCUUUGCUGUUC | 689 | GAACAGCAAAGCAUAACCA | 4520-4538 | 4518 |
| 280 | NGGUUAUGCUUUGCUGUUC | 690 | GAACAGCAAAGCAUAACCN | 4520-4538 | 4518 |
| 281 | NGGUUAUGCUUUGCUGUUN | 691 | NAACAGCAAAGCAUAACCN | 4520-4538 | 4518 |
| 282 | UAAGGUUAUGCUUUGCUGU | 692 | ACAGCAAAGCAUAACCUUA | 4522-4540 | 4520 |
| 283 | NAAGGUUAUGCUUUGCUGU | 693 | ACAGCAAAGCAUAACCUUN | 4522-4540 | 4520 |
| 284 | NAAGGUUAUGCUUUGCUGN | 694 | NCAGCAAAGCAUAACCUUN | 4522-4540 | 4520 |
| 285 | AGAUUCAAGGUUAUGCUUU | 695 | AAAGCAUAACCUUGAAUCU | 4527-4545 | 4525 |

TABLE 2-continued

XDH RNAi Agent Antisense Strand and Sense Strand Core Stretch Base Sequences

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 286 | UGAUUCAAGGUUAUGCUUU | 696 | AAAGCAUAACCUUGAAUCA | 4527-4545 | 4525 |
| 287 | NGAUUCAAGGUUAUGCUUU | 697 | AAAGCAUAACCUUGAAUCN | 4527-4545 | 4525 |
| 288 | NGAUUCAAGGUUAUGCUUN | 698 | NAAGCAUAACCUUGAAUCN | 4527-4545 | 4525 |
| 289 | UUCAAUAAUUGAGUUGGUU | 699 | AACCAACUCAAUUAUUGAA | 4702-4720 | 4700 |
| 290 | NUCAAUAAUUGAGUUGGUU | 700 | AACCAACUCAAUUAUUGAN | 4702-4720 | 4700 |
| 291 | NUCAAUAAUUGAGUUGGUN | 701 | NACCAACUCAAUUAUUGAN | 4702-4720 | 4700 |
| 292 | AGUAAAAUGGAUCACAGGA | 702 | UCCUGUGAUCCAUUUUACU | 5288-5306 | 5286 |
| 293 | UGUAAAAUGGAUCACAGGA | 703 | UCCUGUGAUCCAUUUUACA | 5288-5306 | 5286 |
| 294 | NGUAAAAUGGAUCACAGGA | 704 | UCCUGUGAUCCAUUUUACN | 5288-5306 | 5286 |
| 295 | NGUAAAAUGGAUCACAGGN | 705 | NCCUGUGAUCCAUUUUACN | 5288-5306 | 5286 |
| 296 | UCAUAUGACAGUAAGAAAA | 706 | UUUUCUUACUGUCAUAUGA | 5422-5440 | 5420 |
| 297 | NCAUAUGACAGUAAGAAAA | 707 | UUUUCUUACUGUCAUAUGN | 5422-5440 | 5420 |
| 298 | NCAUAUGACAGUAAGAAAN | 708 | NUUUCUUACUGUCAUAUGN | 5422-5440 | 5420 |
| 299 | UGGAUCUGCAUUUUUCUCC | 709 | GGAGAAAAAUGCAIAUCCA | 124-142 | 122 |
| 300 | NGGAUCUGCAUUUUUCUCC | 710 | GGAGAAAAAUGCAIAUCCN | 124-142 | 122 |
| 301 | NGGAUCUGCAUUUUUCUCN | 711 | NGAGAAAAAUGCAIAUCCN | 124-142 | 122 |
| 302 | UCCAAAAGGGUUGUCUCUG | 712 | CAGAGACAACUCUUUUGGA | 141-159 | 139 |
| 303 | NCCAAAAGGGUUGUCUCUG | 713 | CAGAGACAACUCUUUUGGN | 141-159 | 139 |
| 304 | NCCAAAAGGGUUGUCUCUN | 714 | NAGAGACAACUCUUUUGGN | 141-159 | 139 |
| 305 | UAGACGAUCAUACUUGGAG | 715 | CUCCAAGUAUGAUCIUCUA | 241-259 | 239 |
| 306 | NAGACGAUCAUACUUGGAG | 716 | CUCCAAGUAUGAUCIUCUN | 241-259 | 239 |
| 307 | NAGACGAUCAUACUUGGAN | 717 | NUCCAAGUAUGAUCIUCUN | 241-259 | 239 |
| 308 | UCCUAUUCCUUCCACAGUU | 718 | AACUGUGGAAGGAAUAGGA | 334-352 | 332 |
| 309 | NCCUAUUCCUUCCACAGUU | 719 | AACUGUGGAAGGAAUAGGN | 334-352 | 332 |
| 310 | NCCUAUUCCUUCCACAGUN | 720 | NACUGUGGAAGGAAUAGGN | 334-352 | 332 |
| 311 | UACAUACUCAUGACGAUGC | 721 | GCAUCGUCAUGAGUAUGUA | 432-450 | 430 |
| 312 | NACAUACUCAUGACGAUGC | 722 | GCAUCGUCAUGAGUAUGUN | 432-450 | 430 |
| 313 | NACAUACUCAUGACGAUGN | 723 | NCAUCGUCAUGAGUAUGUN | 432-450 | 430 |
| 314 | UCACAGAUUUCCUUGGAAG | 724 | CUUCCAAGGAAAUCUGUIA | 502-520 | 500 |
| 315 | NCACAGAUUUCCUUGGAAG | 725 | CUUCCAAGGAAAUCUGUIN | 502-520 | 500 |
| 316 | NCACAGAUUUCCUUGGAAN | 726 | NUUCCAAGGAAAUCUGUIN | 502-520 | 500 |
| 317 | UGAACUUCAUCUCAAUGCC | 727 | GGCAUUGAGAUGAAGUUCA | 869-887 | 867 |
| 318 | NGAACUUCAUCUCAAUGCC | 728 | GGCAUUGAGAUGAAGUUCN | 869-887 | 867 |
| 319 | NGAACUUCAUCUCAAUGCN | 729 | NGCAUUGAGAUGAAGUUCN | 869-887 | 867 |
| 320 | AGCAUAUUCUUGAACUUCA | 730 | UGAAGUUCAAGAAUAUGCU | 879-897 | 877 |

TABLE 2-continued

XDH RNAi Agent Antisense Strand and Sense Strand Core Stretch Base Sequences

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 321 | UGCAUAUUCUUGAACUUCA | 731 | UGAAGUUCAAGAAUAUGCA | 879-897 | 877 |
| 322 | NGCAUAUUCUUGAACUUCA | 732 | UGAAGUUCAAGAAUAUGCN | 879-897 | 877 |
| 323 | NGCAUAUUCUUGAACUUCN | 733 | NGAAGUUCAAGAAUAUGCN | 879-897 | 877 |
| 324 | UCAUAGGAAACAGCAUAUU | 734 | AAUAUGCUGUUUCCUAUGA | 890-908 | 888 |
| 325 | NCAUAGGAAACAGCAUAUU | 735 | AAUAUGCUGUUUCCUAUGN | 890-908 | 888 |
| 326 | NCAUAGGAAACAGCAUAUN | 736 | NAUAUGCUGUUUCCUAUGN | 890-908 | 888 |
| 327 | UGGAUCUCUAUGGAGAGCA | 737 | UGCUCUCCAUAGAIAUCCA | 1287-1305 | 1285 |
| 328 | NGGAUCUCUAUGGAGAGCA | 738 | UGCUCUCCAUAGAIAUCCN | 1287-1305 | 1285 |
| 329 | NGGAUCUCUAUGGAGAGCN | 739 | NGCUCUCCAUAGAIAUCCN | 1287-1305 | 1285 |
| 330 | UUUGAAUGCUGAGAAAUAC | 740 | GUAUUUCUCAGCAUUCAAA | 1324-1342 | 1322 |
| 331 | NUUGAAUGCUGAGAAAUAC | 741 | GUAUUUCUCAGCAUUCAAN | 1324-1342 | 1322 |
| 332 | NUUGAAUGCUGAGAAAUAN | 742 | NUAUUUCUCAGCAUUCAAN | 1324-1342 | 1322 |
| 333 | UCUAUGGACUUGAUCUUGG | 743 | CCAAGAUCAAGUCCAUAGA | 1923-1941 | 1921 |
| 334 | NCUAUGGACUUGAUCUUGG | 744 | CCAAGAUCAAGUCCAUAGN | 1923-1941 | 1921 |
| 335 | NCUAUGGACUUGAUCUUGN | 745 | NCAAGAUCAAGUCCAUAGN | 1923-1941 | 1921 |
| 336 | AUGAAACAAACAAACCCUG | 746 | CAGGGUUUGUUUGUUUCAU | 1965-1983 | 1963 |
| 337 | UUGAAACAAACAAACCCUG | 747 | CAGGGUUUGUUUGUUUCAA | 1965-1983 | 1963 |
| 338 | NUGAAACAAACAAACCCUG | 748 | CAGGGUUUGUUUGUUUCAN | 1965-1983 | 1963 |
| 339 | NUGAAACAAACAAACCCUN | 749 | NAGGGUUUGUUUGUUUCAN | 1965-1983 | 1963 |
| 340 | UGGUAGUUCUUCAUAGGUG | 750 | CACCUAUGAAGAACUACCA | 2140-2158 | 2138 |
| 341 | NGGUAGUUCUUCAUAGGUG | 751 | CACCUAUGAAGAACUACCN | 2140-2158 | 2138 |
| 342 | NGGUAGUUCUUCAUAGGUN | 752 | NACCUAUGAAGAACUACCN | 2140-2158 | 2138 |
| 343 | UGAUAAUGGCUGGUAGUUC | 753 | GAACUACCAGCCAUUAUCA | 2150-2168 | 2148 |
| 344 | NGAUAAUGGCUGGUAGUUC | 754 | GAACUACCAGCCAUUAUCN | 2150-2168 | 2148 |
| 345 | NGAUAAUGGCUGGUAGUUN | 755 | NAACUACCAGCCAUUAUCN | 2150-2168 | 2148 |
| 346 | UCUCAAUUGUGAUAAUGGC | 756 | GCCAUUAUCACAAUUGAGA | 2159-2177 | 2157 |
| 347 | NCUCAAUUGUGAUAAUGGC | 757 | GCCAUUAUCACAAUUGAGN | 2159-2177 | 2157 |
| 348 | NCUCAAUUGUGAUAAUGGN | 758 | NCCAUUAUCACAAUUGAGN | 2159-2177 | 2157 |
| 349 | UCUUUCUCGAUCUUCAGCU | 759 | AGCUGAAGAUCGAGAAAGA | 2211-2229 | 2209 |
| 350 | NCUUUCUCGAUCUUCAGCU | 760 | AGCUGAAGAUCGAGAAAGN | 2211-2229 | 2209 |
| 351 | NCUUUCUCGAUCUUCAGCN | 761 | NGCUGAAGAUCGAGAAAGN | 2211-2229 | 2209 |
| 352 | UUUGGAACAGCAAUGGUGC | 762 | GCACCAUUGCUGUUCCAAA | 2322-2340 | 2320 |
| 353 | NUUGGAACAGCAAUGGUGC | 763 | GCACCAUUGCUGUUCCAAN | 2322-2340 | 2320 |
| 354 | NUUGGAACAGCAAUGGUGN | 764 | NCACCAUUGCUGUUCCAAN | 2322-2340 | 2320 |
| 355 | UGUAGACACAAAGAGCUCC | 765 | GGAGCUCUUUGUGUUUACA | 2359-2377 | 2357 |

TABLE 2-continued

XDH RNAi Agent Antisense Strand and Sense Strand Core Stretch Base Sequences

| Antisense Strand SEQ ID No. | Base Sequence (5' → 3') (Shown as an Unmodified Nucleotide Sequence) | Sense Strand SEQ ID No. | Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 356 | NGUAGACACAAAGAGCUCC | 766 | GGAGCUCUUUGUGUUUACN | 2359-2377 | 2357 |
| 357 | NGUAGACACAAAGAGCUCN | 767 | NGAGCUCUUUGUGUUUACN | 2359-2377 | 2357 |
| 358 | UCUGUGUAGACACAAAGAG | 768 | CUCUUUGUGUCUACACAIA | 2363-2381 | 2361 |
| 359 | NCUGUGUAGACACAAAGAG | 769 | CUCUUUGUGUCUACACAIN | 2363-2381 | 2361 |
| 360 | NCUGUGUAGACACAAAGAN | 770 | NUCUUUGUGUCUACACAIN | 2363-2381 | 2361 |
| 361 | UUCCAUAAUACUCUGAGAG | 771 | CUCUCAGAGUAUUAUGGAA | 2698-2716 | 2696 |
| 362 | NUCCAUAAUACUCUGAGAG | 772 | CUCUCAGAGUAUUAUGGAN | 2698-2716 | 2696 |
| 363 | NUCCAUAAUACUCUGAGAN | 773 | NUCUCAGAGUAUUAUGGAN | 2698-2716 | 2696 |
| 364 | UCUCGUUCCAUAAUACUCU | 774 | AGAGUAUUAUGGAACGAIA | 2703-2721 | 2701 |
| 365 | NCUCGUUCCAUAAUACUCU | 775 | AGAGUAUUAUGGAACGAIN | 2703-2721 | 2701 |
| 366 | NCUCGUUCCAUAAUACUCN | 776 | NGAGUAUUAUGGAACGAIN | 2703-2721 | 2701 |
| 367 | AAUGAAACAAACAAACCCU | 777 | AGGGUUUGUUUGUUUCAUU | 1966-1984 | 1964 |
| 368 | UAUGAAACAAACAAACCCU | 778 | AGGGUUUGUUUGUUUCAUA | 1966-1984 | 1964 |
| 369 | NAUGAAACAAACAAACCCU | 779 | AGGGUUUGUUUGUUUCAUN | 1966-1984 | 1964 |
| 370 | NAUGAAACAAACAAACCCN | 780 | NGGGUUUGUUUGUUUCAUN | 1966-1984 | 1964 |
| 371 | AAAUGAAACAAACAAACCC | 781 | GGGUUUGUUUGUUUCAUUU | 1967-1985 | 1965 |
| 372 | UAAUGAAACAAACAAACCC | 782 | GGGUUUGUUUGUUUCAUUA | 1967-1985 | 1965 |
| 373 | NAAUGAAACAAACAAACCC | 783 | GGGUUUGUUUGUUUCAUUN | 1967-1985 | 1965 |
| 374 | NAAUGAAACAAACAAACCN | 784 | NGGUUUGUUUGUUUCAUUN | 1967-1985 | 1965 |
| 375 | UGAAAUGAAACAAACAAAC | 785 | GUUUGUUUGUUUCAUUUCA | 1969-1987 | 1967 |
| 376 | NGAAAUGAAACAAACAAAC | 786 | GUUUGUUUGUUUCAUUUCN | 1969-1987 | 1967 |
| 377 | NGAAAUGAAACAAACAAAN | 787 | NUUUGUUUGUUUCAUUUCN | 1969-1987 | 1967 |
| 378 | AGACGAUCAUACUUGGAGA | 788 | UCUCCAAGUAUGAUCIUCU | 240-258 | 238 |
| 379 | UGACGAUCAUACUUGGAGA | 789 | UCUCCAAGUAUGAUCIUCA | 240-258 | 238 |
| 380 | NGACGAUCAUACUUGGAGA | 790 | UCUCCAAGUAUGAUCIUCN | 240-258 | 238 |
| 381 | NGACGAUCAUACUUGGAGN | 791 | NCUCCAAGUAUGAUCIUCN | 240-258 | 238 |
| 382 | AAGGCAUUCUCAAUCUCCU | 792 | AGGAGAUUGAGAAUICCUU | 486-504 | 484 |
| 383 | UAGGCAUUCUCAAUCUCCU | 793 | AGGAGAUUGAGAAUICCUA | 486-504 | 484 |
| 384 | NAGGCAUUCUCAAUCUCCU | 794 | AGGAGAUUGAGAAUICCUN | 486-504 | 484 |
| 385 | NAGGCAUUCUCAAUCUCCN | 795 | NGGAGAUUGAGAAUICCUN | 486-504 | 484 |
| 386 | UUUCCUUGGAAGGCAUUCU | 796 | AGAAUGCCUUCCAAGGAAA | 495-513 | 493 |
| 387 | NUUCCUUGGAAGGCAUUCU | 797 | AGAAUGCCUUCCAAGGAAN | 495-513 | 493 |
| 388 | NUUCCUUGGAAGGCAUUCN | 798 | NGAAUGCCUUCCAAGGAAN | 495-513 | 493 |
| 389 | UAGAUUUCCUUGGAAGGCA | 799 | UGCCUUCCAAGGAAAUCUA | 499-517 | 497 |
| 390 | NAGAUUUCCUUGGAAGGCA | 800 | UGCCUUCCAAGGAAAUCUN | 499-517 | 497 |

TABLE 2-continued

XDH RNAi Agent Antisense Strand and Sense Strand Core Stretch Base Sequences

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 391 | NAGAUUUCCUUGGAAGGCN | 801 | NGCCUUCCAAGGAAAUCUN | 499-517 | 497 |
| 392 | AUAGGAAACAGCAUAUUCU | 802 | AGAAUAUGCUGUUUCCUAU | 888-906 | 886 |
| 393 | UUAGGAAACAGCAUAUUCU | 803 | AGAAUAUGCUGUUUCCUAA | 888-906 | 886 |
| 394 | NUAGGAAACAGCAUAUUCU | 804 | AGAAUAUGCUGUUUCCUAN | 888-906 | 886 |
| 395 | NUAGGAAACAGCAUAUUCN | 805 | NGAAUAUGCUGUUUCCUAN | 888-906 | 886 |
| 396 | UUGAUGAUGUUCCCUCCAA | 806 | UUGGAGGGAACAUCAUCAA | 1119-1137 | 1117 |
| 397 | NUGAUGAUGUUCCCUCCAA | 807 | UUGGAGGGAACAUCAUCAN | 1119-1137 | 1117 |
| 398 | NUGAUGAUGUUCCCUCCAN | 808 | NUGGAGGGAACAUCAUCAN | 1119-1137 | 1117 |
| 399 | UAGAACUUGAAGAAGAAGC | 809 | GCUUCUUCUUCAAGUUCUA | 1617-1635 | 1615 |
| 400 | NAGAACUUGAAGAAGAAGC | 810 | GCUUCUUCUUCAAGUUCUN | 1617-1635 | 1615 |
| 401 | NAGAACUUGAAGAAGAAGN | 811 | NCUUCUUCUUCAAGUUCUN | 1617-1635 | 1615 |
| 402 | UACCAAUGAUAUGCCCAAC | 812 | GUUGGGCAUAUCAUUGGUA | 2066-2084 | 2064 |
| 403 | NACCAAUGAUAUGCCCAAC | 813 | GUUGGGCAUAUCAUUGGUN | 2066-2084 | 2064 |
| 404 | NACCAAUGAUAUGCCCAAN | 814 | NUUGGGCAUAUCAUUGGUN | 2066-2084 | 2064 |
| 405 | UCAUGGUGUUCUGUGUAGA | 815 | UCUACACAGAACACCAUGA | 2372-2390 | 2370 |
| 406 | NCAUGGUGUUCUGUGUAGA | 816 | UCUACACAGAACACCAUGN | 2372-2390 | 2370 |
| 407 | NCAUGGUGUUCUGUGUAGN | 817 | NCUACACAGAACACCAUGN | 2372-2390 | 2370 |
| 408 | UUGAGAGAGAUCCUGGGUG | 818 | CACCCAGGAUCUCUUUCAA | 2686-2704 | 2684 |
| 409 | NUGAGAGAGAUCCUGGGUG | 819 | CACCCAGGAUCUCUUUCAN | 2686-2704 | 2684 |
| 410 | NUGAGAGAGAUCCUGGGUN | 820 | NACCCAGGAUCUCUUUCAN | 2686-2704 | 2684 |
| 411 | UCAUGAUACUGAGAGCUUG | 821 | CAAGCUCUCAGUAUCAUGA | 2997-3015 | 2995 |
| 412 | NCAUGAUACUGAGAGCUUG | 822 | CAAGCUCUCAGUAUCAUGN | 2997-3015 | 2995 |
| 413 | NCAUGAUACUGAGAGCUUN | 823 | NAAGCUCUCAGUAUCAUGN | 2997-3015 | 2995 |
| 414 | UUGUCAACCUCACUCUUCC | 824 | GGAAGAGUGAGGUUGACAA | 3018-3036 | 3016 |
| 415 | NUGUCAACCUCACUCUUCC | 825 | GGAAGAGUGAGGUUGACAN | 3018-3036 | 3016 |
| 416 | NUGUCAACCUCACUCUUCN | 826 | NGAAGAGUGAGGUUGACAN | 3018-3036 | 3016 |
| 417 | UUUCCAACAAUUCUCCUUG | 827 | CAAGGAGAAUUGUUGGAAA | 3043-3061 | 3041 |
| 418 | NUUCCAACAAUUCUCCUUG | 828 | CAAGGAGAAUUGUUGGAAN | 3043-3061 | 3041 |
| 419 | NUUCCAACAAUUCUCCUUN | 829 | NAAGGAGAAUUGUUGGAAN | 3043-3061 | 3041 |
| 420 | UUGAGUUAGUCUCAAAGCU | 830 | AGCUUUGAGACUAACUCAA | 3500-3518 | 3498 |
| 421 | NUGAGUUAGUCUCAAAGCU | 831 | AGCUUUGAGACUAACUCAN | 3500-3518 | 3498 |
| 422 | NUGAGUUAGUCUCAAAGCN | 832 | NGCUUUGAGACUAACUCAN | 3500-3518 | 3498 |
| 423 | AUGACAAUAUCUGUGCGGA | 833 | UCCGCACAGAUAUUGUCAU | 3600-3618 | 3598 |
| 424 | UUGACAAUAUCUGUGCGGA | 834 | UCCGCACAGAUAUUGUCAA | 3600-3618 | 3598 |
| 425 | NUGACAAUAUCUGUGCGGA | 835 | UCCGCACAGAUAUUGUCAN | 3600-3618 | 3598 |

TABLE 2-continued

XDH RNAi Agent Antisense Strand and Sense Strand Core Stretch Base Sequences

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 426 | NUGACAAUAUCUGUGCGGN | 836 | NCCGCACAGAUAUUGUCAN | 3600-3618 | 3598 |
| 427 | UCAUGACAAUAUCUGUGCG | 837 | CGCACAGAUAUUGUCAUGA | 3602-3620 | 3600 |
| 428 | NCAUGACAAUAUCUGUGCG | 838 | CGCACAGAUAUUGUCAUGN | 3602-3620 | 3600 |
| 429 | NCAUGACAAUAUCUGUGCN | 839 | NGCACAGAUAUUGUCAUGN | 3602-3620 | 3600 |
| 430 | UCAAGAAGAUAGAAGCAG | 840 | CUGCUUCUAUCUUCUUUGA | 3879-3897 | 3877 |
| 431 | NCAAGAAGAUAGAAGCAG | 841 | CUGCUUCUAUCUUCUUUGN | 3879-3897 | 3877 |
| 432 | NCAAAGAAGAUAGAAGCAN | 842 | NUGCUUCUAUCUUCUUUGN | 3879-3897 | 3877 |
| 433 | UCACGUUAUUACCUGUGUG | 843 | CACACAGGUAAUAACGUIA | 3932-3950 | 3930 |
| 434 | NCACGUUAUUACCUGUGUG | 844 | CACACAGGUAAUAACGUIN | 3932-3950 | 3930 |
| 435 | NCACGUUAUUACCUGUGUN | 845 | NACACAGGUAAUAACGUIN | 3932-3950 | 3930 |
| 436 | UAGAACUUGAGGUUAUACA | 846 | UGUAUAACCUCAAGUUCUA | 4396-4414 | 4394 |
| 437 | NAGAACUUGAGGUUAUACA | 847 | UGUAUAACCUCAAGUUCUN | 4396-4414 | 4394 |
| 438 | NAGAACUUGAGGUUAUACN | 848 | NGUAUAACCUCAAGUUCUN | 4396-4414 | 4394 |
| 439 | AUGCUUUGCUGUUCAUUGG | 849 | CCAAUGAACAGCAAAGCAU | 4515-4533 | 4513 |
| 440 | UUGCUUUGCUGUUCAUUGG | 850 | CCAAUGAACAGCAAAGCAA | 4515-4533 | 4513 |
| 441 | NUGCUUUGCUGUUCAUUGG | 851 | CCAAUGAACAGCAAAGCAN | 4515-4533 | 4513 |
| 442 | NUGCUUUGCUGUUCAUUGN | 852 | NCAAUGAACAGCAAAGCAN | 4515-4533 | 4513 |
| 443 | UAGUAUAGAUUCAAGGUUA | 853 | UAACCUUGAAUCUAUACUA | 4533-4551 | 4531 |
| 444 | NAGUAUAGAUUCAAGGUUA | 854 | UAACCUUGAAUCUAUACUN | 4533-4551 | 4531 |
| 445 | NAGUAUAGAUUCAAGGUUN | 855 | NAACCUUGAAUCUAUACUN | 4533-4551 | 4531 |
| 446 | AGAGUAAUCUUGCUUUAUG | 856 | CAUAAAGCAAGAUUACUCU | 4668-4686 | 4666 |
| 447 | UGAGUAAUCUUGCUUUAUG | 857 | CAUAAAGCAAGAUUACUCA | 4668-4686 | 4666 |
| 448 | NGAGUAAUCUUGCUUUAUG | 858 | CAUAAAGCAAGAUUACUCN | 4668-4686 | 4666 |
| 449 | NGAGUAAUCUUGCUUUAUN | 859 | NAUAAAGCAAGAUUACUCN | 4668-4686 | 4666 |
| 450 | AUAGCAUCAUUUCUAGGUG | 860 | CACCUAGAAAUGAUGCUAU | 4845-4863 | 4843 |
| 451 | UUAGCAUCAUUUCUAGGUG | 861 | CACCUAGAAAUGAUGCUAA | 4845-4863 | 4843 |
| 452 | NUAGCAUCAUUUCUAGGUG | 862 | CACCUAGAAAUGAUGCUAN | 4845-4863 | 4843 |
| 453 | NUAGCAUCAUUUCUAGGUN | 863 | NACCUAGAAAUGAUGCUAN | 4845-4863 | 4843 |
| 454 | AGACAGAAGAGACAGAGCU | 864 | AGCUCUGUCUCUUCUIUCU | 5236-5254 | 5234 |
| 455 | UGACAGAAGAGACAGAGCU | 865 | AGCUCUGUCUCUUCUIUCA | 5236-5254 | 5234 |
| 456 | NGACAGAAGAGACAGAGCU | 866 | AGCUCUGUCUCUUCUIUCN | 5236-5254 | 5234 |
| 457 | NGACAGAAGAGACAGAGCN | 867 | NGCUCUGUCUCUUCUIUCN | 5236-5254 | 5234 |
| 458 | AGUAAGAAAACCAAGCCUU | 868 | ($A^{2N}$)AGGCUUGGUUUUCUUACU | 5413-5431 | 5411 |
| 459 | UGUAAGAAAACCAAGCCUU | 869 | ($A^{2N}$)AGGCUUGGUUUUCUUACA | 5413-5431 | 5411 |
| 460 | NGUAAGAAAACCAAGCCUU | 870 | ($A^{2N}$)AGGCUUGGUUUUCUUACN | 5413-5431 | 5411 |

TABLE 2-continued

XDH RNAi Agent Antisense Strand and Sense Strand Core Stretch Base Sequences

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 461 | NGUAAGAAAACCAAGCCUN | 871 | NAGGCUUGGUUUUCUUACN | 5413-5431 | 5411 |
| 462 | AGUAAGAAAACCAAGCCUU | 872 | AAGGCUUGGUUUUCUUACU | 5413-5431 | 5411 |
| 463 | UGUAAGAAAACCAAGCCUU | 873 | AAGGCUUGGUUUUCUUACA | 5413-5431 | 5411 |
| 464 | NGUAAGAAAACCAAGCCUU | 874 | AAGGCUUGGUUUUCUUACN | 5413-5431 | 5411 |
| 465 | NGUAAGAAAACCAAGCCUN | 875 | NAGGCUUGGUUUUCUUACN | 5413-5431 | 5411 |
| 466 | UAUACUUGGAGAGCAUCAC | 876 | GUGAUGCUCUCCAAGUAUA | 233-251 | 231 |
| 467 | NAUACUUGGAGAGCAUCAC | 877 | GUGAUGCUCUCCAAGUAUN | 233-251 | 231 |
| 468 | NAUACUUGGAGAGCAUCAN | 878 | NUGAUGCUCUCCAAGUAUN | 233-251 | 231 |
| 469 | UUGCAGACGAUCAUACUUG | 879 | CAAGUAUGAUCGUCUICAA | 244-262 | 242 |
| 470 | NUGCAGACGAUCAUACUUG | 880 | CAAGUAUGAUCGUCUICAN | 244-262 | 242 |
| 471 | NUGCAGACGAUCAUACUUN | 881 | NAAGUAUGAUCGUCUICAN | 244-262 | 242 |
| 472 | UUGAAUAAAACUCUCAUGC | 882 | GCAUGAGAGUUUUAUUCAA | 1386-1404 | 1384 |
| 473 | NUGAAUAAAACUCUCAUGC | 883 | GCAUGAGAGUUUUAUUCAN | 1386-1404 | 1384 |
| 474 | NUGAAUAAAACUCUCAUGN | 884 | NCAUGAGAGUUUUAUUCAN | 1386-1404 | 1384 |
| 475 | UUGAAUAAAACUCUCAUGC | 885 | GCAUGAGAGUUUU(A$^{2N}$)UUCAA | 1386-1404 | 1384 |
| 476 | NUGAAUAAAACUCUCAUGC | 886 | GCAUGAGAGUUUU(A$^{2N}$)UUCAN | 1386-1404 | 1384 |
| 477 | NUGAAUAAAACUCUCAUGN | 887 | NCAUGAGAGUUUU(A$^{2N}$)UUCAN | 1386-1404 | 1384 |
| 478 | AGAAAAGUGGACGAUCUUG | 888 | CAAGAUCGUCCACUUUUCU | 265-283 | 263 |
| 479 | UGAAAAGUGGACGAUCUUG | 889 | CAAGAUCGUCCACUUUUCU | 265-283 | 263 |
| 480 | NGAAAAGUGGACGAUCUUG | 890 | CAAGAUCGUCCACUUUUCN | 265-283 | 263 |
| 481 | NGAAAAGUGGACGAUCUUN | 891 | NAAGAUCGUCCACUUUUCN | 265-283 | 263 |
| 482 | UAGUUGUCACUGCAACAUG | 892 | CAUGUUGCAGUGACAACUA | 320-338 | 318 |
| 483 | NAGUUGUCACUGCAACAUG | 893 | CAUGUUGCAGUGACAACUN | 320-338 | 318 |
| 484 | NAGUUGUCACUGCAACAUN | 894 | NAUGUUGCAGUGACAACUN | 320-338 | 318 |
| 485 | AUUCCUUCCACAGUUGUCA | 895 | UGACAACUGUGGAAGGAAU | 330-348 | 328 |
| 486 | UUUCCUUCCACAGUUGUCA | 896 | UGACAACUGUGGAAGGAAA | 330-348 | 328 |
| 487 | NUUCCUUCCACAGUUGUCA | 897 | UGACAACUGUGGAAGGAAN | 330-348 | 328 |
| 488 | NUUCCUUCCACAGUUGUCN | 898 | NGACAACUGUGGAAGGAAN | 330-348 | 328 |
| 489 | UGCAUUCUCAAUCUCCUCC | 899 | GGAGGAGAUUGAGAAUGCA | 484-502 | 482 |
| 490 | NGCAUUCUCAAUCUCCUCC | 900 | GGAGGAGAUUGAGAAUGCN | 484-502 | 482 |
| 491 | NGCAUUCUCAAUCUCCUCN | 901 | NGAGGAGAUUGAGAAUGCN | 484-502 | 482 |
| 492 | UUCAAUGCCAAUCUCCGUG | 902 | CACGGAGAUUGGCAUUGAA | 859-877 | 857 |
| 493 | NUCAAUGCCAAUCUCCGUG | 903 | CACGGAGAUUGGCAUUGAN | 859-877 | 857 |
| 494 | NUCAAUGCCAAUCUCCGUN | 904 | NACGGAGAUUGGCAUUGAN | 859-877 | 857 |
| 495 | AUAUUCUUGAACUUCAUCU | 905 | AGAUGAAGUUCAAGAAU(A$^{2N}$)U | 876-894 | 874 |

TABLE 2-continued

XDH RNAi Agent Antisense Strand and Sense Strand Core Stretch Base Sequences

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 496 | UUAUUCUUGAACUUCAUCU | 906 | AGAUGAAGUUCAAGAAU(A$^{2N}$)A | 876-894 | 874 |
| 497 | NUAUUCUUGAACUUCAUCU | 907 | AGAUGAAGUUCAAGAAU(A$^{2N}$)N | 876-894 | 874 |
| 498 | NUAUUCUUGAACUUCAUCN | 908 | NGAUGAAGUUCAAGAAU(A$^{2N}$)N | 876-894 | 874 |
| 499 | AUAUUCUUGAACUUCAUCU | 909 | AGAUGAAGUUCAAGAAUAU | 876-894 | 874 |
| 500 | UUAUUCUUGAACUUCAUCU | 910 | AGAUGAAGUUCAAGAAUAA | 876-894 | 874 |
| 501 | NUAUUCUUGAACUUCAUCU | 911 | AGAUGAAGUUCAAGAAUAN | 876-894 | 874 |
| 502 | NUAUUCUUGAACUUCAUCN | 912 | NGAUGAAGUUCAAGAAUAN | 876-894 | 874 |
| 503 | UUAUGGAGAGCAGUAUCUC | 913 | GAGAUACUGCUCUCCAUAA | 1280-1298 | 1278 |
| 504 | NUAUGGAGAGCAGUAUCUC | 914 | GAGAUACUGCUCUCCAUAN | 1280-1298 | 1278 |
| 505 | NUAUGGAGAGCAGUAUCUN | 915 | NAGAUACUGCUCUCCAUAN | 1280-1298 | 1278 |
| 506 | UAAUGCUGAGAAAUACUCC | 916 | GGAGUAUUUCUCAGCAUUA | 1321-1339 | 1319 |
| 507 | NAAUGCUGAGAAAUACUCC | 917 | GGAGUAUUUCUCAGCAUUN | 1321-1339 | 1319 |
| 508 | NAAUGCUGAGAAAUACUCN | 918 | NGAGUAUUUCUCAGCAUUN | 1321-1339 | 1319 |
| 509 | UGAAUGCUGAGAAAUACUC | 919 | GAGUAUUUCUCAGCAUUCA | 1322-1340 | 1320 |
| 510 | NGAAUGCUGAGAAAUACUC | 920 | GAGUAUUUCUCAGCAUUCN | 1322-1340 | 1320 |
| 511 | NGAAUGCUGAGAAAUACUN | 921 | NAGUAUUUCUCAGCAUUCN | 1322-1340 | 1320 |
| 512 | UCAAUGUCAUCUUCUCUCC | 922 | GGAGAGAAGAUGACAUUGA | 1353-1371 | 1351 |
| 513 | NCAAUGUCAUCUUCUCUCC | 923 | GGAGAGAAGAUGACAUUGN | 1353-1371 | 1351 |
| 514 | NCAAUGUCAUCUUCUCUCN | 924 | NGAGAGAAGAUGACAUUGN | 1353-1371 | 1351 |
| 515 | ACAAAUUCCAGUUAUGUUA | 925 | UAACAUAACUGGAAUUUGU | 2008-2026 | 2006 |
| 516 | UCAAAUUCCAGUUAUGUUA | 926 | UAACAUAACUGGAAUUUGA | 2008-2026 | 2006 |
| 517 | NCAAAUUCCAGUUAUGUUA | 927 | UAACAUAACUGGAAUUUGN | 2008-2026 | 2006 |
| 518 | NCAAAUUCCAGUUAUGUUN | 928 | NAACAUAACUGGAAUUUGN | 2008-2026 | 2006 |
| 519 | UUCAAUUGUGAUAAUGGCU | 929 | AGCCAUUAUCACAAUUGAA | 2158-2176 | 2156 |
| 520 | NUCAAUUGUGAUAAUGGCU | 930 | AGCCAUUAUCACAAUUGAN | 2158-2176 | 2156 |
| 521 | NUCAAUUGUGAUAAUGGCN | 931 | NGCCAUUAUCACAAUUGAN | 2158-2176 | 2156 |
| 522 | AACAUUUUUGCAACAAAGC | 932 | GCUUUGUUGCAAAAAUGUU | 2400-2418 | 2398 |
| 523 | UACAUUUUUGCAACAAAGC | 933 | GCUUUGUUGCAAAAAUGUA | 2400-2418 | 2398 |
| 524 | NACAUUUUUGCAACAAAGC | 934 | GCUUUGUUGCAAAAAUGUN | 2400-2418 | 2398 |
| 525 | NACAUUUUUGCAACAAAGN | 935 | NCUUUGUUGCAAAAAUGUN | 2400-2418 | 2398 |
| 526 | UCAACAUUUUUGCAACAAA | 936 | UUUGUUGCAAAAAUGUUGA | 2402-2420 | 2400 |
| 527 | NCAACAUUUUUGCAACAAA | 937 | UUUGUUGCAAAAAUGUUGN | 2402-2420 | 2400 |
| 528 | NCAACAUUUUUGCAACAAN | 938 | NUUGUUGCAAAAAUGUUGN | 2402-2420 | 2400 |
| 529 | UUUCACUCGAACCACAAUC | 939 | GAUUGUGGUUCGAGUGAAA | 2437-2455 | 2435 |
| 530 | NUUCACUCGAACCACAAUC | 940 | GAUUGUGGUUCGAGUGAAN | 2437-2455 | 2435 |

TABLE 2-continued

XDH RNAi Agent Antisense Strand and Sense Strand Core Stretch Base Sequences

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 531 | NUUCACUCGAACCACAAUN | 941 | NAUUGUGGUUCGAGUGAAN | 2437-2455 | 2435 |
| 532 | UUGGAAGGCAUUCUCAAUC | 942 | GAUUGAGAAUGCCUUCCAA | 490-508 | 488 |
| 533 | NUGGAAGGCAUUCUCAAUC | 943 | GAUUGAGAAUGCCUUCCAN | 490-508 | 488 |
| 534 | NUGGAAGGCAUUCUCAAUN | 944 | NAUUGAGAAUGCCUUCCAN | 490-508 | 488 |

(N = any nucleobase; 1 = hypoxanthine (inosine nucleotide); ($A^{2N}$) = 2-aminoadenine nucleotide)

The XDH RNAi agent sense strands and antisense strands that comprise or consist of the sequences in Table 2 can be modified nucleotides or unmodified nucleotides. In some aspects, the XDH RNAi agents having the sense and antisense strand sequences that comprise or consist of the sequences in Table 2 are all or substantially all modified nucleotides.

In some aspects, the antisense strand of an XDH RNAi agent disclosed herein differs by 0, 1, 2, or 3 nucleotides from any of the antisense strand sequences in Table 2. In some aspects, the sense strand of an XDH RNAi agent disclosed herein differs by 0, 1, 2, or 3 nucleotides from any of the sense strand sequences in Table 2.

As used herein, each N listed in a sequence disclosed in Table 2 may be independently selected from any and all nucleobases (including those found on both modified and unmodified nucleotides). In some aspects, an N nucleotide listed in a sequence disclosed in Table 2 has a nucleobase that is complementary to the N nucleotide at the corresponding position on the other strand. In some aspects, an N nucleotide listed in a sequence disclosed in Table 2 has a nucleobase that is not complementary to the N nucleotide at the corresponding position on the other strand. In some aspects, an N nucleotide listed in a sequence disclosed in Table 2 has a nucleobase that is the same as the N nucleotide at the corresponding position on the other strand. In some aspects, an N nucleotide listed in a sequence disclosed in Table 2 has a nucleobase that is different from the N nucleotide at the corresponding position on the other strand.

Certain modified XDH RNAi agent antisense strands, as well as their underlying unmodified nucleobase sequences, are provided in Table 3. Certain modified XDH RNAi agent sense strands, as well as their underlying unmodified nucleobase sequences, are provided in Table 4. In forming XDH RNAi agents, each of the nucleotides in each of the underlying base sequences listed in Tables 3 and 4, as well as in Table 2, above, can be a modified nucleotide.

The XDH RNAi agents described herein are formed by annealing an antisense strand with a sense strand. A sense strand containing a sequence listed in Table 2 or Table 4, can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some aspects, an XDH RNAi agent antisense strand comprises a nucleotide sequence of any of the sequences in Table 2 or Table 3.

In some aspects, an XDH RNAi agent comprises or consists of a duplex having the nucleobase sequences of the sense strand and the antisense strand of any of the sequences in Table 2, Table 3, or Table 4.

Examples of antisense strands containing modified nucleotides are provided in Table 3 and Table 5C. Examples of sense strands containing modified nucleotides are provided in Table 4 and Table 5C.

As used in Tables 3, 4, and 5C the following notations are used to indicate modified nucleotides and linking groups:
A=adenosine-3'-phosphate;
C=cytidine-3'-phosphate;
G=guanosine-3'-phosphate;
U=uridine-3'-phosphate
I=inosine-3'-phosphate
a=2'-O-methyladenosine-3'-phosphate
as =2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
i=2'-O-methylinosine-3'-phosphate
is =2'-O-methylinosine-3'-phosphorothioate
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
$A_{UNA}$=2',3'-seco-adenosine-3'-phosphate, see Table 6
$A_{UNAS}$=2',3'-seco-adenosine-3'-phosphorothioate, see Table 6
$C_{UNA}$=2',3'-seco-cytidine-3'-phosphate, see Table 6
$C_{UNAS}$=2',3'-seco-cytidine-3'-phosphorothioate, see Table 6
$G_{UNA}$=2',3'-seco-guanosine-3'-phosphate, see Table 6
$G_{UNAS}$=2',3'-seco-guanosine-3'-phosphorothioate, see Table 6
$U_{UNA}$=2',3'-seco-uridine-3'-phosphate, see Table 6

U$_{UNAS}$=2',3'-seco-uridine-3'-phosphorothioate, see Table 6 a_2N=2'-O-methyl-2-aminoadenosine-3'-phosphate, see Table 6 a_2Ns=2'-O-methyl-2-aminoadenosine-3'-phosphorothioate, see Table 6

(invAb)=inverted abasic deoxyribonucleotide, see Table 6

(invAb)s=inverted abasic deoxyribonucleotide-5'-phosphorothioate, see Table 6 cPrpa=5'-cyclopropyl phosphonate-2'-O-methyladenosine-3'-phosphate (see Table 6)

cPrpas=5'-cyclopropyl phosphonate-2'-O-methyladenosine-3'-phosphorothioate (see Table 6)

cPrpu=5'-cyclopropyl phosphonate-2'-O-methyluridine-3'-phosphate (see Table 6)

cPrpus=5'-cyclopropyl phosphonate-2'-O-methyluridine-3'-phosphorothioate (see Table 6)

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides. Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Additionally, for the various aspects disclosed herein, when viewing the respective strand 5'→3', the inverted abasic residues are inserted such that the 3' position of the deoxyribose is linked at the 3' end of the preceding monomer on the respective strand (see, e.g., Table 6). Moreover, as the person of ordinary skill would readily understand and appreciate, while the phosphorothioate chemical structures depicted herein typically show the anion on the sulfur atom, the inventions disclosed herein encompass all phosphorothioate tautomers and resonance structures (e.g., where the sulfur atom has a double-bond and the anion is on an oxygen atom). Unless expressly indicated otherwise herein, such understandings of the person of ordinary skill in the art are used when describing the XDH RNAi agents and compositions of XDH RNAi agents disclosed herein.

Certain examples of targeting ligands, targeting groups, and linking groups used with the XDH RNAi agents disclosed herein are provided below in Table 6. More specifically, targeting groups and linking groups (which together can form a targeting ligand) include (NAG37) and (NAG37)s, for which their chemical structures are provided below in Table 6. Each sense strand and/or antisense strand can have any targeting ligands, targeting groups, or linking groups listed herein, as well as other groups, conjugated to the 5' and/or 3' end of the sequence.

TABLE 3

XDH RNAi Agent Strand Sequences

| Antisense Strand ID: | Modified Antisense Strand (5' → 3') | SEQ ID NO. | Underlying Base Sequence (5' → 3') (Shown as an Unmodified Nucleotide Sequence) | SEQ ID NO. |
| --- | --- | --- | --- | --- |
| AM13029-AS | usUfsgsFgaAfgGfcAfuUgcUfcAfaUgcUfsc | 945 | UUGGAAGGCAUUCUCAAUCUC | 1352 |
| AM13031-AS | usUfsggaAfgGfCfauucUfcAfaucusc | 946 | UUGGAAGGCAUUCUCAAUCUC | 1352 |
| AM13033-AS | asAfscsUfuGfaAfgAfaGfaAfgCfuGfaGfsg | 947 | AACUUGAAGAAGAAGCUGAGG | 1353 |
| AM13035-AS | asGfsasAfcUfuGfaAfgAfaGfaAfgCfuGgsc | 948 | AGAACUUGAAGAAGAAGCUGC | 1354 |
| AM13037-AS | usGfsusAfgAfaCfuUfgAfaGfaAfgfAfaGfsc | 949 | UGUAGAACUUGAAGAAGAAGC | 1355 |
| AM13039-AS | usCfsasUfaGfgUfgAfuUfuUfcAfcCfcCfsu | 950 | UCAUAGGUGAUUUUCACCCCU | 1356 |
| AM13041-AS | usUfsusCfaUfaGfgUfgAfuUfuUfcAfcCfsc | 951 | UUUCAUAGGUGAUUUUCACCC | 1357 |
| AM13043-AS | usCfsusUfcAfuAfgGfuGfaUfuUfuCfaCfsc | 952 | UCUUCAUAGGUGAUUUUCACC | 1358 |
| AM13045-AS | usUfscsUfuCfaUfaGfgUfgAfuUfuUfcAfsc | 953 | UUCUUCAUAGGUGAUUUUCAC | 1359 |
| AM13047-AS | asAfsusUfgUfgAfuAfaUfgGfcUfgGfuAfsg | 954 | AAUUGUGAUAAUGGCUGGUAG | 1360 |
| AM13049-AS | usCfsasUfaAfaAfgGfaGfuUfgUfuCfuUfsc | 955 | UCAUAAAAGGAGUUGUUCUUC | 1361 |
| AM13051-AS | usCfscsAfuAfaAfaGfgAgfUfuGfuUfcUfsc | 956 | UCCAUAAAAGGAGUUGUUCUC | 1362 |
| AM13053-AS | usAfsCfsgUfgUfuAgfUgfCfuUfgUfcUfsc | 957 | UACAGUGUUAGUGCUUGUCUC | 1363 |
| AM13055-AS | usUfsgsUfgUfaCfaUfaCfuCfaUfgAgcGfsa | 958 | UUGUGUACAUACUCAUGACGA | 1364 |
| AM13057-AS | usAfscsCfaGfuUfaUfcAfgCfaUfgUfcCfsu | 959 | UACCAGUUAUCAGCAUGUCCU | 1365 |
| AM13059-AS | usAfsusGfaAfgCfcAfaCfcUfuGfuAfuCfsc | 960 | UAUGAAGCCAACCUUGUAUCC | 1366 |
| AM13061-AS | usCfsusUfcAfuGfaAfgCgcAfaCfcUfuGfsc | 961 | UCUUCAUGAAGCCAACCUUGC | 1367 |
| AM13063-AS | usUfscsUfuCfaUfgAfaGfcCfaAfcCfuUfsg | 962 | UUCUUCAUGAAGCCAACCUUG | 1368 |
| AM13065-AS | usAfsgsUfcUfuCfaUfgAfaGfcCfaAfcCfsu | 963 | UAGUCUUCAUGAAGCCAACCU | 1369 |
| AM13067-AS | usCfsusUfuUfuCfcAfaCfaAfuUfcUfcCfsu | 964 | UCUUUUCCAACAAUUCUCCU | 1370 |
| AM13069-AS | usUfscsUfuCfuUfcAfgAfgCfaAgGfcAfsc | 965 | UUCUACUUCAGAGCAAGCCAC | 1371 |
| AM13071-AS | usAfsusUfuCfuAfcUfuCfaGfaGfcAfaGfsc | 966 | UAUUUCUACUUCAGAGCAAGC | 1372 |
| AM13073-AS | usGfsusCfcAfaUfaUfcAfaUfgGfcAfgGfsg | 967 | UGUCCAAUAUCAAUGGCAGGG | 1373 |
| AM13164-AS | usCfsasGfaAfaAfgUfgGfaCfgAfuCfuUfsg | 968 | UCAGAAAAGUGGACGAUCUUG | 1374 |
| AM13166-AS | asCfsasAfcAfuUfaUfcUfgCfuUfcGfgAfsc | 696 | ACAACAUUAUCUGCUUCGGAC | 1375 |
| AM13168-AS | usCfsasUfaAfuAfcUfcUfgAgfAgfAgAfsc | 970 | UCAUAAUACUCUGAGAGAC | 1376 |
| AM13170-AS | usCfsusUfaUfuCfcAfaAfcUfuGfgUfgGfsg | 971 | UCUUAUUCCAAACUUGGUGGG | 1377 |
| AM13172-AS | usAfsgsUfaAfuCfuUfgCfuUfuAfuGfcAfsg | 972 | UAGUAAUCUUGCUUUAUGCAG | 1378 |
| AM13174-AS | asAfsasGfaAfaUfcUfaGfaAfcAfuUfgUfsc | 973 | AAAGAAAUCUAGAACAUUGUC | 1379 |
| AM13176-AS | usCfsasgaaaagugCfaCfgAfuCfuUfsg | 974 | UCAGAAAAGUGGACGAUCUUG | 1374 |
| AM13177-AS | asCfsasacauUfaUfcUfgCfuUfcggasc | 975 | ACAACAUUAUCUGCUUCGGAC | 1375 |
| AM13179-AS | usCfsasUfaAfuacucUfgAfgAfgagasc | 976 | UCAUAAUACUCUGAGAGAC | 1376 |
| AM13181-AS | asAfsasGfaAfaUfcUfaGfaAfcAfuUfuUfsc | 977 | AAAGAAAUCUAGAACAUUUUC | 1380 |
| AM13204-AS | usCfsasGfaAfaagugGfaCfgAfuCfuUfsg | 978 | UCAGAAAAGUGGACGAUCUUG | 1374 |
| AM13205-AS | usCfsasUfaAfuacucUfgAfgAfgAfgAfsc | 979 | UCAUAAUACUCUGAGAGAC | 1376 |
| AM13206-AS | usCfsusUfaUfuccaaAfcUfuGfgUfggsg | 980 | UCUUAUUCCAAACUUGGUGGG | 1377 |

TABLE 3-continued

XDH RNAi Agent Strand Sequences

| Antisense Strand ID: | Modified Antisense Strand (5' → 3') | SEQ ID NO. | Underlying Base Sequence (5' → 3') (Shown as an Unmodified Nucleotide Sequence) | SEQ ID NO. |
|---|---|---|---|---|
| AM13207-AS | usAfsgsUfaAfucuugCfuUfuAfuGfcAgsg | 981 | UAGUAAUCUUGCUUUAUGCAG | 1378 |
| AM13600-AS | usAfsasCfuUfcacucAfuCfcAfgCfacsu | 982 | UAACUUCACUCAUCCAGCACU | 1381 |
| AM13602-AS | usCfsasAfcuucacuCfaUfcCfagcasc | 983 | UCAACUUCACUCAUCCAGCAC | 1382 |
| AM13604-AS | usGfscsAfacuucacUfcAfuCfcagcsa | 984 | UGCAACUUCACUCAUCCAGCA | 1383 |
| AM13648-AS | usGfsasucauacuuGfgAfgAfgcausc | 985 | UGAUCAUACUUGGAGAGCAUC | 1384 |
| AM13650-AS | usCfsusuguucugcAfgAfcGfaucasc | 986 | UCUUGUUCUGCAGACGAUCAC | 1385 |
| AM13652-AS | usGfsasucuuguucUfgCfaGfacgasc | 987 | UGAUCUUGUUCUGCAGACGAC | 1386 |
| AM13654-AS | usAfsgsuaaaguugCfaCfuGfgcgasc | 988 | UAGUAAAGUUGCACUGGCGAC | 1387 |
| AM13656-AS | usAfsasCfacaaguaAfcCfuUfauccsu | 989 | UAACACAAGUAACCUUAUCCU | 1388 |
| AM13658-AS | usCfsasAfuugugauAfaUfgGfcuggsu | 990 | UCAAUUGUGAUAAUGGCUGGU | 1389 |
| AM13660-AS | usAfsgscaugauacUfgAfgAfgcuusg | 991 | UAGCAUGAUACUGAGAGCUUG | 1390 |
| AM13662-AS | asAfscsUfugucaacCfuCfaCfucuusc | 992 | AACUUGUCAACCUCACUCUUC | 1391 |
| AM13664-AS | usAfsasCfuugucaaCfcUfcAfcucusc | 993 | UAACUUGUCAACCUCACUCUC | 1392 |
| AM13666-AS | usAfsAfsCfaauucucCfuUfgUfugaasc | 994 | UAACAAUUCUCCUUGUUGAAC | 1393 |
| AM13668-AS | usCfsasuguucuguGfuAfuUfguucsc | 995 | UCAUGUUCUGUGGUAUGUUCC | 1394 |
| AM13670-AS | usAfscsUfuUfaauagAfuCfcAfuguusc | 996 | UACUUUAAUGAUCCAUGUUC | 1395 |
| AM13672-AS | usGfsascuuuAfaUfaGfaUfcCfaugusc | 997 | UGACUUUAAUAGAUCCAUGUC | 1396 |
| AM13674-AS | usGfscsauauucacCfaUfuUfaggcsa | 998 | UGCAUAUUCACCAUUUAGGCA | 1397 |
| AM13676-AS | usGfsusuUfuaagcuuCfuAfgAfgguusc | 999 | UGUUUAAGCUUCUAGAGGUUC | 1398 |
| AM13678-AS | usUfsgsuucauuggUfuUfgAfaggcsc | 1000 | UUGUUCAUUGGUUUGAAGGCC | 1399 |
| AM13680-AS | usUfsasUfgCfuuugcUfgUfuCfauugsg | 1001 | UUAUGCUUUGCUGUUCAUUGG | 1400 |
| AM13682-AS | usGfsusUfaugcuuuGfcUfgUfuUfcausc | 1002 | UGUUUAUGCUUUGCUGUUCAUC | 1401 |
| AM13684-AS | asGfsgsUfuaugcuuUfgCfuGfuucasc | 1003 | AGGUUAUGCUUUGCUGUUCAC | 1402 |
| AM13686-AS | usAfsasggUfuaugcUfuUfgCfuguusc | 1004 | UAAGGUUAUGCUUUGCUGUUC | 1403 |
| AM13688-AS | asGfsasUfucaagguUfaUfgCfuuugsc | 1005 | AGAUUCAAGGUUAUGCUUUGC | 1404 |
| AM13690-AS | usUfscsAfauaauugAfgUfuGfguugsg | 1006 | UUCAAUAAUUGAGUUGGUUGG | 1405 |
| AM13692-AS | asGfsusAfaaaugGfaUfcAfcAfggaasg | 1007 | AGUAAAAUGGAUCACAGGAAG | 1406 |
| AM13694-AS | usCfsasUfaugaagUfaAfgAfaaacsc | 1008 | UCAUAUGACAGUAAGAAAACC | 1407 |
| AM13696-AS | usUfsgsgaaggcauUfcUfcGfaucusc | 1009 | UUGGAAGGCAUUCUCGAUCUC | 1408 |
| AM13698-AS | usCfsasUfcauugaaAfaUfgCfcagusc | 1010 | UCAUCAUUGAAAAUGCCAGUC | 1409 |
| AM13700-AS | asAfsasGfacaguuuCfaUfcAfuugasc | 1011 | AAAGACAGUUUCAUCAUUGAC | 1410 |
| AM13702-AS | asAfscsAfcaaguaaCfuCfuCfauccusc | 1012 | AACACAAGUAACCUCAUCCUC | 1411 |
| AM13704-AS | asGfsascaacauugUfcAfgCfuucasg | 1013 | AGACAACAUUGUCAGCUUCAG | 1412 |
| AM13706-AS | usCfsasAfcaucuuuGfcAfaUfaaagsc | 1014 | UCAACAUCUUUGCAAUAAAGC | 1413 |
| AM13708-AS | asGfsasUfuaguuuuAfcAfaAfuccusc | 1015 | AGAUUAGUCUUACAAAUCCUC | 1414 |
| AM13710-AS | usCfsusUfauccaaAfcUfuAfgucgsg | 1016 | UCUUAUUCCAAACUUAGUCGG | 1415 |
| AM13712-AS | usCfsasGfaaaagaaAfgUfgUfgaagsc | 1017 | UCAGAAAAGAAAGUGUGAAGC | 1416 |
| AM13714-AS | usAfsgsAfguuugucUfcAfaAfgcugsc | 1018 | UAGAGUUUGUCUCAAAGCUGC | 1417 |
| AM13716-AS | usUfsgsUfuaagcagUfcAfuUfcUfcusc | 1019 | UUGUUAAGCAGUCAUUCUCUC | 1418 |
| AM13718-AS | usUfsgsGfaaaucugGfaUfaCfuacgsg | 1020 | UUGGAAAUCUGGAUACUACGG | 1419 |
| AM13720-AS | usCfsusUfgaaaaugCfcAfuCfcugcsu | 1021 | UCUUGAAAUGCCAUCCUGCU | 1420 |
| AM13722-AS | asUfsgsAfuuuggauCfaCfaAfuugusc | 1022 | AUGAUUUGGAUCACAAUUGUC | 1421 |
| AM13724-AS | usAfsgsAfauuacucAffaAfCfugccsa | 1023 | UAGAAUUACUCAAAACUGCCA | 1422 |
| AM13726-AS | usGfsasucaaAffAfuGfgAfcUfcagasc | 1024 | UGAUCAAAAUGGACUCAGAC | 1423 |
| AM13728-AS | usAfsasGfaaagcauGfcAfgAfucuasg | 1025 | UAAGAAAGCAUGCAGAUCUAG | 1424 |
| AM13730-AS | usCfsasgsgauauaagCfuCfuCfugaasg | 1026 | UCAGAUAUAAGCUCUCUGAAG | 1425 |
| AM13747-AS | usAfsusGfaagccaaCffCfuGfuAfucsc | 1027 | UAUGAAGCCAACCUUGUAUCC | 1366 |
| AM13748-AS | usAfsusGfaagccaaCfcUfuGfuaucsc | 1028 | UAUGAAGCCAACCUUGUAUCC | 1366 |
| AM13749-AS | usAfsusGfaagC$_{UNA}$caaCfcUfuGfuaucsc | 1029 | UAUGAAGCCAACCUUGUAUCC | 1366 |
| AM13753-AS | usAfsusGfaagucaaCfcUfuGfuaucsc | 1030 | UAUGAAGUCAACCUUGUAUCC | 1426 |
| AM13754-AS | usAfsusGfaagcuaaCfcUfuGfuaucsc | 1031 | UAUGAAGCUAACCUUGUAUCC | 1427 |
| AM13755-AS | cPrpusAfsusGfaagccaaCfcUfuGfuaucsc | 1032 | UAUGAAGCCAACCUUGUAUCC | 1366 |
| AM13758-AS | usCfsusUfcaugaagCfcAfaCfcuugsc | 1033 | UCUUCAUGAAGCCAACCUUGC | 1367 |
| AM13759-AS | cPrpusCfsusUfcaugaagCfcAfaCfcuugsc | 1034 | UCUUCAUGAAGCCAACCUUGC | 1367 |
| AM13761-AS | usCfsusUfcaU$_{UNA}$gaagCfcAfaCfcuugsc | 1035 | UCUUCAUGAAGCCAACCUUGC | 1367 |
| AM13858-AS | usGfsgsAfuCfugcauUfuUfcUfcCfcasc | 1036 | UGGAUCUGCAUUUUCUCCCAC | 1428 |
| AM13860-AS | usCfscsAfaAfagggUfgUfcUfcUfggsa | 1037 | UCCAAAGGGUUGUCUCUGGA | 1429 |
| AM13862-AS | usAfsgsAfcGfaucauAfcUfuGfgAfgasg | 1038 | UAGACGAUCAUACUUGGAGAG | 1430 |
| AM13864-AS | usCfscsUfaUfuccuuCfcAfcAfguusgc | 1039 | UCCUAUUCCUUCCACAGUUGC | 1431 |
| AM13866-AS | usAfscsAfuAfcucauGfaCfgAfuGfccsa | 1040 | UACACUCAUGACGAUGCCA | 1432 |
| AM13868-AS | usCfsasCfaGfauuucCfuUfgGfaAfggsc | 1041 | UCACAGAUUUCCUUGGAAGGC | 1433 |
| AM13870-AS | usGfsasAfcUfucaucUfcAfaUfgccsc | 1042 | UGAACUUCAUCUCAAUGCCAC | 1434 |
| AM13872-AS | asGfscsAfuAfuucuuGfaAfcUfuCfausc | 1043 | AGCAUAUUCUUGAACUUCAUC | 1435 |
| AM13874-AS | usCfsasUfaGfgaaacAfgCfaUfaUfucsc | 1044 | UCAUAGGAAACAGCAUAUUCC | 1436 |
| AM13876-AS | usGfsgsAfuCfucuauGfgAfgAfgCfagsc | 1045 | UGGAUCUCUAUGGAGAGCAGC | 1437 |
| AM13878-AS | usUfsusGfaAfugcugAfgAfgAfaUfacsc | 1046 | UUUGAUGCUGAGAAAUACUC | 1438 |
| AM13880-AS | usCfsusAfuGfgacuuGfaUfcUfuGfgcsg | 1047 | UCUAUGGACUUGAUCUUGGCG | 1439 |
| AM13882-AS | asUfsgsAfaCfaaacAfaAfcCfcUfgsga | 1048 | AUGAACAAACAAACCCUGGA | 1440 |
| AM13884-AS | usGfsgsUfaGfuucuuCfaUfaGfgUfgasc | 1049 | UGGUAGUUCUUCAUAGGUGAC | 1441 |
| AM13886-AS | usGfsasUfaAfuggcuGfgUfaGfuUfcsc | 1050 | UGAUAAUGGCUGGUAGUUCUC | 1442 |
| AM13888-AS | usCfsusCfaAfuugugAfuAfaUfgGfcusg | 1051 | UCUCAAUGUGAUAAUGGCUG | 1443 |
| AM13890-AS | usCfsusUfcUfcgauCfuUfcAfgCfucsa | 1052 | UCUUCUCGAUCUUCAGCUCA | 1444 |
| AM13892-AS | usUfsusGfgAfacagcAfaUfgGfuGfcasg | 1053 | UUUGGAACAGCAAUGGUGCAG | 1445 |

TABLE 3-continued

XDH RNAi Agent Strand Sequences

| Antisense Strand ID: | Modified Antisense Strand (5' → 3') | SEQ ID NO. | Underlying Base Sequence (5' → 3') (Shown as an Unmodified Nucleotide Sequence) | SEQ ID NO. |
|---|---|---|---|---|
| AM13894-AS | usGfsusAfgAfcacaaAfgAfgCfuCfcasc | 1054 | UGUAGACACAAAGAGCUCCAC | 1446 |
| AM13896-AS | usCfsusGfuUfuagacAfcAfaAfgAfgcsu | 1055 | UCUGUGUAGACACAAAGAGCU | 1447 |
| AM13898-AS | usUfscsCfaUfaauacUfcUfgAfgAfgasg | 1056 | UUCCAUAAUACUCUGAGAGAG | 1448 |
| AM13900-AS | usCfsusCfgUfuccauAfaUfaCfuCfugsc | 1057 | UCUCGUUCCAUAAUACUCUGC | 1449 |
| AM14175-AS | cPrpusUfsgsAfaAfcaaaCfaAfcCfcufggsa | 1058 | UUGAAACAAACAAACCCUGGA | 1450 |
| AM14176-AS | cPrpusUfscsCfaUfaauacUfcUfgAfgAfgasg | 1059 | UUCCAUAAUACUCUGAGAGAG | 1448 |
| AM14204-AS | asAfsusGfaaacaaaCfaAfaCfccugsg | 1060 | AAUGAAACAAACAAACCCUGG | 1451 |
| AM14206-AS | asAfsasUfgaaacaaAfcAfaAfcccusg | 1061 | AAAUGAAACAAACAAACCCUG | 1452 |
| AM14208-AS | usGfsasAfaugaaacAfaAfcAfaaccsc | 1062 | UGAAAUGAAACAAACAAACCC | 1453 |
| AM14209-AS | usUfsgsAfaAfcaaaAfaAfcCfcUfggsa | 1063 | UUGAAACAAACAAACCCUGGA | 1450 |
| AM14210-AS | cPrpusUfsgsAfaacaaaCfaAfcCfcUfcuggsa | 1064 | UUGAAACAAACAAACCCUGGA | 1450 |
| AM14211-AS | cPrpuUfgAfaacaaaCfaAfcCfcuggsa | 1065 | UUGAAACAAACAAACCCUGGA | 1450 |
| AM14212-AS | cPrpuUfgAfaacaaaCfaAfcCfcugsgsa | 1066 | UUGAAACAAACAAACCCUGGA | 1450 |
| AM14216-AS | asGfsasCfgaucauaCfuUfgGfagagsc | 1067 | AGACGAUCAUACUUGGAGAGC | 1454 |
| AM14218-AS | asAfsgsGfcauucucAfaUfcUfccucsc | 1068 | AAGGCAUUCUCAAUCUCCUCC | 1455 |
| AM14220-AS | usUfsusCfcuuggaaGfgCfaUfucucsg | 1069 | UUUCCUUGGAAGGCAUUCUCG | 1456 |
| AM14222-AS | usAfsgsAfuuuccuuGfgAfaGfgcausc | 1070 | UAGAUUUCCUUGGAAGGCAUC | 1457 |
| AM14224-AS | asUfsasGfgaaacagCfaUfaCfauucusg | 1071 | AUAGGAAACAGCAUAUUCUUG | 1458 |
| AM14226-AS | usUfsgsAfugauguuCfcCfuCfcaacsg | 1072 | UUGAUGAUGUUCCCUCCAACG | 1459 |
| AM14228-AS | usAfsgsAfacuugaaGfaAfgAfgagcusg | 1073 | UAGAACUUGAAGAAGAAGCUG | 1460 |
| AM14230-AS | usAfscsCfaaugauaUfgCfcCfaacasc | 1074 | UACCAAUGAUAUGCCCAACAC | 1461 |
| AM14232-AS | usCfsasUfggU$_{UNA}$guucUfgUfgUfagacsg | 1075 | UCAUGGUGUUCUGUGUAGACG | 1462 |
| AM14234-AS | usUfsgsAfgagagauCfcUfgGfgugusc | 1076 | UUGAGAGAUCCUGGGUGUC | 1463 |
| AM14236-AS | usCfsasUfgauacugAfgAfgCfuugcsu | 1077 | UCAUGAUACUGAGAGCUUGCU | 1464 |
| AM14238-AS | usUfsgsUfcaaccucAfcUfcUfuccgsa | 1078 | UUGUCAACCUCACUCUUCCGA | 1465 |
| AM14240-AS | usUfsusCfcaacaauUfcUfcCfuugusc | 1079 | UUUCCAACAAUUCUCCUUGUC | 1466 |
| AM14242-AS | usUfsgsAfguuagucUfcAfaAfgcugsc | 1080 | UUGAGUUAGUCUCAAAGCUGC | 1467 |
| AM14244-AS | asUfsgsAfcaauaucUfgUfgCfggagsg | 1081 | AUGACAAUAUCUGUGCGGAGG | 1468 |
| AM14246-AS | usCfsasUfgacaauaUfcUfgUfgcggsa | 1082 | UCAUGACAAUAUCUGUGCGGA | 1469 |
| AM14248-AS | usCfsasAfagaagauAfgAfaGfcagcsc | 1083 | UCAAAGAAGAUAGAAGCAGCC | 1470 |
| AM14250-AS | usCfsascsCfguuauuaCfcUfgUfgugcsu | 1084 | UCACGUUAUUACCUGUGUGCU | 1471 |
| AM14252-AS | usAfsgsAfacuugagGfuUfaUfacagsg | 1085 | UAGAACUUGAGGUUAUACAGG | 1472 |
| AM14254-AS | asUfsgsCfuuugcugUfuCfaUfuggusc | 1086 | AUGCUUUGCUGUUCAUUGGUC | 1473 |
| AM14256-AS | usAfsgsUfauagauuCfaAfgGfuuausg | 1087 | UAGUAUAGAUUCAAGGUUAUG | 1474 |
| AM14258-AS | asGfsasGfuaaucuuGfcUfuUfaugcsc | 1088 | AGAGUAAUCUUGCUUUAUGCC | 1475 |
| AM14260-AS | asUfsasGfcaucauuUfcUfaGfguggsa | 1089 | AUAGCAUCAUUUCUAGGUGGA | 1476 |
| AM14262-AS | asGfsasCfagaagagAfcAfgAfgcuasg | 1090 | AGACAGAAGAGACAGAGCUAG | 1477 |
| AM14264-AS | asGfsusAfagaaaacCfaAfgCfcuuasg | 1091 | AGUAAGAAAACCAAGCCUUAG | 1478 |
| AM14280-AS | usUfscsCfauaauacUfcUfgAfgagasg | 1092 | UUCCAUAAUACUCUGAGAGAG | 1448 |
| AM14281-AS | cPrpusUfscsCfauaauacUfcUfgAfgagasg | 1093 | UUCCAUAAUACUCUGAGAGAG | 1448 |
| AM14282-AS | cPrpuUfcCfauaauacUfcUfgAfgagasg | 1094 | UUCCAUAAUACUCUGAGAGAG | 1448 |
| AM14283-AS | cPrpuUfcCfauaauacUfcUfgAfgagsasg | 1095 | UUCCAUAAUACUCUGAGAGAG | 1448 |
| AM14285-AS | cPrpuUfccauaAfuUfcUfgAfgagasg | 1096 | UUCCAUAAUACUCUGAGAGAG | 1448 |
| AM14288-AS | usAfsusAfcuuggagAfgCfaUfcacusg | 1097 | UAUACUUGGAGAGCAUCACUG | 1479 |
| AM14290-AS | usUfsgsCfagacgauCfUfaCfuuggsc | 1098 | UUGCAGACGAUCAUACUUGGC | 1480 |
| AM14292-AS | usUfsgsAfaUfaaaacUfcUfcAfugccsa | 1099 | UUGAAUAAAACUCUCAUGCCA | 1481 |
| AM14293-AS | cPrpusUfsgsAfaUfaaaacUfcUfcAfugccsa | 1100 | UUGAAUAAAACUCUCAUGCCA | 1482 |
| AM14296-AS | usAfscsUfuGfaAfgAfaGfaAfgCfuGfaGfsg | 1101 | UACUUGAAGAAGAAGCUGAGG | 1482 |
| AM14297-AS | usAfscsUfugaagaaGfaAfgCfugagsg | 1102 | UACUUGAAGAAGAAGCUGAGG | 1482 |
| AM14298-AS | cPrpusAfscsUfugaagaaGfaAfgCfugagsg | 1103 | UACUUGAAGAAGAAGCUGAGG | 1482 |
| AM14299-AS | cPrpuAfcUfugaagaaGfaAfgCfugagsg | 1104 | UACUUGAAGAAGAAGCUGAGG | 1482 |
| AM14301-AS | cPrpuAfcUfugaagaaGfaAfgCfugasgsg | 1105 | UACUUGAAGAAGAAGCUGAGG | 1482 |
| AM14304-AS | cPrpuAfcuugAgagaaGfaAfgfCfugagsg | 1106 | UACUUGAAGAAGAAGCUGAGG | 1482 |
| AM14305-AS | cPrpuAfcuugaAgfaaGfaAfgFfcugagsg | 1107 | UACUUGAAGAAGAAGCUGAGG | 1482 |
| AM14383-AS | cPrpusUfsusGfaAfucugAgfAfgAfgUfagcusc | 1108 | UUUGAAUGCUGAGAAAUACUC | 1438 |
| AM14384-AS | cPrpusUfsusGfaaugcugAgfAfgAfaguacusc | 1109 | UUUGAAUGCUGAGAAAUACUC | 1438 |
| AM14385-AS | cPrpusUfsusgsaaUfgcugAfgAfgAfguacusc | 1110 | UUUGAAUGCUGAGAAAUACUC | 1438 |
| AM14387-AS | cPrpuUfuGgaaugcugAfgAfaAfuacusc | 1111 | UUUGAAUGCUGAGAAAUACUC | 1438 |
| AM14388-AS | cPrpuUfuGfaaugcugAfgAfaAfguacsusc | 1112 | UUUGAAUGCUGAGAAAUACUC | 1438 |
| AM14391-AS | asGfsasAfaAfgguggaCffgAfuCfuUfugusc | 1113 | AGAAAAGUGGACGAUCUUUGC | 1483 |
| AM14393-AS | usAfsgsUfuGfucacuGfcAfaCfaUfggsu | 1114 | UAGUUGUCACUGCAACAUGGU | 1484 |
| AM14395-AS | asUfsusCfcUfuccacAfgUfuGfucacsc | 1115 | AUUCCUUCCACAGUUGUCACC | 1485 |
| AM14397-AS | usGfscsAfuUfcucaaUfcUfcCfuCfcasc | 1116 | UGCAUUCUCAAUCUCCUCCAC | 1486 |
| AM14399-AS | usUfscsAfcAfufgccaaUfcUfcCfgUfgusc | 1117 | UUCAACGCCAAUCUCCGUGUC | 1487 |
| AM14401-AS | asUfsasUfuCfuugaaCfuUfcAfuCfucsg | 1118 | AUAUUCUUGAACUUCAUCUCG | 1488 |
| AM14403-AS | usUfsasUfgGfagagcAfgUfaUfcUfccsu | 1119 | UUAUGGAGAGCAGUAUCUCCU | 1489 |
| AM14405-AS | usAfsasUfgCfugagaAfgaUfaGfcUfCfccsc | 1120 | UAAUGCUGAGAAAUACUCCCC | 1490 |
| AM14407-AS | usGfsasAfuGfcugagaAfgaAfgCfUfccsc | 1121 | UGAAUGCUGAGAAAUACUCCC | 1491 |
| AM14409-AS | usCfsasAfuGfucaucUfcCfuCfuCfcgsg | 1122 | UCAAUGUCAUCUUCUCUCCGG | 1492 |
| AM14411-AS | asCfsasAfaUfuccagUfuAfuGfuUfacsc | 1123 | ACAAAUUCCAGUUAUGUUACC | 1493 |
| AM14413-AS | usUfscsAfaUfugugaUfaAfuGfgCfugsg | 1124 | UUCAAUUGUGAUAAUGGCUGG | 1494 |
| AM14415-AS | asAfscsAfuUfuuugcAfaCfaAfaGfcusc | 1125 | AACAUUUUGCAACAAAGCUC | 1495 |
| AM14417-AS | usCfsasAfcAfuuuuuGfcAfaCfaAfagsc | 1126 | UCAACAUUUUGCAACAAAGC | 1496 |

TABLE 3-continued

XDH RNAi Agent Strand Sequences

| Antisense Strand ID: | Modified Antisense Strand (5' → 3') | SEQ ID NO. | Underlying Base Sequence (5' → 3') (Shown as an Unmodified Nucleotide Sequence) | SEQ ID NO. |
|---|---|---|---|---|
| AM14419-AS | usUfsusCfaCfucgaaCgcAfcAfaUfccsg | 1127 | UCUUAUUCCAAACUUGGUGGG | 1497 |
| AM14522-AS | cPrpusCfsusUfaUfuccaaAfcUfuGfgUfggsg | 1128 | UCUUAUUCCAAACUUGGUGGG | 1377 |
| AM14523-AS | cPrpuCfuUfaUfuccaaAfcUfuGfgUfggsg | 1229 | UCUUAUUCCAAACUUGGUGGG | 1377 |
| AM14524-AS | cPrpuCfuuauuCfaaAfcUfuGfguggsg | 1130 | UCUUAUUCCAAACUUGGUGGG | 1377 |
| AM14527-AS | cPrpuGfcauauucacCfaUfuUfaggcsa | 1131 | UGCAUAUUCACCAUUUAGGCA | 1397 |
| AM14529-AS | cPrpuGfcauaUfucacCfaUfuUfaggcsa | 1132 | UGCAUAUUCACCAUUUAGGCA | 1397 |
| AM14530-AS | cPrpuGfcauauuCfacCfaUfuUfaggcsa | 1133 | UGCAUAUUCACCAUUUAGGCA | 1397 |
| AM14543-AS | usGfscauauucacCfaUfuUfaggcsa | 1134 | UGCAUAUUCACCAUUUAGGCA | 1397 |
| AM14544-AS | usGfscauaUfucacCfaUfuUfaggcsa | 1135 | UGCAUAUUCACCAUUUAGGCA | 1397 |
| AM14545-AS | usGfscauauuCfacCfaUfuUfaggcsa | 1136 | UGCAUAUUCACCAUUUAGGCA | 1397 |
| AM14642-AS | cPrpasUfsgsAfaacaaacAfaAfcCfcuggsa | 1137 | AUGAAACAAACAAACCCUGGA | 1440 |
| AM14643-AS | cPrpasUfsgsAfaacaaacAfaAfcCfcugsgsa | 1138 | AUGAAACAAACAAACCCUGGA | 1440 |
| AM14644-AS | cPrpasUfsgAfaacaaacAfaAfcCfcugsgsa | 1139 | AUGAAACAAACAAACCCUGGA | 1440 |
| AM14645-AS | cPrpaUfgAfaacaaacAfaAfcCfcugsgsa | 1140 | AUGAAACAAACAAACCCUGGA | 1440 |
| AM14647-AS | cPrpasUfsgaaacaAfacAfaAfcCfcugsgsa | 1141 | AUGAAACAAACAAACCCUGGA | 1440 |
| AM14648-AS | cPrpasUfsgaaaCfaaacAfaAfcCfcugsgsa | 1142 | AUGAAACAAACAAACCCUGGA | 1440 |
| AM14649-AS | cPrpasUfsgaAfacaaacAfaAfcCfcugsgsa | 1143 | AUGAAACAAACAAACCCUGGA | 1440 |
| AM14650-AS | cPrpusUfsgAfaaCfaAfacAfaAfcCfcugsgsa | 1144 | AUGAAACAAACAAACCCUGGA | 1440 |
| AM15134-AS | cPrpusUfscCfauaauacUfcUfgAfgagasg | 1145 | UUCCAUAAUACUCUGAGAGAG | 1448 |
| AM15135-AS | cPrpusUfsccCfauaauacUfcUfgAfgagsasg | 1146 | UUCCAUAAUACUCUGAGAGAG | 1448 |
| AM15137-AS | cPrpuUfcCfauaauacUfcUfgAfgagasc | 1147 | UUCCAUAAUACUCUGAGAGAG | 1498 |
| AM15139-AS | cPrpuUfcCfauaauacUfcUfgAfgaggsg | 1148 | UUCCAUAAUACUCUGAGAGGG | 1499 |
| AM15141-AS | cPrpuUfcCfauaauacUfcUfgAfgaggsc | 1149 | UUCCAUAAUACUCUGAGAGGC | 1500 |
| AM15143-AS | cPrpuUfcCfauaauacUfcUfgAgfaggsu | 1150 | UUCCAUAAUACUCUGAGAGGA | 1501 |
| AM15145-AS | cPrpuUfcCfauaauacUfcUfgAfgaggsa | 1151 | UUCCAUAAUACUCUGAGAGGA | 1502 |
| AM15146-AS | cPrpuUfccauAfauacUfcUfgAfgagasg | 1152 | UUCCAUAAUACUCUGAGAGAG | 1448 |
| AM15147-AS | cPrpuGfscsauauuCfacCfaUfuUfaggcsa | 1153 | UGCAUAUUCACCAUUUAGGCA | 1397 |
| AM15148-AS | cPrpusGfscauauuCfacCfaUfuUfaggcsa | 1154 | UGCAUAUUCACCAUUUAGGCA | 1397 |
| AM15149-AS | cPrpusGfscauauuCfacCfaUfuUfaggscsa | 1155 | UGCAUAUUCACCAUUUAGGCA | 1397 |
| AM15150-AS | cPrpuGfcauauuCfacCfaUfuUfaggscsa | 1156 | UGCAUAUUCACCAUUUAGGCA | 1397 |
| AM15151-AS | cPrpusGfscsauaUfucacCfaufuUfaggcsa | 1157 | UGCAUAUUCACCAUUUAGGCA | 1397 |
| AM15152-AS | cPrpusGfscauaUfucacCfaUfuUfaggcsa | 1158 | UGCAUAUUCACCAUUUAGGCA | 1397 |
| AM15153-AS | cPrpusGfscauaUfucacCfaUfuUfaggscsa | 1159 | UGCAUAUUCACCAUUUAGGCA | 1397 |
| AM15154-AS | cPrpuGfcauaUfucacCfaUfuUfaggscsa | 1160 | UGCAUAUUCACCAUUUAGGCA | 1397 |
| AM15285-AS | asUfsgsacaAfuaucUfgUfgCfggagsg | 1161 | AUGACAAUAUCUGUGCGGAGG | 1468 |
| AM15286-AS | asUfsgsacaauAfucUfgUfgCfggagsg | 1162 | AUGACAAUAUCUGUGCGGAGG | 1468 |
| AM15287-AS | cPrpasUfsgsacaauAfucUfgUfgCfggagsg | 1163 | AUGACAAUAUCUGUGCGGAGG | 1468 |
| AM15289-AS | cPrpusUfsgsacaauAfucUfgUfgCfggagsg | 1164 | AUGACAAUAUCUGUGCGGAGG | 1503 |
| AM15290-AS | cPrpaUfgacaauAfucUfgUfgCfggagsg | 1165 | AUGACAAUAUCUGUGCGGAGG | 1468 |
| AM15291-AS | cPrpaUfgacaauAfucUfgUfgCfggasgsg | 1166 | AUGACAAUAUCUGUGCGGAGG | 1468 |
| AM15292-AS | cPrpasUfsgacaauAfucUfgUfgCfggasgsg | 1167 | AUGACAAUAUCUGUGCGGAGG | 1468 |
| AM15294-AS | cPrpasUfsgsacaauAfucUfgUfgCfggasg | 1168 | AUGACAAUAUCUGUGCGGAG | 1504 |
| AM15296-AS | cPrpasUfsgsacaauAfucUfgUfgCfggsgsa | 1169 | AUGACAAUAUCUGUGCGGSA | 1505 |
| AM15606-AS | cPrpusUfsccauaaUfacUfcUfgAfgagsasg | 1170 | UUCCAUAAUACUCUGAGAGAG | 1448 |
| AM15607-AS | cPrpusUfscCfauaauacUfcUfgAfgagsasc | 1171 | UUCCAUAAUACUCUGAGAGAC | 1498 |
| AM15608-AS | cPrpusUfsgaaaCfaaacAfaAfcCfcugsgsa | 1172 | UUGAAACAAACAAACCCUGGA | 1450 |
| AM15626-AS | asUfsgAfaAfcaaacAfaAfcCfcUfgsgsa | 1173 | AUGAAACAAACAAACCCUGGA | 1440 |
| AM15627-AS | asUfsgAfaacaaacAfaAfcCfcugsgsa | 1174 | AUGAAACAAACAAACCCUGGA | 1440 |
| AM17243-AS | asCfsucgUfuccauaaUfaCfucugasgsa | 1672 | ACUCGUUCCAUAAUACUCUGAGA | 1674 |
| AM17245-AS | asUfsccaUfaauacucUfgAfgagagsasu | 1673 | AUCCAUAAUACUCUGAGAGAGAU | 1675 |

TABLE 4

XDH RNAi Agent Strand Sequences

| Sense Strand ID: | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AML3028-SS | (NAG37)s(invAb)sgagauugaGfAfAfugcCfuuccaas(invAb) | 1175 | GAGAUUGAGAAUGCCUUCCAA | 1506 |
| AML3030-SS | (NAG37)s(invAb)sgagauuGfaGfAfAfugccuuccaas(invAb) | 1176 | GAGAUUGAGAAUGCCUUCCAA | 1506 |
| AML3032-SS | (NAG37)s(invAb)scccagcuUfCfUfucuccaaguus(invAb) | 1177 | CCUCAGCUUCCUUCUCAAGUU | 1507 |
| AML3034-SS | (NAG37)s(invAb)sgcagcuucCfUfCfuucaaguucas(invAb) | 1178 | GCAGCUUCCUUCUCAAGUUCA | 1508 |
| AML3036-SS | (NAG37)s(invAb)sgcuucuucCfUfCfaaguucuacas(invAb) | 1179 | GCUUCUUCCUUCAAGUUCUACA | 1509 |
| AML3038-SS | (NAG37)s(invAb)sagggugaaAfAfAfucaccuaugas(invAb) | 1180 | AGGGUGAAAAUCACCUAUGA | 1510 |
| AML3040-SS | (NAG37)s(invAb)sgggugaaaAfUfCfaccuaugaaas(invAb) | 1181 | GGGUGAAAAUCACCUAUGAAA | 1511 |
| AML3042-SS | (NAG37)s(invAb)sggugaaaaUfCfAfccuaugaagas(invAb) | 1182 | GGUGAAAAUCACCUAUGAAGA | 1512 |
| AML3044-SS | (NAG37)s(invAb)sgugaaaauCfAfCfcuaugaagaas(invAb) | 1183 | GUGAAAAUCACCUAUGAAGAA | 1513 |
| AML3046-SS | (NAG37)s(invAb)scuaccagcCfCfAfUfuauacaaauus(invAb) | 1184 | CUACCAGCCCAUUAUACAAAUU | 1514 |
| AML3048-SS | (NAG37)s(invAb)sgaagaacaCfUfCfcuuuuaugas(invAb) | 1185 | GAAGAACAACUCCUUUUAUGA | 1515 |
| AML3050-SS | (NAG37)s(invAb)sgagaacaaCfUfCfcuuuuaugas(invAb) | 1186 | GAGAACAACUCCUUUUAUGGA | 1516 |
| AML3052-SS | (NAG37)s(invAb)sucuccagcAfGfUfaguacacaas(invAb) | 1187 | UCGUCAUGAGUAUGUACACAA | 1517 |
| AML3054-SS | (NAG37)s(invAb)scuaccagcCfCfAfUfauacacaauus(invAb) | 1188 | AGGACAUGCUGAACAAACUGUA | 1518 |
| AML3056-SS | (NAG37)s(invAb)saggacaugCfUfGfauaacugiuas(invAb) | 1189 | AGGACAUGCUGAACAAACUGUA | 1519 |
| AML3058-SS | (NAG37)s(invAb)sggauacaaGfGfufuggcuucauas(invAb) | 1190 | GGAUACAAGGUUGGCUUCAUA | 1520 |
| AML3060-SS | (NAG37)s(invAb)sgcaagguuGfGfCfuucaugaagas(invAb) | 1191 | GCAAGGUUGGCUUCAUGAAGA | 1521 |
| AML3062-SS | (NAG37)s(invAb)scagguugGfCfUfUfcaugaagaas(invAb) | 1992 | CAAGGUUGGCUUCAUGAAGAA | 1522 |
| AML3064-SS | (NAG37)s(invAb)sagguuggcCfUfCfaugaagacuas(invAb) | 1193 | AGGUUGGCUUCAUGAAGACUA | 1523 |
| AML3066-SS | (NAG37)s(invAb)saggagaauUfGfUfGfugaaaaagas(invAb) | 1194 | AGGAGAAUUGUGUGGAAAAGA | 1524 |
| AML3068-SS | (NAG37)s(invAb)sgugcccugCfUfCfugaaguagaas(invAb) | 1195 | GUGGCUUGCUCUGAAGUAGAA | 1525 |
| AML3070-SS | (NAG37)s(invAb)sgcuugcucUfUfGfAfAfguagaaauas(invAb) | 1196 | GCUUGCUCUGAAGUAGAAAUA | 1526 |
| AML3072-SS | (NAG37)s(invAb)scccugccaUfUfGfAfuauauuigacas(invAb) | 1197 | CCCUGCCAUUGAUAUAUUGACA | 1527 |
| AML3163-SS | (NAG37)s(invAb)scaagaucgUfCfCfacuuuucugas(invAb) | 1198 | CAAGAUCGUCCACUUUUCUGA | 1528 |
| AML3165-SS | (NAG37)s(invAb)sguccgaagCfAfGfAfauaaugugus(invAb) | 1199 | GUCCGAAGCAGAAUAAUGUGU | 1529 |
| AML3167-SS | (NAG37)s(invAb)scuagcucCfAfGfAfaguauauaugas(invAb) | 1200 | GUCUCUCCAGAGUAUAUAUGA | 1530 |
| AML3169-SS | (NAG37)s(invAb)sccccaccaGfUfUfuggaauaagas(invAb) | 1201 | CCCACCAGUUUGGAAUAAGA | 1531 |
| AML3171-SS | (NAG37)s(invAb)scugcauaaAfGfCfaagauuacuas(invAb) | 1202 | CUGCAUAAAGCAAGAUUACUA | 1532 |
| AML3173-SS | (NAG37)s(invAb)sgacaauguUfCfUfagaauuucuus(invAb) | 1203 | GACAAUGUUCUAGAAUUCUUU | 1533 |
| AML3175-SS | (NAG37)s(invAb)scaagaucGfUfCfcacUfuuuucugas(invAb) | 1204 | CAAGAUCGUCCACUUUUCUGA | 1528 |
| AML3178-SS | (NAG37)s(invAb)sgucucuccAfGfAfGfuauuaugas(invAb) | 1205 | GUCUCUCCAGAGUAUAUUGA | 1530 |
| AML3180-SS | (NAG37)s(invAb)sgaaaaugUfCfUfagaauuucuuus(invAb) | 1206 | GAAAAUGUUCUAGAAUUCUUU | 1534 |
| AML3599-SS | (NAG37)s(invAb)sagugcuggAfUfGfaguagaaguuas(invAb) | 1207 | AGUGCUGGAUGAGAGAAGUUA | 1535 |
| AML3601-SS | (NAG37)s(invAb)sgcucuigaUfGfAfgugaaguugas(invAb) | 1208 | GGCUIGAUGAGAGUGAAGUUGA | 1536 |
| AML3603-SS | (NAG37)s(invAb)sugcuggauGfAfGfugaaguuicas(invAb) | 1209 | UGCUGGAUGAGAGUGAAGUUCA | 1537 |
| AML3647-SS | (NAG37)s(invAb)sgaugcucuCfCfAfaGfuaugaucas(invAb) | 1210 | GAUGCUCCAAGUAUGAUCA | 1538 |
| AML3649-SS | (NAG37)s(invAb)sgugaucguCfuGfCfAfgaaacaagas(invAb) | 1211 | GUGAUCGUCCAGACAAGAA | 1539 |
| AML3651-SS | (NAG37)s(invAb)sgucgucugCfCfaGfaAfcaagaucas(invAb) | 1212 | GUCGUCUGCAGAACAAGAUCA | 1540 |
| AML3653-SS | (NAG37)s(invAb)sgugccagUfGfCfAfcuuuacuas(invAb) | 1213 | GUCGCCAGUGCAACUUUACUA | 1541 |
| AML3655-SS | (NAG37)s(invAb)saggauaAfgfuUfUfacuugguuas(invAb) | 1214 | AGGAUAAGGUUACUUGUGUUA | 1542 |
| AML3657-SS | (NAG37)s(invAb)saccagccaUfuAfuCfacaauugas(invAb) | 1215 | ACCAGCCAUUAUCACAAUUGA | 1543 |
| AML3659-SS | (NAG37)s(invAb)scaagcucUfcaGfuAfucaugcuas(invAb) | 1216 | CAAGCUCCAGUAUCAUGCUA | 1544 |
| AML3661-SS | (NAG37)s(invAb)sgaagagugAfgGfuUfgacaaguus(invAb) | 1217 | GAAGAGUGAGGUUGACAAGUU | 1545 |

TABLE 4-continued

XDH RNAi Agent Strand Sequences

| Sense Strand ID: | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM13663-SS | (NAG37)s(invAb)sgagugaGfGfUfugacaaguuas(invAb) | 1218 | GAGAGUGAGGUUGACAAGUUA | 1546 |
| AM13665-SS | (NAG37)s(invAb)sguucaacaAfGfGfagaauuguuas(invAb) | 1219 | GUUCAACAAGGAGAAUUGUUA | 1547 |
| AM13667-SS | (NAG37)s(invAb)sggaacaUfaCfcAfcAfcagaacaugas(invAb) | 1220 | GGAACAUACCACAGAACAUGA | 1548 |
| AM13669-SS | (NAG37)s(invAb)sgaacaugGfAfuCfuAfuaaagucas(invAb) | 1221 | GAACAUGGAUCUAUAAAGUCA | 1549 |
| AM13671-SS | (NAG37)s(invAb)sgacaugGfAfuUfuUfaaagucas(invAb) | 1222 | GACAUGGAUCUAUAAAGUCA | 1550 |
| AM13673-SS | (NAG37)s(invAb)sugccuaaAfaUfUfgGfugaauaugcas(invAb) | 1223 | UGCCUAAAUGUGAAUAUGCA | 1551 |
| AM13675-SS | (NAG37)s(invAb)sgaaccucuAfGfAfagcuuaaacas(invAb) | 1224 | GAACCUCUAGAAGCUUAAACA | 1552 |
| AM13677-SS | (NAG37)s(invAb)sggccuucaAfaCfCfAfaugaacaas(invAb) | 1225 | GGCCUUCAAACCAAUGAACAA | 1553 |
| AM13679-SS | (NAG37)s(invAb)sccaaugaAfaCfaGfcaaagcauaas(invAb) | 1226 | CCAAUGAACAGCAAAGCAUAA | 1554 |
| AM13681-SS | (NAG37)s(invAb)sgaugaacaGfCfAfAfagcauaaacas(invAb) | 1227 | GAUGAACAGCAAAGCAUAACA | 1555 |
| AM13683-SS | (NAG37)s(invAb)sgugaacagCfAfAfAfgcauaaccus(invAb) | 1228 | GUGAACAGCAAAGCAUAACCU | 1556 |
| AM13685-SS | (NAG37)s(invAb)sgaacagcaAfaGfCfAfuaaccuuas(invAb) | 1229 | GAACAGCAAAGCAUAACCUUA | 1557 |
| AM13687-SS | (NAG37)s(invAb)sgcaaagcAfUfAfAfccugaaucus(invAb) | 1230 | GCAAAGCAUAACCUGAAUCU | 1558 |
| AM13689-SS | (NAG37)s(invAb)sccaaccaaCfuCfaAfuuaauugaas(invAb) | 1231 | CCAACCAACUCAAUUAUUGAA | 1559 |
| AM13691-SS | (NAG37)s(invAb)sccuuccugUfGfAfUfccauuuuacus(invAb) | 1232 | CUUCCUGUGAUCCAUUUUACU | 1560 |
| AM13693-SS | (NAG37)s(invAb)sgguuuucuUfAfCfugucauaugas(invAb) | 1233 | GGUUUUCUUACUGUCAUAUGA | 1561 |
| AM13695-SS | (NAG37)s(invAb)sgagaucgaGfAfAfUfucaaugaugas(invAb) | 1234 | GAGAUCGAGAAUGCCUUCCAA | 1562 |
| AM13697-SS | (NAG37)s(invAb)sgacuggcaUfUfUfucaaugaugas(invAb) | 1235 | GACUGGCAUUUCAAUGAUGA | 1563 |
| AM13699-SS | (NAG37)s(invAb)sgucaaugaUfGfAfAfaacugucuuus(invAb) | 1236 | GUCAAUGAUGAAAACUGUCUUU | 1564 |
| AM13701-SS | (NAG37)s(invAb)sgaggaugaGfCfUfGfacacugugus(invAb) | 1237 | GAGGAUGAGCUGACACUGUGU | 1565 |
| AM13703-SS | (NAG37)s(invAb)sucugaagcUfGfAfCfaaugugucus(invAb) | 1238 | CUGAAGCUGACAAUGUGUCU | 1566 |
| AM13705-SS | (NAG37)s(invAb)sgcuuuaugCfAfAfaagauguugas(invAb) | 1239 | GCUUUAUGCAAAGAUGUUGA | 1567 |
| AM13707-SS | (NAG37)s(invAb)sgaggauuuGfAfCfugcuuaaucus(invAb) | 1240 | GAGGAUUUGACUGCUUAACU | 1568 |
| AM13709-SS | (NAG37)s(invAb)sccgacuaaGfUfUfuggaauaagas(invAb) | 1241 | CCGACUAAGUUUGGAAUAAGA | 1569 |
| AM13711-SS | (NAG37)s(invAb)sgcuucacacUfUfCfucuuuucugas(invAb) | 1242 | GCUUCACACUUCUCUUUUCUGA | 1570 |
| AM13713-SS | (NAG37)s(invAb)sgcagcuuuGfAfGfacaaacucuas(invAb) | 1243 | GCAGCUUUGAGACAAACUCUA | 1571 |
| AM13715-SS | (NAG37)s(invAb)sgagaaauugGfAfCfugcuuaacaas(invAb) | 1244 | GAGAAAUUGACUGCUUAACAA | 1572 |
| AM13717-SS | (NAG37)s(invAb)sccguaguaUfCfCfAfuuuuugaucas(invAb) | 1245 | CCGUAGUAUCCAGAUUUGAUCA | 1573 |
| AM13719-SS | (NAG37)s(invAb)sagcaggauGfGfCfAfuuucaagas(invAb) | 1246 | AGCAGGAUGGCAUUUCAAGA | 1574 |
| AM13721-SS | (NAG37)s(invAb)sgcaaaugUfGfAfUfccaaaucaus(invAb) | 1247 | GACAAAUGUGAUCCAAAUCAU | 1575 |
| AM13723-SS | (NAG37)s(invAb)sccuccagagAfGfCfuuauaaucugas(invAb) | 1248 | CUUCCAGAGAGCUUAUAUCUGA | 1576 |
| AM13725-SS | (NAG37)s(invAb)sggauacaAfaGfgGfUfuguaauucuas(invAb) | 1249 | UGGCAGUUUUGAGUAAUUCUA | 1577 |
| AM13727-SS | (NAG37)s(invAb)sgucugaguCfCfAfuuuuugaucas(invAb) | 1250 | GUCUGAGUCCAUUUUGAUCA | 1578 |
| AM13729-SS | (NAG37)s(invAb)scuagaucUfGfCfAfuugcuuuuuas(invAb) | 1251 | CUAGAUCUGCAUGCUUUUUA | 1579 |
| AM13746-SS | (NAG37)s(invAb)sgacaauugUfGfAfUfccaaaucaus(invAb) | 1252 | GACAAAUGUGAUCCAAAUCAU | 1520 |
| AM13750-SS | (NAG37)s(invAb)suggcaguuUfUfGfaguaauucuas(invAb) | 1253 | UGGCAGUUUUGAGUAAUUCUA | 1580 |
| AM13751-SS | (NAG37)s(invAb)sggauacaAfaGfGfUfgicuucauas(invAb) | 1254 | GGAUACAAGGUGICUUCAUA | 1581 |
| AM13752-SS | (NAG37)s(invAb)sggauacaAfaGfGfUfuigcuucauas(invAb) | 1255 | GGAUACAAGGUUGCCUGAUA | 1582 |
| AM13756-SS | (NAG37)s(invAb)sggauacaAfaGfGfuggbuccuuucauas(invAb) | 1256 | GGAUACAAGGUGGUUUCAUA | 1520 |
| AM13757-SS | (NAG37)s(invAb)sggauacaAfaGfgfuGfuUfggcuucauas(invAb) | 1257 | GGAUACAAGGUGGCUUCAUA | 1520 |
| AM13760-SS | (NAG37)s(invAb)sgcaaggUfuGfcfuuUfcauGfaaGfaas(invAb) | 1258 | GCAAGGUUGGCUUCAUGAAGA | 1521 |
| AM13857-SS | (NAG37)s(invAb)sgugggagaaAfAfAfugcaiauccas(invAb) | 1259 | GUGGAGAAAAUGCAUAUCCA | 1583 |
| AM13859-SS | (NAG37)s(invAb)succagagaCfAfAfcucuuuuggas(invAb) | 1260 | UCCAGAGACAACUCUUUUGGA | 1584 |
| AM13861-SS | (NAG37)s(invAb)scucuccaaGfUfAfgauclucuas(invAb) | 1261 | CUCUCCAAGUAGAUCUCUA | 1585 |
| AM13863-SS | (NAG37)s(invAb)sgcaacuguGfGfAfaggaauaggas(invAb) | 1262 | GCAACUGUGGAAGGAAUAGGA | 1586 |

TABLE 4-continued

XDH RNAi Agent Strand Sequences

| Sense Strand ID: | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM13865-SS | (NAG37)s(invAb)suggcaucgUfCfAfugaguauguas(invAb) | 1263 | UGGCAUCGCUCAUGAGUAUGUA | 1587 |
| AM13867-SS | (NAG37)s(invAb)sgccuuccaAfGfGfaaaucuguias(invAb) | 1264 | GCCUUCCAAGGAAAUCUGUIA | 1588 |
| AM13869-SS | (NAG37)s(invAb)sguggcauuGfAfGfaugaaguucas(invAb) | 1265 | GUGGCAUUGAGAUGAAGUUCA | 1589 |
| AM13871-SS | (NAG37)s(invAb)sga_2Ngaaguu UfCfAfagaauaugcus(invAb) | 1266 | G(A²ᴺ)UGAAGUUCAAGAAUAUGCU | 1590 |
| AM13873-SS | (NAG37)s(invAb)sggaauaugCfUfGfuuccuaugas(invAb) | 1267 | GGAAUAUGCUGUUCCUAUGA | 1591 |
| AM13875-SS | (NAG37)s(invAb)sgcugcucuCfCfAfuagaiauccas(invAb) | 1268 | GCUGCUCCCAUAGAIAUCCA | 1592 |
| AM13877-SS | (NAG37)s(invAb)sgaguauucUfCfCfagcauucaaas(invAb) | 1269 | GAGUAUUCUCAGCAUUCAAA | 1593 |
| AM13879-SS | (NAG37)s(invAb)scgccaagaUfCfAfagucccauagas(invAb) | 1270 | CGCCAAGAUCAAGUCCAUAGA | 1594 |
| AM13881-SS | (NAG37)s(invAb)succagguGfGfuuuguuucaus(invAb) | 1271 | UCCAGGGUUUGUUUGUUUCAU | 1595 |
| AM13883-SS | (NAG37)s(invAb)sgucacuaUfGfAfagaacuaccas(invAb) | 1272 | GUCACCUAUGAAGAACUACCA | 1596 |
| AM13885-SS | (NAG37)s(invAb)sgagaacuaCfCfAfgccauuaucas(invAb) | 1273 | GAGAACUACCAGCCAUUAUCA | 1597 |
| AM13887-SS | (NAG37)s(invAb)scagccauuAfUfCfacaaugagas(invAb) | 1274 | CAGCCAUUAUCACAAUGAGA | 1598 |
| AM13889-SS | (NAG37)s(invAb)sugagcugaAfGfAfucgagaagas(invAb) | 1275 | UGAGCUGAAGAUCGAGAAGA | 1599 |
| AM13891-SS | (NAG37)s(invAb)scgcaccauUfGfCfuguuccaaas(invAb) | 1276 | CUGCACCAUUGCUGUUCCAAA | 1600 |
| AM13893-SS | (NAG37)s(invAb)sguggagcuCfUfGfuguuuacas(invAb) | 1277 | GUGGAGCUCUUGUGUUUACA | 1601 |
| AM13895-SS | (NAG37)s(invAb)sagcucuuuGfUfGfucuacacaias(invAb) | 1278 | AGCUCUUUGUGUCUACACAIA | 1602 |
| AM13897-SS | (NAG37)s(invAb)scucucucaGfAfGfuauuauggaas(invAb) | 1279 | CUCUCUCCAGAGUAUUAUGGAA | 1603 |
| AM13899-SS | (NAG37)s(invAb)sgcagaguaUfAfGfugaacgaias(invAb) | 1280 | GCAGAGUAUAUGGAACGAIA | 1604 |
| AM14174-SS | (NAG37)s(invAb)sucaggguUfGfUfGfuuuguuucaas(invAb) | 1281 | UCCAGGGUUUGUGUUUGUUUCAA | 1605 |
| AM14203-SS | (NAG37)s(invAb)sccaggguUfGfUfuuguuuucaus(invAb) | 1282 | CCAGGGUUUGUUUUGUUUCAU | 1606 |
| AM14205-SS | (NAG37)s(invAb)scaggguuUfGfUfuuguuucauus(invAb) | 1283 | CAGGGUUUGUUUGUUUCAUU | 1607 |
| AM14207-SS | (NAG37)s(invAb)sggguuuguUfUfGfuuucauucas(invAb) | 1284 | GGGUUUGUUUGUUUCAUUCA | 1608 |
| AM14213-SS | (NAG37)s(invAb)succagguUfuGfUfuguuucaas(invAb) | 1285 | UCCAGGGUUUGUUGUUUCAA | 1605 |
| AM14214-SS | (NAG37)s(invAb)succagguUfuGfUfuuguuucaas(invAb) | 1286 | UCCAGGGUUUGUUUGUUUCAA | 1605 |
| AM14215-SS | (NAG37)s(invAb)scucuccaAfGfUfaugaucucus(invAb) | 1287 | GCUCUCCAAGUAUGAUCUCU | 1609 |
| AM14217-SS | (NAG37)s(invAb)sggagagaUfUfGfagaauiccuus(invAb) | 1288 | GGAGAGAUUGAGAAUUCCUU | 1610 |
| AM14219-SS | (NAG37)s(invAb)scgagaaugCfCfUfuccaagaaas(invAb) | 1289 | CGAGAAUGCCUUCCAAGAAA | 1611 |
| AM14221-SS | (NAG37)s(invAb)sgaugccuuCfCfAfaggaaaucuas(invAb) | 1290 | GAUGCCUUCCAAGGAAAUCUA | 1612 |
| AM14223-SS | (NAG37)s(invAb)sca_2NagaauaUfGfCfuguuccuaus(invAb) | 1291 | C(A²ᴺ)AGAAUAUGCUGUUCCUAU | 1613 |
| AM14225-SS | (NAG37)s(invAb)scguuggaGfGfAfacaucaucaas(invAb) | 1292 | CGUUGGAGGAACAUCAUCAA | 1614 |
| AM14227-SS | (NAG37)s(invAb)scagcucucUfCfUfucaaguucuas(invAb) | 1293 | CAGCUCUUCUUCAAGUUCUA | 1615 |
| AM14229-SS | (NAG37)s(invAb)sguguugcGfcAfUfaucauuggas(invAb) | 1294 | GUGUUGGCCAUAUCAUUGGUA | 1616 |
| AM14231-SS | (NAG37)s(invAb)scgucucaGfCfAfucaacaugas(invAb) | 1295 | CGUUACACCAGCUCAACCAUGA | 1617 |
| AM14233-SS | (NAG37)s(invAb)sgacaccaGfGfAfucucuuucas(invAb) | 1296 | GACACCCAGGAUCUCUUUCAA | 1618 |
| AM14235-SS | (NAG37)s(invAb)sagcaagcuCfUfCfaguaucaugas(invAb) | 1297 | AGCAAGCUCUCAGUAUCAUGA | 1619 |
| AM14237-SS | (NAG37)s(invAb)sucggaagaGfUfGfagguugacaas(invAb) | 1298 | UCGGAAGAGUGAGGUUGACAA | 1620 |
| AM14239-SS | (NAG37)s(invAb)sgacaaggaGfAfAfuuguuggaaas(invAb) | 1299 | GACAAGGAGAAUUGUUGGAAA | 1621 |
| AM14241-SS | (NAG37)s(invAb)sgcagcuuuGfAfGfacuaacucaas(invAb) | 1300 | GCAGCUUUGAGACUAACUCAA | 1622 |
| AM14243-SS | (NAG37)s(invAb)sccuccgcaCfAfGfauauugcaus(invAb) | 1301 | CCUCCGCACAGAUAUUGCAU | 1623 |
| AM14245-SS | (NAG37)s(invAb)succcacaGfUfCfAfauugucaugas(invAb) | 1302 | UCCCACCAAGUCAUAUGUCAUGA | 1624 |
| AM14247-SS | (NAG37)s(invAb)sgcugcuuCfUfAfucucuuugas(invAb) | 1303 | GGCUGCUUCUAUCUCUUUGA | 1625 |
| AM14249-SS | (NAG37)s(invAb)sagcacacaGfGfUfaauaacgias(invAb) | 1304 | AGCACAACAGGUAAUAACCGIA | 1626 |
| AM14251-SS | (NAG37)s(invAb)sccuguauaAfCfCfucaaguucuas(invAb) | 1305 | CCUGUAUAACCUCAAGUUCUA | 1627 |
| AM14253-SS | (NAG37)s(invAb)sgaccaaugAfaGfCfagcaaagcaus(invAb) | 1306 | GACCAAUGAACAGCAAGCAU | 1628 |

TABLE 4-continued

XDH RNAi Agent Strand Sequences

| Sense Strand ID: | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM14255-SS | (NAG37)s(invAb)sca_2NuaaccuUfGfAfaucuauacuas_(invAb) | 1307 | C(A²ⁿ)UAACCUUGAAUCUAUACUA | 1629 |
| AM14257-SS | (NAG37)s(invAb)sggcauaaaGfCfAfagauuacucuus(invAb) | 1308 | GGCAUAAAGCAAGAUUACUCUCU | 1630 |
| AM14259-SS | (NAG37)s(invAb)succaccuadfAfAfaugaugcuaus(invAb) | 1309 | UCCACCUAGAAAUGAUGCUAU | 1631 |
| AM14261-SS | (NAG37)s(invAb)scuagcucuGfCfucucucuiucus(invAb) | 1310 | CUAGCUCUGUCUCUCUUCU | 1632 |
| AM14263-SS | (NAG37)s(invAb)scua_2NaggcuuGfGfuuuucuucus(invAb) | 1311 | CU(A²ⁿ)AGGCUUGGUUUUCUUACU | 1633 |
| AM14284-SS | (NAG37)s(invAb)scucucucaGfaGfuAfuaauggaas(invAb) | 1312 | CUCUCUCAGAGUAUUAUGGAA | 1603 |
| AM14286-SS | (NAG37)s(invAb)scucucucaGfaGfUfauuauggaas(invAb) | 1313 | CUCUCUCAGAGUAUUAUGGAA | 1603 |
| AM14287-SS | (NAG37)s(invAb)scagugaugCfUfCfuccaaguauas(invAb) | 1314 | CAGUGAUGCUCUCCAAGUAUA | 1634 |
| AM14289-SS | (NAG37)s(invAb)sgccaaguaUfGfAfucgucuicaas(invAb) | 1315 | GCCAAGUAUGAUCGUCUICAA | 1635 |
| AM14291-SS | (NAG37)s(invAb)suggcaugaGfAgGfUfuuuauucaas(invAb) | 1316 | UGGCAUGAGAGUUUAUUCAA | 1636 |
| AM14294-SS | (NAG37)s(invAb)suggcaugaGfaGfGfuuuua_2Nuccaas | 1317 | UGGCAUGAGAGUUUU(A²ⁿ)UUCAA | 1367 |
| AM14295-SS | (NAG37)s(invAb)scccagcuUfCfUfucuucaaguas(invAb) | 1318 | CCUCAGCUUCUUCUUCAAGUA | 1638 |
| AM14300-SS | (NAG37)s(invAb)scccagcuUfCfUfucuuuaagtas(invAb) | 1319 | CCUCAGCUUCUUCUUUAAGUA | 1639 |
| AM14302-SS | (NAG37)s(invAb)scccagcuUfCfUfCfuuccaaguas(invAb) | 1320 | CCUCAGCUUCUUCUUCAAGUA | 1638 |
| AM14303-SS | (NAG37)s(invAb)scccagcuUfuqCfuccaaguas(invAb) | 1321 | CCUCAGCUUCUUCUUCAAGUA | 1638 |
| AM14386-SS | (NAG37)s(invAb)sgauauuuCfucAfgcauucaaas(invAb) | 1322 | GAGUAUUUCUCAGCAUUCAAA | 1593 |
| AM14390-SS | (NAG37)s(invAb)sgacaagauCfGfUfcccacuuuucus(invAb) | 1323 | GACAAGAUCGUCCACUUUUCU | 1640 |
| AM14392-SS | (NAG37)s(invAb)saccauguuGfCfAfguagacaacuas(invAb) | 1324 | ACCAUGUUGCAGUGACAACUA | 1641 |
| AM14394-SS | (NAG37)s(invAb)sgugacaaCfUfGfuggaagqaaus(invAb) | 1325 | GGUGACAACUGUGGAAGGAAU | 1642 |
| AM14396-SS | (NAG37)s(invAb)sguggagqaGfAfUfugagaaugcas(invAb) | 1326 | GUGGAGGAGAUUGAGAAUGCA | 1643 |
| AM14398-SS | (NAG37)s(invAb)sgacacggaGfAfUfuggcauugaas(invAb) | 1327 | GACACGGAGAUUGGCAUUGAA | 1644 |
| AM14400-SS | (NAG37)s(invAb)scgagaagucGfGfUfucaagaaua_2Nus(invAb) | 1328 | CGAGAAGUCAAGAAU(A²ⁿ)U | 1645 |
| AM14402-SS | (NAG37)s(invAb)saggagauaCfUfGfcucuccauaas(invAb) | 1329 | AGGAGAUACUGCUCUCCAUAA | 1646 |
| AM14404-SS | (NAG37)s(invAb)sgggagquaUfUfUfcucagcauuas(invAb) | 1330 | GGGAGUAUUUCUCAGCAUUA | 1647 |
| AM14406-SS | (NAG37)s(invAb)sgggagquauUfUfCfucagcauucas(invAb) | 1331 | GGGAGUAUUUCUCAGCAUUCA | 1648 |
| AM14408-SS | (NAG37)s(invAb)sccggagaAgAgGfaagacacauugas(invAb) | 1332 | CCGGAGAGAAGACAAUUGA | 1649 |
| AM14410-SS | (NAG37)s(invAb)sguaacauAgAgCfguggaauuugus(invAb) | 1333 | GGUAACAUAACUGGAAUUGU | 1650 |
| AM14412-SS | (NAG37)s(invAb)sccagccautfAfUfcacaauugaas(invAb) | 1334 | CCAGCCAUUAUCACAAUUGAA | 1651 |
| AM14414-SS | (NAG37)s(invAb)sgcuuugUfUfGfcaaaaaugus(invAb) | 1335 | GAGCUUGUUGCAAAAAUGUU | 1652 |
| AM14416-SS | (NAG37)s(invAb)sgcuuugucCfAfaaaugugas(invAb) | 1336 | GCUUUGUUGCAAAAAUGUUGA | 1653 |
| AM14418-SS | (NAG37)s(invAb)scgqauugGfGfUfucgagqgaaas(invAb) | 1337 | CGGAUGUGGUUCGAGUGAAA | 1654 |
| AM14525-SS | (NAG37)s(invAb)scccaccaafuUfGfgaauaagas(invAb) | 1338 | CCCACCAAGUUGGAAUAAGA | 1531 |
| AM14526-SS | (NAG37)s(invAb)scccaccaaGfuUfGfgaauaagas(invAb) | 1339 | CCCACCAAGUUGGAAUAAGA | 1531 |
| AM14528-SS | (NAG37)s(invAb)sugccuaaaUfgGfGfgaauaugcas(invAb) | 1340 | UGCCUAAAUGGUGAAUAUGCA | 1551 |
| AM14531-SS | (NAG37)s(invAb)sugccuaaaUfgGfUfgaauaugcas(invAb) | 1341 | UGCCUAAAUGGUGAAUAUGCA | 1551 |
| AM14646-SS | (NAG37)s(invAb)succaggguUfuGfUfufuguuucaus(invAb) | 1342 | UCCAGGGUUUGUUUGUUUCAU | 1595 |

TABLE 4-continued

XDH RNAi Agent Strand Sequences

| Sense Strand ID: | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM15136-SS | (NAG37)s(invAb)sgucucucaGfaGfuAfuuauggaas(invAb) | 1343 | GUCUCUCAGAGUAUUAUGGAA | 1655 |
| AM15138-SS | (NAG37)s(invAb)scccucucaGfaGfuAfuuauggaas(invAb) | 1344 | CCCUCUCAGAGUAUUAUGGAA | 1656 |
| AM15140-SS | (NAG37)s(invAb)sgcccucucaGfaGfuAfuuauggaas(invAb) | 1345 | GCCCUCUCAGAGUAUUAUGGAA | 1657 |
| AM15142-SS | (NAG37)s(invAb)saccucucaGfaGfuAfuuauggaas(invAb) | 1346 | ACCUCUCAGAGUAUUAUGGAA | 1658 |
| AM15144-SS | (NAG37)s(invAb)succucucaGfaGfuAfuuauggaas(invAb) | 1347 | UCCUCUCAGAGUAUUAUGGAA | 1659 |
| AM15284-SS | (NAG37)s(invAb)sccuccgacCfaGfaUfauugucaus(invAb) | 1348 | CCUCCGACAGAUAUUGUCAU | 1623 |
| AM15288-SS | (NAG37)s(invAb)sccuccgcacCfaGfaUfauugucaas(invAb) | 1349 | CCUCCGCACAGAUAUUGUCAA | 1660 |
| AM15293-SS | (NAG37)s(invAb)scuccgcaCfaGfaUfauugucaus(invAb) | 1350 | CUCCGCACAGAUAUUGUCAU | 1661 |
| AM15295-SS | (NAG37)s(invAb)succgcaCfaGfaUfauugucaus(invAb) | 1351 | UCCGCACAGAUAUUGUCAU | 1662 |
| AM17242-SS | (NAG37)suscagagUfaUfUfAfuggaacgagus(invAb) | 1676 | UCAGAGUAUAUUGGAACGAGU | 1678 |
| AM17244-SS | (NAG37)scsucucuCfaGfAfGfuauuauggaus(invAb) | 1677 | CUCUCUCAGAGUAUUAUGGAU | 1679 |

(A^{2N}) = 2-aminoadenine nucleotide;
I = hypoxanthine (inosine) nucleotide

The XDH RNAi agents described herein are formed by annealing an antisense strand with a sense strand. A sense strand containing a sequence listed in Table 2, Table 4, or Table 5C can be hybridized to any antisense strand containing a sequence listed in Table 2, Table 3, or Table 5C provided the two sequences have a region of at least 85% complementarity over a contiguous 15, 16, 17, 18, 19, 20, or 21 nucleotide sequence.

In some aspects, the antisense strand of an XDH RNAi agent disclosed herein differs by 0, 1, 2, or 3 nucleotides from any of the antisense strand sequences in Table 3 or Table 5C. In some aspects, the sense strand of an XDH RNAi agent disclosed herein differs by 0, 1, 2, or 3 nucleotides from any of the sense strand sequences in Table 4 or Table 5C.

In some aspects, an XDH RNAi agent antisense strand comprises a nucleotide sequence of any of the sequences in Table 2, Table 3, or Table 5C. In some aspects, an XDH RNAi agent antisense strand comprises the sequence of nucleotides (from 5' end→3' end) at positions 1-17, 2-17, 1-18, 2-18, 1-19, 2-19, 1-20, 2-20, 1-21, or 2-21, of any of the sequences in Table 2, Table 3, or Table 5C. In certain aspects, an XDH RNAi agent antisense strand comprises or consists of a modified sequence of any one of the modified sequences in Table 3 or Table 5C.

In some aspects, an XDH RNAi agent sense strand comprises the nucleotide sequence of any of the sequences in Table 2, Table 4, or Table 5C. In some aspects, an XDH RNAi agent sense strand comprises the sequence of nucleotides (from 5' end→3' end) at positions 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, or 4-21, of any of the sequences in Table 2, Table 4, or Table 5C. In certain aspects, an XDH RNAi agent sense strand comprises or consists of a modified sequence of any one of the modified sequences in Table 4 or Table 5C.

For the XDH RNAi agents disclosed herein, the nucleotide at position 1 of the antisense strand (from 5' end→3' end) can be perfectly complementary to an XDH gene, or can be non-complementary to an XDH gene. In some aspects, the nucleotide at position 1 of the antisense strand (from 5' end→3' end) is a U, A, or dT (or a modified version thereof). In some aspects, the nucleotide at position 1 of the antisense strand (from 5' end→3' end) forms an A:U or U:A base pair with the sense strand.

A sense strand containing a sequence listed in Table 2, Table 4, or Table 5C can be hybridized to any antisense strand containing a sequence listed in Table 2. Table 3, or Table 5C, provided the two sequences have a region of at least 85% complementarity over a contiguous 16, 17, 18, 19, 20, or 21 nucleotide sequence. In some aspects, the XDH RNAi agent has a sense strand consisting of the modified sequence of any of the modified sequences in Table 4 or Table 5C, and an antisense strand consisting of the modified sequence of any of the modified sequences in Table 3 or Table 5C. Certain representative sequence pairings are exemplified by the Duplex ID Nos. shown in Tables 5A, 5B, and 5C.

In some aspects, an XDH RNAi agent comprises, consists of, or consists essentially of a duplex represented by any one of the Duplex ID Nos. presented herein. In some aspects, an XDH RNAi agent comprises the sense strand and antisense strand nucleotide sequences of any of the duplexes represented by any of the Duplex ID NOs. presented herein. In some aspects, an XDH RNAi agent comprises the sense strand and antisense strand nucleotide sequences of any of the duplexes represented by any of the Duplex ID NOs. presented herein and a targeting group and/or linking group wherein the targeting group and/or linking group is covalently linked (i.e., conjugated) to the sense strand or the antisense strand. In some aspects, an XDH RNAi agent includes the sense strand and antisense strand modified nucleotide sequences of any of the Duplex ID NOs. presented herein. In some aspects, an XDH RNAi agent comprises the sense strand and antisense strand modified nucleotide sequences of any of the Duplex ID NOs. presented herein and a targeting group and/or linking group, wherein the targeting group and/or linking group is covalently linked to the sense strand or the antisense strand.

In some aspects, an XDH RNAi agent comprises an antisense strand and a sense strand having the nucleotide sequences of any of the antisense strand/sense strand duplexes of Table 2 or Tables 5A, 5B, and 5C, and further comprises a targeting group or targeting ligand. In some aspects, an XDH RNAi agent comprises an antisense strand and a sense strand having the nucleotide sequences of any of the antisense strand/sense strand duplexes of Table 2 or Tables 5A, 5B, and 5C, and further comprises an asialoglycoprotein receptor ligand targeting group.

A targeting group, with or without a linker, can be linked to the 5' or 3' end of any of the sense and/or antisense strands disclosed in Tables 2, 3, 4, or 5C. A linker, with or without a targeting group, can be attached to the 5' or 3' end of any of the sense and/or antisense strands disclosed in Tables 2, 3, 4, and 5C.

In some aspects, an XDH RNAi agent comprises an antisense strand and a sense strand having the nucleotide sequences of any of the antisense strand/sense strand duplexes of Table 2 or Tables 5A, 5B and 5C, and further comprises a targeting ligand selected from the group consisting of: (NAG37) and (NAG37)s, each as defined in Table 6.

In some aspects, an XDH RNAi agent comprises an antisense strand and a sense strand having the modified nucleotide sequence of any of the antisense strand and/or sense strand nucleotide sequences in Table 3 or Table 4.

In some aspects, an XDH RNAi agent comprises an antisense strand and a sense strand having a modified nucleotide sequence of any of the antisense strand and/or sense strand nucleotide sequences of any of the duplexes Tables 5A, 5B3, and 5C, and further comprises an asialoglycoprotein receptor ligand targeting group.

In some aspects, an XDH RNAi agent comprises, consists of, or consists essentially of any of the duplexes of Tables 5A, 5 SS, and 5C.

TABLE 5A

XDH RNAi Agents Duplexes with Corresponding Sense and Antisense Strand ID Numbers and Sequence ID numbers for the modified and unmodified nucleotide sequences.

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD09217 | AM13029-AS | 945 | 1352 | AM13028-SS | 1175 | 1506 |
| AD09218 | AM13031-AS | 946 | 1352 | AM13030-SS | 1176 | 1506 |
| AD09219 | AM13033-AS | 947 | 1353 | AM13032-SS | 1177 | 1507 |
| AD09220 | AM13035-AS | 948 | 1354 | AM13034-SS | 1178 | 1508 |
| AD09221 | AM13037-AS | 949 | 1355 | AM13036-SS | 1179 | 1509 |
| AD09222 | AM13039-AS | 950 | 1356 | AM13038-SS | 1180 | 1510 |
| AD09223 | AM13041-AS | 951 | 1357 | AM13040-SS | 1181 | 1511 |
| AD09224 | AM13043-AS | 952 | 1358 | AM13042-SS | 1182 | 1512 |
| AD09225 | AM13045-AS | 953 | 1359 | AM13044-SS | 1183 | 1513 |
| AD09226 | AM13047-AS | 954 | 1360 | AM13046-SS | 1184 | 1514 |
| AD09227 | AM13049-AS | 955 | 1361 | AM13048-SS | 1185 | 1515 |
| AD09228 | AM13051-AS | 956 | 1362 | AM13050-SS | 1186 | 1516 |
| AD09229 | AM13053-AS | 957 | 1363 | AM13052-SS | 1187 | 1517 |
| AD09230 | AM13055-AS | 958 | 1364 | AM13054-SS | 1188 | 1518 |
| AD09231 | AM13057-AS | 959 | 1365 | AM13056-SS | 1189 | 1519 |
| AD09232 | AM13059-AS | 960 | 1366 | AM13058-SS | 1190 | 1520 |
| AD09233 | AM13061-AS | 961 | 1367 | AM13060-SS | 1191 | 1521 |
| AD09234 | AM13063-AS | 962 | 1368 | AM13062-SS | 1192 | 1522 |
| AD09235 | AM13065-AS | 963 | 1369 | AM13064-SS | 1193 | 1523 |
| AD09236 | AM13067-AS | 964 | 1370 | AM13066-SS | 1194 | 1524 |
| AD09237 | AM13069-AS | 965 | 1371 | AM13068-SS | 1195 | 1525 |
| AD09238 | AM13071-AS | 966 | 1372 | AM13070-SS | 1196 | 1526 |
| AD09239 | AM13073-AS | 967 | 1373 | AM13072-SS | 1197 | 1527 |
| AD09302 | AM13164-AS | 968 | 1374 | AM13163-SS | 1198 | 1528 |
| AD09303 | AM13166-AS | 969 | 1375 | AM13165-SS | 1199 | 1529 |
| AD09304 | AM13168-AS | 970 | 1376 | AM13167-SS | 1200 | 1530 |
| AD09305 | AM13170-AS | 971 | 1377 | AM13169-SS | 1201 | 1531 |
| AD09306 | AM13172-AS | 972 | 1378 | AM13171-SS | 1202 | 1532 |
| AD09307 | AM13174-AS | 973 | 1379 | AM13173-SS | 1203 | 1533 |
| AD09308 | AM13176-AS | 974 | 1374 | AM13175-SS | 1204 | 1528 |
| AD09309 | AM13177-AS | 975 | 1375 | AM13165-SS | 1199 | 1529 |
| AD09310 | AM13179-AS | 976 | 1376 | AM13178-SS | 1205 | 1530 |
| AD09311 | AM13181-AS | 977 | 1380 | AM13180-SS | 1206 | 1534 |
| AD09323 | AM13204-AS | 978 | 1374 | AM13163-SS | 1198 | 1528 |
| AD09324 | AM13205-AS | 979 | 1376 | AM13167-SS | 1200 | 1530 |
| AD09325 | AM13206-AS | 980 | 1377 | AM13169-SS | 1201 | 1531 |
| AD09326 | AM13207-AS | 981 | 1378 | AM13171-SS | 1202 | 1532 |
| AD09571 | AM13600-AS | 982 | 1381 | AM13599-SS | 1207 | 1535 |
| AD09572 | AM13602-AS | 983 | 1382 | AM13601-SS | 1208 | 1536 |
| AD09573 | AM13604-AS | 984 | 1383 | AM13603-SS | 1209 | 1537 |
| AD09598 | AM13648-AS | 985 | 1384 | AM13647-SS | 1210 | 1538 |
| AD09599 | AM13650-AS | 986 | 1385 | AM13649-SS | 1211 | 1539 |
| AD09600 | AM13652-AS | 987 | 1386 | AM13651-SS | 1212 | 1540 |
| AD09601 | AM13654-AS | 988 | 1387 | AM13653-SS | 1213 | 1541 |
| AD09602 | AM13656-AS | 989 | 1388 | AM13655-SS | 1214 | 1542 |
| AD09603 | AM13658-AS | 990 | 1389 | AM13657-SS | 1215 | 1543 |
| AD09604 | AM13660-AS | 991 | 1390 | AM13659-SS | 1216 | 1544 |
| AD09605 | AM13662-AS | 992 | 1391 | AM13661-SS | 1217 | 1545 |
| AD09606 | AM13664-AS | 993 | 1392 | AM13663-SS | 1218 | 1546 |
| AD09607 | AM13666-AS | 994 | 1393 | AM13665-SS | 1219 | 1547 |
| AD09608 | AM13668-AS | 995 | 1394 | AM13667-SS | 1220 | 1548 |
| AD09609 | AM13670-AS | 996 | 1395 | AM13669-SS | 1221 | 1549 |
| AD09610 | AM13672-AS | 997 | 1396 | AM13671-SS | 1222 | 1550 |
| AD09611 | AM13674-AS | 998 | 1397 | AM13673-SS | 1223 | 1551 |
| AD09612 | AM13676-AS | 999 | 1398 | AM13675-SS | 1224 | 1552 |
| AD09613 | AM13678-AS | 1000 | 1399 | AM13677-SS | 1225 | 1553 |
| AD09614 | AM13680-AS | 1001 | 1400 | AM13679-SS | 1226 | 1554 |
| AD09615 | AM13682-AS | 1002 | 1401 | AM13681-SS | 1227 | 1555 |
| AD09616 | AM13684-AS | 1003 | 1402 | AM13683-SS | 1228 | 1556 |
| AD09617 | AM13686-AS | 1004 | 1403 | AM13685-SS | 1229 | 1557 |
| AD09618 | AM13688-AS | 1005 | 1404 | AM13687-SS | 1230 | 1558 |
| AD09619 | AM13690-AS | 1006 | 1405 | AM13689-SS | 1231 | 1559 |
| AD09620 | AM13692-AS | 1007 | 1406 | AM13691-SS | 1232 | 1560 |
| AD09621 | AM13694-AS | 1008 | 1407 | AM13693-SS | 1233 | 1561 |
| AD09623 | AM13696-AS | 1009 | 1408 | AM13695-SS | 1234 | 1262 |
| AD09624 | AM13698-AS | 1010 | 1409 | AM13697-SS | 1235 | 1563 |
| AD09625 | AM13700-AS | 1011 | 1410 | AM13699-SS | 1236 | 1564 |
| AD09626 | AM13702-AS | 1012 | 1411 | AM13701-SS | 1237 | 1565 |
| AD09627 | AM13704-AS | 1013 | 1412 | AM13703-SS | 1238 | 1566 |
| AD09628 | AM13706-AS | 1014 | 1413 | AM13705-SS | 1239 | 1567 |
| AD09629 | AM13708-AS | 1015 | 1414 | AM13707-SS | 1240 | 1568 |

TABLE 5A-continued

XDH RNAi Agents Duplexes with Corresponding Sense and Antisense Strand ID Numbers and Sequence ID numbers for the modified and unmodified nucleotide sequences.

| Duplex | AS ID | AS modified SEQ ID NO: | AS unmodified SEQ ID NO: | SS ID | SS modified SEQ ID NO: | SS unmodified SEQ ID NO: |
| --- | --- | --- | --- | --- | --- | --- |
| AD09630 | AM13710-AS | 1016 | 1415 | AM13709-SS | 1241 | 1569 |
| AD09631 | AM13712-AS | 1017 | 1416 | AM13711-SS | 1242 | 1570 |
| AD09632 | AM13714-AS | 1018 | 1417 | AM13713-SS | 1243 | 1571 |
| AD09633 | AM13716-AS | 1019 | 1418 | AM13715-SS | 1244 | 1572 |
| AD09634 | AM13718-AS | 1020 | 1419 | AM13717-SS | 1245 | 1573 |
| AD09635 | AM13720-AS | 1021 | 1420 | AM13719-SS | 1246 | 1574 |
| AD09636 | AM13722-AS | 1022 | 1421 | AM13721-SS | 1247 | 1575 |
| AD09637 | AM13724-AS | 1023 | 1422 | AM13723-SS | 1248 | 1576 |
| AD09638 | AM13726-AS | 1024 | 1423 | AM13725-SS | 1249 | 1577 |
| AD09639 | AM13728-AS | 1025 | 1424 | AM13727-SS | 1250 | 1578 |
| AD09640 | AM13730-AS | 1026 | 1425 | AM13729-SS | 1251 | 1579 |
| AD09650 | AM13747-AS | 1027 | 1366 | AM13746-SS | 1252 | 1520 |
| AD09651 | AM13748-AS | 1028 | 1366 | AM13746-SS | 1252 | 1520 |
| AD09652 | AM13749-AS | 1029 | 1366 | AM13746-SS | 1252 | 1520 |
| AD09653 | AM13748-AS | 1028 | 1366 | AM13750-SS | 1253 | 1580 |
| AD09654 | AM13748-AS | 1028 | 1366 | AM13751-SS | 1254 | 1581 |
| AD09655 | AM13748-AS | 1028 | 1366 | AM13752-SS | 1255 | 1582 |
| AD09656 | AM13753-AS | 1030 | 1426 | AM13746-SS | 1252 | 1520 |
| AD09657 | AM13754-AS | 1031 | 1427 | AM13746-SS | 1252 | 1520 |
| AD09658 | AM13755-AS | 1032 | 1366 | AM13746-SS | 1252 | 1520 |
| AD09659 | AM13748-AS | 1028 | 1366 | AM13058-SS | 1190 | 1520 |
| AD09660 | AM13748-AS | 1028 | 1366 | AM13756-SS | 1256 | 1520 |
| AD09661 | AM13748-AS | 1028 | 1366 | AM13757-SS | 1257 | 1520 |
| AD09662 | AM13758-AS | 1028 | 1366 | AM13060-SS | 1191 | 1521 |
| AD09663 | AM13759-AS | 1034 | 1367 | AM13060-SS | 1191 | 1521 |
| AD09664 | AM13758-AS | 1033 | 1367 | AM13760-SS | 1258 | 1521 |
| AD09665 | AM13761-AS | 1035 | 1367 | AM13760-SS | 1258 | 1521 |
| AD09724 | AM13858-AS | 1036 | 1428 | AM13857-SS | 1259 | 1583 |
| AD09725 | AM13860-AS | 1037 | 1429 | AM13859-SS | 1260 | 1584 |
| AD09726 | AM13862-AS | 1038 | 1430 | AM13861-SS | 1261 | 1585 |
| AD09727 | AM13864-AS | 1039 | 1431 | AM13863-SS | 1262 | 1586 |
| AD09728 | AM13866-AS | 1040 | 1432 | AM13865-SS | 1263 | 1587 |
| AD09729 | AM13868-AS | 1041 | 1433 | AM13867-SS | 1264 | 1588 |
| AD09730 | AM13870-AS | 1042 | 1434 | AM13869-SS | 1265 | 1589 |
| AD09731 | AM13872-AS | 1043 | 1435 | AM13871-SS | 1266 | 1590 |
| AD09732 | AM13874-AS | 1044 | 1436 | AM13873-SS | 1267 | 1591 |
| AD09733 | AM13876-AS | 1045 | 1437 | AM13875-SS | 1268 | 1592 |
| AD09734 | AM13878-AS | 1046 | 1438 | AM13877-SS | 1269 | 1593 |
| AD09735 | AM13880-AS | 1047 | 1439 | AM13879-SS | 1270 | 1594 |
| AD09736 | AM13882-AS | 1048 | 1440 | AM13881-SS | 1271 | 1595 |
| AD09737 | AM13884-AS | 1049 | 1441 | AM13883-SS | 1272 | 1596 |
| AD09738 | AM13886-AS | 1050 | 1442 | AM13885-SS | 1273 | 1597 |
| AD09739 | AM13888-AS | 1051 | 1443 | AM13887-SS | 1274 | 1598 |
| AD09740 | AM13890-AS | 1052 | 1444 | AM13889-SS | 1275 | 1599 |
| AD09741 | AM13892-AS | 1053 | 1445 | AM13891-SS | 1276 | 1600 |
| AD09742 | AM13894-AS | 1054 | 1446 | AM13893-SS | 1277 | 1601 |
| AD09743 | AM13896-AS | 1055 | 1447 | AM13895-SS | 1278 | 1602 |
| AD09744 | AM13898-AS | 1056 | 1448 | AM13897-SS | 1279 | 1603 |
| AD09745 | AM13900-AS | 1057 | 1449 | AM13899-SS | 1280 | 1604 |
| AD09937 | AM14175-AS | 1058 | 1450 | AM14174-SS | 1281 | 1605 |
| AD09938 | AM14176-AS | 1059 | 1448 | AM13897-SS | 1279 | 1603 |
| AD09962 | AM14204-AS | 1060 | 1451 | AM14203-SS | 1282 | 1606 |
| AD09963 | AM14206-AS | 1061 | 1452 | AM14205-SS | 1283 | 1607 |
| AD09964 | AM14208-AS | 1062 | 1453 | AM14207-SS | 1284 | 1608 |
| AD09965 | AM14209-AS | 1063 | 1450 | AM14174-SS | 1281 | 1605 |
| AD09966 | AM14210-AS | 1064 | 1450 | AM14174-SS | 1281 | 1605 |
| AD09967 | AM14211-AS | 1065 | 1450 | AM14174-SS | 1281 | 1605 |
| AD09968 | AM14212-AS | 1066 | 1450 | AM14174-SS | 1281 | 1605 |
| AD09969 | AM14211-AS | 1065 | 1450 | AM14213-SS | 1285 | 1605 |
| AD09970 | AM14211-AS | 1065 | 1450 | AM14214-SS | 1286 | 1605 |
| AD09971 | AM14216-AS | 1067 | 1454 | AM14215-SS | 1287 | 1609 |
| AD09972 | AM14218-AS | 1068 | 1455 | AM14217-SS | 1288 | 1610 |
| AD09973 | AM14220-AS | 1069 | 1456 | AM14219-SS | 1289 | 1611 |
| AD09974 | AM14222-AS | 1070 | 1457 | AM14221-SS | 1290 | 1612 |
| AD09975 | AM14224-AS | 1071 | 1458 | AM14223-SS | 1291 | 1613 |
| AD09976 | AM14226-AS | 1072 | 1459 | AM14225-SS | 1292 | 1614 |
| AD09977 | AM14228-AS | 1073 | 1460 | AM14227-SS | 1293 | 1615 |
| AD09978 | AM14230-AS | 1074 | 1461 | AM14229-SS | 1294 | 1616 |
| AD09979 | AM14232-AS | 1075 | 1462 | AM14231-SS | 1295 | 1617 |
| AD09980 | AM14234-AS | 1076 | 1463 | AM14233-SS | 1296 | 1618 |
| AD09981 | AM14236-AS | 1077 | 1464 | AM14235-SS | 1297 | 1619 |

TABLE 5A-continued

XDH RNAi Agents Duplexes with Corresponding Sense and Antisense Strand ID Numbers and Sequence ID numbers for the modified and unmodified nucleotide sequences.

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD09982 | AM14238-AS | 1078 | 1465 | AM14237-SS | 1298 | 1620 |
| AD09983 | AM14240-AS | 1079 | 1466 | AM14239-SS | 1299 | 1621 |
| AD09984 | AM14242-AS | 1080 | 1467 | AM14241-SS | 1300 | 1622 |
| AD09985 | AM14244-AS | 1081 | 1468 | AM14243-SS | 1301 | 1623 |
| AD09986 | AM14246-AS | 1082 | 1469 | AM14245-SS | 1302 | 1624 |
| AD09987 | AM14248-AS | 1083 | 1470 | AM14247-SS | 1303 | 1625 |
| AD09988 | AM14250-AS | 1084 | 1471 | AM14249-SS | 1304 | 1626 |
| AD09989 | AM14252-AS | 1085 | 1472 | AM14251-SS | 1305 | 1627 |
| AD09990 | AM14254-AS | 1086 | 1473 | AM14253-SS | 1306 | 1628 |
| AD09991 | AM14256-AS | 1087 | 1474 | AM14255-SS | 1307 | 1629 |
| AD09992 | AM14258-AS | 1088 | 1475 | AM14257-SS | 1308 | 1630 |
| AD09993 | AM14260-AS | 1089 | 1476 | AM14259-SS | 1309 | 1631 |
| AD09994 | AM14262-AS | 1090 | 1477 | AM14261-SS | 1310 | 1632 |
| AD09995 | AM14264-AS | 1091 | 1478 | AM14263-SS | 1311 | 1633 |
| AD10008 | AM14280-AS | 1092 | 1448 | AM13897-SS | 1279 | 1603 |
| AD10009 | AM14281-AS | 1093 | 1448 | AM13897-SS | 1279 | 1603 |
| AD10010 | AM14282-AS | 1094 | 1448 | AM13897-SS | 1279 | 1603 |
| AD10011 | AM14283-AS | 1095 | 1448 | AM13897-SS | 1279 | 1603 |
| AD10012 | AM14282-AS | 1094 | 1448 | AM14284-SS | 1312 | 1603 |
| AD10013 | AM14285-AS | 1096 | 1448 | AM14284-SS | 1312 | 1603 |
| AD10014 | AM14282-AS | 1094 | 1448 | AM14286-SS | 1313 | 1603 |
| AD10015 | AM14285-AS | 1096 | 1448 | AM14286-SS | 1313 | 1603 |
| AD10016 | AM14288-AS | 1097 | 1479 | AM14287-SS | 1314 | 1634 |
| AD10017 | AM14290-AS | 1098 | 1480 | AM14289-SS | 1315 | 1635 |
| AD10018 | AM14292-AS | 1099 | 1481 | AM14291-SS | 1316 | 1636 |
| AD10019 | AM14293-AS | 1100 | 1482 | AM14291-SS | 1316 | 1636 |
| AD10020 | AM14292-AS | 1099 | 1481 | AM14294-SS | 1317 | 1637 |
| AD10021 | AM14296-AS | 1101 | 1482 | AM14295-SS | 1318 | 1638 |
| AD10022 | AM14297-AS | 1102 | 1482 | AM14295-SS | 1318 | 1638 |
| AD10023 | AM14298-AS | 1103 | 1482 | AM14295-SS | 1318 | 1638 |
| AD10024 | AM14299-AS | 1104 | 1482 | AM14295-SS | 1318 | 1638 |
| AD10025 | AM14299-AS | 1104 | 1482 | AM14300-SS | 1319 | 1639 |
| AD10026 | AM14301-AS | 1105 | 1482 | AM14295-SS | 1318 | 1638 |
| AD10027 | AM14299-AS | 1104 | 1482 | AM14302-SS | 1320 | 1638 |
| AD10028 | AM14299-AS | 1104 | 1482 | AM14303-SS | 1321 | 1638 |
| AD10029 | AM14304-AS | 1106 | 1482 | AM14303-SS | 1321 | 1638 |
| AD10030 | AM14305-AS | 1107 | 1482 | AM14302-SS | 1320 | 1638 |
| AD10091 | AM14383-AS | 1108 | 1438 | AM13877-SS | 1269 | 1593 |
| AD10092 | AM14384-AS | 1109 | 1438 | AM13877-SS | 1269 | 1593 |
| AD10093 | AM14385-AS | 1110 | 1438 | AM13877-SS | 1269 | 1593 |
| AD10094 | AM14384-AS | 1109 | 1438 | AM14386-SS | 1322 | 1593 |
| AD10095 | AM14385-AS | 1110 | 1438 | AM14386-SS | 1322 | 1593 |
| AD10096 | AM14387-AS | 1111 | 1438 | AM13877-SS | 1269 | 1593 |
| AD10097 | AM14388-AS | 1112 | 1438 | AM13877-SS | 1269 | 1593 |
| AD10099 | AM14391-AS | 1113 | 1483 | AM14390-SS | 1323 | 1640 |
| AD10100 | AM14393-AS | 1114 | 1484 | AM14392-SS | 1324 | 1641 |
| AD10101 | AM14395-AS | 1115 | 1485 | AM14394-SS | 1325 | 1642 |
| AD10102 | AM14397-AS | 1116 | 1486 | AM14396-SS | 1326 | 1643 |
| AD10103 | AM14399-AS | 1117 | 1487 | AM14398-SS | 1327 | 1644 |
| AD10104 | AM14401-AS | 1118 | 1488 | AM14400-SS | 1328 | 1645 |
| AD10105 | AM14403-AS | 1119 | 1489 | AM14402-SS | 1329 | 1646 |
| AD10106 | AM14405-AS | 1120 | 1490 | AM14404-SS | 1330 | 1647 |
| AD10107 | AM14407-AS | 1121 | 1491 | AM14406-SS | 1331 | 1648 |
| AD10108 | AM14409-AS | 1122 | 1492 | AM14408-SS | 1332 | 1649 |
| AD10109 | AM14411-AS | 1123 | 1493 | AM14410-SS | 1333 | 1650 |
| AD10110 | AM14413-AS | 1124 | 1494 | AM14412-SS | 1334 | 1651 |
| AD10111 | AM14415-AS | 1125 | 1495 | AM14414-SS | 1335 | 1652 |
| AD10112 | AM14417-AS | 1126 | 1496 | AM14416-SS | 1336 | 1653 |
| AD10113 | AM14419-AS | 1127 | 1497 | AM14418-SS | 1337 | 1654 |
| AD10176 | AM14522-AS | 1128 | 1377 | AM13169-SS | 1201 | 1531 |
| AD10177 | AM14523-AS | 1129 | 1377 | AM13169-SS | 1201 | 1531 |
| AD10178 | AM14524-AS | 1130 | 1377 | AM13169-SS | 1201 | 1531 |
| AD10179 | AM14524-AS | 1130 | 1377 | AM14525-SS | 1338 | 1531 |
| AD10180 | AM14524-AS | 1130 | 1377 | AM14526-SS | 1339 | 1531 |
| AD10181 | AM14527-AS | 1131 | 1397 | AM13673-SS | 1223 | 1551 |
| AD10182 | AM14529-AS | 1132 | 1397 | AM14528-SS | 1340 | 1551 |
| AD10183 | AM14530-AS | 1133 | 1397 | AM14528-SS | 1340 | 1551 |
| AD10184 | AM14529-AS | 1132 | 1397 | AM14531-SS | 1341 | 1551 |
| AD10200 | AM14543-AS | 1134 | 1397 | AM13673-SS | 1223 | 1551 |
| AD10201 | AM14544-AS | 1135 | 1397 | AM13673-SS | 1223 | 1551 |
| AD10202 | AM14545-AS | 1136 | 1397 | AM13673-SS | 1223 | 1551 |

TABLE 5A-continued

XDH RNAi Agents Duplexes with Corresponding Sense and Antisense Strand ID Numbers and Sequence ID numbers for the modified and unmodified nucleotide sequences.

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD10203 | AM14544-AS | 1135 | 1397 | AM14528-SS | 1340 | 1551 |
| AD10204 | AM14545-AS | 1136 | 1397 | AM14528-SS | 1340 | 1551 |
| AD10205 | AM14544-AS | 1135 | 1397 | AM14531-SS | 1341 | 1551 |
| AD10275 | AM14642-AS | 1137 | 1440 | AM13881-SS | 1271 | 1595 |
| AD10276 | AM14643-AS | 1138 | 1440 | AM13881-SS | 1271 | 1595 |
| AD10277 | AM14644-AS | 1139 | 1440 | AM13881-SS | 1271 | 1595 |
| AD10278 | AM14645-AS | 1140 | 1440 | AM13881-SS | 1271 | 1595 |
| AD10279 | AM14644-AS | 1139 | 1440 | AM14646-SS | 1342 | 1595 |
| AD10280 | AM14647-AS | 1141 | 1440 | AM14646-SS | 1342 | 1595 |
| AD10281 | AM14648-AS | 1142 | 1440 | AM14646-SS | 1342 | 1595 |
| AD10282 | AM14649-AS | 1143 | 1440 | AM14646-SS | 1342 | 1595 |
| AD10283 | AM14650-AS | 1144 | 1440 | AM14646-SS | 1342 | 1595 |
| AD10619 | AM14281-AS | 1093 | 1448 | AM14284-SS | 1312 | 1603 |
| AD10620 | AM15134-AS | 1145 | 1448 | AM14284-SS | 1312 | 1603 |
| AD10621 | AM15135-AS | 1146 | 1448 | AM14284-SS | 1312 | 1603 |
| AD10622 | AM14283-AS | 1095 | 1448 | AM14284-SS | 1312 | 1603 |
| AD10623 | AM15137-AS | 1147 | 1498 | AM15136-SS | 1343 | 1655 |
| AD10624 | AM15139-AS | 1148 | 1499 | AM15138-SS | 1344 | 1656 |
| AD10625 | AM15141-AS | 1149 | 1500 | AM15140-SS | 1345 | 1657 |
| AD10626 | AM15143-AS | 1150 | 1501 | AM15142-SS | 1346 | 1658 |
| AD10627 | AM15145-AS | 1151 | 1502 | AM15144-SS | 1347 | 1659 |
| AD10628 | AM15146-AS | 1152 | 1448 | AM14284-SS | 1312 | 1603 |
| AD10629 | AM15147-AS | 1153 | 1397 | AM14528-SS | 1340 | 1551 |
| AD10630 | AM15148-AS | 1154 | 1397 | AM14528-SS | 1340 | 1551 |
| AD10631 | AM15149-AS | 1155 | 1397 | AM14528-SS | 1340 | 1551 |
| AD10632 | AM15150-AS | 1156 | 1397 | AM14528-SS | 1340 | 1551 |
| AD10633 | AM15151-AS | 1157 | 1397 | AM14531-SS | 1341 | 1551 |
| AD10634 | AM15152-AS | 1158 | 1397 | AM14531-SS | 1341 | 1551 |
| AD10635 | AM15153-AS | 1159 | 1397 | AM14531-SS | 1341 | 1551 |
| AD10636 | AM15154-AS | 1160 | 1397 | AM14531-SS | 1341 | 1551 |
| AD10728 | AM14244-AS | 1081 | 1468 | AM15284-SS | 1348 | 1623 |
| AD10729 | AM15285-AS | 1161 | 1468 | AM15284-SS | 1348 | 1623 |
| AD10730 | AM15286-AS | 1162 | 1468 | AM15284-SS | 1348 | 1623 |
| AD10731 | AM15287-AS | 1163 | 1468 | AM15284-SS | 1348 | 1623 |
| AD10732 | AM15289-AS | 1164 | 1503 | AM15288-SS | 1349 | 1660 |
| AD10733 | AM15290-AS | 1165 | 1468 | AM15284-SS | 1348 | 1623 |
| AD10734 | AM15291-AS | 1166 | 1468 | AM15284-SS | 1348 | 1623 |
| AD10735 | AM15292-AS | 1167 | 1468 | AM15284-SS | 1348 | 1623 |
| AD10736 | AM15294-AS | 1168 | 1504 | AM15293-SS | 1350 | 1661 |
| AD10737 | AM15296-AS | 1169 | 1505 | AM15295-SS | 1351 | 1662 |
| AD10952 | AM15606-AS | 1170 | 1448 | AM14284-SS | 1312 | 1603 |
| AD10953 | AM15607-AS | 1171 | 1498 | AM15136-SS | 1343 | 1655 |
| AD10954 | AM15608-AS | 1172 | 1450 | AM14213-SS | 1285 | 1605 |
| AD10967 | AM13882-AS | 1048 | 1440 | AM14646-SS | 1342 | 1595 |
| AD10968 | AM15626-AS | 1173 | 1440 | AM14646-SS | 1342 | 1595 |
| AD10969 | AM15627-AS | 1174 | 1440 | AM14646-SS | 1342 | 1595 |
| AD12167 | AM17243-AS | 1672 | 1674 | AM17242-SS | 1676 | 1678 |
| AD12168 | AM17245-AS | 1673 | 1675 | AM17244-SS | 1677 | 1679 |

TABLE 5B

XDH RNAi Agents Duplexes with Corresponding Sense and Antisense Strand ID Numbers Referencing Position Targeted on XDH Gene (SEQ ID NO: 1)

| Duplex ID | Antisense Strand ID | Sense Strand ID | Targeted XDH Gene Position (Of SEQ ID NO:1) |
|---|---|---|---|
| AD09217 | AM13029-AS | AM13028-SS | 488 |
| AD09218 | AM13031-AS | AM13030-SS | 488 |
| AD09219 | AM13033-AS | AM13032-SS | 1612 |
| AD09220 | AM13035-AS | AM13034-SS | 1614 |
| AD09221 | AM13037-AS | AM13036-SS | 1617 |
| AD09222 | AM13039-AS | AM13038-SS | 2128 |
| AD09223 | AM13041-AS | AM13040-SS | 2130 |
| AD09224 | AM13043-AS | AM13042-SS | 2131 |
| AD09225 | AM13045-AS | AM13044-SS | 2132 |
| AD09226 | AM13047-AS | AM13046-SS | 2153 |
| AD09227 | AM13049-AS | AM13048-SS | 2185 |
| AD09228 | AM13051-AS | AM13050-SS | 2186 |
| AD09229 | AM13053-AS | AM13052-SS | 3272 |
| AD09230 | AM13055-AS | AM13054-SS | 435 |
| AD09231 | AM13057-AS | AM13056-SS | 2571 |
| AD09232 | AM13059-AS | AM13058-SS | 2612 |
| AD09233 | AM13061-AS | AM13060-SS | 2616 |
| AD09234 | AM13063-AS | AM13062-SS | 2617 |

TABLE 5B-continued

XDH RNAi Agents Duplexes with Corresponding Sense and Antisense Strand ID Numbers Referencing Position Targeted on XDH Gene (SEQ ID NO: 1)

| Duplex ID | Antisense Strand ID | Sense Strand ID | Targeted XDH Gene Position (Of SEQ ID NO:1) |
|---|---|---|---|
| AD09235 | AM13065-AS | AM13064-SS | 2619 |
| AD09236 | AM13067-AS | AM13066-SS | 3045 |
| AD09237 | AM13069-AS | AM13068-SS | 3548 |
| AD09238 | AM13071-AS | AM13070-SS | 3551 |
| AD09239 | AM13073-AS | AM13072-SS | 3640 |
| AD09302 | AM13164-AS | AM13163-SS | 265 |
| AD09303 | AM13166-AS | AM13165-SS | 2248 |
| AD09304 | AM13168-AS | AM13167-SS | 2694 |
| AD09305 | AM13170-AS | AM13169-SS | 3083 |
| AD09306 | AM13172-AS | AM13171-SS | 4665 |
| AD09307 | AM13174-AS | AM13173-SS | 4725 |
| AD09308 | AM13176-AS | AM13175-SS | 265 |
| AD09309 | AM13177-AS | AM13165-SS | 2248 |
| AD09310 | AM13179-AS | AM13178-SS | 2694 |
| AD09311 | AM13181-AS | AM13180-SS | 4725 |
| AD09323 | AM13204-AS | AM13163-SS | 265 |
| AD09324 | AM13205-AS | AM13167-SS | 2694 |
| AD09325 | AM13206-AS | AM13169-SS | 3083 |
| AD09326 | AM13207-AS | AM13171-SS | 4665 |
| AD09571 | AM13600-AS | AM13599-SS | 2850 |
| AD09572 | AM13602-AS | AM13601-SS | 2851 |
| AD09573 | AM13604-AS | AM13603-SS | 2852 |
| AD09598 | AM13648-AS | AM13647-SS | 235 |
| AD09599 | AM13650-AS | AM13649-SS | 249 |
| AD09600 | AM13652-AS | AM13651-SS | 252 |
| AD09601 | AM13654-AS | AM13653-SS | 1703 |
| AD09602 | AM13656-AS | AM13655-SS | 2049 |
| AD09603 | AM13658-AS | AM13657-SS | 2155 |
| AD09604 | AM13660-AS | AM13659-SS | 2997 |
| AD09605 | AM13662-AS | AM13661-SS | 3019 |
| AD09606 | AM13664-AS | AM13663-SS | 3020 |
| AD09607 | AM13666-AS | AM13665-SS | 3037 |
| AD09608 | AM13668-AS | AM13667-SS | 4136 |
| AD09609 | AM13670-AS | AM13669-SS | 4149 |
| AD09610 | AM13672-AS | AM13671-SS | 4150 |
| AD09611 | AM13674-AS | AM13673-SS | 4289 |
| AD09612 | AM13676-AS | AM13675-SS | 4446 |
| AD09613 | AM13678-AS | AM13677-SS | 4505 |
| AD09614 | AM13680-AS | AM13679-SS | 4515 |
| AD09615 | AM13682-AS | AM13681-SS | 4517 |
| AD09616 | AM13684-AS | AM13683-SS | 4518 |
| AD09617 | AM13686-AS | AM13685-SS | 4520 |
| AD09618 | AM13688-AS | AM13687-SS | 4525 |
| AD09619 | AM13690-AS | AM13689-SS | 4700 |
| AD09620 | AM13692-AS | AM13691-SS | 5286 |
| AD09621 | AM13694-AS | AM13693-SS | 5420 |
| AD09623 | AM13696-AS | AM13695-SS | N/A (mouse-specific RNAi agent) |
| AD09624 | AM13698-AS | AM13697-SS | N/A (mouse-specific RNAi agent) |
| AD09625 | AM13700-AS | AM13699-SS | N/A (mouse-specific RNAi agent) |
| AD09626 | AM13702-AS | AM13701-SS | N/A (mouse-specific RNAi agent) |
| AD09627 | AM13704-AS | AM13703-SS | N/A (mouse-specific RNAi agent) |
| AD09628 | AM13706-AS | AM13705-SS | N/A (mouse-specific RNAi agent) |
| AD09629 | AM13708-AS | AM13707-SS | N/A (mouse-specific RNAi agent) |
| AD09630 | AM13710-AS | AM13709-SS | N/A (mouse-specific RNAi agent) |
| AD09631 | AM13712-AS | AM13711-SS | N/A (mouse-specific RNAi agent) |
| AD09632 | AM13714-AS | AM13713-SS | N/A (mouse-specific RNAi agent) |
| AD09633 | AM13716-AS | AM13715-SS | N/A (mouse-specific RNAi agent) |
| AD09634 | AM13718-AS | AM13717-SS | N/A (mouse-specific RNAi agent) |
| AD09635 | AM13720-AS | AM13719-SS | N/A (mouse-specific RNAi agent) |
| AD09636 | AM13722-AS | AM13721-SS | N/A (mouse-specific RNAi agent) |
| AD09637 | AM13724-AS | AM13723-SS | N/A (mouse-specific RNAi agent) |
| AD09638 | AM13726-AS | AM13725-SS | N/A (mouse-specific RNAi agent) |
| AD09639 | AM13728-AS | AM13727-SS | N/A (mouse-specific RNAi agent) |
| AD09640 | AM13730-AS | AM13729-SS | N/A (mouse-specific RNAi agent) |
| AD09650 | AM13747-AS | AM13746-SS | 2612 |
| AD09651 | AM13748-AS | AM13746-SS | 2612 |
| AD09652 | AM13749-AS | AM13746-SS | 2612 |
| AD09653 | AM13748-AS | AM13750-SS | 2612 |
| AD09654 | AM13748-AS | AM13751-SS | 2612 |
| AD09655 | AM13748-AS | AM13752-SS | 2612 |
| AD09656 | AM13753-AS | AM13746-SS | 2612 |
| AD09657 | AM13754-AS | AM13746-SS | 2612 |
| AD09658 | AM13755-AS | AM13746-SS | 2612 |
| AD09659 | AM13748-AS | AM13058-SS | 2612 |
| AD09660 | AM13748-AS | AM13756-SS | 2612 |
| AD09661 | AM13748-AS | AM13757-SS | 2612 |
| AD09662 | AM13758-AS | AM13060-SS | 2616 |
| AD09663 | AM13759-AS | AM13060-SS | 2616 |
| AD09664 | AM13758-AS | AM13760-SS | 2616 |
| AD09665 | AM13761-AS | AM13760-SS | 2616 |
| AD09724 | AM13858-AS | AM13857-SS | 122 |
| AD09725 | AM13860-AS | AM13859-SS | 139 |
| AD09726 | AM13862-AS | AM13861-SS | 239 |
| AD09727 | AM13864-AS | AM13863-SS | 332 |
| AD09728 | AM13866-AS | AM13865-SS | 430 |
| AD09729 | AM13868-AS | AM13867-SS | 500 |
| AD09730 | AM13870-AS | AM13869-SS | 867 |
| AD09731 | AM13872-AS | AM13871-SS | 877 |
| AD09732 | AM13874-AS | AM13873-SS | 888 |
| AD09733 | AM13876-AS | AM13875-SS | 1285 |
| AD09734 | AM13878-AS | AM13877-SS | 1322 |
| AD09735 | AM13880-AS | AM13879-SS | 1921 |
| AD09736 | AM13882-AS | AM13881-SS | 1963 |
| AD09737 | AM13884-AS | AM13883-SS | 2138 |
| AD09738 | AM13886-AS | AM13885-SS | 2148 |
| AD09739 | AM13888-AS | AM13887-SS | 2157 |
| AD09740 | AM13890-AS | AM13889-SS | 2209 |
| AD09741 | AM13892-AS | AM13891-SS | 2320 |
| AD09742 | AM13894-AS | AM13893-SS | 2357 |
| AD09743 | AM13896-AS | AM13895-SS | 2361 |
| AD09744 | AM13898-AS | AM13897-SS | 2696 |
| AD09745 | AM13900-AS | AM13899-SS | 2701 |
| AD09937 | AM14175-AS | AM14174-SS | 1963 |
| AD09938 | AM14176-AS | AM13897-SS | 2696 |
| AD09962 | AM14204-AS | AM14203-SS | 1964 |
| AD09963 | AM14206-AS | AM14205-SS | 1965 |
| AD09964 | AM14208-AS | AM14207-SS | 1967 |
| AD09965 | AM14209-AS | AM14174-SS | 1963 |
| AD09966 | AM14210-AS | AM14174-SS | 1963 |
| AD09967 | AM14211-AS | AM14174-SS | 1963 |
| AD09968 | AM14212-AS | AM14174-SS | 1963 |
| AD09969 | AM14211-AS | AM14213-SS | 1963 |
| AD09970 | AM14211-AS | AM14214-SS | 1963 |
| AD09971 | AM14216-AS | AM14215-SS | 238 |
| AD09972 | AM14218-AS | AM14217-SS | 484 |
| AD09973 | AM14220-AS | AM14219-SS | 493 |
| AD09974 | AM14222-AS | AM14221-SS | 497 |
| AD09975 | AM14224-AS | AM14223-SS | 886 |
| AD09976 | AM14226-AS | AM14225-SS | 1117 |
| AD09977 | AM14228-AS | AM14227-SS | 1615 |
| AD09978 | AM14230-AS | AM14229-SS | 2064 |
| AD09979 | AM14232-AS | AM14231-SS | 2370 |
| AD09980 | AM14234-AS | AM14233-SS | 2684 |
| AD09981 | AM14236-AS | AM14235-SS | 2995 |
| AD09982 | AM14238-AS | AM14237-SS | 3016 |
| AD09983 | AM14240-AS | AM14239-SS | 3041 |

TABLE 5B-continued

XDH RNAi Agents Duplexes with Corresponding Sense and Antisense Strand ID Numbers Referencing Position Targeted on XDH Gene (SEQ ID NO: 1)

| Duplex ID | Antisense Strand ID | Sense Strand ID | Targeted XDH Gene Position (Of SEQ ID NO:1) |
|---|---|---|---|
| AD09984 | AM14242-AS | AM14241-SS | 3498 |
| AD09985 | AM14244-AS | AM14243-SS | 3598 |
| AD09986 | AM14246-AS | AM14245-SS | 3600 |
| AD09987 | AM14248-AS | AM14247-SS | 3877 |
| AD09988 | AM14250-AS | AM14249-SS | 3930 |
| AD09989 | AM14252-AS | AM14251-SS | 4394 |
| AD09990 | AM14254-AS | AM14253-SS | 4513 |
| AD09991 | AM14256-AS | AM14255-SS | 4531 |
| AD09992 | AM14258-AS | AM14257-SS | 4666 |
| AD09993 | AM14260-AS | AM14259-SS | 4843 |
| AD09994 | AM14262-AS | AM14261-SS | 5234 |
| AD09995 | AM14264-AS | AM14263-SS | 5411 |
| AD10008 | AM14280-AS | AM13897-SS | 2696 |
| AD10009 | AM14281-AS | AM13897-SS | 2696 |
| AD10010 | AM14282-AS | AM13897-SS | 2696 |
| AD10011 | AM14283-AS | AM13897-SS | 2696 |
| AD10012 | AM14282-AS | AM14284-SS | 2696 |
| AD10013 | AM14285-AS | AM14284-SS | 2696 |
| AD10014 | AM14282-AS | AM14286-SS | 2696 |
| AD10015 | AM14285-AS | AM14286-SS | 2696 |
| AD10016 | AM14288-AS | AM14287-SS | 231 |
| AD10017 | AM14290-AS | AM14289-SS | 242 |
| AD10018 | AM14292-AS | AM14291-SS | 1384 |
| AD10019 | AM14293-AS | AM14291-SS | 1384 |
| AD10020 | AM14292-AS | AM14294-SS | 1384 |
| AD10021 | AM14296-AS | AM14295-SS | 1612 |
| AD10022 | AM14297-AS | AM14295-SS | 1612 |
| AD10023 | AM14298-AS | AM14295-SS | 1612 |
| AD10024 | AM14299-AS | AM14295-SS | 1612 |
| AD10025 | AM14299-AS | AM14300-SS | 1612 |
| AD10026 | AM14301-AS | AM14295-SS | 1612 |
| AD10027 | AM14299-AS | AM14302-SS | 1612 |
| AD10028 | AM14299-AS | AM14303-SS | 1612 |
| AD10029 | AM14304-AS | AM14303-SS | 1612 |
| AD10030 | AM14305-AS | AM14302-SS | 1612 |
| AD10091 | AM14383-AS | AM13877-SS | 1322 |
| AD10092 | AM14384-AS | AM13877-SS | 1322 |
| AD10093 | AM14385-AS | AM13877-SS | 1322 |
| AD10094 | AM14384-AS | AM14386-SS | 1322 |
| AD10095 | AM14385-AS | AM14386-SS | 1322 |
| AD10096 | AM14387-AS | AM13877-SS | 1322 |
| AD10097 | AM14388-AS | AM13877-SS | 1322 |
| AD10099 | AM14391-AS | AM14390-SS | 263 |
| AD10100 | AM14393-AS | AM14392-SS | 318 |
| AD10101 | AM14395-AS | AM14394-SS | 328 |
| AD10102 | AM14397-AS | AM14396-SS | 482 |
| AD10103 | AM14399-AS | AM14398-SS | 857 |
| AD10104 | AM14401-AS | AM14400-SS | 874 |
| AD10105 | AM14403-AS | AM14402-SS | 1278 |
| AD10106 | AM14405-AS | AM14404-SS | 1319 |
| AD10107 | AM14407-AS | AM14406-SS | 1320 |
| AD10108 | AM14409-AS | AM14408-SS | 1351 |
| AD10109 | AM14411-AS | AM14410-SS | 2006 |
| AD10110 | AM14413-AS | AM14412-SS | 2156 |
| AD10111 | AM14415-AS | AM14414-SS | 2398 |
| AD10112 | AM14417-AS | AM14416-SS | 2400 |
| AD10113 | AM14419-AS | AM14418-SS | 2435 |
| AD10176 | AM14522-AS | AM13169-SS | 3083 |
| AD10177 | AM14523-AS | AM13169-SS | 3083 |
| AD10178 | AM14524-AS | AM13169-SS | 3083 |
| AD10179 | AM14524-AS | AM14525-SS | 3083 |
| AD10180 | AM14524-AS | AM14526-SS | 3083 |
| AD10181 | AM14527-AS | AM13673-SS | 4289 |
| AD10182 | AM14529-AS | AM14528-SS | 4289 |
| AD10183 | AM14530-AS | AM14528-SS | 4289 |
| AD10184 | AM14529-AS | AM14531-SS | 4289 |
| AD10200 | AM14543-AS | AM13673-SS | 4289 |
| AD10201 | AM14544-AS | AM13673-SS | 4289 |
| AD10202 | AM14545-AS | AM13673-SS | 4289 |
| AD10203 | AM14544-AS | AM14528-SS | 4289 |
| AD10204 | AM14545-AS | AM14528-SS | 4289 |
| AD10205 | AM14544-AS | AM14531-SS | 4289 |
| AD10275 | AM14642-AS | AM13881-SS | 1963 |
| AD10276 | AM14643-AS | AM13881-SS | 1963 |
| AD10277 | AM14644-AS | AM13881-SS | 1963 |
| AD10278 | AM14645-AS | AM13881-SS | 1963 |
| AD10279 | AM14644-AS | AM14646-SS | 1963 |
| AD10280 | AM14647-AS | AM14646-SS | 1963 |
| AD10281 | AM14648-AS | AM14646-SS | 1963 |
| AD10282 | AM14649-AS | AM14646-SS | 1963 |
| AD10283 | AM14650-AS | AM14646-SS | 1963 |
| AD10619 | AM14281-AS | AM14284-SS | 2696 |
| AD10620 | AM15134-AS | AM14284-SS | 2696 |
| AD10621 | AM15135-AS | AM14284-SS | 2696 |
| AD10622 | AM14283-AS | AM14284-SS | 2696 |
| AD10623 | AM15137-AS | AM15136-SS | 2696 |
| AD10624 | AM15139-AS | AM15138-SS | 2696 |
| AD10625 | AM15141-AS | AM15140-SS | 2696 |
| AD10626 | AM15143-AS | AM15142-SS | 2696 |
| AD10627 | AM15145-AS | AM15144-SS | 2696 |
| AD10628 | AM15146-AS | AM14284-SS | 2696 |
| AD10629 | AM15147-AS | AM14528-SS | 4289 |
| AD10630 | AM15148-AS | AM14528-SS | 4289 |
| AD10631 | AM15149-AS | AM14528-SS | 4289 |
| AD10632 | AM15150-AS | AM14528-SS | 4289 |
| AD10633 | AM15151-AS | AM14531-SS | 4289 |
| AD10634 | AM15152-AS | AM14531-SS | 4289 |
| AD10635 | AM15153-AS | AM14531-SS | 4289 |
| AD10636 | AM15154-AS | AM14531-SS | 4289 |
| AD10728 | AM14244-AS | AM15284-SS | 3598 |
| AD10729 | AM15285-AS | AM15284-SS | 3598 |
| AD10730 | AM15286-AS | AM15284-SS | 3598 |
| AD10731 | AM15287-AS | AM15284-SS | 3598 |
| AD10732 | AM15289-AS | AM15288-SS | 3598 |
| AD10733 | AM15290-AS | AM15284-SS | 3598 |
| AD10734 | AM15291-AS | AM15284-SS | 3598 |
| AD10735 | AM15292-AS | AM15284-SS | 3598 |
| AD10736 | AM15294-AS | AM15293-SS | 3598 |
| AD10737 | AM15296-AS | AM15295-SS | 3598 |
| AD10952 | AM15606-AS | AM14284-SS | 2696 |
| AD10953 | AM15607-AS | AM15136-SS | 2696 |
| AD10954 | AM15608-AS | AM14213-SS | 1963 |
| AD10967 | AM13882-AS | AM14646-SS | 1963 |
| AD10968 | AM15626-AS | AM14646-SS | 1963 |
| AD10969 | AM15627-AS | AM14646-SS | 1963 |
| AD12167 | AM17243-AS | AM17242-SS | 2701 |
| AD12168 | AM17245-AS | AM17244-SS | 2696 |

TABLE 5C

XDH RNAi Agent Duplexes Showing Chemically Modified Antisense Strand and Sense Strand Sequences

| Sense Strand ID: | Modified Antisense Strand (5' → 3') | SEQ ID NO. | Modified Sense Strand (5' → 3') | SEQ ID NO. |
|---|---|---|---|---|
| AD09217 | usUfsgsGfaAfgGfcAfuUfcUfcAfaUfcUfsc | 945 | (NAG37)s(invAb)sgagauugaGfAfAfugccuuccaas(invAb) | 1175 |
| AD09218 | usUfsggaAfgGfCfauucUfcAfaucusc | 946 | (NAG37)s(invAb)sgagauuGfaGfAfAfugccuuccaas(invAb) | 1176 |
| AD09219 | asAfscsUfuGfaAfgAfaGfAfAfgCfuGfaGfsg | 947 | (NAG37)s(invAb)sccucagcuUfCfUfucuucaaguus(invAb) | 1177 |

TABLE 5C-continued

XDH RNAi Agent Duplexes Showing Chemically Modified Antisense Strand and Sense Strand Sequences

| Sense Strand ID: | Modified Antisense Strand (5' → 3') | SEQ ID NO. | Modified Sense Strand (5' → 3') | SEQ ID NO. |
|---|---|---|---|---|
| AD09220 | asGfsasAfcUfuGfaAfgAfaGfaAfgCfuGfsc | 948 | (NAG37)s(invAb)sgcagcuucUfUfCfuucaaguucus(invAb) | 1178 |
| AD09221 | usGfsusAfgAfaCfuUfgAfaGfaAfgAfaGfsc | 949 | (NAG37)s(invAb)sgcuucuucUfUfCfaaguucuacas(invAb) | 1179 |
| AD09222 | usCfsasUfaGfgUfgAfuUfuUfcAfcCfcCfsu | 950 | (NAG37)s(invAb)sggggugaAfAfAfucaccuaugas(invAb) | 1180 |
| AD09223 | usUfsusCfaUfaGfgUfgAfuUfuUfcAfcCfsc | 951 | (NAG37)s(invAb)sgggugaaaAfUfCfaccuaugaaas(invAb) | 1181 |
| AD09224 | usCfsusUfcAfuAfgGfuGfaUfuUfuCfaCfsc | 952 | (NAG37)s(invAb)sggugaaaaUfCfAfccuaugaagas(invAb) | 1182 |
| AD09225 | usUfscsUfuCfaUfaGfgUfgAfuUfuUfcAfsc | 953 | (NAG37)s(invAb)sgugaaaauCfAfCfcuaugaagaas(invAb) | 1183 |
| AD09226 | asAfsusUfgUfgAfuAfaUfgGfcUfgGfuAfsg | 954 | (NAG37)s(invAb)scuaccagcCfAfUfuaucacaauus(invAb) | 1184 |
| AD09227 | usCfsasUfaAfaAfgGfaAfcUfgUfuCfuUfsc | 955 | (NAG37)s(invAb)sgaagaacaAfCfUfccuuuuaugas(invAb) | 1185 |
| AD09228 | usCfscsAfuAfaAfaGfgAfgUfuGfuUfcUfsc | 956 | (NAG37)s(invAb)sgagaacaaCfUfCfcuuuuauggas(invAb) | 1186 |
| AD09229 | usAfscsAfgUfgUfuAfgUfgCfuUfgUfcUfsc | 957 | (NAG37)s(invAb)sgagacaagCfAfCfuaacacuguas(invAb) | 1187 |
| AD09230 | usUfsgsUfgUfaCfaUfaCfuCfaUfgAfcGfsa | 958 | (NAG37)s(invAb)sucgucaugAfGfUfauguacacaas(invAb) | 1188 |
| AD09231 | usAfscsCfaGfuUfaUfcAfgCfuAfgUfcCfsu | 959 | (NAG37)s(invAb)saggacaugCfUfGfauaacugiuas(invAb) | 1189 |
| AD09232 | usAfsusGfaAfgCfcAfaCfcUfuGfuAfuCfsc | 960 | (NAG37)s(invAb)sggauacaaGfUfGfuggcuucauas(invAb) | 1190 |
| AD09233 | usCfsusUfcAfuAfgCfcAfaCfcUfuCfuGfsc | 961 | (NAG37)s(invAb)sgcaagguuGfGfCfuuucaugaagas(invAb) | 1191 |
| AD09234 | usUfscsUfuCfaUfgAfaGfcCfaAfcCfuUfsg | 962 | (NAG37)s(invAb)scaagguugGfCfUfucaugaagaas(invAb) | 1192 |
| AD09235 | usAfsgsUfcUfuCfaUfgAfaGfcCfaAfcCfsu | 963 | (NAG37)s(invAb)sagguuggcUfUfCfaugaagacuas(invAb) | 1193 |
| AD09236 | usCfsusUfuUfuCfcAfaCfaAfuUfcUfcCfsu | 964 | (NAG37)s(invAb)saggagaauUfGfUfuggaaaaagas(invAb) | 1194 |
| AD09237 | usUfscsUfaCfuUfcAfgAfgCfaAfgCfcAfsc | 965 | (NAG37)s(invAb)sguggcuugCfUfCfugaaguagaas(invAb) | 1195 |
| AD09238 | usAfsusUfuCfuAfcUfuCfaGfaGfcAfaGfsc | 966 | (NAG37)s(invAb)sgcuugcucUfGfAfaguagaaaas(invAb) | 1196 |
| AD09239 | usGfsusCfcAfaUfaUfcAfaUfgGfcAfgGfsg | 967 | (NAG37)s(invAb)scccugccaUfUfGfauauuigacas(invAb) | 1197 |
| AD09302 | usCfsasGfaAfaAfgUfgGfaCfgAfuCfuUfsg | 968 | (NAG37)s(invAb)scaagaucgUfCfCfacuuuucugas(invAb) | 1198 |
| AD09303 | asCfsasAfcAfuUfaUfcUfgCfuUfcGfgAfsc | 969 | (NAG37)s(invAb)sguccgaagCfAfGfauaauguugus(invAb) | 1199 |
| AD09304 | usCfsasUfaAfuAfcUfcUfgAfgAfgAfgAfsc | 970 | (NAG37)s(invAb)sgucucucuCfAfGfaguauuaugas(invAb) | 1200 |
| AD09305 | usCfsusUfaUfuCfcAfaCfaAfcUfuGfgUfgGfsg | 971 | (NAG37)s(invAb)scccaccaaUfUfGfuggaauaagas(invAb) | 1201 |
| AD09306 | usAfsgsUfaAfuUfcUfgCfuUfuAfuGfcAfsg | 972 | (NAG37)s(invAb)scugcauaaAfGfCfaagauuacuas(invAb) | 1202 |
| AD09307 | asAfsgsGfaAfaUfcUfaGfaAfcAfuUfgUfsc | 973 | (NAG37)s(invAb)sgacaauguUfCfUfagauuucuus(invAb) | 1203 |
| AD09308 | usCfsasgaaaagugGfaCfgAfuCfuUfsg | 974 | (NAG37)s(invAb)scaagaucgUfcCfaCfuuuucugas(invAb) | 1204 |
| AD09309 | asCfsasacauUfaUfcUfgCfuUfcggasc | 975 | (NAG37)s(invAb)sguccgaagCfAfGfauaauguugus(invAb) | 1199 |
| AD09310 | usCfsasUfaAfuacucUfgAfgAfgagasc | 976 | (NAG37)s(invAb)sgucucucuCfaGfaGfuaauuaugas(invAb) | 1205 |
| AD09311 | asAfsgsGfaAfaUfcUfaGfaAfcAfuUfuUfsc | 977 | (NAG37)s(invAb)sgaaaauguUfCfUfagauuucuus(invAb) | 1206 |
| AD09323 | usCfsasGfaAfaagugGfaCfgAfuCfuUfsg | 978 | (NAG37)s(invAb)scaagaucgUfCfCfacuuuucugas(invAb) | 1198 |
| AD09324 | usCfsasUfaAfuacucUfgAfgAfgAfgAfsc | 979 | (NAG37)s(invAb)sgucucucuCfAfGfaguauuaugas(invAb) | 1200 |
| AD09325 | usCfsusUfaUfuccaaAfcUfuGfgUfggsg | 980 | (NAG37)s(invAb)sccaccaaGfUfUfuggaauaagas(invAb) | 1201 |
| AD09326 | usAfsgsUfaAfuUfcuugCfuUfuAfuGfcAfsg | 981 | (NAG37)s(invAb)scugcauaaAfGfCfaagauuacuas(invAb) | 1202 |
| AD09571 | usAfsasCfuUfcacucAfuCfcAfgCfcacsu | 982 | (NAG37)s(invAb)sagugcuggAfUfGfagugaaguuas(invAb) | 1207 |
| AD09572 | usCfsasAfcuucacUfaUfcCfagcasc | 983 | (NAG37)s(invAb)sgugcuigaUfGfAfugugaaguuas(invAb) | 1208 |
| AD09573 | usGfscsAfacuucacUfcAfuCfcagcsa | 984 | (NAG37)s(invAb)sugcuggauGfAfUfgaaguuicas(invAb) | 1209 |
| AD09598 | usGfsasucauacuuGfaGfaAfgcausc | 985 | (NAG37)s(invAb)sgaugcucuCfcAfaGfuauagaucas(invAb) | 1210 |
| AD09599 | usCfsusuguucugcAfgAfcGfuacasc | 986 | (NAG37)s(invAb)sgugaucguCfuGfcAfgaacaagas(invAb) | 1211 |
| AD09600 | usGfsasucuuguucUfgCfaGfacgasc | 987 | (NAG37)s(invAb)sgucgucugCfaGfaAfcaagaucas(invAb) | 1212 |
| AD09601 | usAfsgsuaaaguugCfaCfuGfgcgasc | 988 | (NAG37)s(invAb)sgucgccagUfGfCfaAfcuuuacuas(invAb) | 1213 |
| AD09602 | usAfsasCfacaaguaAfcCfuUfauccsu | 989 | (NAG37)s(invAb)sggauaAfgGfuUfacuuguguuas(invAb) | 1214 |
| AD09603 | usCfsasAfuugugauAfaUfgGfcuggsu | 990 | (NAG37)s(invAb)saccagccaUfUfAfuCfacaauugas(invAb) | 1215 |
| AD09604 | usAfsgscaugauacUfgAfgAfgcuusg | 991 | (NAG37)s(invAb)scaagcucuCfaGfuAfucaugcuas(invAb) | 1216 |
| AD09605 | asAfsfcUfugucaacCfuCfaCffucuusc | 992 | (NAG37)s(invAb)sgaagagugAfGfGfuUfgcaaguus(invAb) | 1217 |
| AD09606 | usAfsasCfuugucaaCfcUfcAffcucusc | 993 | (NAG37)s(invAb)sgagagugaGfGfUfugacaaguuas(invAb) | 1218 |
| AD09607 | usAfsasCfaauucucCffuUfgUfugaasc | 994 | (NAG37)s(invAb)sguucaacaAfGfFfagaaauguuas(invAb) | 1219 |
| AD09608 | usCfsasuguucuguGffgUfaUfguucsc | 995 | (NAG37)s(invAb)sggaacaUfaCfcAfcagaacaugas(invAb) | 1220 |
| AD09609 | usAfscsUfuUfaauagAfuCfcAfugusc | 996 | (NAG37)s(invAb)sgaacauggAfuCfuAfuuaaaguas(invAb) | 1221 |
| AD09610 | usGfsascuuuAfaUfaGfaUfcCfaugusc | 997 | (NAG37)s(invAb)sgacauggaUfcUfaUfuaaaguas(invAb) | 1222 |
| AD09611 | usGfscsauauucacCfaUfuUfaggcsa | 998 | (NAG37)s(invAb)sugccuaAfaUfgFfugaauaugcas(invAb) | 1223 |
| AD09612 | usGfsusUfuaagcuuCfuAfgAfguusc | 999 | (NAG37)s(invAb)sgaaccucuAfGfGfafagcuuaaacas(invAb) | 1224 |
| AD09613 | usUfsgsuucauuggUfuUfgAfaggcsc | 1000 | (NAG37)s(invAb)sggccuucaAfaCfCfAfaugaacaas(invAb) | 1225 |
| AD09614 | usUfsasUfgCfuuuugcUfgUfuCffauugsg | 1001 | (NAG37)s(invAb)sccaaugAfaCfaGfcaaagcauaas(invAb) | 1226 |
| AD09615 | usGfsusUfaugcuuuGfcUfgUfuCfausc | 1002 | (NAG37)s(invAb)sgaugaacaGfcAfFAfagcauaacas(invAb) | 1227 |
| AD09616 | asGfsgsUfuaugcuuUfgCfuGfuucasc | 1003 | (NAG37)s(invAb)sgugaacagCfAfAfagcauaaccus(invAb) | 1228 |
| AD09617 | usAfsasggguuaugcUfuUfgCffuguusc | 1004 | (NAG37)s(invAb)sgaacagcaAfaGfcAfuaaccuuas(invAb) | 1229 |
| AD09618 | asGfsasUfucaagguUfaUfgCfuuusg | 1005 | (NAG37)s(invAb)scaaagcaUfAfAfccuugaaucus(invAb) | 1230 |
| AD09619 | usUfscsAfauaaauugAfgUfuUfgfuugsg | 1006 | (NAG37)s(invAb)sccaaccaaCfuCfaAfuuuauugaas(invAb) | 1231 |
| AD09620 | asGfsusAfaaauggaUfcAfcAfggaasg | 1007 | (NAG37)s(invAb)scuuccuguGfaFfccauuuuaucs(invAb) | 1232 |
| AD09621 | usCfsasUfaugacagUfaAfgAfaacsc | 1008 | (NAG37)s(invAb)sgguuucuUfAfCfugucauaugas(invAb) | 1233 |
| AD09623 | usUfsgsgaaggcauUfcUfcGfaucusc | 1009 | (NAG37)s(invAb)sgagacgaUfAfAfugccuuccaas(invAb) | 1234 |
| AD09624 | usCfsasUfcauugaaAfaUfgCfcagusc | 1010 | (NAG37)s(invAb)sgacuggaUfUfUfucaaugaugas(invAb) | 1235 |
| AD09625 | asAfsasGfacaguuuCfaUfcAfuugasc | 1011 | (NAG37)s(invAb)sgucaaugaUfGfAfaacugucuuus(invAb) | 1236 |
| AD09626 | asAfscscsacaaguaaCfcUfcAffuccusc | 1012 | (NAG37)s(invAb)sgaggaugaGfFfGfuacuuuguuus(invAb) | 1237 |
| AD09627 | asGfsasacauugUfcAfgCffucasg | 1013 | (NAG37)s(invAb)scugaagcuGfAfCfaaguguicuas(invAb) | 1238 |
| AD09628 | usCfsasacacucuuGfcAfaUfaaagsc | 1014 | (NAG37)s(invAb)sgcuuuauUfGfCfAfaagauguuas(invAb) | 1239 |
| AD09629 | asGfsusUfagucuuAfcAfaAfuccusc | 1015 | (NAG37)s(invAb)sgaggauuUfGfAfagacuaaucus(invAb) | 1240 |
| AD09630 | usCfsusUfauuccaaAfcUfuAfgucgsg | 1016 | (NAG37)s(invAb)sccgacuaaGfUfUfuggaauaagas(invAb) | 1241 |
| AD09631 | usCfsasGfaaaagaAfgUfgUfgaagsc | 1017 | (NAG37)s(invAb)sgcuucacaCfUfUfucuuuucugas(invAb) | 1242 |
| AD09632 | usAfsgsAfguuugucUfcAfaAfgcugsc | 1018 | (NAG37)s(invAb)sgcagcuuuGfAfGfacaaacucuas(invAb) | 1243 |
| AD09633 | usUfsgsUfuaagcagUfcAfaUfuUfcusc | 1019 | (NAG37)s(invAb)sgaaauuUfAfCfugcuuaacaas(invAb) | 1244 |
| AD09634 | usUfsgsGfaaaucgGfaUfaCfuacgsg | 1020 | (NAG37)s(invAb)sccguaguUfCfCfagauuuuccaas(invAb) | 1245 |
| AD09635 | usCfsusUfgaaaugCfcAfuCfucgcsu | 1021 | (NAG37)s(invAb)sagcaggauGfCfFfauuuucaagas(invAb) | 1246 |
| AD09636 | asUfsgsAfuuuggauCfaCfaAfuugusc | 1022 | (NAG37)s(invAb)sgacaauugUfGfAfuccaaaucaus(invAb) | 1247 |

TABLE 5C-continued

XDH RNAi Agent Duplexes Showing Chemically Modified Antisense Strand and Sense Strand Sequences

| Sense Strand ID: | Modified Antisense Strand (5' → 3') | SEQ ID NO. | Modified Sense Strand (5' → 3') | SEQ ID NO. |
|---|---|---|---|---|
| AD09637 | usAfsgsAfauuacucAfaAfaCfugccsa | 1023 | (NAG37)s(invAb)suggcaguuUfUfGfaguaauucuas(invAb) | 1248 |
| AD09638 | usGfsasucaaAfAfauGfgAfcUfcagasc | 1024 | (NAG37)s(invAb)sgucugaguCfCfAfuuuuugaucas(invAb) | 1249 |
| AD09639 | usAfsasGfaaagcauGfcAfgAfucuasg | 1025 | (NAG37)s(invAb)scuagaucuCfCfAfugcuuucuuas(invAb) | 1250 |
| AD09640 | usCfsasgauauaagCfuCfuCfugaasg | 1026 | (NAG37)s(invAb)scuuccagagAfGfCfuauaaucugas(invAb) | 1251 |
| AD09650 | usCfsusGfaagccaaCfcUfuGfuAfucsc | 1027 | (NAG37)s(invAb)sggauacAfaGfgUfuggcuucauas(invAb) | 1252 |
| AD09651 | usAfsusGfaagccaaCfcUfuGfuaucsc | 1028 | (NAG37)s(invAb)sggauacAfaGfgUfuggcuucauas(invAb) | 1252 |
| AD09652 | usAfsusGfaagCuNAcaaCfcUfuGfuaucsc | 1029 | (NAG37)s(invAb)sggauacAfaGfgUfuggcuucauas(invAb) | 1252 |
| AD09653 | usAfsusGfaagccaaCfcUfuGfuaucsc | 1028 | (NAG37)s(invAb)sggauacAfaGfgUfugicuucauas(invAb) | 1253 |
| AD09654 | usAfsusGfaagccaaCfcUfuGfuaucsc | 1028 | (NAG37)s(invAb)sggauacAfaGfgUfuigcuucauas(invAb) | 1254 |
| AD09655 | usAfsusGfaagccaaCfcUfuGfuaucsc | 1028 | (NAG37)s(invAb)sggauacAfaGfgUfugguuucauas(invAb) | 1255 |
| AD09656 | usAfsusGfaagucaaCfcUfuGfuaucsc | 1030 | (NAG37)s(invAb)sggauacAfaGfgUfuggcuucauas(invAb) | 1252 |
| AD09657 | usAfsusGfaagcuaaCfcUfuGfuaucsc | 1031 | (NAG37)s(invAb)sggauacAfaGfgUfuggcuucauas(invAb) | 1252 |
| AD09658 | cPrpusAfsusGfaagccaaCfcUfuGfuaucsc | 1032 | (NAG37)s(invAb)sggauacAfaGfgUfuggcuucauas(invAb) | 1252 |
| AD09659 | usAfsusGfaagccaaCfcUfuGfuaucsc | 1028 | (NAG37)s(invAb)sggauacaaGfGfUfuggcuucauas(invAb) | 1190 |
| AD09660 | usAfsusGfaagccaaCfcUfuGfuaucsc | 1028 | (NAG37)s(invAb)sggauacaaGfgUfUfggcuucauas(invAb) | 1256 |
| AD09661 | usAfsusGfaagccaaCfcUfuGfuaucsc | 1028 | (NAG37)s(invAb)sggauacaaGfgUfiuGfgcuucauas(invAb) | 1257 |
| AD09662 | usCfsusUfcaugaagCfcAfaCfcuugsc | 1028 | (NAG37)s(invAb)sgcaagguuGfGfCfuucaugaagas(invAb) | 1191 |
| AD09663 | cPrpusCfsusUfcaugaagCfcAfaCfcuugsc | 1034 | (NAG37)s(invAb)sgcaagguuGfGfCfuucaugaagas(invAb) | 1191 |
| AD09664 | usCfsusUfcaugaagCfcAfaCfcuugsc | 1033 | (NAG37)s(invAb)sgcaagguuGfgCfuUfcaugaagas(invAb) | 1258 |
| AD09665 | usCfsusUfcaUuNAgaagCfcAfaCfcuugsc | 1035 | (NAG37)s(invAb)sgcaagguuGfgCfuUfcaugaagas(invAb) | 1258 |
| AD09724 | usGfsgsAfuCfugcauUfuUfuCfuCfcasc | 1036 | (NAG37)s(invAb)sguggagaaAfAfAfugcaiauccas(invAb) | 1259 |
| AD09725 | usCfscsAfaAfaggguUfgUfcUfcUfggsa | 1037 | (NAG37)s(invAb)succagagaCfAfAfcucuuuuggas(invAb) | 1260 |
| AD09726 | usAfsgsAfcGfaucauAfcUfuGfgAfgasg | 1038 | (NAG37)s(invAb)scucuccaaGfUfAfugauciucuas(invAb) | 1261 |
| AD09727 | usCfscsUfaUfuccuuCfcAfcAfgUfugsc | 1039 | (NAG37)s(invAb)sgcaacuguGffGfAfaggaauaggas(invAb) | 1262 |
| AD09728 | usAfscsAfuAfcucauGfaCfgAfuUfgccsa | 1040 | (NAG37)s(invAb)suggcaucgUfCfAfugaguauguas(invAb) | 1263 |
| AD09729 | usCfsasCfaGfauuucCfuUfgGfaAfggsc | 1041 | (NAG37)s(invAb)sgccuuccaAfGfGfaaaucuguias(invAb) | 1264 |
| AD09730 | usGfsasAfcUfucaucUfcAfaUfgCfcasc | 1042 | (NAG37)s(invAb)sguggcauuGfAfGfaugaaguucas(invAb) | 1265 |
| AD09731 | asGfscsAfuAfuucucuGfaAfcUfuCfausc | 1043 | (NAG37)s(invAb)sga_2NuagaaguUfCfAfagaauaugcus(invAb) | 1266 |
| AD09732 | usCfsasUfaGfgaaacAfgCfaUfaUfucsc | 1044 | (NAG37)s(invAb)sggaauaugCfUfGfuuuccuaugas(invAb) | 1267 |
| AD09733 | usGfsgsAfuCfucuauGfaAfgAfgCfagsc | 1045 | (NAG37)s(invAb)sgcugcucuCfCfAfuagaiauccas(invAb) | 1268 |
| AD09734 | usUfsusGfaAfugcugAfgAfaAfuAfucsc | 1046 | (NAG37)s(invAb)sgaguauuuCfUfCfagcauucaaas(invAb) | 1269 |
| AD09735 | usCfsusAfuGfgacuuGffaUfcUfuGfgcsg | 1047 | (NAG37)s(invAb)scgccaagaUfCfAfaguccauagas(invAb) | 1270 |
| AD09736 | asUfsgsAfaAfcaaacAfaAfcCfcUfggsa | 1048 | (NAG37)s(invAb)succagggUfUfGfuuuguuucaas(invAb) | 1271 |
| AD09737 | usGfsgsUfaGfuucuuCfaUfaGfgUfgasc | 1049 | (NAG37)s(invAb)sgucaccuaUfGfAfagaacuaccas(invAb) | 1272 |
| AD09738 | usGfsasUfaAfuggcuGfgUfaGfuUfcusc | 1050 | (NAG37)s(invAb)sgagaacuaCfCfAfgccauuaucas(invAb) | 1273 |
| AD09739 | usCfsusCfaAfuugugAfuAfaUfgGfcusg | 1051 | (NAG37)s(invAb)scagccauuAfUfCfacaauugagas(invAb) | 1274 |
| AD09740 | usCfsusUfuCfucgauCfuUfcAfgCfucsa | 1052 | (NAG37)s(invAb)sugagcugaAfGfAfucgagaaagas(invAb) | 1275 |
| AD09741 | usUfsusGfgAfacagcAfaUfgGfuGfcasg | 1053 | (NAG37)s(invAb)scugcaccaUfUfGfcuguuccaaas(invAb) | 1276 |
| AD09742 | usGfsusAfgAfcacaaAfgAfgCfuCfcasc | 1054 | (NAG37)s(invAb)sguggagcuCfUfUfuguguuuacas(invAb) | 1277 |
| AD09743 | usCfsusGfuGfuagacAfcAfaAfgAfgcsu | 1055 | (NAG37)s(invAb)sagcucuuuGfUfGfucuacacaias(invAb) | 1278 |
| AD09744 | usUfscsCfaUfaauacUfcUfgAfgAfgasg | 1056 | (NAG37)s(invAb)scucucucaCfAfGfuauuauggaas(invAb) | 1279 |
| AD09745 | usCfsusCfgUfuccauAfaUfaCfuCfugsc | 1057 | (NAG37)s(invAb)scagaguaUfAfAfuggaacgaias(invAb) | 1280 |
| AD09937 | cPrpusUfsgsAfaAfcaaacAfaAfcCfcUfggsa | 1058 | (NAG37)s(invAb)succagggUfUfGfuuuguuucaas(invAb) | 1281 |
| AD09938 | cPrpusUfscsCfaUfaauacUfcUfgAfgAfgasg | 1059 | (NAG37)s(invAb)scucucucaGfAfGfuauuauggaas(invAb) | 1279 |
| AD09962 | asAfsusGfaaacaaaCfaAfaCfcccugsg | 1060 | (NAG37)s(invAb)scagggguuUfUfGfuuugcaauus(invAb) | 1282 |
| AD09963 | asAfsasUfgaaacaaAfcAfaAfcccusg | 1061 | (NAG37)s(invAb)scagggguuUfUfGfuuugucauuus(invAb) | 1283 |
| AD09964 | usGfsasAfaugaaacAfaAfcAfaaccsc | 1062 | (NAG37)s(invAb)sggguuuguUfUfGfuuucauucas(invAb) | 1284 |
| AD09965 | usUfsgsAfaAfcaaacAfaAfcCfcUfggsa | 1063 | (NAG37)s(invAb)succagggUfUfGfuuuguuucaas(invAb) | 1281 |
| AD09966 | cPrpusUfsgsAfaacaaacAfaAfcCfcuggsa | 1064 | (NAG37)s(invAb)succagggUfUfGfuuuguuucaas(invAb) | 1281 |
| AD09967 | cPrpuUfgAfaacaaacAfaAfcCfcuggsa | 1065 | (NAG37)s(invAb)succagggUfUfGfuuuguuucaas(invAb) | 1281 |
| AD09968 | cPrpuUfgAfaacaaacAfaAfcCfcugsgsa | 1066 | (NAG37)s(invAb)succagggUfUfGfuuuguuucaas(invAb) | 1281 |
| AD09969 | cPrpuUfgAfaacaaacAfaAfcCfcuggsa | 1065 | (NAG37)s(invAb)succagggUfufGfuUfuguuucaas(invAb) | 1285 |
| AD09970 | cPrpuUfgAfaacaaacAfaAfcCfcuggsa | 1065 | (NAG37)s(invAb)succagggUfuGfUfuguuucaas(invAb) | 1286 |
| AD09971 | asUfsgsAfcGfaucauaCfuUfgGfgagasg | 1067 | (NAG37)s(invAb)sgcucuccaAfGfUfaugauciucus(invAb) | 1287 |
| AD09972 | asAfsgsGfcauucucAfaUfcUfcucsc | 1068 | (NAG37)s(invAb)sggaggagaUfUfGfagaauiccuus(invAb) | 1288 |
| AD09973 | usUfsusCfcuuggaaGfgCfaUfucucsg | 1069 | (NAG37)s(invAb)scgagaaugCfCfUfuccaaggaaas(invAb) | 1289 |
| AD09974 | usAfsgsAfuuuccuuGfgAfaGfgcausc | 1070 | (NAG37)s(invAb)sgaugccuuCfCfAfaggaaaucuas(invAb) | 1290 |
| AD09975 | asUfsgGfgaaacagCfaUfaUfucuusg | 1071 | (NAG37)s(invAb)sca_2NagaauaUfGfCfuguuuccuaus(invAb) | 1291 |
| AD09976 | usUfsgsAfugauguuCfcCfuCfcAfcaacsg | 1072 | (NAG37)s(invAb)scguuggagGffGfAfacaucaucaas(invAb) | 1292 |
| AD09977 | usAfsgsAfacuugaaGfaAfgAfagcusg | 1073 | (NAG37)s(invAb)scagcuucuUfCfUfucaaguucas(invAb) | 1293 |
| AD09978 | usAfscsCfaaugauaUfgCfcCfaacasc | 1074 | (NAG37)s(invAb)sguguuugggCfAfUfaucauuggas(invAb) | 1294 |
| AD09979 | usCfsasUfggUuNAguucUfgUfgUfagacsg | 1075 | (NAG37)s(invAb)scgucucuacaCfAfGfaacaccaugas(invAb) | 1295 |
| AD09980 | usUfsgsAfgagagauCfcUfgGfguguusc | 1076 | (NAG37)s(invAb)sgacacccaGfGfAfucucuuucaas(invAb) | 1296 |
| AD09981 | usCfsasUfgaucugAfgAfgCfuugcsu | 1077 | (NAG37)s(invAb)sagcaagcuCfUfCfaguaucaugas(invAb) | 1297 |
| AD09982 | usUfsgsUfcaaccucAfcUfcUfuccgsa | 1078 | (NAG37)s(invAb)sucggaagaGfUfGffagguugacaas(invAb) | 1298 |
| AD09983 | usUfsusCfcaacaauUfcUfcCfuuugsc | 1079 | (NAG37)s(invAb)sgacaaaggAfGfAfauugugggaas(invAb) | 1299 |
| AD09984 | usUfsgsAfguuagucUfcAfaAfgcugsc | 1080 | (NAG37)s(invAb)sgcagcuuuGfAfGfacuaacucaas(invAb) | 1300 |
| AD09985 | asUfsgsAfcaauaucUfgUfgCfggagsg | 1081 | (NAG37)s(invAb)sccuccgcaCfAfGfauauugucaus(invAb) | 1301 |
| AD09986 | usCfsasUfgacaauaUfcUfgUfgcggsa | 1082 | (NAG37)s(invAb)succgcacaGfAfUfauugucaugas(invAb) | 1302 |
| AD09987 | usCfsasAfagaagauAfgAfaGfcagcsc | 1083 | (NAG37)s(invAb)sggcugcuuCfUfAfucuucuuugas(invAb) | 1303 |
| AD09988 | usCfsasCfguuauuaCfcUfgUfgugcsu | 1084 | (NAG37)s(invAb)sagcacacaGfGfUfaauaacguias(invAb) | 1304 |
| AD09989 | usAfsgsAfacuugagGfuUfaUfacagsg | 1085 | (NAG37)s(invAb)sccuguauaAfCfCfucaaguucas(invAb) | 1305 |
| AD09990 | asUfsgsCfuuugcugUffCfaUfuggusc | 1086 | (NAG37)s(invAb)sgaccaaugAfAfCfagcaaagcaus(invAb) | 1306 |
| AD09991 | usAfsgsUfauagauuCfaAfgGfuuausg | 1087 | (NAG37)s(invAb)sca_2NuaaccuUfGfAfaucuauacuas(invAb) | 1307 |
| AD09992 | asGfsasGfuaaucuuGfcCfuUfuUfaugcsc | 1088 | (NAG37)s(invAb)sggcauaaaGfCfAfagauuacucus(invAb) | 1308 |

TABLE 5C-continued

XDH RNAi Agent Duplexes Showing Chemically Modified Antisense Strand and Sense Strand Sequences

| Sense Strand ID: | Modified Antisense Strand (5' → 3') | SEQ ID NO. | Modified Sense Strand (5' → 3') | SEQ ID NO. |
|---|---|---|---|---|
| AD09993 | asUfsasGfcaucauuUfcUfaGfguggsa | 1089 | (NAG37)s(invAb)succaccuaGfAfAfaugaugcuaus(invAb) | 1309 |
| AD09994 | asGfsasCfagaagagAfcAfgAfgcuasg | 1090 | (NAG37)s(invAb)scuagcucuGfUfCfucuucuiucus(invAb) | 1310 |
| AD09995 | asGfsusAfagaaaacCfaAfgCfcuuasg | 1091 | (NAG37)s(invAb)scua_2NaggcuUfGfGfuuuucuuacus(invAb) | 1311 |
| AD10008 | usUfscsCfauaauacUfcUfgAfgagasg | 1092 | (NAG37)s(invAb)scucucucaGfAfGfuauuauggaas(invAb) | 1279 |
| AD10009 | cPrpusUfscsCfauaauacUfcUfgAfgagasg | 1093 | (NAG37)s(invAb)scucucucaGfAfGfuauuauggaas(invAb) | 1279 |
| AD10010 | cPrpuUfcCfauaauacUfcUfgAfgagasg | 1094 | (NAG37)s(invAb)scucucucaGfAfGfuauuauggaas(invAb) | 1279 |
| AD10011 | cPrpuUfcCfauaauacUfcUfgAfgagsasg | 1095 | (NAG37)s(invAb)scucucucaGfAfGfuauuauggaas(invAb) | 1279 |
| AD10012 | cPrpuUfcCfauaauacUfcUfgAfgagasg | 1094 | (NAG37)s(invAb)scucucucaGfaGfuAfuuauggaas(invAb) | 1312 |
| AD10013 | cPrpuUfccauaaUfacUfcUfgAfgagasg | 1096 | (NAG37)s(invAb)scucucucaGfaGfuAfuuauggaas(invAb) | 1312 |
| AD10014 | cPrpuUfcCfauaauacUfcUfgAfgagasg | 1094 | (NAG37)s(invAb)scucucucaGfaGfUfauuauggaas(invAb) | 1313 |
| AD10015 | cPrpuUfccauaaUfacUfcUfgAfgagasg | 1096 | (NAG37)s(invAb)scucucucaGfaGfUfauuauggaas(invAb) | 1313 |
| AD10016 | usAfsusAfcuuggagAfgCfaUfcacusg | 1097 | (NAG37)s(invAb)scagugaugCfUfCfuccaaguauas(invAb) | 1314 |
| AD10017 | usUfsgsCfagacgauCfaUfaCfuuggsc | 1098 | (NAG37)s(invAb)sgccaaguaUfGfAfucgucuicaas(invAb) | 1315 |
| AD10018 | usUfsgsAfaUfaaaacUfcUfcAfugccsa | 1099 | (NAG37)s(invAb)suggcaugaGfAfGfuuuuauucaas(invAb) | 1316 |
| AD10019 | cPrpusUfsgsAfaUfaaaacUfcUfcAfugccsa | 1100 | (NAG37)s(invAb)suggcaugaGfAfGfuuuuauucaas(invAb) | 1316 |
| AD10020 | usUfsgsAfaUfaaaacUfcUfcAfugccsa | 1099 | (NAG37)s(invAb)suggcaugaGfAfGfuuuuua_2Nuucaas(invAb) | 1317 |
| AD10021 | usAfscsUfuGfaAfgAfaGfaAfgCfuGfaGfsg | 1101 | (NAG37)s(invAb)sccucagcuUfCfUfucuucaaguas(invAb) | 1318 |
| AD10022 | usAfscsUfugaagaaGfaAfgCfugagsg | 1102 | (NAG37)s(invAb)sccucagcuUfCfUfucuucaaguas(invAb) | 1318 |
| AD10023 | cPrpusAfscsUfugaagaaGfaAfgCfugagsg | 1103 | (NAG37)s(invAb)sccucagcuUfCfUfucuucaaguas(invAb) | 1318 |
| AD10024 | cPrpuAfcUfugaagaaGfaAfgCfugagsg | 1104 | (NAG37)s(invAb)sccucagcuUfCfUfucuucaaguas(invAb) | 1318 |
| AD10025 | cPrpuAfcUfugaagaaGfaAfgCfugagsg | 1104 | (NAG37)s(invAb)sccucagcuUfCfUfucuuuaaguas(invAb) | 1319 |
| AD10026 | cPrpuAfcUfugaagaaGfaAfgCfugasgsg | 1105 | (NAG37)s(invAb)sccucagcuUfCfUfucuucaaguas(invAb) | 1318 |
| AD10027 | cPrpuAfcUfugaagaaGfaAfgCfugagsg | 1104 | (NAG37)s(invAb)sccucagcuUfcUfUfcuucaaguas(invAb) | 1320 |
| AD10028 | cPrpuAfcUfugaagaaGfaAfgCfugagsg | 1104 | (NAG37)s(invAb)sccucagcuUfcUfuCfuucaaguas(invAb) | 1321 |
| AD10029 | cPrpuAfcuugAfagaaGfaAfgCfugagsg | 1106 | (NAG37)s(invAb)sccucagcuUfcUfuCfuucaaguas(invAb) | 1321 |
| AD10030 | cPrpuAfcuugaaGfaaGfaAfgCfugagsg | 1107 | (NAG37)s(invAb)sccucagcuUfcUfUfcuucaaguas(invAb) | 1320 |
| AD10091 | cPrpuUfsusGfaAfugcugAfgAfaAfuAfcusc | 1108 | (NAG37)s(invAb)sgaguauuuCfUfCfagcauucaaas(invAb) | 1269 |
| AD10092 | cPrpusUfsusGfaaugcugAfgAfaAfuacusc | 1109 | (NAG37)s(invAb)sgaguauuuCfUfCfagcauucaaas(invAb) | 1269 |
| AD10093 | cPrpusUfsusgaaUfgcugAfgAfaAfuacusc | 1110 | (NAG37)s(invAb)sgaguauuuCfUfCfagcauucaaas(invAb) | 1269 |
| AD10094 | cPrpusUfsusGfaaugcugAfgAfaAfuacusc | 1109 | (NAG37)s(invAb)sgaguauuuCfuCfAfgcauucaaas(invAb) | 1322 |
| AD10095 | cPrpusUfsusgaaUfgcugAfgAfaAfuacusc | 1110 | (NAG37)s(invAb)sgaguauuuCfuCfAfgcauucaaas(invAb) | 1322 |
| AD10096 | cPrpuUfuGfaaugcugAfgAfaAfuacusc | 1111 | (NAG37)s(invAb)sgaguauuuCfUfCfagcauucaaas(invAb) | 1269 |
| AD10097 | cPrpuUfuGfaaugcugAfgAfaAfuacsusc | 1112 | (NAG37)s(invAb)sgaguauuuCfUfCfagcauucaaas(invAb) | 1269 |
| AD10099 | asGfsasAfaAfguggaCfgAfuCfuUfgusc | 1113 | (NAG37)s(invAb)sgacaagauCfGfUfccacuuuucus(invAb) | 1323 |
| AD10100 | usAfsgsUfuGfucacuGfcAfaCfaUfggsu | 1114 | (NAG37)s(invAb)saccauguuGfCfAfgugacaacuas(invAb) | 1324 |
| AD10101 | asUfsusCfcUfuccacAfgUfuGfuCfacsc | 1115 | (NAG37)s(invAb)sggugacaaCfUfGfuggaaggaaus(invAb) | 1325 |
| AD10102 | usGfscsAfuUfcucaaUfcUfcCfuUfcasc | 1116 | (NAG37)s(invAb)sguggaggaGfAfUfugagaaugcas(invAb) | 1326 |
| AD10103 | usUfscsAfaUfgccaaUfcUfcCfgUfgusc | 1117 | (NAG37)s(invAb)sgacacggaGfAfUfuggcauugaas(invAb) | 1327 |
| AD10104 | asUfsasUfuCfuugaaCfuUfcAfuCfucsg | 1118 | (NAG37)s(invAb)scgagaugaAfGfUfucaagaaua_2Nus(invAb) | 1328 |
| AD10105 | usUfsasUfgGfagagcAfgUfaUfcUfccsu | 1119 | (NAG37)s(invAb)saggagauaCfUfGfcucuccauaas(invAb) | 1329 |
| AD10106 | usAfsasUfgCfugagaAfaUfaCfuCfccsc | 1120 | (NAG37)s(invAb)sggggaguaUfUfUfcucagcauuas(invAb) | 1330 |
| AD10107 | usGfsasAfuGfcugagAfaAfuAfcUfccsc | 1121 | (NAG37)s(invAb)sgggaguauUfUfCfucagcauucas(invAb) | 1331 |
| AD10108 | usCfsasAfuGfucaucUfuCfuCfuCfcgsg | 1122 | (NAG37)s(invAb)sccggagagAfAfGfaugacauugas(invAb) | 1332 |
| AD10109 | asCfsasAfaUfuccagUfuAfuUfgUfacsc | 1123 | (NAG37)s(invAb)sgguaacauAfAfCfuggaauugus(invAb) | 1333 |
| AD10110 | usUfscsAfuUfugugaUfaAfuUfgCfugsg | 1124 | (NAG37)s(invAb)sccagccauUfAfUfcacaauugaas(invAb) | 1334 |
| AD10111 | asAfscsAfuUfuuugcAfuaCfaAfaGfcusc | 1125 | (NAG37)s(invAb)sgagcuuugUfUfGfcaaaaauguus(invAb) | 1335 |
| AD10112 | usCfsasAfcAfuuuuuGfcAfaCfaAfagsc | 1126 | (NAG37)s(invAb)sgcuuuguGfCfAfaaaauguugas(invAb) | 1336 |
| AD10113 | usUfsusCfaCfucgaaCfcAfcAfaUfccsg | 1127 | (NAG37)s(invAb)scggauuguGffGfUfucgagugaaas(invAb) | 1337 |
| AD10176 | cPrpusCfsusUfaUfuccaaAfcUfuGfgUfggsg | 1128 | (NAG37)s(invAb)scccaccaaGfUfUfuggaauaagas(invAb) | 1201 |
| AD10177 | cPrpuCfuUfaUfuccaaAfcUfuGfgUfggsg | 1129 | (NAG37)s(invAb)scccaccaaGfUfUfuggaauaagas(invAb) | 1201 |
| AD10178 | cPrpuCfuuauucCfaaAfcUfuGfguggsg | 1130 | (NAG37)s(invAb)scccaccaaGfUfUfuggaauaagas(invAb) | 1201 |
| AD10179 | cPrpuCfuuauucCfaaAfcUfuGfguggsg | 1130 | (NAG37)s(invAb)scccaccaaGfuUfGfaauaagas(invAb) | 1338 |
| AD10180 | cPrpuCfuuauucCfaaAfcUfuGfguggsg | 1130 | (NAG37)s(invAb)scccaccaaGfuUfUfggaauaagas(invAb) | 1339 |
| AD10181 | cPrpuGfcauuucacCfaUfuUfaggcsa | 1131 | (NAG37)s(invAb)sugccuaAfaUfgGfugaauaugcas(invAb) | 1223 |
| AD10182 | cPrpuGfcauaUfucacCfaUfiUfaggcsa | 1132 | (NAG37)s(invAb)sugccuaaaUfgGfuGfaauaugcas(invAb) | 1340 |
| AD10183 | cPrpuGfcauauuCfacCfaUfiUfaggcsa | 1133 | (NAG37)s(invAb)sugccuaaaUfgGfuGfaauaugcas(invAb) | 1340 |
| AD10184 | cPrpuGfcauaUfucacCfaUfiUfaggcsa | 1132 | (NAG37)s(invAb)sugccuaaaUfgGfUfgaauaugcas(invAb) | 1341 |
| AD10200 | usGfscauauucacCfaUfiUfaggcsa | 1134 | (NAG37)s(invAb)sugccuaAfaUfgGfugaauaugcas(invAb) | 1223 |
| AD10201 | usGfscauaUfucacCfaUfiUfaggcsa | 1135 | (NAG37)s(invAb)sugccuaAfaUfgGfugaauaugcas(invAb) | 1223 |
| AD10202 | usGfscauauuCfacCfaUfiUfaggcsa | 1136 | (NAG37)s(invAb)sugccuaAfaUfgGfugaauaugcas(invAb) | 1223 |
| AD10203 | usGfscauaUfucacCfaUfiUfaggcsa | 1135 | (NAG37)s(invAb)sugccuaaaUfgGfuGfaauaugcas(invAb) | 1340 |
| AD10204 | usGfscauauuCfacCfaUfiUfaggcsa | 1136 | (NAG37)s(invAb)sugccuaaaUfgGfuGfaauaugcas(invAb) | 1340 |
| AD10205 | usGfscauaUfucacCfaUfiUfaggcsa | 1135 | (NAG37)s(invAb)sugccuaaaUfgGfUfgaauaugcas(invAb) | 1341 |
| AD10275 | cPrpasUfsgsAfaacaaacAfaAfcCfcugsa | 1137 | (NAG37)s(invAb)succaggguUfUfGfuuuguuucaus(invAb) | 1271 |
| AD10276 | cPrpasUfsgsAfaacaaacAfaAfcCfcugsgsa | 1138 | (NAG37)s(invAb)succaggguUfUfGfuuuguuucaus(invAb) | 1271 |
| AD10277 | cPrpasUfsgAfaacaaacAfaAfcCfcugsgsa | 1139 | (NAG37)s(invAb)succaggguUfUfGfuuuguuucaus(invAb) | 1271 |
| AD10278 | cPrpaUfgAfaacaaacAfaAfcCfcugsgsa | 1140 | (NAG37)s(invAb)succaggguUfUfGfuuuguuucaus(invAb) | 1271 |
| AD10279 | cPrpasUfsgAfaacaaacAfaAfcCfcugsgsa | 1139 | (NAG37)s(invAb)succaggguUfuGfuUfuguuucaus(invAb) | 1342 |
| AD10280 | cPrpasUfsgaaacaAfacAfaAfcCfcugsgsa | 1141 | (NAG37)s(invAb)succaggguUfuGfuUfuguuucaus(invAb) | 1342 |
| AD10281 | cPrpasUfsgaaaCfaaacAfaAfcCfcugsgsa | 1142 | (NAG37)s(invAb)succaggguUfuGfuUfuguuucaus(invAb) | 1342 |
| AD10282 | cPrpasUfsgaAfacaaacAfaAfcCfcugsgsa | 1143 | (NAG37)s(invAb)succaggguUfuGfuUfuguuucaus(invAb) | 1342 |
| AD10283 | cPrpasUfsgAfaaCfaAfacAfaAfcCfcugsgsa | 1144 | (NAG37)s(invAb)succaggguUfuGfuUfuguuucaus(invAb) | 1342 |
| AD10619 | cPrpusUfscsCfauaauacUfcUfgAfgagasg | 1093 | (NAG37)s(invAb)scucucucaGfaGfuAfuuauggaas(invAb) | 1312 |
| AD10620 | cPrpuUfscCfauaauacUfcUfgAfgagasg | 1145 | (NAG37)s(invAb)scucucucaGfaGfuAfuuauggaas(invAb) | 1312 |
| AD10621 | cPrpuUfscCfauaauacUfcUfgAfgagsasg | 1146 | (NAG37)s(invAb)scucucucaGfaGfuAfuuauggaas(invAb) | 1312 |

TABLE 5C-continued

XDH RNAi Agent Duplexes Showing Chemically Modified Antisense Strand and Sense Strand Sequences

| Sense Strand ID: | Modified Antisense Strand (5' → 3') | SEQ ID NO. | Modified Sense Strand (5' → 3') | SEQ ID NO. |
|---|---|---|---|---|
| AD10622 | cPrpuUfcCfauaauacUfcUfgAfgagsasg | 1095 | (NAG37)s(invAb)scucucucaGfaGfuAfuuauggaas(invAb) | 1312 |
| AD10623 | cPrpuUfcCfauaauacUfcUfgAfgagasc | 1147 | (NAG37)s(invAb)sgucucucaGfaGfuAfuuauggaas(invAb) | 1343 |
| AD10624 | cPrpuUfcCfauaauacUfcUfgAfgaggsg | 1148 | (NAG37)s(invAb)scccucucaGfaGfuAfuuauggaas(invAb) | 1344 |
| AD10625 | cPrpuUfcCfauaauacUfcUfgAfgaggsc | 1149 | (NAG37)s(invAb)sgccucucaGfaGfuAfuuauggaas(invAb) | 1345 |
| AD10626 | cPrpuUfcCfauaauacUfcUfgAfgaggsu | 1150 | (NAG37)s(invAb)saccucucaGfaGfuAfuuauggaas(invAb) | 1346 |
| AD10627 | cPrpuUfcCfauaauacUfcUfgAfgaggsa | 1151 | (NAG37)s(invAb)succucucaGfaGfuAfuuauggaas(invAb) | 1347 |
| AD10628 | cPrpuUfccauAfauacUfcUfgAfgagasg | 1152 | (NAG37)s(invAb)scucucucaGfaGfuAfuuauggaas(invAb) | 1312 |
| AD10629 | cPrpusGfscsauauuCfacCfaUfuUfaggcsa | 1153 | (NAG37)s(invAb)sugccuaaaUfgGfuGfaauaugcas(invAb) | 1340 |
| AD10630 | cPrpusGfscauauuCfacCfaUfuUfaggcsa | 1154 | (NAG37)s(invAb)sugccuaaaUfgGfuGfaauaugcas(invAb) | 1340 |
| AD10631 | cPrpusGfscauauuCfacCfaUfuUfaggscsa | 1155 | (NAG37)s(invAb)sugccuaaaUfgGfuGfaauaugcas(invAb) | 1340 |
| AD10632 | cPrpuGfcauauuCfacCfaUfuUfaggscsa | 1156 | (NAG37)s(invAb)sugccuaaaUfgGfuGfaauaugcas(invAb) | 1340 |
| AD10633 | cPrpusGfscsauaUfucacCfaUfuUfaggcsa | 1157 | (NAG37)s(invAb)sugccuaaaUfgGfUfgaauaugcas(invAb) | 1341 |
| AD10634 | cPrpusGfscauaUfucacCfaUfuUfaggcsa | 1158 | (NAG37)s(invAb)sugccuaaaUfgGfUfgaauaugcas(invAb) | 1341 |
| AD10635 | cPrpusGfscauaUfucacCfaUfuUfaggscsa | 1159 | (NAG37)s(invAb)sugccuaaaUfgGfUfgaauaugcas(invAb) | 1341 |
| AD10636 | cPrpuGfcauaUfucacCfaUfuUfaggscsa | 1160 | (NAG37)s(invAb)sugccuaaaUfgGfUfgaauaugcas(invAb) | 1341 |
| AD10728 | asUfsgsAfcaauaucUfgUfgCfggagsg | 1081 | (NAG37)s(invAb)sccuccgcaCfaGfaUfauugucaus(invAb) | 1348 |
| AD10729 | asUfsgsacaAfuaucUfgUfgCfggagsg | 1161 | (NAG37)s(invAb)sccuccgcaCfaGfaUfauugucaus(invAb) | 1348 |
| AD10730 | asUfsgsacaauAfucUfgUfgCfggagsg | 1162 | (NAG37)s(invAb)sccuccgcaCfaGfaUfauugucaus(invAb) | 1348 |
| AD10731 | cPrpasUfsgsacaauAfucUfgUfgCfggagsg | 1163 | (NAG37)s(invAb)sccuccgcaCfaGfaUfauugucaus(invAb) | 1348 |
| AD10732 | cPrpusUfsgsacaauAfucUfgUfgCfggagsg | 1164 | (NAG37)s(invAb)sccuccgcaCfaGfaUfauugucaas(invAb) | 1349 |
| AD10733 | cPrpaUfgacaauAfucUfgUfgCfggagsg | 1165 | (NAG37)s(invAb)sccuccgcaCfaGfaUfauugucaus(invAb) | 1348 |
| AD10734 | cPrpaUfgacaauAfucUfgUfgCfggasgsg | 1166 | (NAG37)s(invAb)sccuccgcaCfaGfaUfauugucaus(invAb) | 1348 |
| AD10735 | cPrpasUfsgacaauAfucUfgUfgCfggasgsg | 1167 | (NAG37)s(invAb)sccuccgcaCfaGfaUfauugucaus(invAb) | 1348 |
| AD10736 | cPrpasUfsgsacaauAfucUfgUfgCfggasg | 1168 | (NAG37)s(invAb)scuccgcaCfaGfaUfauugucaus(invAb) | 1350 |
| AD10737 | cPrpasUfsgsacaauAfucUfgUfgCfggsa | 1169 | (NAG37)s(invAb)succgcaCfaGfaUfauugucaus(invAb) | 1351 |
| AD10952 | cPrpuUfsccauaaUfacUfcUfgAfgagsasg | 1170 | (NAG37)s(invAb)scucucucaGfaGfuAfuuauggaas(invAb) | 1312 |
| AD10953 | cPrpuUfscCfauaauacUfcUfgAfgagsasc | 1171 | (NAG37)s(invAb)sgucucucaGfaGfuAfuuauggaas(invAb) | 1343 |
| AD10954 | cPrpusUfsgaaaCfaaacAfaAfcCfcugsgsa | 1172 | (NAG37)s(invAb)succaggguUfuGfuUfuguuucaas(invAb) | 1285 |
| AD10967 | asUfsgsAfaAfcaaacAfaAfcCfcUfggsa | 1048 | (NAG37)s(invAb)succaggguUfuGfuUfuguuucaus(invAb) | 1342 |
| AD10968 | asUfsgAfaAfcaaacAfaAfcCfcUfgsgsa | 1173 | (NAG37)s(invAb)succaggguUfuGfuUfuguuucaus(invAb) | 1342 |
| AD10969 | asUfsgAfaacaaacAfaAfcCfcugsgsa | 1174 | (NAG37)s(invAb)succaggguUfuGfuUfuguuucaus(invAb) | 1342 |
| AD12167 | asCfsucgUfuccauaaUfaCfucugasgsa | 1672 | (NAG37)suscagagUfaUfUfAfuggaacgagus(invAb) | 1676 |
| AD12168 | asUfsccaUfaauacucUfgAfgagagsasu | 1673 | (NAG37)scsucucuCfaGfAfGfuauuauggaus(invAb) | 1677 |

In some aspects, an XDH RNAi agent is prepared or provided as a salt, mixed salt, or a free-acid. The RNAi agents described herein, upon delivery to a cell expressing an XDH gene, inhibit or knockdown expression of one or more XDH genes in vivo and/or in vitro.

Targeting Ligands or Groups, Linking Groups, and Delivery Vehicles

In some aspects, an XDH RNAi agent is conjugated to one or more non-nucleotide groups including, but not limited to, a targeting group, a linking group, a targeting ligand, a delivery polymer, or a delivery vehicle. The non-nucleotide group can enhance targeting, delivery or attachment of the RNAi agent. Examples of targeting groups and linking groups are provided in Table 6. The non-nucleotide group can be covalently linked to the 3' and/or 5' end of either the sense strand and/or the antisense strand. In some aspects, an XDH RNAi agent contains a non-nucleotide group linked to the 3' and/or 5' end of the sense strand. In some aspects, a non-nucleotide group is linked to the 5' end of an XDH RNAi agent sense strand. A non-nucleotide group may be linked directly or indirectly to the RNAi agent via a linker/linking group. In some aspects, a non-nucleotide group is linked to the RNAi agent via a labile, cleavable, or reversible bond or linker.

In some aspects, a non-nucleotide group enhances the pharmacokinetic or biodistribution properties of an RNAi agent or conjugate to which it is attached to improve cell- or tissue-specific distribution and cell-specific uptake of the RNAi agent or conjugate. In some aspects, a non-nucleotide group enhances endocytosis of the RNAi agent.

Targeting groups or targeting moieties enhance the pharmacokinetic or biodistribution properties of a conjugate or RNAi agent to which they are attached to improve cell-specific (including, in some cases, organ specific) distribution and cell-specific (or organ specific) uptake of the conjugate or RNAi agent. A targeting group can be monovalent, divalent, trivalent, tetravalent, or have higher valency for the target to which it is directed. Representative targeting groups include, without limitation, compounds with affinity to cell surface molecules, cell receptor ligands, haptens, antibodies, monoclonal antibodies, antibody fragments, and antibody mimics with affinity to cell surface molecules.

In some aspects, a targeting group is linked to an RNAi agent using a linker, such as a PEG linker or one, two, or three abasic and/or ribitol (abasic ribose) residues, which can in some instances serve as linkers. In some aspects, a targeting ligand comprises a galactose-derivative cluster.

The XDH RNAi agents described herein can be synthesized having a reactive group, such as an amino group (also referred to herein as an amine), at the 5'-terminus and/or the 3'-terminus. The reactive group can be used subsequently to attach a targeting moiety using methods typical in the art.

In some aspects, a targeting group comprises an asialoglycoprotein receptor ligand. As used herein, an asialoglycoprotein receptor ligand is a ligand that contains a moiety having affinity for the asialoglycoprotein receptor. As noted herein, the asialoglycoprotein receptor is highly expressed on hepatocytes. In some aspects, an asialoglycoprotein receptor ligand includes or consists of one or more galactose derivatives. As used herein, the term galactose derivative includes both galactose and derivatives of galactose having affinity for the asialoglycoprotein receptor that is equal to or greater than that of galactose. Galactose derivatives include, but are not limited to: galactose, galactosamine, N-formyl-galactosamine, N-acetyl-galactosamine, N-propionyl-galactosamine, N-n-butanoyl-galactosamine, and N-iso-butanoyl-galactos-amine (see for example: S. T. Iobst and K. Drickamer, J. B. C., 1996, 271, 6686). Galactose derivatives, and clusters of galactose derivatives, that are useful for in vivo targeting of oligonucleotides and other molecules to the liver are known in the art (see, for example, Baenziger and Fiete, 1980, Cell, 22, 611-620; Connolly et al., 1982, J. Biol. Chem., 257, 939-945).

Galactose derivatives have been used to target molecules to hepatocytes in vivo through their binding to the asialoglycoprotein receptor expressed on the surface of hepatocytes. Binding of asialoglycoprotein receptor ligands to the asialoglycoprotein receptor(s) facilitates cell-specific targeting to hepatocytes and endocytosis of the molecule into hepatocytes. Asialoglycoprotein receptor ligands can be monomeric (e.g., having a single galactose derivative, also referred to as monovalent or monodentate) or multimeric (e.g., having multiple galactose derivatives). The galactose derivative or galactose derivative cluster can be attached to the 3' or 5' end of the sense or antisense strand of the RNAi agent using methods known in the art. The preparation of targeting ligands, such as galactose derivative clusters, is described in, for example, International Patent Application Publication No. WO 2018/044350 to Arrowhead Pharmaceuticals, Inc., and International Patent Application Publication No. WO 2017/156012 to Arrowhead Pharmaceuticals, Inc., the contents of both of which are incorporated by reference herein in their entirety.

As used herein, a galactose derivative cluster comprises a molecule having two to four terminal galactose derivatives. A terminal galactose derivative is attached to a molecule through its C-1 carbon. In some aspects, the galactose derivative cluster is a galactose derivative trimer (also referred to as tri-antennary galactose derivative or tri-valent galactose derivative). In some aspects, the galactose derivative cluster comprises N-acetyl-galactosamine moieties. In some aspects, the galactose derivative cluster comprises three N-acetyl-galactosamine moieties. In some aspects, the galactose derivative cluster is a galactose derivative tetramer (also referred to as tetra-antennary galactose derivative or tetra-valent galactose derivative). In some aspects, the galactose derivative cluster comprises four N-acetyl-galactosamine moieties.

As used herein, a galactose derivative trimer contains three galactose derivatives, each linked to a central branch point. As used herein, a galactose derivative tetramer contains four galactose derivatives, each linked to a central branch point. The galactose derivatives can be attached to the central branch point through the C-1 carbons of the saccharides. In some aspects, the galactose derivatives are linked to the branch point via linkers or spacers. In some aspects, the linker or spacer is a flexible hydrophilic spacer, such as a PEG group (see, e.g., U.S. Pat. No. 5,885,968; Biessen et al. J. Med. Chem. 1995 Vol. 39 p. 1538-1546). In some aspects, the PEG spacer is a $PEG_3$ spacer. The branch point can be any small molecule which permits attachment of three galactose derivatives and further permits attachment of the branch point to the RNAi agent. An example of branch point group is a di-lysine or di-glutamate. Attachment of the branch point to the RNAi agent can occur through a linker or spacer. In some aspects, the linker or spacer comprises a flexible hydrophilic spacer, such as, but not limited to, a PEG spacer. In some aspects, the linker comprises a rigid linker, such as a cyclic group. In some aspects, a galactose derivative comprises or consists of N-acetyl-galactosamine.

In some aspects, the galactose derivative cluster is comprised of a galactose derivative tetramer, which can be, for example, an N-acetyl-galactosamine tetramer.

Certain aspects of the present disclosure include pharmaceutical compositions for delivering an XDH RNAi agent to a liver cell in vivo. Such pharmaceutical compositions can include, for example, an XDH RNAi agent conjugated to a galactose derivative cluster. In some aspects, the galactose derivative cluster is comprised of a galactose derivative trimer, which can be, for example, an N-acetyl-galactosamine trimer, or galactose derivative tetramer, which can be, for example, an N-acetyl-galactosamine tetramer.

A targeting ligand or targeting group can be linked to the 3' or 5' end of a sense strand or an antisense strand of an XDH RNAi agent disclosed herein.

Targeting ligands include, but are not limited to (NAG37) and (NAG37)s as defined in Table 6. Other targeting groups and targeting ligands, including galactose cluster targeting ligands, are known in the art.

In some aspects, a linking group is conjugated to the RNAi agent. The linking group facilitates covalent linkage of the agent to a targeting group, delivery polymer, or delivery vehicle. The linking group can be linked to the 3' and/or the 5' end of the RNAi agent sense strand or antisense strand. In some aspects, the linking group is linked to the RNAi agent sense strand. In some aspects, the linking group is conjugated to the 5' or 3' end of an RNAi agent sense strand. In some aspects, a linking group is conjugated to the 5' end of an RNAi agent sense strand. Examples of linking groups, can include, but are not limited to: reactive groups such a primary amines and alkynes, alkyl groups, abasic nucleotides, ribitol (abasic ribose), and/or PEG groups.

In some aspects, a targeting group is linked internally to a nucleotide on the sense strand and/or the antisense strand of the RNAi agent. In some aspects, a targeting group is linked to the RNAi agent via a linker.

A linker or linking group is a connection between two atoms that links one chemical group (such as an RNAi agent) or segment of interest to another chemical group (such as a targeting group or delivery polymer) or segment of interest via one or more covalent bonds. A labile linkage contains a labile bond. A linkage can optionally include a spacer that increases the distance between the two joined atoms. A spacer can further add flexibility and/or length to the linkage. Spacers include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

In some aspects, when two or more RNAi agents are included in a single composition, each of the RNAi agents may be linked to the same targeting group or two a different targeting groups (i.e., targeting groups having different chemical structure). In some aspects, targeting groups are linked to the XDH RNAi agents disclosed herein without the use of an additional linker. In some aspects, the targeting group itself is designed having a linker or other site to facilitate conjugation readily present. In some aspects, when two or more XDH RNAi agents are included in a single molecule, each of the RNAi agents may utilize the same linker or different linkers (i.e., linkers having different chemical structures).

Any of the XDH RNAi agent nucleotide sequences listed in Tables 2, 3, 4, or 5C, whether modified or unmodified, can contain 3' and/or 5' targeting group(s) or linking group(s).

Any of the XDH RNAi agent sequences listed in Table 3 or 4, or are otherwise described herein, which contain a 3' or 5' targeting group or linking group, can alternatively contain no 3' or 5' targeting group or linking group, or can contain a different 3' or 5' targeting group or linking group including, but not limited to, those depicted in Table 6. Any of the XDH RNAi agent duplexes listed in Tables 5A, 5B and 5C, whether modified or unmodified, can further comprise a targeting group or linking group, including, but not limited to, those depicted in Table 6, and the targeting group or linking group can be attached to the 3' or 5' terminus of either the sense strand or the antisense strand of the XDH RNAi agent duplex.

Examples of targeting groups and linking groups (which when combined can form targeting ligands) are provided in Table 6. Table 4 and Table 5C provide several aspects of XDH RNAi agent sense strands having a targeting group or linking group linked to the 5' or 3' end.

TABLE 6

Structures Representing Various Modified Nucleotides, Targeting Ligands or Targeting Groups, Capping Residues, and Linking Groups

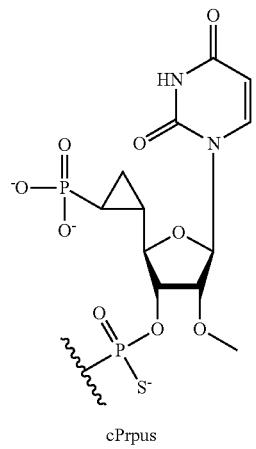

cPrpus

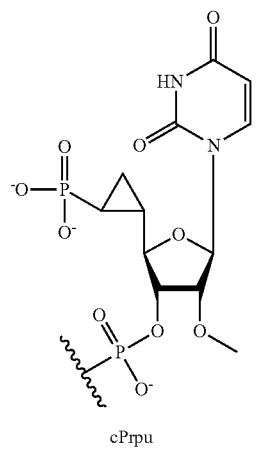

cPrpu

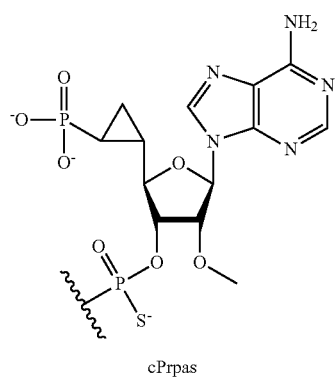

cPrpas

TABLE 6-continued
Structures Representing Various Modified Nucleotides, Targeting Ligands or Targeting Groups, Capping Residues, and Linking Groups
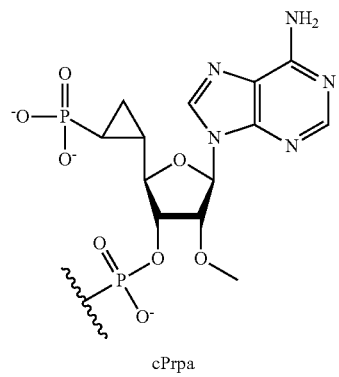
cPrpa
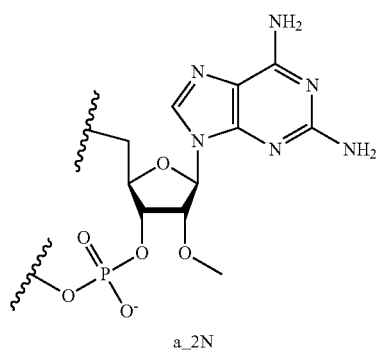
a_2N
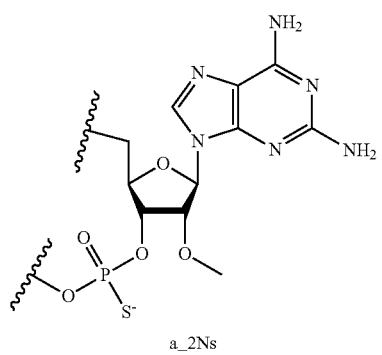
a_2Ns
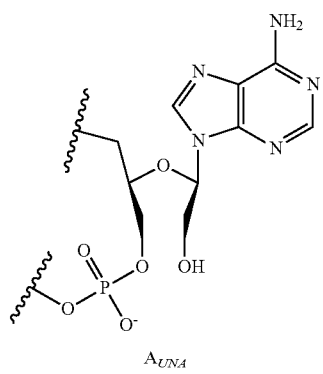
$A_{UNA}$ TABLE 6-continued
Structures Representing Various Modified Nucleotides, Targeting Ligands or Targeting Groups, Capping Residues, and Linking Groups
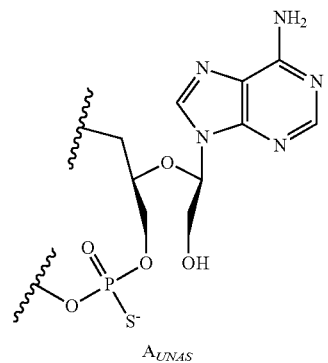
A<sub>UNAS</sub>
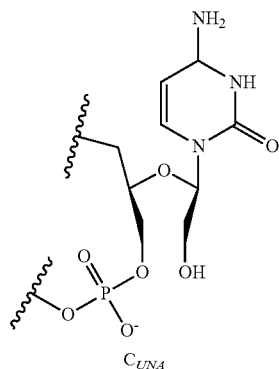
C<sub>UNA</sub>
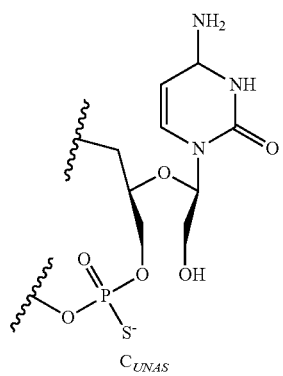
C<sub>UNAS</sub>
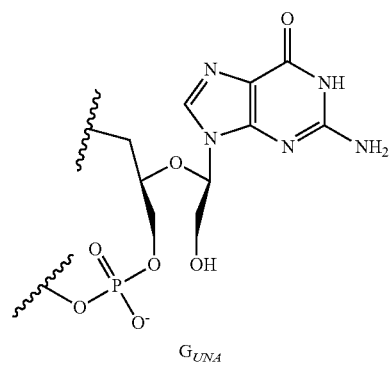
G<sub>UNA</sub>

TABLE 6-continued
Structures Representing Various Modified Nucleotides, Targeting Ligands or Targeting Groups, Capping Residues, and Linking Groups
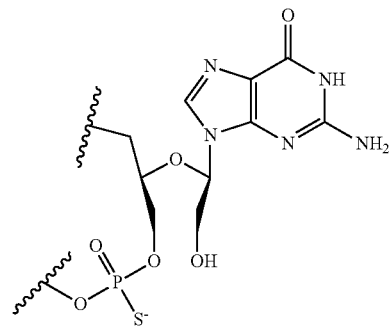 [SMILES: *C[C@H](COP(=O)([S-])O*)O[C@H](CO)n1cnc2c(=O)[nH]c(N)nc21]
G<sub>UNAS</sub>
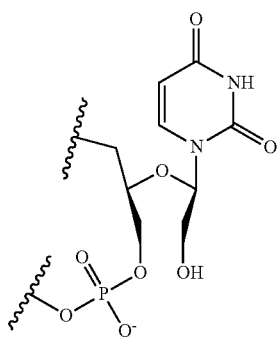 [SMILES: *C[C@H](COP(=O)([O-])O*)O[C@H](CO)n1ccc(=O)[nH]c1=O]
U<sub>UNA</sub>
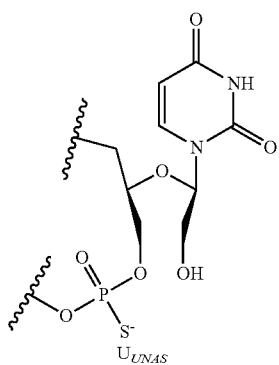
U<sub>UNAS</sub>
When positioned internally:
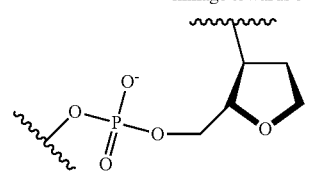
linkage towards 5' end
linkage towards 3' end
(invAb)

TABLE 6-continued
Structures Representing Various Modified Nucleotides, Targeting Ligands or Targeting Groups, Capping Residues, and Linking Groups
When positioned internally:
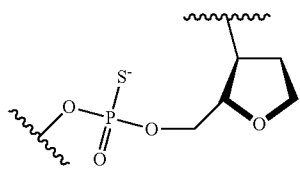
(invAb)s
When positioned at the 3' terminal end:
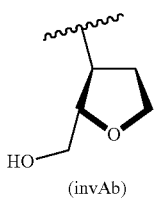
(invAb)
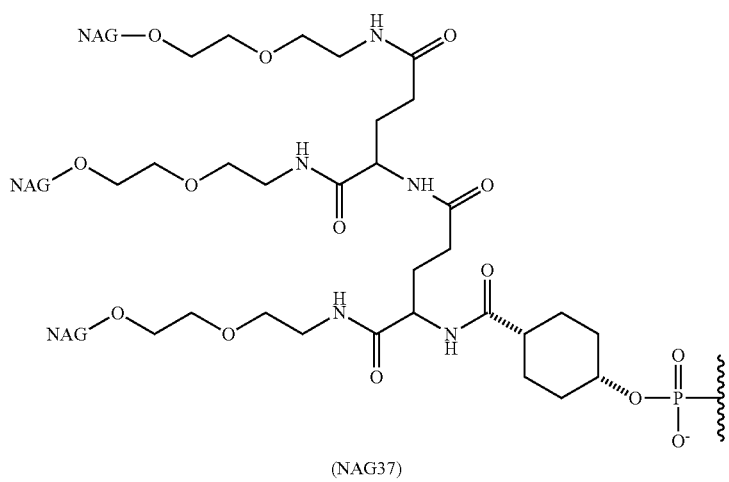
(NAG37)
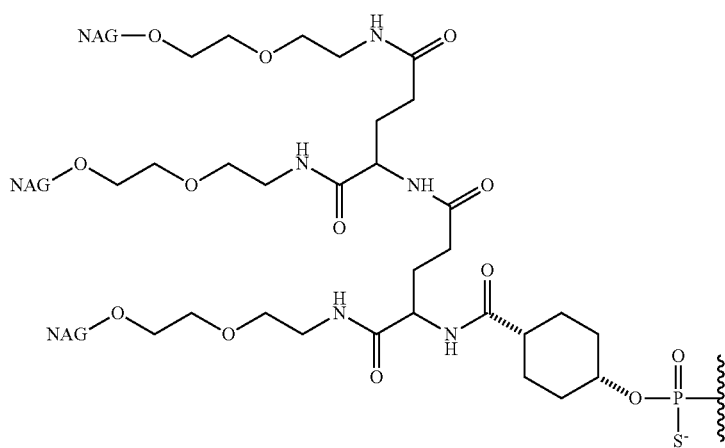
(NAG37)s TABLE 6-continued Structures Representing Various Modified Nucleotides, Targeting Ligands or Targeting Groups, Capping Residues, and Linking Groups

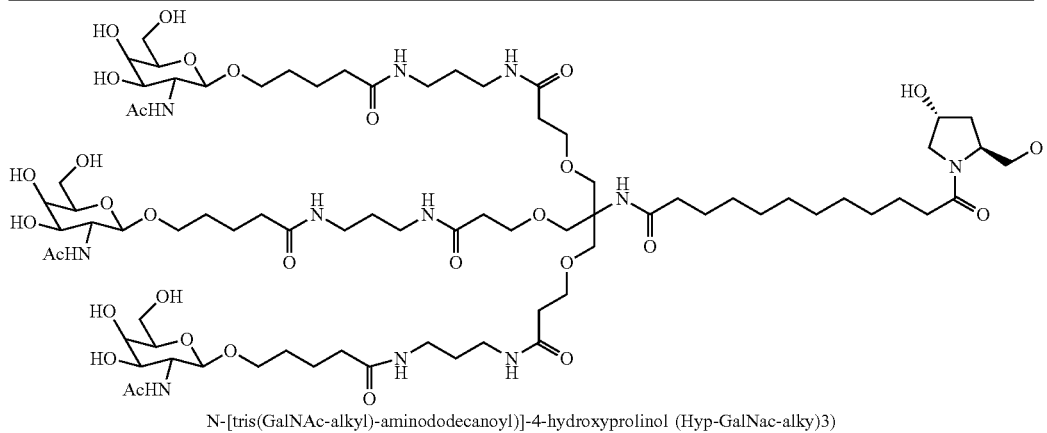

N-[tris(GalNAc-alkyl)-aminododecanoyl)]-4-hydroxyprolinol (Hyp-GalNac-alky)3)

In each of the above structures in Table 6, NAG comprises an N-acetyl-galactosamine or another galactose derivative, as would be understood by a person of ordinary skill in the art to be attached in view of the structures above and description provided herein. Other linking groups known in the art may be used.

In some aspects, a delivery vehicle can be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine. In some aspects, the RNAi agents can be combined with lipids, nanoparticles, polymers, liposomes, micelles, DPCs or other delivery systems available in the art. The RNAi agents can also be chemically conjugated to targeting groups, lipids (including, but not limited to cholesterol and cholesteryl derivatives), nanoparticles, polymers, liposomes, micelles, DPCs (see, for example WO 2000/053722, WO 2008/0022309, WO 2011/104169, and WO 2012/083185, WO 2013/032829, WO 2013/158141, each of which is incorporated herein by reference), hydrogels, cyclodextrins, biodegradable nanocapsules, and bioadhesive microspheres, proteinaceous vectors, or other delivery systems suitable for nucleic acid or oligonucleotide delivery as known and available in the art.

Pharmaceutical Compositions and Formulations

The XDH RNAi agents disclosed herein can be prepared as pharmaceutical compositions or formulations (also referred to herein as "medicaments"). In some aspects, pharmaceutical compositions include at least one XDH RNAi agent. These pharmaceutical compositions are particularly useful in the inhibition of the expression of the target mRNA in a target cell, a group of cells, a tissue, or an organism.

The pharmaceutical compositions can be used to treat a subject having a disease, disorder, or condition that would benefit from reduction in the level of the target XDH mRNA, or inhibition in expression of the target gene. The pharmaceutical compositions can be used to treat a subject at risk of developing a disease, disorder, symptom, or condition that would benefit from reduction of the level of the target mRNA or an inhibition in expression the target gene. In one embodiment, the method includes administering an XDH RNAi agent linked to a targeting ligand as described herein, to a subject to be treated. In some aspects, one or more pharmaceutically acceptable excipients (including vehicles, carriers, diluents, and/or delivery polymers) are added to the pharmaceutical compositions that include an XDH RNAi agent, thereby forming a pharmaceutical formulation or medicament suitable for in vivo delivery to a subject, including a human.

The pharmaceutical compositions that include an XDH RNAi agent and methods disclosed herein decrease the level of the target mRNA in a cell, group of cells, group of cells, tissue, organ, or subject, including by administering to the subject a therapeutically effective amount of a herein described XDH RNAi agent, thereby inhibiting the expression of XDH mRNA in the subject. In some aspects, the subject has been previously identified as having a pathogenic upregulation of the target gene in hepatocytes. In some aspects, the subject has been previously identified or diagnosed as having gout or hyperuricemia. In some aspects, the subject has been suffering from symptoms associated with gout or hyperuricemia. In some aspects, the subject would benefit from a reduction of XDH gene expression in the subject's liver.

In some aspects, the described pharmaceutical compositions including an XDH RNAi agent are used for treating or managing clinical presentations associated with gout or hyperuricemia. In some aspects, a therapeutically (including prophylactically) effective amount of one or more of pharmaceutical compositions is administered to a subject in need of such treatment. In some aspects, administration of any of the disclosed XDH RNAi agents can be used to decrease the number, severity, and/or frequency of symptoms of a disease in a subject.

The described pharmaceutical compositions that include an XDH RNAi agent can be used to treat at least one symptom in a subject having a disease or disorder that would benefit from reduction or inhibition in expression of XDH mRNA and/or a reduction in serum uric acid levels. Measuring serum uric acid levels can be conducted in accordance with established methods known in the art.

In some aspects, the subject is administered a therapeutically effective amount of one or more pharmaceutical compositions that include an XDH RNAi agent thereby treating the symptom. In other aspects, the subject is administered a prophylactically effective amount of one or more XDH RNAi agents, thereby preventing or inhibiting the at least one symptom.

The route of administration is the path by which an XDH RNAi agent is brought into contact with the body. In general, methods of administering drugs and oligonucleotides and nucleic acids for treatment of a mammal are well known in the art and can be applied to administration of the compositions described herein. The XDH RNAi agents disclosed herein can be administered via any suitable route in a preparation appropriately tailored to the particular route. Thus, herein described pharmaceutical compositions can be administered by injection, for example, intravenously, intramuscularly, intracutaneously, subcutaneously, intraarticularly, or intraperitoneally. In some aspects, the herein described pharmaceutical compositions are administered via subcutaneous injection.

The pharmaceutical compositions including an XDH RNAi agent described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with the compositions described herein. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain aspects, the compositions are administered by subcutaneous or intravenous infusion or injection.

In some aspects, the pharmaceutical compositions described herein comprise one or more pharmaceutically acceptable excipients. The pharmaceutical compositions described herein are formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical Ingredient (API, therapeutic product, e.g., XDH RNAi agent) that are intentionally included in the drug delivery system. Excipients do not exert or are not intended to exert a therapeutic effect at the intended dosage. Excipients can act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, detergents, dextran, dextrose, diluents, disintegrants, emulsifiers, extenders, fillers, flavors, glidants, humectants, lubricants, oils, polymers, preservatives, saline, salts, solvents, sugars, surfactants, suspending agents, sustained release matrices, sweeteners, thickening agents, tonicity agents, vehicles, water-repelling agents, and wetting agents.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor® EL™ (BASF, Parsippany, N.J.) or phosphate buffered saline (PBS). Suitable carriers should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

In some aspects, pharmaceutical formulations that include the XDH RNAi agents disclosed herein suitable for subcutaneous administration can be prepared in an aqueous sodium phosphate buffer (e.g., the XDH RNAi agent formulated in 0.5 mM sodium phosphate monobasic, 0.5 mM sodium phosphate dibasic, in water). In some aspects, pharmaceutical formulations that include the XDH RNAi agents disclosed herein suitable for subcutaneous administration can be prepared in water for injection (sterile water). XDH RNAi agents disclosed herein suitable for subcutaneous administration can be prepared in isotonic saline (0.9%).

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for oral administration of the XDH RNAi agents disclosed herein can also be prepared. In some aspects, the XDH RNAi agents disclosed herein are administered orally. In some aspects, the XDH RNAi agents disclosed herein are formulated in a capsule for oral administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The XDH RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, analgesics, antihistamines, or anti-inflammatory agents (e.g., acetaminophen, NSAIDs, diphenhydramine, etc.). It is also envisioned that cells, tissues, or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic, or preventive result.

In some aspects, the methods disclosed herein further comprise the step of administering a second therapeutic or treatment in addition to administering an RNAi agent disclosed herein. In some aspects, the second therapeutic is another XDH RNAi agent (e.g., an XDH RNAi agent that targets a different sequence within the XDH target). In other aspects, the second therapeutic can be a small molecule drug, an antibody, an antibody fragment, or an aptamer.

In some aspects, the described XDH RNAi agent(s) are optionally combined with one or more additional therapeutics. The XDH RNAi agent and additional therapeutic(s) can be administered in a single composition or they can be administered separately. In some aspects, the one or more additional therapeutics is administered separately in separate dosage forms from the RNAi agent (e.g., the XDH RNAi agent is administered by subcutaneous injection, while the additional therapeutic involved in the method of treatment dosing regimen is administered orally). In some aspects, the described XDH RNAi agent(s) are administered to a subject in need thereof via subcutaneous injection, and the one or more optional additional therapeutics are administered orally, which together provide for a treatment regimen for diseases and conditions associated with gout or hyperuricemia. In some aspects, the described XDH RNAi agent(s) are administered to a subject in need thereof via subcutaneous injection, and the one or more optional additional therapeutics are administered via a separate subcutaneous injection. In some aspects, the XDH RNAi agent and one or more additional therapeutics are combined into a single dosage form (e.g., a "cocktail" formulated into a single composition for subcutaneous injection). The XDH RNAi agents, with or without the one or more additional therapeutics, can be combined with one or more excipients to form pharmaceutical compositions.

Generally, an effective amount of an XDH RNAi agent will be in the range of from about 0.1 to about 100 mg/kg of body weight/dose, e.g., from about 1.0 to about 50 mg/kg of body weight/dose. In some aspects, an effective amount of an active compound will be in the range of from about 0.25 to about 5 mg/kg of body weight per dose. In some aspects, an effective amount of an active ingredient will be in the range of from about 0.5 to about 4 mg/kg of body weight per dose. In some aspects, an effective amount of an XDH RNAi agent may be a fixed dose. In some aspects, the fixed dose is in the range of from about 5 mg to about 1,000 mg of XDH RNAi agent. In some aspects, the fixed does is in the range of 50 to 400 mg of XDH RNAi agent. Dosing may be weekly, bi-weekly, monthly, quarterly, or at any other interval depending on the dose of XDH RNAi agent administered, the activity level of the particular XDH RNAi agent, and the desired level of inhibition for the particular subject. The Examples herein show suitable levels for inhibition in certain animal species. The amount administered will depend on such variables as the overall health status of the patient or subject, the relative biological efficacy of the compound delivered, the formulation of the drug, the presence and types of excipients in the formulation, and the route of administration. Also, it is to be understood that the initial dosage administered can be increased beyond the above upper level to rapidly achieve the desired blood-level or tissue level, or the initial dosage can be smaller than the optimum.

For treatment of disease or for formation of a medicament or composition for treatment of a disease, the pharmaceutical compositions described herein including an XDH RNAi agent can be combined with an excipient or with a second therapeutic agent or treatment including, but not limited to: a second or other RNAi agent, a small molecule drug, an antibody, an antibody fragment, peptide and/or an aptamer.

The described XDH RNAi agents, when added to pharmaceutically acceptable excipients or adjuvants, can be packaged into kits, containers, packs, or dispensers. The pharmaceutical compositions described herein may be packaged in pre-filled syringes, pen injectors, autoinjectors, infusion bags/devices, or vials.

Methods of Treatment and Inhibition of Expression

The XDH RNAi agents disclosed herein can be used to treat a subject (e.g., a human or other mammal) having a disease or disorder that would benefit from administration of the RNAi agent. In some aspects, the RNAi agents disclosed herein can be used to treat a subject (e.g., a human) that would benefit from reduction and/or inhibition in expression of XDH mRNA and/or XDH protein levels, which can lead to a reduction in serum uric acid levels in, for example, a subject that has been diagnosed with or is suffering from symptoms related to gout or hyperuricemia.

In some aspects, the subject is administered a therapeutically effective amount of any one or more XDH RNAi agents. Treatment of a subject can include therapeutic and/or prophylactic treatment. The subject is administered a therapeutically effective amount of any one or more XDH RNAi agents described herein. The subject can be a human, patient, or human patient. The subject may be an adult, adolescent, child, or infant. Administration of a pharmaceutical composition described herein can be to a human being or animal.

The XDH RNAi agents described herein can be used to treat at least one symptom in a subject having an XDH-related disease or disorder, or having a disease or disorder that is mediated at least in part by XDH gene expression. In some aspects, the XDH RNAi agents are used to treat or manage a clinical presentation of a subject with a disease or disorder that would benefit from or be mediated at least in part by a reduction in XDH mRNA. The subject is administered a therapeutically effective amount of one or more of the XDH RNAi agents or XDH RNAi agent-containing compositions described herein. In some aspects, the methods disclosed herein comprise administering a composition comprising an XDH RNAi agent described herein to a subject to be treated. In some aspects, the subject is administered a prophylactically effective amount of any one or more of the described XDH RNAi agents, thereby treating the subject by preventing or inhibiting the at least one symptom.

In certain aspects, the present disclosure provides methods for treatment of diseases, disorders, conditions, or pathological states mediated at least in part by XDH gene expression, in a patient in need thereof, wherein the methods include administering to the patient any of the XDH RNAi agents described herein.

In some aspects, the RNAi agent comprises an antisense strand comprising an unmodified nucleic acid sequence of AM15135, AM14244, AM15149, AM13882, AM14216, AM14387, AM14240, AM14238, or AM14236, and a sense strand comprising an unmodified nucleic acid sequence of AM14284, AM14243, AM14528, AM13881, AM14215, AM13877, AD14239, AD14237, or AD14235.

In some aspects, the XDH RNAi agent comprises an antisense strand comprising a modified nucleic acid sequence of AM15135, AM14244, AM15149, AM13882, AM14216, AM14387, AM14240, AM14238, or AM14236, and a sense strand comprising a modified nucleic acid sequence of AM14284, AM14243, AM14528, AM13881, AM14215, AM13877, AD14239, AD14237, or AD14235.

In some aspects, the RNAi agent comprises an antisense strand comprising a nucleic acid sequence of UUCCAUAAUACUCUGAGAGAG (SEQ ID NO:1448) and a sense strand comprising a nucleic acid sequence of CUCUCUCAGAGUAUUAUGGAA (SEQ ID NO:1603). In some aspects, a nucleic acid sequence of the antisense strand comprises a nucleic acid sequence of cPrpusUfscCfauaauacUfcUfgAfgagsasg (SEQ ID NO:1146) and a nucleic acid sequence of the sense strand comprises a nucleic acid sequence of cucucucaGfaGfuAfuuauggaa (SEQ ID NO: 1663) or (invAb)scucucucaGfaGfuAfuuauggaas(invAb) (SEQ ID NO:1680).

In some aspects, the RNAi agent comprises an antisense strand comprising a nucleic acid sequence of AUGACAAUAUCUGUGCGGAGG (SEQ ID NO:1468) and a sense strand comprising a nucleic acid sequence of CCUCCGCACAGAUAUUGUCAU (SEQ ID NO:1623). In some aspects, a nucleic acid sequence of the antisense strand comprises asUfsgsAfcaauaucUfgUfgCfggagsg (SEQ ID NO:1081) and a nucleic acid sequence of the sense strand comprises a nucleic acid sequence of ccuccgcaCfAfGfauauugucau (SEQ ID NO:1664) or (invAb)sccuccgcaCfAfGfauauugucaus(invAb) (SEQ ID NO:1681).

In some aspects, the RNAi agent comprises an antisense sequence comprising a nucleic acid sequence of UGCAUAUUCACCAUUUAGGCA (SEQ ID NO:1397) and a sense strand comprising a nucleic acid sequence of UGCCUAAAUGGUGAAUAUGCA (SEQ ID NO:1551). In some aspects, a nucleic acid sequence of the antisense strand comprises cPrpusGfscauauuCfacCfaUfuUfaggscsa (SEQ ID NO: 1155) and a nucleic acid sequence of the sense strand comprises ugccuaaaUfgGfuGfaauaugca (SEQ ID NO:1665) or (invAb)sugccuaaaUfgGfuGfaauaugcas(invAb) (SEQ ID NO:1682).

In some aspects, the RNAi agent comprises an antisense sequence comprising a nucleic acid sequence of AUGAAACAAACAAACCCUGGA (SEQ ID NO:1440) and a sense strand comprising a nucleic acid sequence of UCCAGGGUUUGUUUGUUUCAU (SEQ ID NO:1595). In some aspects, a nucleic acid sequence of the antisense strand comprises asUfsgsAfaAfcaaacAfaAfcCfcUfggsa (SEQ ID NO:1048) and a nucleic acid sequence of the sense strand comprises uccaggguUfUfGfuuuguuucau (SEQ ID NO: 1666) or (invAb)succaggguUfUfGfuuuguuucaus (invAb) (SEQ ID NO:1683).

In some aspects, the RNAi agent comprises an antisense sequence comprising a nucleic acid sequence of AGACGAUCAUACUUGGAGAGC (SEQ ID NO:1454) and a sense strand comprising a nucleic acid sequence of GCUCUCCAAGUAUGAUCIUCU (SEQ ID NO:1609). In some aspects, a nucleic acid sequence of the antisense strand comprises asGfsasCfgaucauaCfuUfgGfagagsc (SEQ ID NO:1067) and a nucleic acid sequence of the sense strand comprises gcucuccaAfGfUfaugauciucu (SEQ ID NO:1667) or (invAb)sgcucuccaAfGfUfaugauciucus(invAb) (SEQ ID NO:1684).

In some aspects, the RNAi agent comprises an antisense sequence comprising a nucleic acid sequence of UUUGAAUGCUGAGAAAUACUC (SEQ ID NO:1438) and a sense strand comprising a nucleic acid sequence of GAGUAUUUCUCAGCAUUCAAA (SEQ ID NO:1593). In some aspects, a nucleic acid sequence of the antisense strand comprises cPrpuUfuGfaaugcugAfgAfaAfuacusc (SEQ ID NO:1111) and a nucleic acid sequence of the sense strand comprises gaguauuuCfUfCfagcauucaaa (SEQ ID NO:1668) or (invAb)sgaguauuuCfUfCfagcauucaaas(invAb) (SEQ ID NO:1685).

In some aspects, the RNAi agent comprises an antisense sequence comprising a nucleic acid sequence of UUUCCAACAAUUCUCCUUGUC (SEQ ID NO:1466) and a sense strand comprising a nucleic acid sequence of GACAAGGAGAAUUGUUGGAAA (SEQ ID NO:1621). In some aspects, a nucleic acid sequence of the antisense strand comprises usUfsusCfcaacaauUfcUfcCfuugusc (SEQ ID NO:1079) and a nucleic acid sequence of the sense strand comprises gacaaggaGfAfAfuuguuggaaa (SEQ ID NO:1669) or (invAb)sgacaaggaGfAfAfuuguuggaaas(invAb) (SEQ ID NO:1686).

In some aspects, the RNAi agent comprises an antisense sequence comprising a nucleic acid sequence of UUGUCAACCUCACUCUUCCGA (SEQ ID NO:1465) and a sense strand comprising a nucleic acid sequence of UCGGAAGAGUGAGGUUGACAA (SEQ ID NO:1620). In some aspects, a nucleic acid sequence of the antisense strand comprises usUfsgsUfcaaccucAfcUfcUfuccgsa (SEQ ID NO:1078) and a nucleic acid sequence of the sense strand comprises ucggaagaGfUfGfagguugacaa (SEQ ID NO:1670) or (invAb)sucggaagaGfUfGfagguugacaas(invAb) (SEQ ID NO:1687).

In some aspects, the RNAi agent comprises an antisense sequence comprising a nucleic acid sequence of UCAUGAUACUGAGAGCUUGCU (SEQ ID NO:1464) and a sense strand comprising a nucleic acid sequence of AGCAAGCUCUCAGUAUCAUGA (SEQ ID NO:1619). In some aspects, a nucleic acid sequence of the antisense strand comprises usCfsasUfgauacugAfgAfgCfuugcsu (SEQ ID NO:1077) and a nucleic acid sequence of the sense strand comprises agcaagcuCfUfCfaguaucauga (SEQ ID NO:1671) or (invAb)sagcaagcuCfUfCfaguaucaugas(invAb) (SEQ ID NO:1688).

In some aspects, the 5' end of the sense strand is coupled to a targeting ligand comprising the structure of (NAG37)s.

In some aspects, the gene expression level and/or mRNA level of an XDH gene in a subject to whom a described XDH RNAi agent is administered is reduced by at least about 30%, 35% 40%, 45%, 50%, 55% 60%, 65%, 70%, 75%, 80%, 85%, 95%, 96%, 97%, 98%, 99%, or greater than 99% relative to the subject prior to being administered the XDH RNAi agent or to a subject not receiving the XDH RNAi agent. The gene expression level and/or mRNA level in the subject may be reduced in a cell, group of cells, and/or tissue of the subject. In some aspects, the XDH gene expression is inhibited by at least about 30%, 35%, 40%, 45% 50%, 55%, 60%, 65%, or greater than 65% in the cytoplasm of hepatocytes relative to the subject prior to being administered the XDH RNAi agent or to a subject not receiving the XDH RNAi agent.

In some aspects, the XDH protein expression level in a subject to whom a described XDH RNAi agent has been administered is reduced by at least about 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the XDH RNAi agent or to a subject not receiving the XDH RNAi agent. The protein expression level in the subject may be reduced in a cell, group of cells, tissue, blood, and/or other fluid of the subject.

A reduction in XDH mRNA expression levels and XDH protein expression levels can be assessed by any methods known in the art. As used herein, a reduction or decrease in XDH mRNA level and/or protein level are collectively referred to herein as a reduction or decrease in XDH or inhibiting or reducing the gene expression of XDH. The Examples set forth herein illustrate known methods for assessing inhibition of XDH gene expression. The person of ordinary skill in the art would further know suitable methods for assessing inhibition of XDH gene expression in vivo and/or in vitro.

In some aspects, disclosed herein are methods of treatment (including prophylactic or preventative treatment) of diseases, disorders, or symptoms caused by caused by gout and/or hyperuricemia, wherein the methods include administering to a subject in need thereof a therapeutically effective amount of an XDH RNAi agent that includes an antisense strand that is at least partially complementary to the portion of the XDH mRNA having the sequence in Table 1. In some aspects, disclosed herein are methods of treatment (including prophylactic or preventative treatment) of diseases or symptoms caused by caused by gout or hyperuricemia, wherein the methods include administering to a subject in need thereof a therapeutically effective amount of an XDH RNAi agent that includes an antisense strand comprising the sequence of any of the sequences in Tables 2, 3 or 5C, and a sense strand that comprises any of the sequences in Tables 2, 4, or 5C that is at least partially complementary to the antisense strand. In some aspects, disclosed herein are methods of treatment (including prophylactic or preventative treatment) of diseases or symptoms caused by gout or hyperuricemia, wherein the methods include administering to a subject in need thereof a therapeutically effective amount of an XDH RNAi agent that includes a sense strand that comprises any of the sequences in Tables 2, 4, or 5C, and an antisense strand comprising the sequence of any of the sequences in Tables 2, 3, or 5C that is at least partially complementary to the sense strand.

In some aspects, the RNAi agent comprises an antisense strand comprising an unmodified nucleic acid sequence of AM15135, AM14244, AM15149, AM13882, AM14216, AM14387, AM14240, AM14238, or AM14236, and a sense strand comprising an unmodified nucleic acid sequence of AM14284, AM14243, AM14528, AM13881, AM14215, AM13877, AD14239, AD14237, or AD14235.

In some aspects, The RNAi agent comprises an antisense strand comprising a modified nucleic acid sequence of AM15135, AM14244, AM15149, AM13882, AM14216, AM14387, AM14240, AM14238, or AM14236, and a sense strand comprising a modified nucleic acid sequence of AM14284, AM14243, AM14528, AM13881, AM14215, AM13877, AD14239, AD14237, or AD14235.

In some aspects, the RNAi agent comprises an antisense strand comprising a nucleic acid sequence of UUCCAUAAUACUCUGAGAGAG (SEQ ID NO:1448) and a sense strand comprising a nucleic acid sequence of CUCUCUCAGAGUAUUAUGGAA (SEQ ID NO:1603). In some aspects, a nucleic acid sequence of the antisense strand comprises cPrpusUfscCfauaauacUfcUfgAfgagsasg (SEQ ID NO:1146) and a nucleic acid sequence of the sense strand comprises cucucucaGfaGfuAfuuauggaa (SEQ ID NO:1663) or (invAb)scucucucaGfaGfuAfuuauggaas(invAb) (SEQ ID NO:1680).

In some aspects, the RNAi agent comprises an antisense strand comprising a nucleic acid sequence of AUGACAAUAUCUGUGCGGAGG (SEQ ID NO:1468) and a sense strand comprising a nucleic acid sequence of CCUCCGCACAGAUAUUGUCAU (SEQ ID NO:1623). In some aspects, a nucleic acid sequence of the antisense strand comprises asUfsgsAfcaauaucUfgUfgCfggagsg (SEQ ID NO:1081) and a nucleic acid sequence of the sense strand comprises ccuccgcaCfAfGfauauugucau (SEQ ID NO:1664) or (invAb)sccuccgcaCfAfGfauauugucaus(invAb) (SEQ ID NO:1681).

In some aspects, the RNAi agent comprises an antisense sequence comprising a nucleic acid sequence of UGCAUAUUCACCAUUUAGGCA (SEQ ID NO:1397) and a sense strand comprising a nucleic acid sequence of UGCCUAAAUGGUGAAUAUGCA (SEQ ID NO:1551). In some aspects, a nucleic acid sequence of the antisense strand comprises cPrpusGfscauauuCfacCfaUfuUfaggscsa (SEQ ID NO:1155) and a nucleic acid sequence of the sense strand comprises ugccuaaaUfgGfuGfaauaugca (SEQ ID NO:1665) or (invAb)sugccuaaaUfgGfuGfaauaugcas(invAb) (SEQ ID NO:1682).

In some aspects, the RNAi agent comprises an antisense sequence comprising a nucleic acid sequence of AUGAAACAAACAAACCCUGGA (SEQ ID NO:1440) and a sense strand comprising a nucleic acid sequence of UCCAGGGUUUGUUUGUUUCAU (SEQ ID NO:1595). In some aspects, a nucleic acid sequence of the antisense strand comprises asUfsgsAfaAfcaaacAfaAfcCfcUfggsa (SEQ ID NO:1048) and a nucleic acid sequence of the sense strand comprises uccaggguUfUfGfuuuguuucau (SEQ ID NO: 1666) or (invAb)succaggguUfUfGfuuuguuucaus (invAb) (SEQ ID NO:1683).

In some aspects, the RNAi agent comprises an antisense sequence comprising a nucleic acid sequence of AGACGAUCAUACUUGGAGAGC (SEQ ID NO:1454) and a sense strand comprising a nucleic acid sequence of GCUCUCCAAGUAUGAUCIUCU (SEQ ID NO:1609). In some aspects, a nucleic acid sequence of the antisense strand comprises asGfsasCfgaucauaCfuUfgGfagagsc (SEQ ID NO:1067) and a nucleic acid sequence of the sense strand comprises asGfsasCfgaucauaCfuUfgGfagagsc (SEQ ID NO:1067) and a nucleic acid sequence of the sense strand comprises gcucuccaAfGfUfaugauciucu (SEQ ID NO:1667) or (invAb)sgcucuccaAfGfUfaugauciucus(invAb) (SEQ ID NO:1684).

In some aspects, the RNAi agent comprises an antisense sequence comprising a nucleic acid sequence of UUUGAAUGCUGAGAAAUACUC (SEQ ID NO:1438) and a sense strand comprising a nucleic acid sequence of GAGUAUUUCUCAGCAUUCAAA (SEQ ID NO:1593). In some aspects, a nucleic acid sequence of the antisense strand comprises cPrpuUfuGfaaugcugAfgAfaAfuacusc (SEQ ID NO:1111) and a nucleic acid sequence of the sense strand comprises gaguauuuCfUfCfagcauucaaa (SEQ ID NO:1668) or (invAb)sgaguauuuCfUfCfagcauucaaas(invAb) (SEQ ID NO:1685).

In some aspects, the RNAi agent comprises an antisense sequence comprising a nucleic acid sequence of UUUCCAACAAUUCUCCUUGUC (SEQ ID NO:1466) and a sense strand comprising a nucleic acid sequence of GACAAGGAGAAUUGUUGGAAA (SEQ ID NO:1621). In some aspects, a nucleic acid sequence of the antisense strand comprises usUfsusCfcaacaauUfcUfcCfuugusc (SEQ ID NO:1079) and a nucleic acid sequence of the sense strand comprises gacaaggaGfAfAfuuguuggaaa (SEQ ID NO:1669) or (invAb)sgacaaggaGfAfAfuuguuggaaas(invAb) (SEQ ID NO:1686).

In some aspects, the RNAi agent comprises an antisense sequence comprising a nucleic acid sequence of UUGUCAACCUCACUCUUCCGA (SEQ ID NO:1465) and a sense strand comprising a nucleic acid sequence of UCGGAAGAGUGAGGUUGACAA (SEQ ID NO:1620). In some aspects, a nucleic acid sequence of the antisense strand comprises usUfsgsUfcaaccucAfcUfcUfuccgsa (SEQ ID NO:1078) and a nucleic acid sequence of the sense strand comprises ucggaagaGfUfGfagguugacaa (SEQ ID NO:1670) or (invAb)sucggaagaGfUfGfagguugacaas(invAb) (SEQ ID NO:1687).

In some aspects, the RNAi agent comprises an antisense sequence comprising a nucleic acid sequence of UCAUGAUACUGAGAGCUUGCU (SEQ ID NO:1464) and a sense strand comprising a nucleic acid sequence of AGCAAGCUCUCAGUAUCAUGA (SEQ ID NO:1619). In some aspects, a nucleic acid sequence of the antisense strand comprises usCfsasUfgauacugAfgAfgCfuugcsu (SEQ ID NO:1077) and a nucleic acid sequence of the sense strand comprises agcaagcuCfUfCfaguaucauga (SEQ ID NO:1671) or (invAb)sagcaagcuCfUfCfaguaucaugas(invAb) (SEQ ID NO:1688).

In some aspects, the 5' end of the sense strand is coupled to a targeting ligand comprising the structure of (NAG37)s.

In some aspects, disclosed herein are methods for inhibiting expression of an XDH gene in a cell, wherein the methods include administering to the cell an XDH RNAi agent that includes an antisense strand that is at least partially complementary to the portion of the XDH mRNA having the sequence in Table 1. In some aspects, disclosed herein are methods of inhibiting expression of an XDH gene in a cell, wherein the methods include administering to a cell an XDH RNAi agent that includes an antisense strand comprising the sequence of any of the sequences in Tables 2, 3, or 5C and a sense strand that comprises any of the sequences in Tables 2, 4, or 5C that is at least partially complementary to the antisense strand. In some aspects, disclosed herein are methods of inhibiting expression of an XDH gene in a cell, wherein the methods include administering an XDH RNAi agent that includes a sense strand that comprises any of the sequences in Tables 2, 4, or 5C, and an antisense strand that includes the sequence of any of the sequences in Tables 2, 3, or 5C that is at least partially complementary to the sense strand.

In some aspects, the XDH RNAi agents are administered to a subject in need thereof as a first line therapy. In some aspects, the XDH RNAi agents are administered to a subject in need thereof as a second line therapy. In certain aspects, the XDH RNAi agents are administered as a second line therapy to patients who have failed one or more first line standard of care therapies. In certain aspects, the XDH RNAi agents are administered as a maintenance therapy following the administration of one or more prior therapies. In certain aspects, the XDH RNAi agents administered as a maintenance therapy following the administration of one or more standard of care therapies. In some aspects, the XDH RNAi agents administered in combination with one or more additional therapies. In some aspects, the one or more additional therapies is a standard of care therapy. In some aspects, the one or more additional therapies is an oral therapy.

Provided herein are methods for treating gout using the XDH RNAi agents described herein, for example, RNAi agent comprising an antisense strand comprising an unmodified nucleic acid sequence of AM15135, AM14244, AM15149, AM13882, AM14216, AM14387, AM14240, AM14238, or AM14236, and a sense strand comprising an unmodified nucleic acid sequence of AM14284, AM14243, AM14528, AM13881, AM14215, AM13877, AD14239, AD14237, or AD14235. In some aspects, the gout is uncontrolled gout. In some aspects, the oligonucleotide, composition, or pharmaceutical composition described herein is administered as a second line therapy to patients who have failed allopurinol and/or febuxostat. In some aspects, the oligonucleotide, composition, or pharmaceutical composition described herein is administered prior to KRYSTEXXA. In some aspects, the oligonucleotide, composition, or pharmaceutical composition described herein is administered as a maintenance therapy following the administration of KRYSTEXXA.

The use of XDH RNAi agents provides methods for therapeutic (including prophylactic) treatment of diseases/disorders associated with gout, hyperuricemia, elevated serum uric acid levels, or elevated XDH gene expression. The described XDH RNAi agents mediate RNA interference to inhibit the expression of one or more genes necessary for production of XDH protein. XDH RNAi agents can also be used to treat or prevent various diseases, disorders, or conditions, including gout. Furthermore, compositions for delivery of XDH RNAi agents to liver cells, and specifically to hepatocytes, in vivo, are described.

Cells, Tissues, Organs, and Non-Human Organisms

Cells, tissues, organs, and non-human organisms that include at least one of the XDH RNAi agents described herein are contemplated. The cell, tissue, organ, or non-human organism is made by delivering the RNAi agent to the cell, tissue, organ or non-human organism.

Illustrative Embodiments

Provided here are illustrative embodiments of the disclosed technology. These embodiments are illustrative only and do not limit the scope of the present disclosure or of the claims attached hereto.

Embodiment 1. An RNAi agent for inhibiting expression of an XDH gene, comprising:

an antisense strand comprising at least 15 contiguous nucleotides differing by 0, 1, 2, or 3, nucleotides from any one of the sequences antisense strand sequences disclosed in Table 2, Table 3, or Table 5C; and a sense strand comprising a nucleotide sequence that is at least partially complementary to the antisense strand.

Embodiment 2. An RNAi agent for inhibiting expression of an XDH gene, comprising:
a sense strand comprising at least 15 contiguous nucleotides differing by 0, 1, 2, or 3 nucleotides from a stretch of the same length of nucleotides of SEQ ID NO: 1; and an antisense strand comprising a nucleotide sequences that is at least partially complementary to the sense strand.

Embodiment 3. The RNAi agent of embodiment 1, wherein the antisense strand comprises nucleotides at positions 2-18 of any one of the antisense strand sequences of Table 2, Table 3, or Table 5C.

Embodiment 4. The RNAi agent of embodiment 1 or embodiment 2, wherein the sense strand comprises a nucleotide sequence of at least 15 contiguous nucleotides differing by 0 or 1 nucleotide from any one of the sense strand sequences of Table 2, Table 4, or Table 5C, and wherein the sense strand has a region of at least 85% complementarity over the 15 contiguous nucleotides to the antisense strand.

Embodiment 5. The RNAi agent of any one of embodiments 1-4, wherein at least one nucleotide of the RNAi agent is a modified nucleotide or includes a modified internucleoside linkage.

Embodiment 6. The RNAi agent of any one of aspects 1-5, wherein all or substantially all of the nucleotides of the sense and/or antisense strand of the RNAi agent are modified nucleotides.

Embodiment 7. The RNAi agent of any one of aspects 5-6, wherein the modified nucleotide is selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate containing nucleotide, cyclopropyl phosphonate containing nucleotide, and 3'-O-methyl nucleotide.

Embodiment 8. The RNAi agent of embodiment 7, wherein all or substantially all of the modified nucleotides are 2'-O-methyl nucleotides, 2'-fluoro nucleotides, or combinations thereof.

Embodiment 9. The RNAi agent of any one of aspects 1-8, wherein the antisense strand comprises the nucleotide sequence of any one of the modified antisense strand sequences of Table 3 or Table 5C.

Embodiment 10. The RNAi agent of any one of aspects 1-9, wherein the sense strand comprises the nucleotide sequence of any of the modified sense strand sequences of Table 4 or Table 5C.

Embodiment 11. The RNAi agent of embodiment 1, wherein the antisense strand comprises the nucleotide sequence of any one of the modified sequences of Table 5C and the sense strand comprises the nucleotide sequence of any one of the modified sequences of Table 5C.

Embodiment 12. The RNAi agent of any one of aspects 1-11, wherein the RNAi agent is linked to a targeting ligand.

Embodiment 13. The RNAi agent of embodiment 12, wherein the targeting ligand comprises n-acetyl-galactosamine.

Embodiment 14. The RNAi agent of embodiment 12 or 13, wherein the targeting ligand comprises the structure of (NAG37) or (NAG37)s.

Embodiment 15. The RNAi agent of any one of aspects 11-14, wherein the targeting ligand is linked to the sense strand.

Embodiment 16. The RNAi agent of embodiment 15, wherein the targeting ligand is linked to the 5' terminal end of the sense strand.

Embodiment 17. The RNAi agent of any one of aspects 1-16, wherein the sense strand is between 15 and 30 nucleotides in length, and the antisense strand is between 18 and 30 nucleotides in length.

Embodiment 18. The RNAi agent of embodiment 17, wherein the sense strand and the antisense strand are each between 18 and 27 nucleotides in length.

Embodiment 19. The RNAi agent of embodiment 18, wherein the sense strand and the antisense strand are each between 18 and 24 nucleotides in length.

Embodiment 20. The RNAi agent of embodiment 19, wherein the sense strand and the antisense strand are each 21 nucleotides in length.

Embodiment 21. The RNAi agent of any one of aspects 17-20, wherein the RNAi agent has two blunt ends.

Embodiment 22. The RNAi agent of any one of aspects 1-21, wherein the sense strand comprises one or two terminal caps.

Embodiment 23. The RNAi agent of any one of aspects 1-22, wherein the sense strand comprises one or two inverted abasic residues.

Embodiment 24. The RNAi agent of embodiment 1, wherein the RNAi agent is comprised of a sense strand and an antisense strand that form a duplex sequence of any one of the duplexes as listed in Table 5A, Table 5B, or Table 5C.

Embodiment 25. The RNAi agent of any one of aspects 1-23, wherein the sense strand further includes inverted abasic residues at the 3' terminal end of the nucleotide sequence, at the 5' end of the nucleotide sequence, or at both.

Embodiment 26. The RNAi agent of embodiment 1, comprising an antisense strand that comprises, consists of, or consists essentially of a modified nucleotide sequence that differs by 0 or 1 nucleotide from one of the antisense strand nucleotide sequences of Table 3 or Table 5C, wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpa and cPrpu represent 5'-cyclopropyl phosphonate-2'-O-methyl adenosine and 5'-cyclopropyl phosphonate-2'-O-methyl uridine, respectively; $C_{UNA}$ and $U_{UNA}$ represent 2',3'-seco-cytidine and 2',3'-seco-uridine, respectively; s represents a phosphorothioate linkage; and wherein all or substantially all of the nucleotides on the sense strand are modified nucleotides.

Embodiment 27. The RNAi agent of embodiment 1, wherein the sense strand comprises, consists of, or consists essentially of a modified nucleotide sequence that differs by 0 or 1 nucleotide from one of the nucleotide sequences of Table 4 or Table 5C, wherein a, c, g, i, and u represent 2'-O-methyl adenosine, cytidine, guanosine, inosine, and uridine, respectively; Af, Cf, Gf, and Uf represent 2'-fluoro adenosine, cytidine, guanosine, and uridine, respectively; a_2N represents 2'-O-methyl-2-aminoadenosine; s represents a phosphorothioate linkage; and wherein all or substantially all of the nucleotides on the antisense strand are modified nucleotides.

Embodiment 28. The RNAi agent of any one of aspects 24-27, wherein the sense strand includes inverted abasic residues at the 3' terminal end of the nucleotide sequence, at the 5' end of the nucleotide sequence, or at both.

Embodiment 29. The RNAi agent of any one of aspects 24-28, wherein the sense strand of the RNAi agent is linked to a targeting ligand.

Embodiment 30. The RNAi agent of embodiment 29, wherein the targeting ligand has affinity for the asialoglycoprotein receptor.

Embodiment 31. The RNAi agent of embodiment 30, wherein the targeting ligand comprises N-acetyl-galactosamine.

Embodiment 32. The RNAi agent of embodiment 1, wherein the targeting ligand comprises:

consists of a modified nucleotide sequence of Table 4 or Table 5C, wherein a, c, g, i, and u represent 2'-O-methyl adenosine, cytidine, guanosine, inosine, and uridine, respectively; Af, Cf, Gf, and Uf represent 2'-fluoro adenosine, cytidine, guanosine, and uridine, respectively; cPrpa and cPrpu represent 5'-cyclopropyl phosphonate-2'-O-methyl adenosine and 5'-cyclopropyl phosphonate-2'-O-methyl uridine, respectively; a_2N represents 2'-O-methyl-2-aminoadenosine; CUNA and UUNA represent 2',3'-seco-cytidine and 2',3'-seco-uridine, respectively; s represents a phosphoroth-

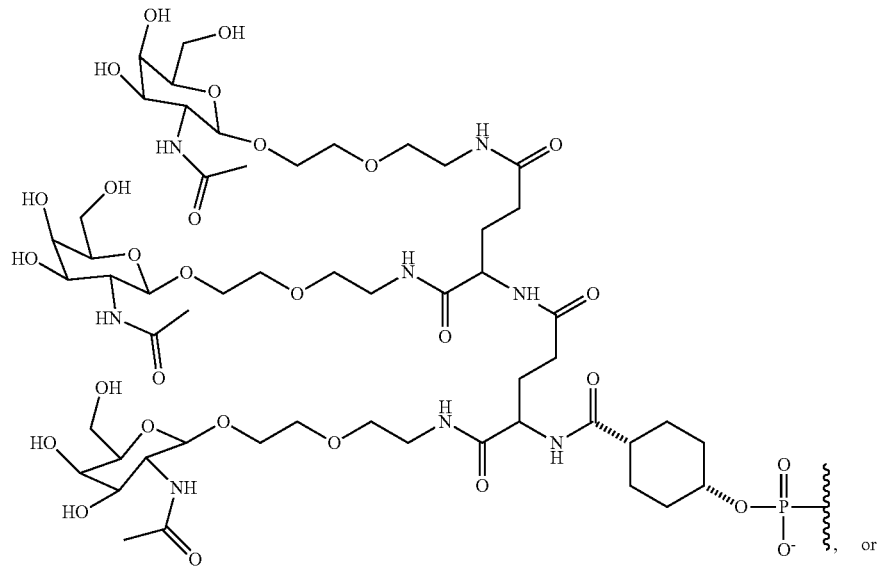

, or

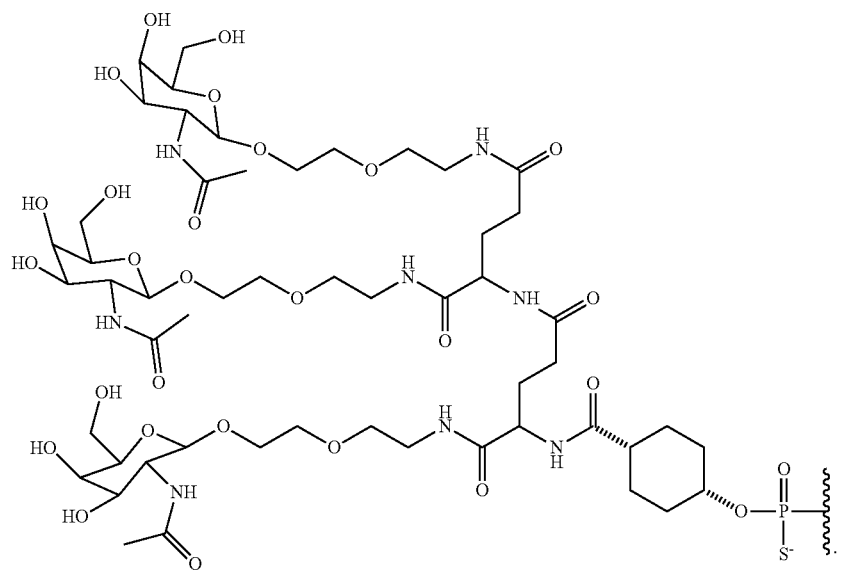

.

Embodiment 33. The RNAi agent of embodiment 1, wherein the antisense strand consists of a modified nucleotide sequence of Table 3 or Table 5C and the sense strand ioate linkage; (invAb) represents an inverted abasic deoxyribose residue; and (NAG37)s has the following chemical structure:

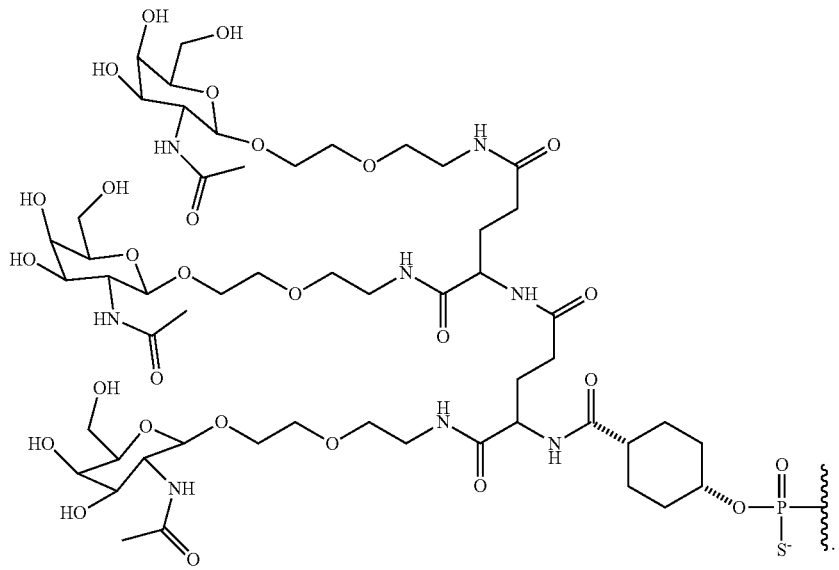

Embodiment 34. The RNAi agent of any one of embodiments 1-3, wherein a nucleic acid sequence of the antisense strand comprises an unmodified nucleic acid sequence of AM15135, AM14244, AM15149, AM13882, AM14216, AM14387, AM14240, AM14238, or AM14236, and a nucleic acid sequence of the sense strand comprises an unmodified nucleic acid sequence of AM14284, AM14243, AM14528, AM13881, AM14215, AM13877, AD14239, AD14237, or AD14235.

Embodiment 35. The RNAi agent of any one of embodiments 1-3, wherein a nucleic acid sequence of the antisense strand comprises a modified nucleic acid sequence of AM15135, AM14244, AM15149, AM13882, AM14216, AM14387, AM14240, AM14238, or AM14236, and a nucleic acid sequence of the sense strand comprises a modified nucleic acid sequence of AM14284, AM14243, AM14528, AM13881, AM14215, AM13877, AD14239, AD14237, or AD14235.

Embodiment 36. The RNAi agent of any one of embodiments 1-3, wherein a nucleic acid sequence of the antisense strand comprises UUCCAUAAUACUCUGAGAGAG (SEQ ID NO:1448) and a nucleic acid sequence of the sense strand comprises CUCUCUCAGAGUAUUAUGGAA (SEQ ID NO:1603).

Embodiment 37. The RNAi agent of any one of embodiments 1-3, wherein a nucleic acid sequence of the antisense strand comprises cPrpusUfscCfauaauacUfcUfgAfgagsasg (SEQ ID NO:1146) and a nucleic acid sequence of the sense strand comprises cucucucaGfaGfuAfuuauggaa (SEQ ID NO: 1663), wherein lower case (n)=2'-O-Me; Nf=2'-F; cPrpn=5'-cyclopropyl phosphonate-2'-O-methyl; (and s=phosphorothioate backbone modification.

Embodiment 38. The RNAi agent of any one of embodiments 1-3, wherein a nucleic acid sequence of the antisense strand comprises cPrpusUfscCfauaauacUfcUfgAfgagsasg (SEQ ID NO:1146) and the sense strand comprises (invAb)scucucucaGfaGfuAfuuauggaas(invAb) (SEQ ID NO:1680) wherein lower case (n)=2'-O-Me; Nf=2'-F; cPrpn=5'-cyclopropyl phosphonate-2'-O-methyl; (invAb)=inverted abasic residue; and s=phosphorothioate backbone modification.

Embodiment 39. The RNAi agent of any one of embodiments 1-3, wherein a nucleic acid sequence of the antisense strand comprises AUGACAAUAUCUGUGCGGAGG (SEQ ID NO:1468) and a nucleic acid sequence of the sense strand comprises CCUCCGCACAGAUAUUGUCAU (SEQ ID NO:1623).

Embodiment 40. The RNAi agent of any one of embodiments 1-3, wherein a nucleic acid sequence of the antisense strand comprises asUfsgsAfcaauaucUfgUfgCfggagsg (SEQ ID NO:1081) and a nucleic acid sequence of the sense strand comprises ccuccgcaCfAfGfauauugucau (SEQ ID NO:1664), wherein lower case (n)=2'-O-Me; Nf=2'-F; and s=phosphorothioate backbone modification.

Embodiment 41. The RNAi agent of any one of embodiments 1-3, wherein a nucleic acid sequence of the antisense strand comprises asUfsgsAfcaauaucUfgUfgCfggagsg (SEQ ID NO:1081) and the sense strand comprises (invAb)sccuccgcaCfAfGfauauugucaus(invAb) (SEQ ID NO:1681) wherein lower case (n)=2'-O-Me; Nf=2'-F; (invAb)=inverted abasic residue; and s=phosphorothioate backbone modification.

Embodiment 42. The RNAi agent of any one of embodiments 1-3, wherein a nucleic acid sequence of the antisense strand comprises UGCAUAUUCACCAUUUAGGCA (SEQ ID NO:1397) and a nucleic acid sequence of the sense strand comprises UGCCUAAAUGGUGAAUAUGCA (SEQ ID NO:1551).

Embodiment 43. The RNAi agent of any one of embodiments 1-3, wherein a nucleic acid sequence of the antisense strand comprises cPrpusGfscauauuCfacCfaUfuUfaggscsa (SEQ ID NO:1155) and a nucleic acid sequence of the sense strand comprises ugccuaaaUfgGfuGfaauaugca (SEQ ID NO:1665), wherein lower case (n)=2'-O-Me; Nf=2'-F; and s=phosphorothioate backbone modification.

Embodiment 44. The RNAi agent of any one of embodiments 1-3, wherein a nucleic acid sequence of the antisense strand comprises cPrpusGfscauauuCfacCfaUfuUfaggscsa (SEQ ID NO: 1155) and the sense strand comprises (invAb)sugccuaaaUfgGfuGfaauaugcas(invAb) (SEQ ID NO:1682), wherein lower case (n)=2'-O-Me; Nf=2'-F; (invAb)=inverted abasic residue; and s=phosphorothioate backbone modification.

Embodiment 45. The RNAi agent of any one of embodiments 1-3, wherein a nucleic acid sequence of the antisense strand comprises AUGAAACAAACAAACCCUGGA (SEQ ID NO:1440) and a nucleic acid sequence of the sense strand comprises UCCAGGGUUUGUUUGUUUCAU (SEQ ID NO:1595).

Embodiment 46. The RNAi agent of any one of embodiments 1-3, wherein a nucleic acid sequence of the antisense strand comprises asUfsgsAfaAfcaaacAfaAfcCfcUfggsa (SEQ ID NO:1048) and a nucleic acid sequence of the sense strand comprises uccagggUfUfGfuuuguuucau (SEQ ID NO:1666), wherein lower case (n)=2'-O-Me; Nf=2'-F; and s=phosphorothioate backbone modification.

Embodiment 47. The RNAi agent of any one of embodiments 1-3, wherein a nucleic acid sequence of the antisense strand comprises asUfsgsAfaAfcaaacAfaAfcCfcUfggsa (SEQ ID NO:1048) and the sense strand comprises (invAb)succagggUfUfGfuuuguuucaus(invAb) (SEQ ID NO:1683), wherein lower case (n)=2'-O-Me; Nf=2'-F; (invAb)=inverted abasic residue; and s=phosphorothioate backbone modification.

Embodiment 48. The RNAi agent of any one of embodiments 1-3, wherein a nucleic acid sequence of the antisense strand comprises AGACGAUCAUACUUGGAGAGC (SEQ ID NO:1454) and a nucleic acid sequence of the sense strand comprises GCUCUCCAAGUAUGAUCIUCU (SEQ ID NO:1609).

Embodiment 49. The RNAi agent of any one of embodiments 1-3, wherein a nucleic acid sequence of the antisense strand comprises asGfsasCfgaucauaCfuUfgGfagagsc (SEQ ID NO:1067) and a nucleic acid sequence of the sense strand comprises gcucuccaAfGfUfaugauciucu (SEQ ID NO:1667), wherein lower case (n)=2'-O-Me; Nf=2'-F; and s=phosphorothioate backbone modification.

Embodiment 50. The RNAi agent of any one of embodiments 1-3, wherein a nucleic acid sequence of the antisense strand comprises asGfsasCfgaucauaCfuUfgGfagagsc (SEQ ID NO:1067) and the sense strand comprises (invAb)sgcucuccaAfGfUfaugauciucus(invAb) (SEQ ID NO: 1684), wherein lower case (n)=2'-O-Me; Nf=2'-F; (invAb)=inverted abasic residue; and s=phosphorothioate backbone modification.

Embodiment 51. The RNAi agent of any one of embodiments 1-3, wherein a nucleic acid sequence of the antisense strand comprises UUUGAAUGCUGAGAAAUACUC (SEQ ID NO:1438) and a nucleic acid sequence of the sense strand comprises GAGUAUUUCUCAGCAUUCAAA (SEQ ID NO:1593).

Embodiment 52. The RNAi agent of any one of embodiments 1-3, wherein a nucleic acid sequence of the antisense strand comprises cPrpuUfuGfaaugcugAfgAfaAfuacusc (SEQ ID NO:1111) and a nucleic acid sequence of the sense strand comprises gaguauuuCfUfCfagcauucaaa (SEQ ID NO:1668), wherein lower case (n)=2'-O-Me; Nf=2'-F; cPrpn=5'-cyclopropyl phosphonate-2'-O-methyl; and s=phosphorothioate backbone modification.

Embodiment 53. The RNAi agent of any one of embodiments 1-3, wherein a nucleic acid sequence of the antisense strand comprises cPrpuUfuGfaaugcugAfgAfaAfuacusc (SEQ ID NO:1111) and the sense strand comprises (invAb)sgaguauuuCfJfCfagcauucaaas(invAb) (SEQ ID NO:1685), wherein lower case (n)=2'-O-Me; Nf=2'-F; cPrpn=5'-cyclopropyl phosphonate-2'-O-methyl; (invAb)=inverted abasic residue; and s=phosphorothioate backbone modification.

Embodiment 54. The RNAi agent of any one of embodiments 1-3, wherein a nucleic acid sequence of the antisense strand comprises UUUCCAACAAUUCUCCUUGUC (SEQ ID NO:1466) and a nucleic acid sequence of the sense strand comprises GACAAGGAGAAUUGUUGGAAA (SEQ ID NO:1621).

Embodiment 55. The RNAi agent of any one of embodimentsl-3, wherein a nucleic acid sequence of the antisense strand comprises usUfsusCfcaacaauUfcUfcCfuugusc (SEQ ID NO:1079) and a nucleic acid sequence of the sense strand comprises gacaaggaGfAfAfuuguuggaaa (SEQ ID NO:1669), wherein lower case (n)=2'-O-Me; Nf=2'-F; and s=phosphorothioate backbone modification.

Embodiment 56. The RNAi agent of any one of embodimentsl-3, wherein a nucleic acid sequence of the antisense strand comprises usUfsusCfcaacaauUfcUfcCfuugusc (SEQ ID NO:1079) and the sense strand comprises (invAb)sgacaaggaGfAfAfuuguuggaaas(invAb) (SEQ ID NO:1686), wherein lower case (n)=2'-O-Me; Nf=2'-F; (invAb)=inverted abasic residue; and s=phosphorothioate backbone modification.

Embodiment 57. The RNAi agent of any one of embodiments 1-3, wherein a nucleic acid sequence of the antisense strand comprises UUGUCAACCUCACUCUUCCGA (SEQ ID NO:1465) and a nucleic acid sequence of the sense strand comprises UCGGAAGAGUGAGGUUGACAA (SEQ ID NO:1620).

Embodiment 58. The RNAi agent of any one of embodiments 1-3, wherein a nucleic acid sequence of the antisense strand comprises usUfsgsUfcaaccucAfcUfcUfuccgsa (SEQ ID NO:1078) and a nucleic acid sequence of the sense strand comprises ucggaagaGfUfGfagguugacaa (SEQ ID NO:1670), wherein lower case (n)=2'-O-Me; Nf=2'-F; and s=phosphorothioate backbone modification.

Embodiment 59. The RNAi agent of any one of embodiments 1-3, wherein a nucleic acid sequence of the antisense strand comprises usUfsgsUfcaaccucAfcUfcUfuccgsa (SEQ ID NO:1078) and the sense strand comprises (invAb)sucggaagaGfUfGfagguugacaas(invAb) (SEQ ID NO: 1687), wherein lower case (n)=2'-O-Me; Nf=2'-F; (invAb)=inverted abasic residue; and s=phosphorothioate backbone modification.

Embodiment 60. The RNAi agent of any one of embodiments 1-3, wherein a nucleic acid sequence of the antisense strand comprises UCAUGAUACUGAGAGCUUGCU (SEQ ID NO:1464) and a nucleic acid sequence of the sense strand comprises AGCAAGCUCUCAGUAUCAUGA (SEQ ID NO:1619).

Embodiment 61. The RNAi agent of any one of embodiments 1-3, wherein a nucleic acid sequence of the antisense strand comprises usCfsasUfgauacugAfgAfgCfuugcsu (SEQ ID NO:1077) and a nucleic acid sequence of the sense strand comprises agcaagcuCfJfCfaguaucauga (SEQ ID NO:1671), wherein lower case (n)=2'-O-Me; Nf=2'-F; and s=phosphorothioate backbone modification.

Embodiment 62. The RNAi agent of any one of embodiments 1-3, wherein a nucleic acid sequence of the antisense strand comprises usCfsasUfgauacugAfgAfgCfuugcsu (SEQ ID NO:1077) and the sense strand comprises (invAb)sagcaagcuCfJfCfaguaucaugas(invAb) (SEQ ID NO:1688), wherein lower case (n)=2'-O-Me; Nf=2'-F; (invAb)=inverted abasic residue; and s=phosphorothioate backbone modification.

Embodiment 63. The RNAi agent of any one of embodiments 31-62, wherein the 5' end of the sense strand is coupled to a targeting ligand comprising the structure of (NAG37) or (NAG37)s.

Embodiment 64. The RNAi agent of any one of embodiments 31-62, wherein the 5' end of the sense strand is coupled to a targeting ligand comprising the structure of (NAG37)s.

Embodiment 65. The RNAi agent of any one of embodiments 31-64, wherein RNAi agent is a pharmaceutically acceptable salt.

Embodiment 66. A composition comprising the RNAi agent of any one of embodiments 1-65, wherein the composition further comprises a pharmaceutically acceptable excipient.

Embodiment 67. A method for inhibiting expression of an XDH gene in a cell, the method comprising introducing into a cell an effective amount of an RNAi agent of any one of embodiments 1-66 or the composition of embodiment 66.

Embodiment 68. The method of embodiment 67, wherein the cell is within a subject.

Embodiment 69. The method of embodiment 68, wherein the subject is a human subject.

Embodiment 70. The method of any one of embodiments 67-69, wherein the XDH gene expression is inhibited by at least about 30%.

Embodiment 71. The method of any one of embodiments 67-70, wherein the XDH activity is reduced by at least about 40%, about 45%, about 50%, about 55%, about 60%, about 65%, or about 70%.

Embodiment 72. A method of treating an XDH-related disease, disorder, or symptom, the method comprising administering to a human subject in need thereof a therapeutically effective amount of the composition of embodiment 66.

Embodiment 73. The method of embodiment 72, wherein the disease is gout.

Embodiment 74. The method of any one of embodiments 67-73, wherein the RNAi agent is administered at a dose of about 0.05 mg/kg to about 5.0 mg/kg of body weight of the human subject.

Embodiment 75. The method of any one of embodiments 67-74, wherein the RNAi agent is administered in two or more doses.

Embodiment 76. A single-stranded antisense compound for inhibiting an XDH gene, comprising an antisense nucleotide sequence having at least 15 contiguous nucleotides differing by 0, 1, 2, or 3 nucleotides, wherein the nucleotides are complementary to any of the target nucleotide sequences of Table 1.

Embodiment 77. A single-stranded antisense compound for inhibiting an XDH gene, comprising at least 15 contiguous nucleotides differing by 0, 1, 2, or 3 nucleotides of any of the antisense strand sequences disclosed in Table 2, Table 3, or Table 5C.

The above provided embodiments and items are now illustrated with the following, non-limiting examples.

EXAMPLES

Example 1. Synthesis of XDH RNAi Agents

XDH RNAi agent duplexes shown in Tables 5A, 5B, and 5C, above, were synthesized in accordance with the following general procedures:
A. Synthesis.
The sense and antisense strands of the RNAi agents were synthesized according to phosphoramidite technology on solid phase used in oligonucleotide synthesis. Such standard synthesis is generally known in the art. Depending on the scale, either a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, Pa., USA). The monomer positioned at the 3' end of the respective strand was attached to the solid support as a starting point for synthesis. All RNA and 2'-modified RNA phosphoramidites were purchased from Thermo Fisher Scientific (Milwaukee, Wis., USA) or Hongene Biotech (Shanghai, PRC). The 2'-O-methyl phosphoramidites included the following: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl amidites. 5'-(4,4'-Dimethoxytrityl)-2',3'-seco-uridine, 2'-benzoyl-3'-[(2-cyanoethyl)-(N,N-diisopropyl)]-phosphoramidite was also purchased from Thermo Fisher Scientific or Hongene Biotech. 5'-dimethoxytrityl-2'-O-methyl-inosine-3'-O-(2-cyanoethyl-N,N-diisopropylamino) phosphoramidites were purchased from Glen Research (Virginia) or Hongene Biotech. The cyclopropyl phosphonate phosphoramidites were synthesized in accordance with International Patent Application Publication No. WO 2017/214112 (see also Altenhofer et. al., Chem. Communications (Royal Soc. Chem.), 7 (July 221)). The inverted abasic (3'-O-dimethoxytrityl-2'-deoxyribose-5'-O-(2-cyanoethyl-N,N-diisopropylamino) phosphoramidites were purchased from ChemGenes (Wilmington, Mass., USA) or SAFC (St Louis, Mo., USA). 5'-O-dimethoxytrityl-$N^2$,$N^6$-(phenoxyacetate)-2'-O-methyl-diaminopurine-3'-O-(2-cyanoethyl-N,N-diisopropylamino) phosphoramidites were obtained from ChemGenes or Hongene Biotech.

Targeting ligand-containing phosphoramidites were dissolved in anhydrous dichloromethane or anhydrous acetonitrile (50 mM), while all other amidites were dissolved in anhydrous acetonitrile (50 mM), or anhydrous dimethylformamide and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 12 min (RNA), 15 min (targeting ligand), 90 sec (2'-OMe), and 60 sec (2'-F). In order to introduce phosphorothioate linkages, a 100 mM solution of 3-phenyl 1,2,4-dithiazoline-5-one (POS, obtained from PolyOrg, Inc., Leominster, Mass., USA) in anhydrous Acetonitrile was employed. Unless specifically identified as a "naked" RNAi agent having no targeting ligand present, each of the XDH RNAi agent duplexes synthesized and tested in the following Examples utilized N-acetyl-galactosamine as "NAG" in the targeting ligand chemical structures represented in Table 6. (NAG37) and (NAG37)s targeting ligand phosphoramidite compounds can be synthesized in accordance with International Patent Application Publication No. WO 2018/044350 to Arrowhead Pharmaceuticals, Inc.

B. Cleavage and Deprotection of Support Bound Oligomer.
After finalization of the solid phase synthesis, the dried solid support was treated with a 1:1 volume solution of 40 wt. % methylamine in water and 28% ammonium hydroxide solution (Aldrich) for 1.5 hours at 30° C. The solution was evaporated and the solid residue was reconstituted in water (see below).

129

C. Purification.

Crude oligomers were purified by anionic exchange HPLC using a TSKgel SuperQ-5PW 13 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 26/40 column packed with Sephadex G-25 fine with a running buffer of filtered DI water or 100 mM ammonium bicarbonate, pH 6.7 and 20% Acetonitrile.

D. Annealing.

Complementary strands were mixed by combining equimolar RNA solutions (sense and antisense) in 1× Phosphate-Buffered Saline (Corning, Cellgro) to form the RNAi agents. Some RNAi agents were lyophilized and stored at −15 to −25° C. Duplex concentration was determined by measuring the solution absorbance on a UV-Vis spectrometer in 1× Phosphate-Buffered Saline. The solution absorbance at 260 nm was then multiplied by a conversion factor and the dilution factor to determine the duplex concentration. The conversion factor used was either 0.050 mg/(mL-cm) or was calculated from an experimentally determined extinction coefficient.

Example 2. XDH-GLuc AAV Mouse Model

To evaluate certain XDH RNAi agents, an XDH-GLuc (*Gaussia* Luciferase) AAV (Adeno-associated virus) mouse model was used. Six- to eight-week-old male C57BL/6 mice were transduced with XDH-GLuc AAV serotype 8, administered at least 14 days prior to administration of an XDH RNAi agent or control. Two types of XDH-GLuc AAV were used. The genome of the first XDH-GLuc AAV contains the 80-2899 region of the human XDH cDNA sequence (GenBank NM_000379.4 (SEQ ID NO:1)) inserted into the 3' UTR of the GLuc reporter gene sequence. The genome of the second XDH-GLuc AAV contains the 2820-5715 region of the human XDH cDNA sequence (GenBank NM_000379.4 (SEQ ID NO:1)) inserted into the 3' UTR of the GLuc reporter gene sequence. 5E12 to 1E13 GC/kg of the respective virus in PBS in a total volume of 10 mL/kg animal's body weight was injected into mice via the tail vein to create XDH-GLuc AAV model mice. Inhibition of expression of XDH by an XDH RNAi agent results in concomitant inhibition of GLuc expression, which is measured. Prior to administration of a treatment (between day −7 and day 1 pre-dose), GLuc expression levels in serum were measured by the Pierce™ *Gaussia* Luciferase Glow Assay Kit (Thermo Fisher Scientific), and the mice were grouped according to average GLuc levels.

Mice were anesthetized with 2-3% isoflurane and blood samples were collected from the submandibular area into serum separation tubes (Sarstedt AG & Co., Nümbrecht, Germany). Blood was allowed to coagulate at ambient temperature for 20 min. The tubes were centrifuged at 8,000×g for 3 min to separate the serum and stored at 4° C. Serum was collected and measured by the Pierce™ *Gaussia* Luciferase Glow Assay Kit according to the manufacturer's instructions. Serum GLuc levels for each animal can be normalized to the control group of mice injected with vehicle control in order to account for the non-treatment related shift in XDH expression with this model. To do so, first, the GLuc level for each animal at a time point was divided by the pre-treatment level of expression in that animal (Day 1) in order to determine the ratio of expression "normalized to pre-treatment". Expression at a specific time point was then normalized to the control group by dividing the "normalized to pre-treatment" ratio for an individual animal by the average "normalized to pre-treatment" ratio of all mice in the normal vehicle control group. Alternatively, the serum GLuc levels for each animal was assessed by normalizing to pre-treatment levels only.

Example 3. In Vivo Testing of XDH RNAi Agents in XDH-GLuc AAV Mice

The XDH-GLUC AAV mouse model described in Example 2, above, using the XDH-GLuc AAV containing the 80-2899 region of the human XDH cDNA sequence was used. At day 1, each mouse was given a single subcutaneous administration of 250 μl/25 g animal weight containing either 2.0 mg/kg (mpk) of an XDH RNAi agent formulated in isotonic saline, or vehicle control (isotonic saline with no RNAi agent), according to the following Table 7.

TABLE 7

Targeted Positions and Dosing Groups of Example 3

| Group | Targeted Gene Position (within SEQ ID NO: 1) | RNAi Agent and Dose | Dosing Regimen |
| --- | --- | --- | --- |
| 1 | N/A | Saline (no RNAi agent) | Single injection on day 1 |
| 2 | 488 | 2.0 mg/kg AD09218 | Single injection on day 1 |
| 3 | 122 | 2.0 mg/kg AD09724 | Single injection on day 1 |
| 4 | 249 | 2.0 mg/kg AD09599 | Single injection on day 1 |
| 5 | 252 | 2.0 mg/kg AD09600 | Single injection on day 1 |
| 6 | 1285 | 2.0 mg/kg AD09733 | Single injection on day 1 |
| 7 | 2209 | 2.0 mg/kg AD09740 | Single injection on day 1 |
| 8 | 1963 | 2.0 mg/kg AD09736 | Single injection on day 1 |
| 9 | 1963 | 2.0 mg/kg AD09937 | Single injection on day 1 |
| 10 | 2696 | 2.0 mg/kg AD09744 | Single injection on day 1 |
| 11 | 2696 | 2.0 mg/kg AD09938 | Single injection on day 1 |
| 12 | 2616 | 2.0 mg/kg AD09663 | Single injection on day 1 |

Each of the XDH RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agent AD09218 (Group 2) included nucleotide sequences that were designed to inhibit expression of an XDH gene at position 488 of the gene; the XDH RNAi agent AD09724 (Group 3) included nucleotide sequences that were designed to inhibit expression of an XDH gene at position 122 of the gene; the XDH RNAi agent AD09599 (Group 4) included nucleotide sequences that were designed to inhibit expression of an XDH gene at position 249 of the gene; the XDH RNAi agent AD09600 (Group 5) included nucleotide sequences that were designed to inhibit expression of an XDH gene at position 252 of the gene; the XDH RNAi agent AD09733 (Group 6) included nucleotide sequences that were designed to inhibit expression of an XDH gene at position 1285 of the gene; the XDH RNAi agent AD09740 (Group 7) included nucleotide sequences that were designed to inhibit expression of an XDH gene at position 2209 of the gene; the XDH RNAi agents AD09736 (Group 8) and AD09937 (Group 9) included nucleotide sequences that were designed to inhibit expression of an XDH gene at position 1963 of the gene; the XDH RNAi agents AD09744

(Group 10) and AD09938 (Group 11) included nucleotide sequences that were designed to inhibit expression of an XDH gene at position 2696 of the gene; and the XDH RNAi agent AD09663 (Group 12) included nucleotide sequences that were designed to inhibit expression of an XDH gene at position 2616 of the gene. (See, e.g., SEQ ID NO:1 and Table 2 for the XDH gene referenced).

While it has been previously reported that an RNAi agent targeting position 488 of the XDH gene can be active in vitro and in vivo in mice and in rats, the nucleotide sequence of an RNAi agent targeting this position is compromised and unsuitable for therapeutic use. More specifically, the seed region (2 to 7 nt) of the RNAi agent targeting position 488 matches perfectly with that of a known human microRNA (miRNA), thus this agent is expected to result in undesired silencing of hundreds of potential off-targets mimicking the known miRNA (See, e.g., Kamola et al., The siRNA Non-seed Region and Its Target Sequences Are Auxiliary Determinants of Off-Target Effects, 11(12) PLoS Comput Biol (2015)). In addition, the core 17-mer sequence (nucleotides located at positions 2-18 of the antisense strand (5'→3')) of the RNAi agent targeting position 488 is complementary to transcripts of four human genes with only one mismatch, hence bearing an additional risk of reducing the expression of these four genes through a different off-target mechanism. Thus, the RNAi agent of Group 2 is not a viable candidate for human therapeutic treatment.

The injections were performed between the skin and muscle (i.e. subcutaneous injections) into the loose skin over the neck and shoulder area. Four (4) mice in each group were tested (n=4). Serum was collected on day 1 (pre-treatment), day 8, day 15, and day 22, and XDH expression levels were determined pursuant to the procedure set forth in Example 2, above. Data from the experiment are shown in the following Table 8:

TABLE 8

Average XDH Normalized to Pre-Treatment & Control in XDH-GLUC AAV Mice from Example 3

| Group ID | Day 8 | | Day 15 | | Day 22 | |
| --- | --- | --- | --- | --- | --- | --- |
| | Avg XDH | Std Dev (+/-) | Avg XDH | Std Dev (+/-) | Avg XDH | Std Dev (+/-) |
| Group 1 (Saline vehicle) | 1.000 | 0.105 | 1.000 | 0.020 | 1.000 | 0.096 |
| Group 2 (2.0 mg/kg AD09218) | 0.601 | 0.094 | 0.505 | 0.085 | 0.531 | 0.103 |
| Group 3 (2.0 mg/kg AD09724) | 1.115 | 0.149 | 0.890 | 0.095 | 0.964 | 0.208 |
| Group 4 (2.0 mg/kg AD09599) | 1.009 | 0.088 | 0.872 | 0.096 | 0.991 | 0.092 |
| Group 5 (2.0 mg/kg AD09600) | 0.874 | 0.292 | 0.865 | 0.415 | 0.927 | 0.348 |
| Group 6 (2.0 mg/kg AD09733) | 1.024 | 0.054 | 0.896 | 0.129 | 1.209 | 0.262 |
| Group 7 (2.0 mg/kg AD09740) | 0.963 | 0.083 | 0.793 | 0.103 | 1.132 | 0.084 |
| Group 8 (2.0 mg/kg AD09736) | 0.607 | 0.154 | 0.521 | 0.111 | 0.809 | 0.135 |
| Group 9 (2.0 mg/kg AD09937) | 0.673 | 0.148 | 0.593 | 0.120 | 0.748 | 0.108 |
| Group 10 (2.0 mg/kg AD09744) | 0.679 | 0.084 | 0.694 | 0.078 | 0.934 | 0.163 |
| Group 11 (2.0 mg/kg AD09938) | 0.552 | 0.076 | 0.478 | 0.076 | 0.711 | 0.095 |
| Group 12 (2.0 mg/kg AD09663) | 0.826 | 0.102 | 0.849 | 0.435 | 1.246 | 0.895 |

As shown in Table 8, above, as expected the RNAi agent of Group 2 (targeting position 488) was active and showed reductions of approximately 49.5% on day 15 (0.505). The RNAi agents of Group 8 (AD09736) and Group 9 (AD09937), both of which target the XDH gene at position 1963, showed generally comparable reductions of XDH (reductions of 47.9% and 40.7% on day 15, respectively) with Group 2. Similarly, the RNAi agents of Group 10 (AD09744) and Group 11 (AD09938), both of which target the XDH gene at position 2696, showed generally comparable reductions of XDH (showing reductions of 30.6% and 52.2%) with Group 2.

Example 4. In Vivo Testing of XDH RNAi Agents in XDH-GLuc AAV Mice

The XDH-GLUC AAV mouse model described in Example 2, above, using the XDH-GLuc AAV containing the 80-2899 region of the human XDH cDNA sequence was used. At day 1, each mouse was given a single subcutaneous administration of 250 µl/25 g animal weight containing either 2.0 mg/kg (mpk) of an XDH RNAi agent formulated in isotonic saline, or vehicle control (isotonic saline with no RNAi agent), according to the following Table 9.

TABLE 9

Targeted Positions and Dosing Groups of Example 4

| Group | Targeted Gene Position (within SEQ ID NO: 1) | RNAi Agent and Dose | Dosing Regimen |
| --- | --- | --- | --- |
| 1 | N/A | Saline (no RNAi agent) | Single injection on day 1 |
| 2 | 1963 | 2.0 mg/kg AD09736 | Single injection on day 1 |
| 3 | 1963 | 2.0 mg/kg AD09965 | Single injection on day 1 |
| 4 | 1963 | 2.0 mg/kg AD09937 | Single injection on day 1 |
| 5 | 1963 | 2.0 mg/kg AD09966 | Single injection on day 1 |
| 6 | 1963 | 2.0 mg/kg AD09967 | Single injection on day 1 |
| 7 | 1963 | 2.0 mg/kg AD09968 | Single injection on day 1 |
| 8 | 1963 | 2.0 mg/kg AD09969 | Single injection on day 1 |
| 9 | 1963 | 2.0 mg/kg AD09970 | Single injection on day 1 |
| 10 | 1964 | 2.0 mg/kg AD09962 | Single injection on day 1 |
| 11 | 1965 | 2.0 mg/kg AD09963 | Single injection on day 1 |
| 12 | 1967 | 2.0 mg/kg AD09964 | Single injection on day 1 |

Each of the XDH RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents AD09736 (Group 2), AD09965 (Group 3), AD09937 (Group 4), AD09966 (Group 5), AD09967 (Group 6), AD09968 (Group 7), AD09969 (Group 8), and AD09970 (Group 9) all included nucleotide sequences that were designed to inhibit expression of an XDH gene at position 1963 of the gene; the XDH RNAi agent AD09962 (Group 10) included nucleotide sequences that were designed to inhibit expression of an XDH gene at position 1964 of the gene; the XDH RNAi agent AD09963 (Group 11) included nucleotide sequences that were designed to inhibit expression of an XDH gene at position 1965 of the gene; and the XDH RNAi agent AD09964 (Group 12) included nucleotide sequences that were designed to inhibit expression of an XDH gene at position 1967 of the gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8, day 15, and day 22, and XDH expression levels were determined pursuant to the procedure set forth in Example 2, above. Data from the experiment are shown in the following Table 10:

TABLE 10

Average XDH Normalized to Pre-Treatment & Control in XDH-GLUC AAV Mice from Example 4

| Groupd ID | Day 8 | | Day 15 | | Day 22 | |
|---|---|---|---|---|---|---|
| | Avg XDH | Std Dev (+/−) | Avg XDH | Std Dev (+/−) | Avg XDH | Std Dev (+/−) |
| Group 1 (Saline vehicle) | 1.000 | 0.136 | 1.000 | 0.205 | 1.000 | 0.110 |
| Group 2 (2.0 mg/kg AD09218) | 0.625 | 0.146 | 0.603 | 0.078 | 0.642 | 0.066 |
| Group 3 (2.0 mg/kg AD09965) | 0.812 | 0.143 | 0.623 | 0.182 | 0.670 | 0.198 |
| Group 4 (2.0 mg/kg AD09937) | 0.502 | 0.045 | 0.581 | 0.183 | 0.528 | 0.099 |
| Group 5 (2.0 mg/kg AD09966) | 0.486 | 0.093 | 0.469 | 0.173 | 0.502 | 0.207 |
| Group 6 (2.0 mg/kg AD09967) | 0.644 | 0.065 | 0.490 | 0.141 | 0.483 | 0.084 |
| Group 7 (2.0 mg/kg AD09968) | 0.551 | 0.244 | 0.599 | 0.234 | 0.554 | 0.168 |
| Group 8 (2.0 mg/kg AD09969) | 0.603 | 0.105 | 0.573 | 0.078 | 0.611 | 0.118 |
| Group 9 (2.0 mg/kg AD09970) | 0.659 | 0.228 | 0.618 | 0.230 | 0.621 | 0.110 |
| Group 10 (2.0 mg/kg AD09962) | 0.820 | 0.161 | 0.818 | 0.132 | 0.744 | 0.093 |
| Group 11 (2.0 mg/kg AD09963) | 0.793 | 0.061 | 0.743 | 0.065 | 0.722 | 0.095 |
| Group 12 (2.0 mg/kg AD09664) | 0.836 | 0.088 | 0.783 | 0.146 | 0.683 | 0.058 |

As shown in Table 10, above, the RNAi agents of Groups 2-9, which all included nucleotide sequences targeting position 1963 of the XDH gene, reported substantial inhibitory activity, with certain XDH RNAi agents achieving greater than 50% inhibition in vivo. Further, the XDH RNAi agents of each of Groups 2-9, all of which target position 1963 of the XDH gene, generally showed an increase in inhibition of XDH gene expression of approximately 20-35% compared to sequences targeting neighboring positions of an XDH gene, shown in Groups 10-12 (Compare, for example, Group 5 (AD09600) at day 15 showing 53.1% inhibition (0.469) with Groups 10-12 at day 15 showing 18.2% inhibition (0.818); 25.7% inhibition (0.743); and 21.7% inhibition (0.783), respectively).

Example 5. In Vivo Testing of XDH RNAi Agents in XDH-GLuc AAV Mice

The XDH-GLUC AAV mouse model described in Example 2, above, using the XDH-GLuc AAV containing the 80-2899 region of the human XDH cDNA sequence was used. At day 1, each mouse was given a single subcutaneous administration of 250 µl/25 g animal weight containing either 2.0 mg/kg (mpk) of an XDH RNAi agent formulated in isotonic saline, or vehicle control (isotonic saline with no RNAi agent), according to the following Table 11.

TABLE 11

Targeted Positions and Dosing Groups of Example 5

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 2696 | 2.0 mg/kg AD09744 | Single injection on day 1 |
| 3 | 2696 | 2.0 mg/kg AD09938 | Single injection on day 1 |
| 4 | 2696 | 2.0 mg/kg AD10008 | Single injection on day 1 |
| 5 | 2696 | 2.0 mg/kg AD10009 | Single injection on day 1 |

TABLE 11-continued

Targeted Positions and Dosing Groups of Example 5

| Group | Targeted Gene Position (within SEQ ID NO: 1) | RNAi Agent and Dose | Dosing Regimen |
|---|---|---|---|
| 6 | 2696 | 2.0 mg/kg AD10010 | Single injection on day 1 |
| 7 | 2696 | 2.0 mg/kg AD10011 | Single injection on day 1 |
| 8 | 2696 | 2.0 mg/kg AD10012 | Single injection on day 1 |
| 9 | 2696 | 2.0 mg/kg AD10013 | Single injection on day 1 |
| 10 | 2696 | 2.0 mg/kg AD10014 | Single injection on day 1 |
| 11 | 2696 | 2.0 mg/kg AD10015 | Single injection on day 1 |

Each of the XDH RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents of Groups 2-11 all included nucleotide sequences that were designed to inhibit expression of an XDH gene at position 2696 of the gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8 (and planned to be collected on days 15, and day 22), and XDH expression levels were determined pursuant to the procedure set forth in Example 2, above. Data from the experiment through day 22 are shown in the following Table 12:

TABLE 12

Average XDH Normalized to Pre-Treatment & Control in XDH-GLUC AAV Mice from Example 5

| | Day 8 | | Day 15 | | Day 22 | |
|---|---|---|---|---|---|---|
| Groupd ID | Avg XDH | Std Dev (+/−) | Avg XDH | Std Dev (+/−) | Avg XDH | Std Dev (+/−) |
| Group 1 (Saline vehicle) | 1.000 | 0.183 | 1.000 | 0.274 | 1.000 | 0.213 |
| Group 2 (2.0 mg/kg AD09744) | 0.818 | 0.161 | 0.615 | 0.092 | 0.800 | 0.255 |
| Group 3 (2.0 mg/kg AD09938) | 0.669 | 0.120 | 0.606 | 0.099 | 0.699 | 0.128 |
| Group 4 (2.0 mg/kg AD10008) | 0.786 | 0.140 | 0.627 | 0.248 | 0.744 | 0.102 |
| Group 5 (2.0 mg/kg AD10009) | 0.671 | 0.364 | 0.457 | 0.133 | 0.550 | 0.241 |
| Group 6 (2.0 mg/kg AD10010) | 0.591 | 0.134 | 0.535 | 0.103 | 0.494 | 0.105 |
| Group 7 (2.0 mg/kg AD10011) | 0.589 | 0.280 | 0.432 | 0.169 | 0.546 | 0.144 |
| Group 8 (2.0 mg/kg AD10012) | 0.362 | 0.077 | 0.295 | 0.055 | 0.369 | 0.029 |
| Group 9 (2.0 mg/kg AD10013) | 0.393 | 0.073 | 0.482 | 0.054 | 0.577 | 0.061 |
| Group 10 (2.0 mg/kg AD10014) | 0.423 | 0.055 | 0.426 | 0.082 | 0.548 | 0.100 |
| Group 11 (2.0 mg/kg AD10015) | 0.502 | 0.034 | 0.477 | 0.056 | 0.535 | 0.077 |

As shown in Table 12, each of the RNAi agents of Groups 2-11, which all included nucleotide sequences targeting position 2696 of the XDH gene, reported substantial inhibitory activity of XDH gene expression.

Example 6. In Vivo Testing of XDH RNAi Agents in XDH-GLuc AAV Mice

The XDH-GLUC AAV mouse model described in Example 2, above, using the XDH-GLuc AAV containing the 80-2899 region of the human XDH cDNA sequence was used. At day 1, each mouse was given a single subcutaneous administration of 250 µl/25 g animal weight containing either 2.0 mg/kg (mpk) of an XDH RNAi agent formulated in isotonic saline, or vehicle control (isotonic saline with no RNAi agent), according to the following Table 13.

TABLE 13

Targeted Positions and Dosing Groups of Example 6

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 488 | 2.0 mg/kg AD09218 | Single injection on day 1 |
| 3 | 231 | 2.0 mg/kg AD10016 | Single injection on day 1 |
| 4 | 242 | 2.0 mg/kg AD10017 | Single injection on day 1 |
| 5 | 1322 | 2.0 mg/kg AD09734 | Single injection on day 1 |
| 6 | 1322 | 2.0 mg/kg AD10091 | Single injection on day 1 |
| 7 | 1322 | 2.0 mg/kg AD10092 | Single injection on day 1 |
| 8 | 1322 | 2.0 mg/kg AD10093 | Single injection on day 1 |
| 9 | 1322 | 2.0 mg/kg AD10094 | Single injection on day 1 |
| 10 | 1322 | 2.0 mg/kg AD10095 | Single injection on day 1 |
| 11 | 1322 | 2.0 mg/kg AD10096 | Single injection on day 1 |
| 12 | 1322 | 2.0 mg/kg AD10097 | Single injection on day 1 |

Each of the XDH RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agent AD09218 (Group 2) included nucleotide sequences that were designed to inhibit expression of an XDH gene at position 488 of the gene; the XDH RNAi agent AD10016 (Group 3) included nucleotide sequences that were designed to inhibit expression of an XDH gene at position 231 of the gene; the XDH RNAi agent AD10017 (Group 4) included nucleotide sequences that were designed to inhibit expression of an XDH gene at position 242 of the gene; and the XDH RNAi agents AD09734 (Group 5), AD10091 (Group 6), AD10092 (Group 7), AD10093 (Group 8), AD10094 (Group 9), AD10095 (Group 10), AD10096 (Group 11), and AD10097 (Group 12) included nucleotide sequences that were designed to inhibit expression of an XDH gene at position 1322 of the gene. (See, e.g., SEQ ID NO:1 and Table 2 for the XDH gene referenced).

As noted in Example 3, above, the RNAi agent targeting position 488 of the XDH gene (Group 2), while previously reported to be active in vivo in mice and rats, includes a compromised nucleotide sequence and is unsuitable for therapeutic use due to toxicity concerns.

The injections were performed between the skin and muscle (i.e. subcutaneous injections) into the loose skin over the neck and shoulder area. Four (4) mice in each group were tested (n=4). Serum was collected on day 1 (pre-treatment), day 8 (and planned for days 15 and day 22), and XDH expression levels were determined pursuant to the procedure set forth in Example 2, above. Data from the experiment through day 8 are shown in the following Table 14:

TABLE 14

Average XDH Normalized to Pre-Treatment & Control in XDH-GLUC AAV Mice from Example 6

| | Day 8 | | Day 15 | | Day 22 | |
|---|---|---|---|---|---|---|
| Groupd ID | Avg XDH | Std Dev (+/−) | Avg XDH | Std Dev (+/−) | Avg XDH | Std Dev (+/−) |
| Group 1 (Saline vehicle) | 1.000 | 0.069 | 1.000 | 0.046 | 1.000 | 0.058 |
| Group 2 (2.0 mg/kg AD09218) | 0.550 | 0.223 | 0.489 | 0.204 | 0.461 | 0.116 |

TABLE 14-continued

Average XDH Normalized to Pre-Treatment & Control in XDH-GLUC AAV Mice from Example 6

| | Day 8 | | Day 15 | | Day 22 | |
|---|---|---|---|---|---|---|
| Groupd ID | Avg XDH | Std Dev (+/−) | Avg XDH | Std Dev (+/−) | Avg XDH | Std Dev (+/−) |
| Group 3 (2.0 mg/kg AD10016) | 0.652 | 0.098 | 0.700 | 0.115 | 0.620 | 0.092 |
| Group 4 (2.0 mg/kg AD10017) | 0.645 | 0.085 | 0.640 | 0.154 | 0.632 | 0.064 |
| Group 5 (2.0 mg/kg AD09734) | 0.718 | 0.059 | 0.705 | 0.119 | 0.632 | 0.087 |
| Group 6 (2.0 mg/kg AD10091) | 0.673 | 0.112 | 0.757 | 0.157 | 0.673 | 0.100 |
| Group 7 (2.0 mg/kg AD10092) | 0.757 | 0.031 | 0.694 | 0.085 | 0.633 | 0.089 |
| Group 8 (2.0 mg/kg AD10093) | 0.717 | 0.039 | 0.752 | 0.117 | 0.634 | 0.082 |
| Group 9 (2.0 mg/kg AD10094) | 0.728 | 0.071 | 0.727 | 0.219 | 0.664 | 0.106 |
| Group 10 (2.0 mg/kg AD10095) | 0.805 | 0.193 | 0.776 | 0.110 | 0.767 | 0.170 |
| Group 11 (2.0 mg/kg AD10096) | 0.536 | 0.044 | 0.587 | 0.147 | 0.561 | 0.093 |
| Group 12 (2.0 mg/kg AD10097) | 0.839 | 0.383 | 0.952 | 0.450 | 1.033 | 0.632 |

Example 7. In Vivo Testing of XDH RNAi Agents in XDH-GLuc AAV Mice

The XDH-GLUC AAV mouse model described in Example 2, above, using the XDH-GLuc AAV containing the 2820-5715 region of the human XDH cDNA sequence was used. At day 1, each mouse was given a single subcutaneous administration of 250 µl/25 g animal weight containing either 2.0 mg/kg (mpk) of an XDH RNAi agent formulated in isotonic saline, or vehicle control (isotonic saline with no RNAi agent), according to the following Table 15.

TABLE 15

Targeted Positions and Dosing Groups of Example 7

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 3083 | 2.0 mg/kg AD09325 | Single injection on day 1 |
| 3 | 2995 | 2.0 mg/kg AD09981 | Single injection on day 1 |
| 4 | 3016 | 2.0 mg/kg AD09982 | Single injection on day 1 |
| 5 | 3041 | 2.0 mg/kg AD09983 | Single injection on day 1 |
| 6 | 3498 | 2.0 mg/kg AD09984 | Single injection on day 1 |
| 7 | 3598 | 2.0 mg/kg AD09985 | Single injection on day 1 |
| 8 | 3877 | 2.0 mg/kg AD09987 | Single injection on day 1 |
| 9 | 4394 | 2.0 mg/kg AD09989 | Single injection on day 1 |

Each of the XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agent AD09325 (Group 2) included nucleotide sequences that were designed to inhibit expression of an XDH gene at position 3083 of the gene; the XDH RNAi agent AD09981 (Group 3) included nucleotide sequences that were designed to inhibit expression of an XDH gene at position 2995 of the gene; the XDH RNAi agent AD09982 (Group 4) included nucleotide sequences that were designed to inhibit expression of an XDH gene at position 3016 of the gene; the XDH RNAi agent AD09983 (Group 5) included nucleotide sequences that were designed to inhibit expression of an XDH gene at position 3041 of the gene; the XDH RNAi agent AD09984 (Group 6) included nucleotide sequences that were designed to inhibit expression of an XDH gene at position 3498 of the gene; the XDH RNAi agent AD09985 (Group 7) included nucleotide sequences that were designed to inhibit expression of an XDH gene at position 3598 of the gene; the XDH RNAi agent AD09987 (Group 8) included nucleotide sequences that were designed to inhibit expression of an XDH gene at position 3877 of the gene; and the XDH RNAi agent AD09989 (Group 9) included nucleotide sequences that were designed to inhibit expression of an XDH gene at position 4394 of the gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8, day 15, and day 22, and XDH expression levels were determined pursuant to the procedure set forth in Example 2, above. Data from the experiment are shown in the following Table 16:

TABLE 16

Average XDH Normalized to Pre-Treatment & Control in XDH-GLUC AAV Mice from Example 7

| | Day 8 | | Day 15 | | Day 22 | |
|---|---|---|---|---|---|---|
| Groupd ID | Avg XDH | Std Dev (+/−) | Avg XDH | Std Dev (+/−) | Avg XDH | Std Dev (+/−) |
| Group 1 (Saline vehicle) | 1.000 | 0.375 | 1.000 | 0.397 | 1.000 | 0.397 |
| Group 2 (2.0 mg/kg AD09325) | 0.513 | 0.078 | 0.823 | 0.154 | 0.823 | 0.154 |
| Group 3 (2.0 mg/kg AD09981) | 0.600 | 0.040 | 0.681 | 0.129 | 0.681 | 0.129 |
| Group 4 (2.0 mg/kg AD09982) | 0.592 | 0.058 | 0.631 | 0.137 | 0.631 | 0.137 |
| Group 5 (2.0 mg/kg AD09983) | 0.596 | 0.066 | 0.574 | 0.087 | 0.574 | 0.087 |

TABLE 16-continued

Average XDH Normalized to Pre-Treatment & Control in XDH-GLUC AAV Mice from Example 7

| Groupd ID | Day 8 | | Day 15 | | Day 22 | |
|---|---|---|---|---|---|---|
| | Avg XDH | Std Dev (+/−) | Avg XDH | Std Dev (+/−) | Avg XDH | Std Dev (+/−) |
| Group 6 (2.0 mg/kg AD09984) | 0.724 | 0.043 | 0.941 | 0.221 | 0.941 | 0.221 |
| Group 7 (2.0 mg/kg AD09985) | 0.472 | 0.076 | 0.449 | 0.092 | 0.449 | 0.092 |
| Group 8 (2.0 mg/kg AD09987) | 0.691 | 0.225 | 0.751 | 0.149 | 0.751 | 0.149 |
| Group 9 (2.0 mg/kg AD09989) | 0.585 | 0.076 | 0.757 | 0.120 | 0.757 | 0.120 |

As shown in Table 16, each of the RNAi agents of Groups 2-9, reported inhibition of XDH gene expression.

Example 8. In Vivo Testing of XDH RNAi Agents in XDH-GLuc AAV Mice

The XDH-GLUC AAV mouse model described in Example 2, above, using the XDH-GLuc AAV containing the 2820-5715 region of the human XDH cDNA sequence was used. At day 1, each mouse was given a single subcutaneous administration of 250 µl/25 g animal weight containing either 2.0 mg/kg (mpk) of an XDH RNAi agent formulated in isotonic saline, or vehicle control (isotonic saline with no RNAi agent), according to the following Table 17.

TABLE 17

Targeted Positions and Dosing Groups of Example 8

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 3083 | 2.0 mg/kg AD09325 | Single injection on day 1 |
| 3 | 3600 | 2.0 mg/kg AD09986 | Single injection on day 1 |
| 4 | 3930 | 2.0 mg/kg AD09988 | Single injection on day 1 |
| 5 | 4513 | 2.0 mg/kg AD09990 | Single injection on day 1 |
| 6 | 4531 | 2.0 mg/kg AD09991 | Single injection on day 1 |
| 7 | 4666 | 2.0 mg/kg AD09992 | Single injection on day 1 |
| 8 | 4843 | 2.0 mg/kg AD09993 | Single injection on day 1 |
| 9 | 5234 | 2.0 mg/kg AD09994 | Single injection on day 1 |
| 10 | 5411 | 2.0 mg/kg AD09995 | Single injection on day 1 |
| 11 | 4136 | 2.0 mg/kg AD09608 | Single injection on day 1 |

Each of the XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents in Groups 2-11 each included nucleotide sequences that were designed to inhibit expression of an XDH gene at the specific positions of the gene as set forth in Table 17, above. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8 (and planned to be collected on days 15, and day 22), and XDH expression levels were determined pursuant to the procedure set forth in Example 2, above. Data from the experiment through day 8 are shown in the following Table 18:

TABLE 18

Average XDH Normalized to Pre-Treatment & Control in XDH-GLUC AAV Mice from Example 8

| Groupd ID | Day 8 | | Day 15 | | Day 22 | |
|---|---|---|---|---|---|---|
| | Avg XDH | Std Dev (+/−) | Avg XDH | Std Dev (+/−) | Avg XDH | Std Dev (+/−) |
| Group 1 (Saline vehicle) | 1.000 | 0.119 | 1.000 | 0.059 | 1.000 | 0.177 |
| Group 2 (2.0 mg/kg AD09325) | 0.650 | 0.022 | 0.628 | 0.083 | 0.548 | 0.143 |
| Group 3 (2.0 mg/kg AD09986) | 0.999 | 0.145 | 0.628 | 0.090 | 0.625 | 0.086 |
| Group 4 (2.0 mg/kg AD09988) | 0.616 | 0.163 | 0.746 | 0.284 | 0.756 | 0.149 |
| Group 5 (2.0 mg/kg AD09990) | 0.617 | 0.190 | 0.901 | 0.197 | 0.971 | 0.283 |
| Group 6 (2.0 mg/kg AD09991) | 0.883 | 0.154 | 0.782 | 0.134 | 0.728 | 0.156 |
| Group 7 (2.0 mg/kg AD09992) | 1.020 | 0.074 | 0.808 | 0.039 | 0.788 | 0.074 |
| Group 8 (2.0 mg/kg AD09993) | 0.961 | 0.048 | 0.775 | 0.122 | 0.831 | 0.169 |
| Group 9 (2.0 mg/kg AD09994) | 1.334 | 0.237 | 1.005 | 0.121 | 1.193 | 0.357 |
| Group 10 (2.0 mg/kg AD09995) | 0.795 | 0.095 | 0.729 | 0.120 | 0.777 | 0.137 |
| Group 11 (2.0 mg/kg AD09608) | 0.993 | 0.103 | 0.744 | 0.267 | 0.435 | 0.088 |

Example 9. In Vivo Testing of XDH RNAi Agents in Wild-Type Mice

Certain XDH RNAi agents have sufficient homology with the mouse XDH gene transcript that they are suitable to be examined for XDH gene expression inhibitory activity in wild-type mice. At day 1, six- to eight-week-old female C57bl/6 mice were given a single subcutaneous administration of 200 µl/20 g animal weight containing 1.0 mg/kg (mpk) of an XDH RNAi agent formulated in isotonic saline, or vehicle control (isotonic saline with no RNAi agent), according to the following Table 19.

TABLE 19

Targeted Positions and Dosing Groups of Example 9

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 488 | 1.0 mg/kg AD09217 | Single injection on day 1 |
| 3 | 488 | 1.0 mg/kg AD09218 | Single injection on day 1 |
| 4 | 1612 | 1.0 mg/kg AD09219 | Single injection on day 1 |
| 5 | 1614 | 1.0 mg/kg AD09220 | Single injection on day 1 |
| 6 | 1617 | 1.0 mg/kg AD09221 | Single injection on day 1 |
| 7 | 2128 | 1.0 mg/kg AD09222 | Single injection on day 1 |
| 8 | 2130 | 1.0 mg/kg AD09223 | Single injection on day 1 |
| 9 | 2131 | 1.0 mg/kg AD09224 | Single injection on day 1 |
| 10 | 2132 | 1.0 mg/kg AD09225 | Single injection on day 1 |
| 11 | 2153 | 1.0 mg/kg AD09226 | Single injection on day 1 |
| 12 | 2185 | 1.0 mg/kg AD09227 | Single injection on day 1 |
| 13 | 2186 | 1.0 mg/kg AD09228 | Single injection on day 1 |
| 14 | 3272 | 1.0 mg/kg AD09229 | Single injection on day 1 |

Each of the XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents in Groups 2-14 each included nucleotide sequences that, while also being homologous to the mouse XDH gene transcript, were designed to inhibit expression of an XDH gene at the specific positions of the human XDH gene as set forth in Table 19, above. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Mice were euthanized on study day 10, and total RNA was isolated from both livers following collection and homogenization. Mouse XDH mRNA expression was quantitated by probe-based quantitative PCR, normalized to mouse beta-actin expression, and expressed as fraction of vehicle control group (geometric mean, +/−95% confidence interval).

TABLE 20

Average Relative Mouse XDH mRNA at Sacrifice (Day 10) in Example 9

| Group ID | Average Relative mXDH mRNA | Low (error) | High (error) |
|---|---|---|---|
| Group 1 (No Treatment) | 1.000 | 0.197 | 0.246 |
| Group 2 (1.0 mg/kg AD09217) | 0.600 | 0.100 | 0.119 |
| Group 3 (1.0 mg/kg AD09218) | 0.628 | 0.132 | 0.167 |
| Group 4 (1.0 mg/kg AD09219) | 0.649 | 0.071 | 0.080 |
| Group 5 (1.0 mg/kg AD09220) | 0.943 | 0.157 | 0.188 |
| Group 6 (1.0 mg/kg AD09221) | 1.174 | 0.205 | 0.249 |
| Group 7 (1.0 mg/kg AD09222) | 1.098 | 0.242 | 0.310 |
| Group 8 (1.0 mg/kg AD09223) | 1.196 | 0.191 | 0.228 |
| Group 9 (1.0 mg/kg AD09224) | 1.348 | 0.179 | 0.207 |
| Group 10 (1.0 mg/kg AD09225) | 1.663 | 0.241 | 0.281 |
| Group 11 (1.0 mg/kg AD09226) | 1.711 | 0.126 | 0.136 |
| Group 12 (1.0 mg/kg AD09227) | 0.912 | 0.047 | 0.050 |
| Group 13 (1.0 mg/kg AD09228) | 0.983 | 0.114 | 0.128 |
| Group 14 (1.0 mg/kg AD09229) | 1.023 | 0.117 | 0.132 |

The data were normalized to the non-treatment group (Group 1). As noted above in, for example, Example 3, the RNAi agent targeting position 488 of the XDH gene of Group 2 (AD09217) and Group 3 (AD09218), while being previously identified as having activity in mice and rats in vivo, includes a compromised nucleotide sequence and is unsuitable for therapeutic use due to toxicity concerns. As shown in Table 20, above, the XDH RNAi agent AD09219 (Group 4), which targets position 1612 of the XDH gene transcript, showed mRNA reductions of approximately 35.1% (0.649) in mice, which was generally comparable to the reductions exhibited by the XDH RNAi agents of Group 2 (40% inhibition; (0.600)) and Group 3 (37.2% inhibition; (0.628)), which both included RNAi agents having sequences targeting position 488 of the XDH gene which as noted above has toxicity concerns.

Example 10. In Vivo Testing of XDH RNAi Agents in Wild-Type Mice

Certain XDH RNAi agents have sufficient homology with the mouse XDH gene transcript that they are suitable to be examined for XDH gene expression inhibitory activity in wild-type mice. At day 1, six- to eight-week-old male C57bl/6 mice were given a single subcutaneous administration of 200 l/20 g animal weight containing 1.0 mg/kg (mpk) of an XDH RNAi agent formulated in isotonic saline, or vehicle control (isotonic saline with no RNAi agent), according to the following Table 21.

TABLE 21

Targeted Positions and Dosing Groups of Example 10

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 1612 | 1.0 mg/kg AD09219 | Single injection on day 1 |
| 3 | 1612 | 1.0 mg/kg AD10021 | Single injection on day 1 |
| 4 | 1612 | 1.0 mg/kg AD10022 | Single injection on day 1 |
| 5 | 1612 | 1.0 mg/kg AD10023 | Single injection on day 1 |
| 6 | 1612 | 1.0 mg/kg AD10024 | Single injection on day 1 |
| 7 | 1612 | 1.0 mg/kg AD10025 | Single injection on day 1 |
| 8 | 1612 | 1.0 mg/kg AD10026 | Single injection on day 1 |
| 9 | 1612 | 1.0 mg/kg AD10027 | Single injection on day 1 |
| 10 | 1612 | 1.0 mg/kg AD10028 | Single injection on day 1 |
| 11 | 1612 | 1.0 mg/kg AD10029 | Single injection on day 1 |
| 12 | 1612 | 1.0 mg/kg AD10030 | Single injection on day 1 |

Each of the XDH RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents in Groups 2-14 each included nucleotide sequences that, while also being homologous to the mouse XDH gene transcript, were designed to inhibit expression of an XDH gene at positions 1612 of the human XDH gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Mice were euthanized on study day 8, and total RNA was isolated from both livers following collection and homogenization. Mouse XDH mRNA expression was quantitated by probe-based quantitative PCR, normalized to mouse beta-actin expression, and expressed as fraction of vehicle control group (geometric mean, +/−95% confidence interval).

TABLE 22

Average Relative Mouse XDH mRNA at Sacrifice (Day 8) in Example 10

| Group ID | Average Relative mXDH mRNA | Low (error) | High (error) |
| --- | --- | --- | --- |
| Group 1 (No Treatment) | 1.000 | 0.242 | 0.319 |
| Group 2 (1.0 mg/kg AD09219) | 0.607 | 0.044 | 0.048 |
| Group 3 (1.0 mg/kg AD10021) | 0.653 | 0.139 | 0.177 |
| Group 4 (1.0 mg/kg AD10022) | 0.711 | 0.055 | 0.060 |
| Group 5 (1.0 mg/kg AD10023) | 0.609 | 0.067 | 0.076 |
| Group 6 (1.0 mg/kg AD10024) | 0.703 | 0.116 | 0.139 |
| Group 7 (1.0 mg/kg AD10025) | 0.659 | 0.083 | 0.095 |
| Group 8 (1.0 mg/kg AD10026) | 0.561 | 0.093 | 0.111 |
| Group 9 (1.0 mg/kg AD10027) | 0.540 | 0.090 | 0.108 |
| Group 10 (1.0 mg/kg AD10028) | 0.631 | 0.054 | 0.059 |
| Group 11 (1.0 mg/kg AD10029) | 0.440 | 0.042 | 0.046 |
| Group 12 (1.0 mg/kg AD10030) | 0.550 | 0.118 | 0.150 |

The data were normalized to the non-treatment group (Group 1). As shown in Table 22, above, each of the XDH RNAi agents targeting position 1612 (Groups 2-12) showed mouse mRNA reductions.

Example 11. In Vivo Testing of XDH RNAi Agents in Wild-Type Rats

Certain XDH RNAi agents have sufficient homology with the rat XDH gene transcript that they are suitable to be examined for XDH gene expression inhibitory activity in wild-type rats. At day 1, male Sprague Dawley rats were given a single subcutaneous administration of 4 mL/1 kg animal weight containing a dose of an XDH RNAi agent formulated in isotonic saline, or vehicle control (isotonic saline with no RNAi agent), according to the following Table 23.

TABLE 23

Targeted Positions and Dosing Groups of Example 11

| Group | Targeted Gene Position (within SEQ ID NO: 1) | RNAi Agent and Dose | Dosing Regimen |
| --- | --- | --- | --- |
| 1 | N/A | Saline (no RNAi agent) | Single injection on day 1 |
| 2 | 488 | 10.0 mg/kg AD09218 | Single injection on day 1 |
| 3 | 488 | 3.0 mg/kg AD09218 | Single injection on day 1 |
| 4 | 488 | 1.0 mg/kg AD09218 | Single injection on day 1 |
| 5 | 488 | 0.3 mg/kg AD09218 | Single injection on day 1 |
| 6 | 2612 | 10.0 mg/kg AD09651 | Single injection on day 1 |
| 7 | 2612 | 3.0 mg/kg AD09651 | Single injection on day 1 |
| 8 | 2612 | 1.0 mg/kg AD09651 | Single injection on day 1 |
| 9 | 2612 | 0.3 mg/kg AD09651 | Single injection on day 1 |
| 10 | 2616 | 10.0 mg/kg AD09663 | Single injection on day 1 |
| 11 | 2616 | 3.0 mg/kg AD09663 | Single injection on day 1 |
| 12 | 2616 | 1.0 mg/kg AD09663 | Single injection on day 1 |
| 13 | 2616 | 0.3 mg/kg AD09663 | Single injection on day 1 |

Each of the XDH RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agent in Groups 2-5 (AD09218) included nucleotide sequences that, while also being homologous to the rat XDH gene transcript, were designed to inhibit expression of an XDH gene at position 488 of the human XDH gene; the XDH RNAi agent in Groups 6-9 (AD09651) included nucleotide sequences that, while also being homologous to the rat XDH gene transcript, were designed to inhibit expression of an XDH gene at position 2612 of the human XDH gene; and the XDH RNAi agents in Groups 10-13 (AD09663) included nucleotide sequences that, while also being homologous to the rat XDH gene transcript, were designed to inhibit expression of an XDH gene at position 2616 of the human XDH gene. (See, e.g., SEQ ID NO:1 and Table 2 for the XDH gene referenced).

The injections were performed between the skin and muscle (i.e. subcutaneous injections) into the loose skin over the neck and shoulder area. Four (4) rats in each group were tested (n=4). Rats were euthanized on study day 10, and total RNA was isolated from both livers following collection and homogenization. Rat XDH mRNA expression was quantitated by probe-based quantitative PCR, normalized to rat beta-actin expression, and expressed as fraction of vehicle control group (geometric mean, +/−95% confidence interval).

TABLE 24

Average Relative Mouse XDH mRNA at Sacrifice (Day 10) in Example 11

| Group ID | Average Relative rXDH mRNA | Low (error) | High (error) |
| --- | --- | --- | --- |
| Group 1 (No Treatment) | 1.000 | 0.164 | 0.197 |
| Group 2 (10.0 mg/kg AD09218) | 0.207 | 0.079 | 0.128 |
| Group 3 (3.0 mg/kg AD09218) | 0.295 | 0.105 | 0.163 |
| Group 4 (1.0 mg/kg AD09218) | 0.369 | 0.061 | 0.072 |
| Group 5 (0.3 mg/kg AD09218) | 0.556 | 0.086 | 0.102 |
| Group 6 (10.0 mg/kg AD09651) | 0.209 | 0.056 | 0.076 |
| Group 7 (3.0 mg/kg AD09651) | 0.271 | 0.045 | 0.054 |
| Group 8 (1.0 mg/kg AD09651) | 0.625 | 0.111 | 0.135 |

TABLE 24-continued

Average Relative Mouse XDH
mRNA at Sacrifice (Day 10) in Example 11

| Group ID | Average Relative rXDH mRNA | Low (error) | High (error) |
|---|---|---|---|
| Group 9 (0.3 mg/kg AD09651) | 0.828 | 0.114 | 0.132 |
| Group 10 (10.0 mg/kg AD09663) | 0.122 | 0.045 | 0.072 |
| Group 11 (3.0 mg/kg AD09663) | 0.213 | 0.060 | 0.083 |
| Group 12 (1.0 mg/kg AD09663) | 0.428 | 0.094 | 0.120 |
| Group 13 (0.3 mg/kg AD09663) | 0.481 | 0.112 | 0.146 |

The data were normalized to the non-treatment group (Group 1). As noted above in, for example, Example 3, the RNAi agent targeting position 488 of the XDH gene of Groups 2-5 (AD09218), while being previously identified as having activity in rats in vivo, includes a compromised nucleotide sequence and is unsuitable for therapeutic use due to toxicity concerns. As shown in Table 24, the XDH RNAi agent AD09651 (Groups 6-9), which targets position 2612 of the XDH gene transcript, and the XDH RNAi agent AD09663 (Groups 10-13), which targets position 2616, both showed dose-dependent mRNA reductions that were comparable to AD09218 (targeting position 488 of the XDH gene).

Example 12. In Vivo Testing of XDH RNAi Agents in Cynomolgus Monkeys

XDH RNAi agents AD09325 and AD09307 were evaluated in cynomolgus monkeys (cynos). On day 1, three male cynos for each group (n=3) were administered a subcutaneous injection of 0.3 mL/kg (approximately 1.5 mL volume, depending on animal mass) containing 3.0 mg/kg (10 mg/mL) of the respective XDH RNAi agent, formulated in isotonic saline.

TABLE 25

Targeted Positions and Dosing Groups of Example 12

| Group | Targeted Gene Position (within SEQ ID NO: 1) | RNAi Agent and Dose | Dosing Regimen (on day 1) |
|---|---|---|---|
| A | 3083 | 3.0 mg/kg AD09325 | Single subcutaneous injection |
| B | 4725 | 3.0 mg/kg AD09307 | Single subcutaneous injection |

The XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agent in Groups A (AD09325) included nucleotide sequences that were designed to inhibit expression of a human XDH gene at position 3083; and the XDH RNAi agent in Group B (AD09307) included nucleotide sequences that were designed to inhibit expression of an XDH gene at position 4725. (See, e.g., SEQ ID NO:1 and Table 2 for the XDH gene referenced).

On days −8 (8 days before dose) and 15, survival liver biopsies were taken. On the date of each biopsy collection, cynos were anesthetized and laparoscopy was used to extract two liver tissue samples approximately 80 mg to 120 mg each, and aliquots of approximately 50 mg were snap-frozen and stored at −70° C. until analysis. On day 29, cynos were euthanized and aliquots of approximately 50 mg liver samples were collected. The biopsy samples were then homogenized, and levels of cyno XDH (cXDH) mRNA in the cyno livers were measured by RT-qPCR using a housekeeping gene as reference. Resulting values were then normalized to the pre-dose (in this case, at day −8) cXDH mRNA measurements. The resulting mRNA data are reflected in the following Table 26:

TABLE 26

Cyno XDH mRNA Levels Normalized to Pre-Dose (Day −8) from Example 12 for each Group (n = 3)

| | Relative cXDH mRNA Expression | Low Error | High Error | Relative eXDH mRNA Expression | Low Error | High Error |
|---|---|---|---|---|---|---|
| | Day −8 | | | Day 15 | | |
| Group A: AD09325 | 1.000 | 0.211 | 0.268 | 0.609 | 0.097 | 0.115 |
| Group B: AD09307 | 1.000 | 0.339 | 0.512 | 1.139 | 0.316 | 0.437 |
| | Day 29 | | | | | |
| Group A: AD09325 | 1.178 | 0.286 | 0.378 | | | |
| Group B: AD09307 | 1.591 | 0.509 | 0.748 | | | |

As shown in Table 26, XDH RNAi agent AD09325, which was designed to target position 3083 of the XDH gene, showed 39% inhibition of cXDH mRNA at Day 15 and returned to baseline by day 29. XDH RNAi agent AD09307, which was designed to target position 4725 of the XDH gene, showed no inhibitory activity at either of the time points measured.

Example 13. In Vivo Testing of XDH RNAi Agents in Cynomolgus Monkeys

XDH RNAi agents AD09734, AD09651, AD09663, and AD09611 were evaluated in cynomolgus monkeys (cynos). On days 1 and 31, three male cynos for each group (n=3) were administered a subcutaneous injection of 0.3 mL/kg (approximately 1.5 mL volume, depending on animal mass) containing 3.0 mg/kg (10 mg/mL) of the respective XDH RNAi agent, formulated in isotonic saline.

TABLE 27

Targeted Positions and Dosing Groups of Example 13

| Group | Targeted Gene Position (within SEQ ID NO: 1) | RNAi Agent and Dose | Dosing Regimen (on days 1 and 31) |
|---|---|---|---|
| 1 | 1322 | 3.0 mg/kg AD09734 | Two subcutaneous injections |
| 2 | 2612 | 3.0 mg/kg AD09651 | Two subcutaneous injections |
| 3 | 2616 | 3.0 mg/kg AD09663 | Two subcutaneous injections |
| 4 | 4289 | 3.0 mg/kg AD09611 | Two subcutaneous injections |

The XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents included nucleotide sequences that were designed to inhibit expression of a human XDH gene at the specific positions as shown in Table 27, above. (See, e.g., SEQ ID NO:1 and Table 2 for the XDH gene referenced).

On days −14 or −7 (pre-dose), 15, 43, and 80 (for Group 4 only) liver biopsies were taken. On the date of each biopsy collection, cynos were anesthetized and laparoscopy was used to extract two liver tissue samples approximately 80 mg to 120 mg each, and aliquots of approximately 50 mg were snap-frozen and stored at −70° C. until analysis. The biopsy samples were then homogenized, and levels of cXDH mRNA in the cyno livers were measured by RT-qPCR using a housekeeping gene as reference. Resulting values were then normalized to the pre-dose (in this case, at day −14 or −7, depending on the animals) cXDH mRNA measurements. Batch analysis of samples across timepoints was performed where applicable. The resulting mRNA data are reflected in the following Table 28:

TABLE 28

Cyno XDH mRNA Levels Normalized to Pre-Dose (Day −14 or −7) from Example 13 for each Group (n = 3)

| | Relative eXDH mRNA Expression | Low Error | High Error | Low Error | High Error | Relative eXDH mRNA Expression |
|---|---|---|---|---|---|---|
| | Pre-Dose (Day −14 or Day −7) | | | Day 15 | | |
| Group 1: AD09734 | 1.000 | 0.127 | 0.145 | 0.351 | 0.028 | 0.031 |
| Group 2: AD09651 | 1.000 | 0.170 | 0.205 | 0.433 | 0.131 | 0.188 |
| Group 3: AD09663 | 1.000 | 0.374 | 0.597 | 0.621 | 0.274 | 0.489 |
| Group 4: AD09611 | 1.000 | 0.202 | 0.254 | 0.570 | 0.122 | 0.156 |
| | Day 43 | | | Day 80 | | |
| Group 1: AD09734 | 0.434 | 0.134 | 0.194 | | | |
| Group 2: AD09651 | 0.342 | 0.074 | 0.094 | | | |
| Group 3: AD09663 | 0.605 | 0.316 | 0.662 | | | |
| Group 4: AD09611 | 0.239 | 0.015 | 0.016 | 0.493 | 0.090 | 0.110 |

As shown in Table 28, each of the XDH RNAi agents showed inhibition of XDH gene expression.

XDH Activity Assay. Using RNAScope (see, e.g., RNAscope, A Novel in Situ RNA Analysis Platform for Formalin-Fixed, Paraffin-Embedded Tissues, J Mol Diagn. 2012 January; 14(1): 22-29), it was determined that XDH mRNA transcripts are partitioned between both nuclear and cytosolic compartments. As translation to XDH protein only occurs in the cytoplasm, inhibition of cytoplasmic mRNA transcripts is considered therapeutically relevant. Measurement of XDH mRNA transcripts using q-PCR from whole liver homogenate, as explained in Table 28, is therefore not necessarily reflective of determining therapeutically relevant XDH inhibition as it measures the presence of XDH mRNA in both the cytosolic and nucleic compartments. Thus, to obtain a more accurate assessment of the inhibitory activity of the various XDH RNAi agents disclosed herein, an XDH activity assay was developed capable of indirectly measuring the amount of XDH protein inhibited by the XDH RNAi agents through the RNA interference mechanism.

More specifically, XDH activity was assessed using the following method: frozen cyno liver biopsy samples were homogenized in buffer containing 100 mM oxonic acid to inhibit endogenous uricase activity which is known to degrade uric acid. Liver homogenates were purified using Sephadex G25 spin columns, and protein concentrations adjusted to 0.5 μg/μl total protein (lysate). XDH activity was measured by liquid-chromatography mass spectrometry (LCMS) as the conversion of xanthine to uric acid at 37° C. within a 30-minute timeframe. The amount of uric acid generated over time is an indirect measure of the amount of cXDH protein present in the lysate; accordingly, the less uric acid identified, the less cXDH protein was present in lysate, thereby indicating a more potent XDH RNAi agent for reducing XDH protein. The resulting XDH activity data (normalized to pre-dose) are shown in Table 29.

TABLE 29

Cyno XDH Activity Levels Normalized to Pre-Dose (Day −14 or −7) from Example 13 for each Group (n = 3)

| | Pre-Dose (Day −14 or Day −7) | | Day 15 | | Day 43 | | Day 80 | |
|---|---|---|---|---|---|---|---|---|
| | Relative XDH Activity | Std Dev (+/−) | Relative XDH Activity | Std Dev (+/−) | Relative XDH Activity | Std Dev (+/−) | Relative XDH Activity | Std Dev (+/−) |
| Group 1: AD09734 | 1.000 | 0.042 | 0.363 | 0.056 | 0.240 | 0.056 | | |
| Group 2: AD09651 | 1.000 | 0.026 | 0.511 | 0.121 | 0.289 | 0.053 | | |
| Group 3: AD09663 | 1.000 | 0.003 | 0.412 | 0.219 | 0.247 | 0.164 | | |
| Group 4: AD09611 | 1.000 | 0.025 | 0.555 | 0.115 | 0.226 | 0.057 | 0.268 | 0.082 |

As shown in Table 29, through day 43 each of the RNAi agents tested above showed XDH activity reductions of greater than 70%. Further, RNAi agent AD09611 showed substantial reductions of XDH activity that were maintained for seven weeks post the last dose (day 31).

Example 14. In Vivo Testing of XDH RNAi Agents in XDH-GLuc AAV Mice

The XDH-GLUC AAV mouse model described in Example 2, above, using the XDH-GLuc AAV containing the 2820-5715 region of the human XDH cDNA sequence was used. At day 1, each mouse was given a single subcutaneous administration of 250 µl/25 g animal weight containing either 2.0 mg/kg (mpk) of an XDH RNAi agent formulated in isotonic saline, or vehicle control (isotonic saline with no RNAi agent), according to the following Table 30.

TABLE 30

Targeted Positions and Dosing Groups of Example 14

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 4289 | 2.0 mg/kg AD09611 | Single injection on day 1 |
| 3 | 4289 | 2.0 mg/kg AD10183 | Single injection on day 1 |
| 4 | 4289 | 2.0 mg/kg AD10629 | Single injection on day 1 |
| 5 | 4289 | 2.0 mg/kg AD10630 | Single injection on day 1 |
| 6 | 4289 | 2.0 mg/kg AD10631 | Single injection on day 1 |
| 7 | 4289 | 2.0 mg/kg AD10632 | Single injection on day 1 |
| 8 | 4289 | 2.0 mg/kg AD10184 | Single injection on day 1 |
| 9 | 4289 | 2.0 mg/kg AD10633 | Single injection on day 1 |
| 10 | 4289 | 2.0 mg/kg AD10634 | Single injection on day 1 |
| 11 | 4289 | 2.0 mg/kg AD10635 | Single injection on day 1 |
| 12 | 4289 | 2.0 mg/kg AD10636 | Single injection on day 1 |

Each of the XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents in Groups 2-12 each included nucleotide sequences that were designed to inhibit expression of an XDH gene at position 4289 of the gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8, and day 15, and XDH expression levels were determined pursuant to the procedure set forth in Example 2, above. Data from the experiment through day 22 are shown in Table 31:

TABLE 31

Average XDH Normalized to Pre-Treatment & Control in XDH-GLUC AAV Mice from Example 14

| | Day 8 | | Day 15 | | Day 22 | |
|---|---|---|---|---|---|---|
| Groupd ID | Avg XDH | Std Dev (+/−) | Avg XDH | Std Dev (+/−) | Avg XDH | Std Dev (+/−) |
| Group 1 (Saline vehicle) | 1.000 | 0.164 | 1.000 | 0.044 | 1.000 | 0.085 |
| Group 2 (2.0 mg/kg AD09611) | 0.877 | 0.113 | 0.710 | 0.100 | 0.629 | 0.148 |
| Group 3 (2.0 mg/kg AD10183) | 0.585 | 0.084 | 0.402 | 0.082 | 0.432 | 0.098 |
| Group 4 (2.0 mg/kg AD10629) | 0.548 | 0.119 | 0.443 | 0.127 | 0.501 | 0.195 |
| Group 5 (2.0 mg/kg AD10630) | 0.708 | 0.076 | 0.609 | 0.130 | 0.497 | 0.045 |
| Group 6 (2.0 mg/kg AD10631) | 0.523 | 0.035 | 0.398 | 0.090 | 0.477 | 0.080 |
| Group 7 (2.0 mg/kg AD10632) | 0.679 | 0.248 | 0.583 | 0.125 | 0.574 | 0.314 |
| Group 8 (2.0 mg/kg AD10184) | 0.573 | 0.051 | 0.501 | 0.029 | 0.529 | 0.070 |
| Group 9 (2.0 mg/kg AD10633) | 0.686 | 0.153 | 0.544 | 0.080 | 0.562 | 0.111 |
| Group 10 (2.0 mg/kg AD10634) | 0.680 | 0.136 | 0.572 | 0.088 | 0.615 | 0.092 |
| Group 11 (2.0 mg/kg AD10635) | 0.764 | 0.178 | 0.678 | 0.105 | 0.674 | 0.083 |
| Group 12 (2.0 mg/kg AD10636) | 0.555 | 0.068 | 0.440 | 0.091 | 0.488 | 0.126 |

Example 15. In Vivo Testing of XDH RNAi Agents in XDH-GLuc AAV Mice

The XDH-GLUC AAV mouse model described in Example 2, using the XDH-GLuc AAV containing the 80-2899 region of the human XDH cDNA sequence was used. At day 1, each mouse was given a single subcutaneous administration of 250 µl/25 g animal weight containing either 1.0 mg/kg (mpk) or 3.0 mg/kg (mpk) of an XDH RNAi agent formulated in isotonic saline, or vehicle control (isotonic saline with no RNAi agent), according to Table 32.

TABLE 32

Targeted Positions and Dosing Groups of Example 15

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 1963 | 3.0 mg/kg AD09736 | Single injection on day 1 |
| 3 | 1963 | 1.0 mg/kg AD09736 | Single injection on day 1 |
| 4 | 1963 | 3.0 mg/kg AD09937 | Single injection on day 1 |
| 5 | 1963 | 1.0 mg/kg AD09937 | Single injection on day 1 |
| 6 | 1963 | 3.0 mg/kg AD09967 | Single injection on day 1 |
| 7 | 1963 | 1.0 mg/kg AD09967 | Single injection on day 1 |
| 8 | 1963 | 3.0 mg/kg AD10278 | Single injection on day 1 |
| 9 | 1963 | 1.0 mg/kg AD10278 | Single injection on day 1 |
| 10 | 1963 | 3.0 mg/kg AD10281 | Single injection on day 1 |
| 11 | 1963 | 1.0 mg/kg AD10281 | Single injection on day 1 |

Each of the XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents of Groups 2-11 all included nucleotide sequences that were designed to inhibit expression of an XDH gene at position 1963 of the gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8, and day 22, and XDH expression levels were determined pursuant to the procedure set forth in Example 2, above. Data from the experiment through day 22 are shown in Table 33:

TABLE 33

Average XDH Normalized to Pre-Treatment & Control in XDH-GLUC AAV Mice from Example 15

| Group ID | Day 8 Avg XHD | Std Dev (+/−) | Day 22 Avg XHD | Std Dev (+/−) |
|---|---|---|---|---|
| Group 1 (Saline vehicle) | 1.000 | 0.202 | 1.000 | 0.112 |
| Group 2 (3.0 mg/kg AD09736) | 0.587 | 0.080 | 0.682 | 0.182 |
| Group 3 (1.0 mg/kg AD09736) | 1.100 | 0.292 | 1.063 | 0.212 |
| Group 4 (3.0 mg/kg AD09937) | 0.554 | 0.211 | 0.547 | 0.214 |
| Group 5 (1.0 mg/kg AD09937) | 0.914 | 0.175 | 0.851 | 0.175 |
| Group 6 (3.0 mg/kg AD09967) | 0.638 | 0.035 | 0.696 | 0.139 |
| Group 7 (1.0 mg/kg AD09967) | 0.838 | 0.103 | 0.790 | 0.149 |
| Group 8 (3.0 mg/kg AD10278) | 0.518 | 0.036 | 0.678 | 0.112 |
| Group 9 (1.0 mg/kg AD10278) | 1.209 | 0.116 | 0.940 | 0.266 |
| Group 10 (3.0 mg/kg AD10281) | 0.769 | 0.184 | 0.762 | 0.145 |
| Group 11 (1.0 mg/kg AD10281) | 1.224 | 0.172 | 0.995 | 0.160 |

Example 16. In Vivo Testing of XDH RNAi Agents in XDH-GLuc AAV Mice

The XDH-GLUC AAV mouse model described in Example 2, above, using the XDH-GLuc AAV containing the 2820-5715 region of the human XDH cDNA sequence was used. At day 1, each mouse was given a single subcutaneous administration of 250 μl/25 g animal weight containing either 4.0 mg/kg (mpk), 2.0 mg/kg (mpk), 1.0 mg/kg (mpk) of an XDH RNAi agent formulated in isotonic saline, or vehicle control (isotonic saline with no RNAi agent), according to Table 34.

TABLE 34

Targeted Positions and Dosing Groups of Example 16

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 4289 | 4.0 mg/kg AD09611 | Single injection on day 1 |
| 3 | 4289 | 2.0 mg/kg AD09611 | Single injection on day 1 |
| 4 | 4289 | 1.0 mg/kg AD09611 | Single injection on day 1 |
| 5 | 4289 | 4.0 mg/kg AD10183 | Single injection on day 1 |
| 6 | 4289 | 2.0 mg/kg AD10183 | Single injection on day 1 |
| 7 | 4289 | 1.0 mg/kg AD10183 | Single injection on day 1 |
| 8 | 4289 | 4.0 mg/kg AD10631 | Single injection on day 1 |
| 9 | 4289 | 2.0 mg/kg AD10631 | Single injection on day 1 |
| 10 | 4289 | 1.0 mg/kg AD10631 | Single injection on day 1 |
| 11 | 4289 | 4.0 mg/kg AD10184 | Single injection on day 1 |
| 12 | 4289 | 2.0 mg/kg AD10184 | Single injection on day 1 |
| 13 | 4289 | 1.0 mg/kg AD10184 | Single injection on day 1 |

Each of the XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents in Groups 2-13 each included nucleotide sequences that were designed to inhibit expression of an XDH gene at position 4289 of the gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8, day 15, and day 22, and XDH expression levels were determined pursuant to the procedure set forth in Example 2. Data from the experiment through day 22 are shown in Table 35:

TABLE 35

Average XDH Normalized to Pre-Treatment & Control in XDH-GLUC AAV Mice from Example 16

| Groupd ID | Day 8 Avg XDH | Std Dev (+/−) | Day 15 Avg XDH | Std Dev (+/−) | Day 22 Avg XDH | Std Dev (+/−) |
|---|---|---|---|---|---|---|
| Group 1 (Saline vehicle) | 1.000 | 0.167 | 1.000 | 0.099 | 1.000 | 0.048 |
| Group 2 (4.0 mg/kg AD09611) | 0.808 | 0.086 | 0.810 | 0.089 | 0.958 | 0.118 |
| Group 3 (2.0 mg/kg AD09611) | 1.100 | 0.224 | 0.998 | 0.383 | 1.245 | 0.476 |
| Group 4 (1.0 mg/kg AD09611) | 0.917 | 0.198 | 0.941 | 0.224 | 0.780 | 0.544 |
| Group 5 (4.0 mg/kg AD10183) | 0.636 | 0.140 | 0.642 | 0.044 | 0.797 | 0.112 |
| Group 6 (2.0 mg/kg AD10183) | 0.768 | 0.059 | 0.672 | 0.206 | 0.870 | 0.079 |
| Group 7 (1.0 mg/kg AD10183) | 0.841 | 0.111 | 0.792 | 0.266 | 0.938 | 0.122 |
| Group 8 (4.0 mg/kg AD10631) | 0.755 | 0.110 | 0.677 | 0.094 | 0.664 | 0.126 |
| Group 9 (2.0 mg/kg AD10631) | 0.852 | 0.066 | 0.755 | 0.103 | 0.869 | 0.149 |
| Group 10 (1.0 mg/kg AD10631) | 0.884 | 0.153 | 0.954 | 0.128 | 1.060 | 0.071 |
| Group 11 (4.0 mg/kg AD10184) | 0.640 | 0.079 | 0.663 | 0.055 | 0.680 | 0.068 |
| Group 12 (2.0 mg/kg AD10184) | 0.729 | 0.049 | 0.746 | 0.126 | 0.811 | 0.116 |
| Group 13 (1.0 mg/kg AD10184) | 0.807 | 0.069 | 0.730 | 0.090 | 0.796 | 0.119 |

Example 17. In Vivo Testing of XDH RNAi Agents in XDH-GLuc AAV Mice

The XDH-GLUC AAV mouse model described in Example 2, using the XDH-GLuc AAV containing the 2820-5715 region of the human XDH cDNA sequence was used. At day 1, each mouse was given a single subcutaneous administration of 200 μl/20 g animal weight containing either 4.0 mg/kg (mpk), 2.0 mg/kg (mpk), 1.0 mg/kg (mpk) of an XDH RNAi agent formulated in isotonic saline, or vehicle control (isotonic saline with no RNAi agent), according to Table 36.

TABLE 36

Targeted Positions and Dosing Groups of Example 17

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 3598 | 4.0 mg/kg AD09985 | Single injection on day 1 |
| 3 | 3598 | 2.0 mg/kg AD09985 | Single injection on day 1 |
| 4 | 3598 | 1.0 mg/kg AD09985 | Single injection on day 1 |
| 5 | 3598 | 4.0 mg/kg AD10729 | Single injection on day 1 |
| 6 | 3598 | 2.0 mg/kg AD10729 | Single injection on day 1 |
| 7 | 3598 | 1.0 mg/kg AD10729 | Single injection on day 1 |
| 8 | 3598 | 4.0 mg/kg AD10730 | Single injection on day 1 |
| 9 | 3598 | 2.0 mg/kg AD10730 | Single injection on day 1 |
| 10 | 3598 | 1.0 mg/kg AD10730 | Single injection on day 1 |
| 11 | 3598 | 4.0 mg/kg AD10734 | Single injection on day 1 |
| 12 | 3598 | 2.0 mg/kg AD10734 | Single injection on day 1 |
| 13 | 3598 | 1.0 mg/kg AD10734 | Single injection on day 1 |

Each of the XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents in Groups 2-13 each included nucleotide sequences that were designed to inhibit expression of an XDH gene at position 3598 of the gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8, day 15, and day 22, and XDH expression levels were determined pursuant to the procedure set forth in Example 2, above. Data from the experiment through day 22 are shown in Table 37:

TABLE 37

Average XDH Normalized to Pre-Treatment & Control in XDH-GLUC AAV Mice from Example 17

| | Day 8 | | Day 15 | | Day 22 | |
|---|---|---|---|---|---|---|
| Groupd ID | Avg XDH | Std Dev (+/−) | Avg XDH | Std Dev (+/−) | Avg XDH | Std Dev (+/−) |
| Group 1 (Saline vehicle) | 1.000 | 0.294 | 1.000 | 0.350 | 1.000 | 0.156 |
| Group 2 (4.0 mg/kg AD09985) | 0.342 | 0.061 | 0.340 | 0.052 | 0.320 | 0.074 |
| Group 3 (2.0 mg/kg AD09985) | 0.464 | 0.065 | 0.443 | 0.076 | 0.457 | 0.108 |
| Group 4 (1.0 mg/kg AD09985) | 0.527 | 0.163 | 0.509 | 0.075 | 0.487 | 0.094 |
| Group 5 (4.0 mg/kg AD10729) | 0.393 | 0.081 | 0.379 | 0.074 | 0.359 | 0.045 |
| Group 6 (2.0 mg/kg AD10729) | 0.504 | 0.176 | 0.447 | 0.132 | 0.394 | 0.176 |
| Group 7 (1.0 mg/kg AD10729) | 0.480 | 0.168 | 0.535 | 0.279 | 0.486 | 0.205 |
| Group 8 (4.0 mg/kg AD10730) | 0.322 | 0.035 | 0.316 | 0.046 | 0.244 | 0.064 |
| Group 9 (2.0 mg/kg AD10730) | 0.467 | 0.076 | 0.397 | 0.052 | 0.360 | 0.113 |
| Group 10 (1.0 mg/kg AD10730) | 0.560 | 0.114 | 0.540 | 0.079 | 0.536 | 0.068 |
| Group 11 (4.0 mg/kg AD10734) | 0.369 | 0.048 | 0.340 | 0.074 | 0.278 | 0.025 |
| Group 12 (2.0 mg/kg AD10734) | 0.574 | 0.338 | 0.467 | 0.255 | 0.432 | 0.299 |
| Group 13 (1.0 mg/kg AD10734) | 0.616 | 0.198 | 0.617 | 0.086 | 0.389 | 0.076 |

Example 18. In Vivo Testing of XDH RNAi Agents in XDH-GLuc AAV Mice

The XDH-GLUC AAV mouse model described in Example 2, using the XDH-GLuc AAV containing the 80-2899 and 2820-5715 regions of the human XDH cDNA sequence was used. At day 1, each mouse was given a single subcutaneous administration of 200 μl/20 g animal weight containing either 4.0 mg/kg (mpk), 2.0 mg/kg (mpk), 1.0 mg/kg (mpk) of an XDH RNAi agent formulated in isotonic saline, or vehicle control (isotonic saline with no RNAi agent), according to Table 38.

TABLE 38

Targeted Positions and Dosing Groups of Example 18

| Group | Targeted Gene Position (within SEQ ID NO: 1) | RNAi Agent and Dose | Dosing Regimen |
|---|---|---|---|
| 1 | 2696 | Saline (no RNAi agent) | Single injection on day 1 |
| 2 | 2696 | 4.0 mg/kg AD09744 | Single injection on day 1 |
| 3 | 2696 | 2.0 mg/kg AD09744 | Single injection on day 1 |
| 4 | 2696 | 1.0 mg/kg AD09744 | Single injection on day 1 |
| 5 | 2696 | 4.0 mg/kg AD10621 | Single injection on day 1 |
| 6 | 2696 | 2.0 mg/kg AD10621 | Single injection on day 1 |
| 7 | 2696 | 1.0 mg/kg AD10621 | Single injection on day 1 |
| 8 | 1963 | 4.0 mg/kg AD09736 | Single injection on day 1 |
| 9 | 1963 | 2.0 mg/kg AD09736 | Single injection on day 1 |
| 10 | 1963 | 1.0 mg/kg AD09736 | Single injection on day 1 |
| 11 | 1963 | 4.0 mg/kg AD09937 | Single injection on day 1 |
| 12 | 1963 | 2.0 mg/kg AD09937 | Single injection on day 1 |
| 13 | 1963 | 1.0 mg/kg AD09937 | Single injection on day 1 |

Each of the XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents in Groups 2-13 each included nucleotide sequences that were designed to inhibit expression of an XDH gene at positions 2696 and 1963 of the gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8, day 15, and day 22, and XDH expression levels were determined pursuant to the procedure set forth in Example 2. Data from the experiment through day 22 are shown in Table 39:

TABLE 39A

Average XDH Normalized to Pre-Treatment in XDH-GLUC AAV Mice from Example 18

| Group ID | Day 8 Avg XDH | Day 8 Std Dev (+/−) | Day 15 Avg XDH | Day 15 Std Dev (+/−) | Day 22 Avg XDH | Day 22 Std Dev (+/−) |
|---|---|---|---|---|---|---|
| Group 1 (Saline vehicle) | 1.183 | 0.346 | 1.164 | 0.468 | 1.448 | 0.573 |
| Group 2 (4.0 mg/kg AD09744) | 0.538 | 0.113 | 0.404 | 0.106 | 0.601 | 0.062 |
| Group 3 (2.0 mg/kg AD09744) | 0.704 | 0.210 | 0.663 | 0.165 | 0.950 | 0.214 |
| Group 4 (1.0 mg/kg AD09744) | 0.903 | 0.100 | 0.842 | 0.154 | 1.101 | 0.249 |
| Group 5 (4.0 mg/kg AD10621) | 0.406 | 0.226 | 0.366 | 0.293 | 0.650 | 0.532 |
| Group 6 (2.0 mg/kg AD10621) | 0.521 | 0.261 | 0.411 | 0.225 | 0.640 | 0.343 |
| Group 7 (1.0 mg/kg AD10621) | 0.580 | 0.202 | 0.467 | 0.227 | 0.669 | 0.361 |
| Group 8 (4.0 mg/kg AD09736) | 0.870 | 0.117 | 0.732 | 0.045 | 1.084 | 0.195 |
| Group 9 (2.0 mg/kg AD09736) | 0.867 | 0.088 | 0.809 | 0.100 | 1.187 | 0.254 |
| Group 10 (1.0 mg/kg AD09736) | 1.313 | 0.177 | 1.199 | 0.185 | 1.344 | 0.185 |
| Group 11 (4.0 mg/kg AD09937) | 0.540 | .0164 | 0.588 | 0.268 | 0.780 | 0.257 |
| Group 12 (2.0 mg/kg AD09937) | 0.636 | 0.249 | 0.812 | 0.480 | 0.846 | 0.312 |
| Group 13 (1.0 mg/kg AD09937) | 0.927 | 0.215 | 0.932 | 0.127 | 1.011 | 0.057 |

TABLE 39B

Average XDH Normalized to Pre-Treatment & Control in XDH-GLUC AAV Mice from Example 18

| Group ID | Day 8 Avg XDH | Day 8 Std Dev (+/−) | Day 15 Avg XDH | Day 15 Std Dev (+/−) | Day 22 Avg XDH | Day 22 Std Dev (+/−) |
|---|---|---|---|---|---|---|
| Group 1 (Saline vehicle) | 1.000 | 0.292 | 1.000 | 0.403 | 1.000 | 0.396 |
| Group 2 (4.0 mg/kg AD09744) | 0.455 | 0.095 | 0.347 | 0.091 | 0.415 | 0.043 |
| Group 3 (2.0 mg/kg AD09744) | 0.595 | 0.178 | 0.570 | 0.142 | 0.656 | 0.147 |
| Group 4 (1.0 mg/kg AD09744) | 0.763 | 0.084 | 0.724 | 0.132 | 0.760 | 0.172 |
| Group 5 (4.0 mg/kg AD10621) | 0.343 | 0.191 | 0.315 | 0.252 | 0.449 | 0.367 |
| Group 6 (2.0 mg/kg AD10621) | 0.441 | 0.220 | 0.353 | 0.193 | 0.442 | 0.237 |
| Group 7 (1.0 mg/kg AD10621) | 0.491 | 0.171 | 0.402 | 0.195 | 0.462 | 0.249 |
| Group 8 (4.0 mg/kg AD09736) | 0.736 | 0.099 | 0.629 | 0.039 | 0.748 | 0.135 |
| Group 9 (2.0 mg/kg AD09736) | 0.733 | 0.075 | 0.696 | 0.086 | 0.820 | 0.175 |
| Group 10 (1.0 mg/kg AD09736) | 1.110 | 0.150 | 1.031 | 0.159 | 0.928 | 0.128 |
| Group 11 (4.0 mg/kg AD09937) | 0.457 | 0.139 | 0.505 | 0.230 | 0.538 | 0.171 |
| Group 12 (2.0 mg/kg AD09937) | 0.538 | 0.210 | 0.698 | 0.413 | 0.584 | 0.216 |
| Group 13 (1.0 mg/kg AD09937) | 0.783 | 0.182 | 0.801 | 0.109 | 0.698 | 0.039 |

Example 19. In Vivo Testing of XDH RNAi Agents in XDH-GLuc AAV Mice

The XDH-GLUC AAV mouse model described in Example 2, using the XDH-GLuc AAV containing the 80-2899 region of the human XDH cDNA sequence was used. At day 1, each mouse was given a single subcutaneous administration of 200 µl/20 g animal weight containing either 4.0 mg/kg (mpk), 2.0 mg/kg (mpk) of an XDH RNAi agent formulated in isotonic saline, or vehicle control (isotonic saline with no RNAi agent), according to Table 40.

TABLE 40

Targeted Positions and Dosing Groups of Example 19

| Group | Targeted Gene Position (within SEQ ID NO: 1) | RNAi Agent and Dose | Dosing Regimen |
|---|---|---|---|
| 1 | 1963 | Saline (no RNAi agent) | Single injection on day 1 |
| 2 | 1963 | 4.0 mg/kg AD09736 | Single injection on day 1 |
| 3 | 1963 | 2.0 mg/kg AD09736 | Single injection on day 1 |

TABLE 40-continued

Targeted Positions and Dosing Groups of Example 19

| Group | Targeted Gene Position (within SEQ ID NO: 1) | RNAi Agent and Dose | Dosing Regimen |
|---|---|---|---|
| 4 | 1963 | 4.0 mg/kg AD10967 | Single injection on day 1 |
| 5 | 1963 | 2.0 mg/kg AD10967 | Single injection on day 1 |

TABLE 40-continued

Targeted Positions and Dosing Groups of Example 19

| Group | Targeted Gene Position (within SEQ ID NO: 1) | RNAi Agent and Dose | Dosing Regimen |
|---|---|---|---|
| 6 | 1963 | 4.0 mg/kg AD10968 | Single injection on day 1 |
| 7 | 1963 | 2.0 mg/kg AD10968 | Single injection on day 1 |
| 8 | 1963 | 4.0 mg/kg AD10969 | Single injection on day 1 |
| 9 | 1963 | 2.0 mg/kg AD10969 | Single injection on day 1 |

Each of the XDH RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents in Groups 2-9 each included nucleotide sequences that were designed to inhibit expression of an XDH gene at position 1963 of the gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8, day 15, and day 22, and XDH expression levels were determined pursuant to the procedure set forth in Example 2. Data from the experiment through day 22 are shown in Table 41:

TABLE 41

Average XDH Normalized to Pre-Treatment & Control in XDH-GLUC AAV Mice from Example 19

| Group ID | Day 8 Avg XDH | Day 8 Std Dev (+/−) | Day 15 Avg XDH | Day 15 Std Dev (+/−) | Day 22 Avg XDH | Day 22 Std Dev (+/−) |
|---|---|---|---|---|---|---|
| Group 1 (Saline vehicle) | 1.000 | 0.158 | 1.000 | 0.166 | 1.000 | 0.077 |
| Group 2 (4.0 mg/kg AD09736) | 0.607 | 0.088 | 0.704 | 0.077 | 0.635 | 0.230 |
| Group 3 (2.0 mg/kg AD09736) | 0.738 | 0.199 | 0.742 | 0.085 | 0.991 | 0.061 |
| Group 4 (4.0 mg/kg AD10967) | 0.468 | 0.115 | 0.542 | 0.083 | 0.714 | 0.131 |
| Group 5 (2.0 mg/kg AD10967) | 0.746 | 0.099 | 0.826 | 0.047 | 0.940 | 0.203 |
| Group 6 (4.0 mg/kg AD10968) | 0.520 | 0.131 | 0.488 | 0.149 | 0.685 | 0.176 |
| Group 7 (2.0 mg/kg AD10968) | 0.534 | 0.148 | 0.597 | 0.135 | 0.827 | 0.155 |
| Group 8 (4.0 mg/kg AD10969) | 0.614 | 0.194 | 0.617 | 0.211 | 0.758 | 0.264 |
| Group 9 (2.0 mg/kg AD10969) | 0.728 | 0.274 | 0.711 | 0.244 | 0.984 | 0.440 |

Example 20. In Vivo Testing of XDH RNAi Agents in XDH-GLuc AAV Mice

The XDH-GLUC AAV mouse model described in Example 2, using the XDH-GLuc AAV containing the 2820-5715 region of the human XDH cDNA sequence was used. At day 1, each mouse was given a single subcutaneous administration of 200 μl/20 g animal weight containing either 4.0 mg/kg (mpk), 2.0 mg/kg (mpk), 1.0 mg/kg (mpk) of an XDH RNAi agent formulated in isotonic saline, or vehicle control (isotonic saline with no RNAi agent), according to Table 42.

TABLE 42

Targeted Positions and Dosing Groups of Example 20

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 4289 | 4.0 mg/kg AD09611 | Single injection on day 1 |
| 3 | 4289 | 2.0 mg/kg AD09611 | Single injection on day 1 |
| 4 | 4289 | 1.0 mg/kg AD09611 | Single injection on day 1 |
| 5 | 4289 | 4.0 mg/kg AD10631 | Single injection on day 1 |
| 6 | 4289 | 2.0 mg/kg AD10631 | Single injection on day 1 |
| 7 | 4289 | 1.0 mg/kg AD10631 | Single injection on day 1 |
| 8 | 3598 | 4.0 mg/kg AD09985 | Single injection on day 1 |
| 9 | 3598 | 2.0 mg/kg AD09985 | Single injection on day 1 |
| 10 | 3598 | 1.0 mg/kg AD09985 | Single injection on day 1 |

Each of the XDH RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents in Groups 2-10 each included nucleotide sequences that were designed to inhibit expression of an XDH gene at positions 4289 and 3598 of the gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8, day 15, and day 22, and XDH expression levels were determined pursuant to the procedure set forth in Example 2. Data from the experiment through day 22 are shown in Table 43:

TABLE 43

Average XDH Normalized to Pre-Treatment & Control in XDH-GLUC AAV Mice from Example 20

| | Day 8 | | Day 15 | | Day 22 | |
|---|---|---|---|---|---|---|
| Group ID | Avg XDH | Std Dev (+/−) | Avg XDH | Std Dev (+/−) | Avg XDH | Std Dev (+/−) |
| Group 1 (Saline vehicle) | 1.000 | 0.209 | 1.000 | 0.098 | 1.000 | 0.222 |
| Group 2 (4.0 mg/kg AD09611) | 0.892 | 0.047 | 0.777 | 0.181 | 0.829 | 0.213 |
| Group 3 (2.0 mg/kg AD09611) | 0.703 | 0.168 | 0.699 | 0.159 | 0.789 | 0.209 |
| Group 4 (1.0 mg/kg AD09611) | 0.868 | 0.183 | 0.843 | 0.071 | 0.729 | 0.136 |
| Group 5 (4.0 mg/kg AD10631) | 0.642 | 0.082 | 0.651 | 0.058 | 0.644 | 0.153 |
| Group 6 (2.0 mg/kg AD10631) | 0.660 | 0.192 | 0.594 | 0.082 | 0.557 | 0.102 |
| Group 7 (1.0 mg/kg AD10631) | 0.626 | 0.060 | 0.649 | 0.089 | 0.720 | 0.143 |
| Group 8 (4.0 mg/kg AD09985) | 0.600 | 0.360 | 0.600 | 0.341 | 0.586 | 0.209 |
| Group 9 (2.0 mg/kg AD09985) | 0.576 | 0.119 | 0.519 | 0.025 | 0.619 | 0.088 |
| Group 10 (1.0 mg/kg AD09985) | 0.710 | 0.163 | 0.641 | 0.086 | 0.631 | 0.136 |

Example 21. In Vivo Testing of XDH RNAi Agents in Cynomolgus Monkeys

XDH RNAi agent AD09611, which was previously evaluated in cynomolgus monkeys (cynos) in the study described in Example 13, was further evaluated in cynomolgus monkeys (cynos). On days 1, 15, and 29, three male cynos for each group (n=3) were administered a subcutaneous injection of 0.3 mL/kg (approximately 1.5 mL volume, depending on animal mass) containing 3.0 mg/kg (10 mg/mL) of the respective XDH RNAi agent, formulated in isotonic saline.

TABLE 44

Targeted Positions and Dosing Groups of Example 21

| Group | Targeted Gene Position (within SEQ ID NO: 1) | RNAi Agent and Dose | Dosing Regimen (on days 1, 15, and 29) |
|---|---|---|---|
| 1 | 4289 | 3.0 mg/kg AD09611 | Three subcutaneous injections |
| 2 | 4289 | 3.0 mg/kg AD09611 | Three subcutaneous injections |

The XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents included nucleotide sequences that were designed to inhibit expression of a human XDH gene at the specific positions as shown in Table 43, above. (See, e.g., SEQ ID NO:1 and Table 2 for the XDH gene referenced).

On days −14, 29, 57, and 85, liver biopsies were taken from Group 1 animals. On days −7, 43, 71, and 99, liver biopsies were taken from Group 2 animals. On the date of each biopsy collection, cynos were sedated and Menghini technique was used to extract two liver tissue samples, and aliquots of approximately 10 mg were snap-frozen and stored at −70° C. until analysis. The biopsy samples were then homogenized, and levels of cXDH mRNA in the cyno livers were measured by RT-qPCR using a housekeeping gene as reference. Resulting values were then normalized to the pre-dose (in this case, at day −14 or −7, depending on the animals) cXDH mRNA measurements. The resulting mRNA data are reflected in the following Table 45:

TABLE 45

Cyno XDH mRNA Levels Normalized to Pre-Dose (Day −14 or −7) from Example 21 for each Group (n = 3)

| | Relative cXDH mRNA Expression | Low Error | High Error | Relative cXDH mRNA Expression | Low Error | High Error |
|---|---|---|---|---|---|---|
| | Pre-Dose (Day −14 or Day −7) | | | Day 29 | | |
| Group 1: AD09611 | 1.000 | 0.177 | 0.215 | 0.595 | 0.097 | 0.116 |
| Group 2: AD09611 | 1.000 | 0.083 | 0.091 | NA | NA | NA |
| | Day 43 | | | Day 57 | | |
| Group 1: AD09611 | | | | 0.429 | 0.105 | 0.138 |
| Group 2: AD09611 | 0.604 | 0.060 | 0.067 | | | |
| | Day 71 | | | Day 85 | | |
| Group 1: AD09611 | | | | 0.560 | 0.079 | 0.092 |
| Group 2: AD09611 | 0.758 | 0.121 | 0.144 | | | |
| | Day 99 | | | | | |
| Group 1: AD09611 | | | | | | |
| Group 2: AD09611 | 0.950 | 0.066 | 0.071 | | | |

Additionally, XDH activity was assessed using the XDH Activity Assay method described in Example 13. The resulting XDH activity data are shown in Table 46.

TABLE 46

Cyno XDH Activity Levels Normalized to Pre-Dose (Day −14 or −7) from Example 21 for each Group (n = 3)

|  | Relative XDH Activity | Std Dev (+/−) | Relative XDH Activity | Std Dev (+/−) | Relative XDH Activity | Std Dev (+/−) | Relative XDH Activity | Std Dev (+/−) |
|---|---|---|---|---|---|---|---|---|
|  | Pre-Dose (Day −14 or Day −7) | | Day 29 | | Day 43 | | Day 57 | |
| Group 1: AD09611 | 1.000 | 0.01 | 0.290 | 0.004 | | | 0.391 | 0.15 |
| Group 2: AD09611 | 1.000 | 0.012 | | | 0.394 | 0.066 | | |
|  | Day 71 | | Day 85 | | Day 99 | | | |
| Group 1: AD09611 | | | 0.341 | 0.079 | | | | |
| Group 2: AD09611 | 0.357 | 0.098 | | | 0.465 | 0.067 | | |

As shown in Table 46, AD09611 showed XDH activity reductions of up to 70% as measured on day 29, and reductions were maintained at greater than 50% through day 99.

Example 22. In Vivo Testing of XDH RNAi Agents in Cynomolgus Monkeys

XDH RNAi agents AD10631, AD09736, AD10621, and AD09985 were evaluated in cynomolgus monkeys (cynos). On days 1, 15, and 29, three male cynos for each group (n=3) were administered a subcutaneous injection of 0.3 mL/kg (approximately 1.5 mL volume, depending on animal mass) containing 3.0 mg/kg (10 mg/mL) of the respective XDH RNAi agent, formulated in isotonic saline.

TABLE 47

Targeted Positions and Dosing Groups of Example 22

| Group | Targeted Gene Position (within SEQ ID NO: 1) | RNAi Agent and Dose | Dosing Regimen (on days 1, 15, and 29) |
|---|---|---|---|
| 1 | 4289 | 3.0 mg/kg AD10631 | Three subcutaneous injections |
| 2 | 1963 | 3.0 mg/kg AD09736 | Three subcutaneous injections |
| 3 | 2696 | 3.0 mg/kg AD10621 | Three subcutaneous injections |
| 4 | 3598 | 3.0 mg/kg AD09985 | Three subcutaneous injections |

The XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents included nucleotide sequences that were designed to inhibit expression of a human XDH gene at the specific positions as shown in Table 47. (See, e.g., SEQ ID NO:1 and Table 2 for the XDH gene referenced). As noted herein, AD10631 was designed to target position 4289 and was comprised of a chemically modified nucleotide sequence similar to AD09611, but included a 5'-cyclopropyl-phosphonate modified nucleotide at the 5' terminal end of the antisense strand.

On days −7, 43, 71, and 99, liver biopsies were taken. On the date of each biopsy collection, cynos were sedated and 3.5 mm×310 mm clamshell biopsy forceps were used to extract one liver tissue sample approximately 160 mg to 240 mg, and aliquots of approximately 50 mg were snap-frozen and stored at −70° C. until analysis. The biopsy samples were then homogenized, and levels of cXDH mRNA in the cyno livers were measured by RT-qPCR using a housekeeping gene as reference. Resulting values were then normalized to the pre-dose (in this case, at day −7) cXDH mRNA measurements. The resulting mRNA data are reflected in Table 48:

TABLE 48

Cyno XDH mRNA Levels Normalized to Pre-Dose (Day −7) from Example 22 for each Group (n = 3)

|  | Relative cXDH mRNA Expression | Low Error | High Error | Relative cXDH mRNA Expression | Low Error | High Error |
|---|---|---|---|---|---|---|
|  | Pre-Dose (Day −7) | | | Day 43 | | |
| Group 1: AD10631 | 1.000 | 0.093 | 0.102 | 0.459 | 0.062 | 0.072 |
| Group 2: AD09736 | 1.000 | 0.120 | 0.136 | 0.420 | 0.076 | 0.092 |
| Group 3: AD10621 | 1.000 | 0.113 | 0.127 | 0.373 | 0.025 | 0.027 |
| Group 4: AD09985 | 1.000 | 0.084 | 0.091 | 0.413 | 0.081 | 0.101 |
|  | Day 71 | | | Day 99 | | |
| Group 1: AD10631 | 0.413 | 0.036 | 0.040 | 0.595 | 0.055 | 0.060 |
| Group 2: AD09736 | 0.478 | 0.072 | 0.085 | 0.502 | 0.126 | 0.168 |
| Group 3: AD10621 | 0.397 | 0.029 | 0.031 | 0.477 | 0.038 | 0.042 |
| Group 4: AD09985 | 0.339 | 0.047 | 0.055 | 0.459 | 0.107 | 0.140 |

Additionally, XDH activity was assessed using the XDH Activity Assay method described in Example 13. The resulting XDH activity data are shown in Table 49.

TABLE 49

Cyno XDH Activity Levels Normalized to Pre-Dose (Day −7)
from Example 22 for each Group (n = 3)

|  | Pre-Dose (Day −7) | | Day 43 | | Day 71 | | Day 98 | |
| --- | --- | --- | --- | --- | --- | --- | --- | --- |
|  | Relative XDH Activity | Std Dev (+/−) | Relative XDH Activity | Std Dev (+/−) | Relative XDH Activity | Std Dev (+/−) | Relative XDH Activity | Std Dev (+/−) |
| Group 1: AD10631 | 1 | 0.000 | 0.268 | 0.060 | 0.273 | 0.049 | 0.553 | 0.135 |
| Group 2: AD09736 | 1 | 0.000 | 0.091 | 0.019 | 0.130 | 0.036 | 0.232 | 0.069 |
| Group 3: AD10621 | 1 | 0.000 | 0.052 | 0.004 | 0.161 | 0.063 | 0.186 | 0.080 |
| Group 4: AD09985 | 1 | 0.000 | 0.074 | 0.011 | 0.146 | 0.044 | 0.199 | 0.149 |

As noted above, each of AD09736 (Group 2), AD010621 (Group 3), and AD09985 (Group 4) obtained 90% or greater reductions in XDH activity, indicating these are highly potent XDH RNAi agents capable of reducing XDH protein expression by 90% in liver cells (hepatocytes). AD10631 was reported to have a 74% reduction in XDH activity, which is similar to what was seen with the XDH activity assay performed on cyno liver biopsy samples administered AD09611 (which targeted the same position on the XDH gene as AD10631) as reported in Example 13 and Example 21.

Example 23. In Vitro Testing of XDH RNAi Agents

Candidate sequence duplexes shown below in Table 50 were tested in vitro. The XDH RNAi agents were prepared in accordance with the procedures set forth in Example 1. The XDH RNAi agents included modified nucleotides that were conjugated at the 5′ terminal end of the sense strand to a targeting ligand that included three N-acetyl-galactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand).

TABLE 50

XDH RNAi Agents Tested for In Vitro Free Uptake Assay in Primary Human and Cynomolgus Monkey Hepatocytes

| RNAi Agent | Targeted Gene Position (within SEQ ID NO: 1) |
| --- | --- |
| AD09218 | 488 |
| AD09744 | 2696 |
| AD10012 | 2696 |
| AD10621 | 2696 |
| AD09736 | 1963 |
| AD09937 | 1963 |
| AD10278 | 1963 |
| AD09218 | 488 |
| AD09985 | 3598 |
| AD10731 | 3598 |
| AD09611 | 4289 |
| AD10184 | 4289 |
| AD10631 | 4289 |

Evaluation of XDH RNAi agents in vitro was performed by seeding primary human or cynomolgus monkey hepatocytes cells. Cells were seeded at 25,000 cells per well in 50 μL culture medium in 96-well collagen coated plate. Cells were treated with each of the XDH RNAi agent duplexes shown in Table 50 immediately after cells were seeded by adding 50 μL per well at 2× the final concentration, followed by gentle mixing and incubation at 37° C., 5% $CO_2$, for 48 hours without disturbing the cells. Isolation and purification of RNA was completed using a commercially available kit according to the manufacturer's instructions (Zymo Quick-RNA Miniprep Kit (Zymo Research, Irvine, Calif.)). Relative expression of each of the XDH RNAi agents was determined by qRT-PCR by comparing the expression levels of XDH mRNA to an endogenous control (PPIA).

A serial dilution of the RNAi agents was performed and the data curve fit to calculate the dose (concentration) required to knock down gene expression by 50% ("EC50," or effective concentration estimated to reduce gene expression by 50%). Residual XDH gene activity and EC50 of the XDH RNAi agents are shown below in Tables 51 and 52. Thus, for example, for RNAi agent AD10012, in primary human hepatocytes, at 1 nM, results in 0.2485 residual XDH gene relative expression, or 75.15% XDH gene knockdown. As further provided in Table 51, AD10012 was reported to have an EC50 of 0.012 nM (6 point repeat with free uptake in primary human hepatocytes), meaning AD10012 achieves 50% XDH gene knockdown at 0.012 nM concentration.

TABLE 51

In vitro inhibition of XDH RNAi Agents by free uptake in primary human hepatocytes

| RNAi Agent | RNAi Agent Concentration | | | | | | | | | | | | EC50 (nM) |
|---|---|---|---|---|---|---|---|---|---|---|---|---|---|
| | 0.01 nM Avg | SD | 0.1 nM | SD | 1 nM | SD | 10 nM | SD | 100 nM | SD | 1000 nM | SD | |
| AD09218 | 1.1908 | 0.4415 | 0.7427 | 0.2296 | 0.3515 | 0.1042 | 0.3459 | 0.1794 | 0.2624 | 0.0653 | 0.3672 | 0.1138 | 0.073 |
| AD09744 | 1.1048 | 0.2004 | 0.6711 | 0.0780 | 0.6122 | 0.0581 | 0.1599 | 0.0769 | 0.3055 | 0.0624 | 0.3551 | 0.1225 | 0.098 |
| AD10012 | 0.8735 | 0.0804 | 0.3435 | 0.0463 | 0.2485 | 0.0293 | 0.1707 | 0.1403 | 0.1840 | 0.0354 | 0.2882 | 0.1552 | 0.012 |
| AD10621 | 0.6962 | 0.1486 | 0.3373 | 0.0537 | 0.2388 | 0.0516 | 0.1614 | 0.0148 | 0.1714 | 0.0338 | 0.1947 | 0.0297 | 0.033 |
| AD09736 | 0.6916 | 0.0306 | 0.3905 | 0.0993 | 0.2970 | 0.0661 | 0.1534 | 0.0956 | 0.2394 | 0.0955 | 0.1572 | 0.0313 | 0.059 |
| AD09937 | 0.7534 | 0.1915 | 0.3373 | 0.0449 | 0.1919 | 0.0562 | 0.2224 | 0.0745 | 0.1309 | 0.0274 | 0.1282 | 0.0160 | 0.029 |
| AD10278 | 0.8245 | 0.1510 | 0.3776 | 0.0823 | 0.2635 | 0.0463 | 0.2347 | 0.0524 | 0.1359 | 0.0275 | 0.1295 | 0.0362 | 0.036 |
| AD09218 | 0.7578 | 0.4480 | 0.4888 | 0.0416 | 0.4312 | 0.1623 | 0.2016 | 0.0565 | 0.1651 | 0.0731 | 0.2039 | 0.0753 | 0.035 |
| AD09985 | 0.9439 | 0.0347 | 0.7353 | 0.1957 | 0.3808 | 0.1059 | 0.2642 | 0.0402 | 0.2657 | 0.0527 | 0.2820 | 0.1093 | 0.190 |
| AD10731 | 0.9885 | 0.0470 | 0.5503 | 0.0816 | 0.3282 | 0.0367 | 0.3649 | 0.1127 | 0.2777 | 0.0134 | 0.2634 | 0.0412 | 0.042 |
| AD09611 | 0.9968 | 0.0629 | 1.0892 | 0.2769 | 0.9445 | 0.0773 | 0.7137 | 0.1343 | 0.4735 | 0.0527 | 0.3751 | 0.0702 | 9.607 |
| AD10184 | 0.9568 | 0.1924 | 0.6296 | 0.0664 | 0.3272 | 0.0500 | 0.2448 | 0.0108 | 0.1962 | 0.0357 | 0.1766 | 0.0323 | 0.117 |
| AD10631 | 0.9386 | 0.0626 | 0.4900 | 0.1062 | 0.3561 | 0.0780 | 0.3252 | 0.1326 | 0.2606 | 0.0450 | 0.1594 | 0.0271 | 0.040 |

TABLE 52

In vitro inhibition of XDH RNAi Agents by free uptake in primary cynomolgus monkey hepatocytes

| RNAi Agent | RNAi Agent Concentration | | | | | | | | | | | | EC50, number of repeat points EC50 (nM), 6x |
|---|---|---|---|---|---|---|---|---|---|---|---|---|---|
| | 0.06 nM | SD | 0.49 nM | SD | 3.91 nM | SD | 31.25 nM | SD | 250 nM | SD | 2000 nM | SD | |
| AD09218 | 0.7835 | 0.1158 | 0.5673 | 0.0789 | 0.5559 | 0.1965 | 0.3457 | 0.1295 | 0.3402 | 0.0323 | 0.3044 | 0.0532 | 3.767 |
| AD09744 | 0.7400 | 0.0417 | 0.5543 | 0.0606 | 0.4657 | 0.0987 | 0.3451 | 0.0901 | 0.3667 | 0.0903 | 0.3446 | 0.1180 | 0.5439 |
| AD10012 | 0.6654 | 0.0098 | 0.4408 | 0.1139 | 0.3365 | 0.0168 | 0.2600 | 0.0335 | 0.2525 | 0.0334 | 0.2234 | 0.0236 | 0.3707 |
| AD10621 | 0.5571 | 0.1315 | 0.4494 | 0.1035 | 0.3046 | 0.1092 | 0.3036 | 0.0667 | 0.2430 | 0.0764 | 0.1819 | 0.0379 | 1.03 |
| AD09736 | 0.5093 | 0.0602 | 0.3650 | 0.0643 | 0.2476 | 0.0325 | 0.2683 | 0.0184 | 0.1759 | 0.0188 | 0.2002 | 0.0517 | 0.4216 |
| AD09937 | 0.5609 | 0.0444 | 0.3441 | 0.0388 | 0.2705 | 0.0203 | 0.2531 | 0.0565 | 0.1845 | 0.0197 | 0.1933 | 0.0394 | 0.2249 |
| AD10278 | 0.4772 | 0.0029 | 0.3957 | 0.0457 | 0.2929 | 0.0667 | 0.2837 | 0.0210 | 0.1784 | 0.0163 | 0.2003 | 0.0536 | 1.918 |
| AD09218 | 0.8383 | 0.2444 | 0.6405 | 0.1284 | 0.5279 | 0.0812 | 0.3616 | 0.0964 | 0.2885 | 0.0710 | 0.3272 | 0.0644 | 2.04 |
| AD09985 | 0.8656 | 0.0630 | 0.5815 | 0.0823 | 0.5065 | 0.0684 | 0.4399 | 0.0955 | 0.2934 | 0.0512 | 0.2938 | 0.0481 | 0.4581 |
| AD10731 | 0.7837 | 0.1459 | 0.4582 | 0.1026 | 0.3867 | 0.1169 | 0.4410 | 0.1221 | 0.2709 | 0.0683 | 0.2992 | 0.0018 | 0.09407 |
| AD09611 | 0.6219 | 0.0679 | 0.8340 | 0.1089 | 0.3923 | 0.1597 | 0.5281 | 0.1568 | 0.4321 | 0.0247 | 0.3780 | 0.0137 | 20.19 |
| AD10184 | 0.6263 | 0.0080 | 0.4306 | 0.0235 | 0.4214 | 0.0468 | 0.3293 | 0.0610 | 0.2743 | 0.0341 | 0.1787 | 0.0679 | 0.5228 |
| AD10631 | 0.5973 | 0.0231 | 0.5815 | 0.0713 | 0.5537 | 0.1817 | 0.5543 | 0.1779 | 0.3033 | 0.0283 | 0.3341 | 0.0497 | 77.08 |

Example 24. In Vivo Testing of XDH RNAi Agents in XDH-GLuc AAV Mice

The XDH-GLUC AAV mouse model described in Example 2, using the XDH-GLuc AAV containing the 80-2899 region of the human XDH cDNA sequence was used. At day 1, each mouse was given a single subcutaneous administration of 250 μl/25 g animal weight containing 2.0 mg/kg (mpk) of an XDH RNAi agent formulated in isotonic saline, or vehicle control (isotonic saline with no RNAi agent), according to Table 53.

TABLE 53

Targeted Positions and Dosing Groups of Example 24

| Group | Targeted Gene Position (within SEQ ID NO: 1) | RNAi Agent and Dose | Dosing Regimen |
|---|---|---|---|
| 1 | 2696 | Saline (no RNAi agent) | Single injection on day 1 |
| 2 | 2696 | 2.0 mg/kg AD09744 | Single injection on day 1 |
| 3 | 2696 | 2.0 mg/kg AD10012 | Single injection on day 1 |
| 4 | 2696 | 2.0 mg/kg AD10619 | Single injection on day 1 |

TABLE 53-continued

Targeted Positions and Dosing Groups of Example 24

| Group | Targeted Gene Position (within SEQ ID NO: 1) | RNAi Agent and Dose | Dosing Regimen |
|---|---|---|---|
| 5 | 2696 | 2.0 mg/kg AD10620 | Single injection on day 1 |
| 6 | 2696 | 2.0 mg/kg AD10621 | Single injection on day 1 |
| 7 | 2696 | 2.0 mg/kg AD10622 | Single injection on day 1 |
| 8 | 2696 | 2.0 mg/kg AD10623 | Single injection on day 1 |
| 9 | 2696 | 2.0 mg/kg AD10624 | Single injection on day 1 |
| 10 | 2696 | 2.0 mg/kg AD10625 | Single injection on day 1 |
| 11 | 2696 | 2.0 mg/kg AD10626 | Single injection on day 1 |
| 12 | 2696 | 2.0 mg/kg AD10627 | Single injection on day 1 |

Each of the XDH RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents in Groups 2-12 each included nucleotide sequences that were designed to inhibit expression of an XDH gene at position 2696 of the gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8, day 15, and day 22, and XDH expression levels were determined pursuant to the procedure set forth in Example 2. Data from the experiment through day 22 are shown in Table 54:

TABLE 54

Average XDH Normalized to Pre-Treatment & Control in XDH-GLUC AAV Mice from Example 24

| | Day 8 | | Day 15 | | Day 22 | |
|---|---|---|---|---|---|---|
| Group ID | Avg XDH | Std Dev (+/−) | Avg XDH | Std Dev (+/−) | Avg XDH | Std Dev (+/−) |
| Group 1 (Saline vehicle) | 1.000 | 0.107 | 1.000 | 0.172 | 1.000 | 0.233 |
| Group 2 (2.0 mg/kg AD09744) | 0.585 | 0.079 | 0.616 | 0.024 | 0.659 | 0.088 |
| Group 3 (2.0 mg/kg AD10012) | 0.336 | 0.034 | 0.305 | 0.014 | 0.343 | 0.018 |
| Group 4 (2.0 mg/kg AD10619) | 0.397 | 0.034 | 0.415 | 0.011 | 0.415 | 0.046 |
| Group 5 (2.0 mg/kg AD10620) | 0.394 | 0.049 | 0.326 | 0.046 | 0.306 | 0.053 |
| Group 6 (2.0 mg/kg AD10621) | 0.403 | 0.038 | 0.312 | 0.049 | 0.348 | 0.026 |
| Group 7 (2.0 mg/kg AD10622) | 0.382 | 0.068 | 0.317 | 0.061 | 0.338 | 0.065 |
| Group 8 (2.0 mg/kg AD10623) | 0.280 | 0.124 | 0.268 | 0.053 | 0.258 | 0.137 |
| Group 9 (2.0 mg/kg AD10624) | 0.302 | 0.069 | 0.362 | 0.091 | 0.376 | 0.174 |
| Group 10 (2.0 mg/kg AD10625) | 0.341 | 0.048 | 0.342 | 0.096 | 0.412 | 0.079 |
| Group 11 (2.0 mg/kg AD10626) | 0.436 | 0.078 | 0.394 | 0.063 | 0.415 | 0.035 |
| Group 12 (2.0 mg/kg AD10627) | 0.317 | 0.041 | 0.325 | 0.023 | 0.322 | 0.041 |

Example 25. In Vivo Testing of XDH RNAi Agents in Cynomolgus Monkeys

XDH RNAi agents AD10621 and AD09985 were evaluated in cynomolgus monkeys (cynos). On day 1, three male cynos for each group (n=3) were administered a subcutaneous injection of 0.3 mL/kg (approximately 1.5 mL volume, depending on animal mass) containing 3 mg/kg or 1 mg/kg of the respective XDH RNAi agent, formulated in isotonic saline.

TABLE 55

Targeted Positions and Dosing Groups of Example 22

| Group | Targeted Gene Position (within SEQ ID NO: 1) | RNAi Agent and Dose | Dosing Regimen (on day 1) |
|---|---|---|---|
| 1 | 2696 | 3.0 mg/kg AD10621 | Single subcutaneous injection |
| 2 | 3598 | 3.0 mg/kg AD09985 | Single subcutaneous injection |
| 3 | 2696 | 1.0 mg/kg AD10621 | Single subcutaneous injection |
| 4 | 3598 | 1.0 mg/kg AD09985 | Single subcutaneous injection |

The XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents included nucleotide sequences that were designed to inhibit expression of a human XDH gene at the specific positions as shown in Table 55. (See, e.g., SEQ ID NO:1 and Table 2 for the XDH gene referenced).

On days −6 (day −3 for one of the animals), 29, 55, and 99 (day 100 for one of the animals), liver biopsies were taken. On the date of each biopsy collection, cynos were sedated and needles were used to extract two liver tissue samples approximately 20 mg each. Samples were weighed, snap-frozen and stored at −70° C. until analysis. The biopsy samples were then homogenized, and levels of cXDH mRNA in the cyno livers were measured by RT-qPCR using a housekeeping gene as reference. Resulting values were then normalized to the pre-dose (in this case, at day −6 or day −3) cXDH mRNA measurements. The resulting mRNA data are reflected in Table 56:

TABLE 56

Cyno XDH mRNA Levels Normalized to Pre-Dose (Day −6 or Day −3) from Example 25 for each Group (n = 3)

| | Relative cXDH mRNA Expression | Low Error | High Error | Relative cXDH mRNA Expression | Low Error | High Error |
|---|---|---|---|---|---|---|
| | Pre-Dose (Day −6 or Day −3) | | | Day 29 | | |
| Group 1: AD10621 | 1.000 | 0.107 | 0.120 | 0.585 | 0.098 | 0.118 |
| Group 2: AD09985 | 1.000 | 0.039 | 0.041 | 0.695 | 0.072 | 0.080 |
| Group 3: AD10621 | 1.000 | 0.114 | 0.128 | 0.864 | 0.138 | 0.165 |
| Group 4: AD09985 | 1.000 | 0.121 | 0.138 | 0.691 | 0.131 | 0.162 |
| | Day 55 | | | Day 99 or Day 100 | | |
| Group 1: AD10621 | 0.687 | 0.052 | 0.056 | 0.793 | 0.082 | 0.092 |
| Group 2: AD09985 | 0.708 | 0.087 | 0.100 | 0.678 | 0.121 | 0.148 |
| Group 3: AD10621 | 0.666 | 0.148 | 0.190 | 0.693 | 0.125 | 0.153 |
| Group 4: AD09985 | 0.720 | 0.112 | 0.132 | 0.676 | 0.149 | 0.191 |

Additionally, XDH activity was assessed using the XDH Activity Assay method described in Example 13. The resulting XDH activity data are shown in Table 57.

TABLE 57

Cyno XDH Activity Levels Normalized to Pre-Dose (Day −6) from Example 25 for each Group (n = 3)

|  | Pre-Dose (Day −6 or Day −3) | | Day 29 | | Day 55 | | Day 99 or Day 100 | |
| --- | --- | --- | --- | --- | --- | --- | --- | --- |
|  | Relative XDH Activity | Std Dev (+/−) | Relative XDH Activity | Std Dev (+/−) | Relative XDH Activity | Std Dev (+/−) | Relative XDH Activity | Std Dev (+/−) |
| Group 1: AD10621 | 1 | 0.000 | 0.153 | 0.0048 | 0.399 | 0.2224 | 0.855 | 0.2914 |
| Group 2: AD09985 | 1 | 0.000 | 0.109 | 0.0139 | 0.221 | 0.1523 | 0.649 | 0.1959 |
| Group 3: AD10621 | 1 | 0.000 | 0.236 | 0.0452 | 0.343 | 0.3047 | 0.681 | 0.0675 |
| Group 4: AD09985 | 1 | 0.000 | 0.506 | 0.2290 | 0.517 | 0.2206 | 1.215 | 0.1157 |

As noted above, each of AD10621 (Group 1) and AD09985 (Group 2) obtained ~85% or greater reductions in XDH activity, indicating these are highly potent XDH RNAi agents capable of reducing XDH protein expression by ~85% in liver cells (hepatocytes).

Example 26. In Vivo Testing of XDH RNAi Agents in XDH-GLuc AAV Mice

The XDH-GLUC AAV mouse model described in Example 2, above, using the XDH-GLuc AAV containing the 80-2899 region of the human XDH cDNA sequence was used. At day 1, each mouse was given a single subcutaneous administration of 250 μl/25 g animal weight containing either 2.0 mg/kg (mpk) of an XDH RNAi agent formulated in isotonic saline, or vehicle control (isotonic saline with no RNAi agent), according to the following Table 58.

TABLE 58

Targeted Positions and Dosing Groups of Example 26

| Group | Targeted Gene Position (within SEQ ID NO: 1) | RNAi Agent and Dose | Dosing Regimen |
| --- | --- | --- | --- |
| 1 | N/A | Saline (no RNAi agent) | Single injection on day 1 |
| 2 | 488 | 2.0 mg/kg AD09218 | Single injection on day 1 |
| 3 | 139 | 2.0 mg/kg AD09725 | Single injection on day 1 |
| 4 | 235 | 2.0 mg/kg AD09598 | Single injection on day 1 |
| 5 | 239 | 2.0 mg/kg AD09726 | Single injection on day 1 |
| 6 | 332 | 2.0 mg/kg AD09727 | Single injection on day 1 |
| 7 | 2320 | 2.0 mg/kg AD09741 | Single injection on day 1 |

TABLE 58-continued

Targeted Positions and Dosing Groups of Example 26

| Group | Targeted Gene Position (within SEQ ID NO: 1) | RNAi Agent and Dose | Dosing Regimen |
| --- | --- | --- | --- |
| 8 | 2357 | 2.0 mg/kg AD09742 | Single injection on day 1 |
| 9 | 2361 | 2.0 mg/kg AD09743 | Single injection on day 1 |
| 10 | 2696 | 2.0 mg/kg AD09744 | Single injection on day 1 |
| 11 | 2701 | 2.0 mg/kg AD09745 | Single injection on day 1 |

Each of the XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents of Groups 2-11 all included nucleotide sequences that were designed to inhibit expression of an XDH gene at the positions of the gene listed on Table 58. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8, day 15 and day 22, and XDH expression levels were determined pursuant to the procedure set forth in Example 2, above. Data from the experiment through day 22 are shown in the following Table 59:

TABLE 59

Average XDH Normalized to Pre-Treatment & Control in XDH-GLUC AAV Mice from Example 26

|  | Day 8 | | Day 15 | | Day 22 | |
| --- | --- | --- | --- | --- | --- | --- |
| Group ID | Avg XDH | Std Dev (+/−) | Avg XDH | Std Dev (+/−) | Avg XDH | Std Dev (+/−) |
| Group 1 (Saline vehicle) | 1.000 | 0.066 | 1.000 | 0.104 | 1.000 | 0.084 |
| Group 2 2.0 mg/kg AD09218 | 0.350 | 0.043 | 0.376 | 0.038 | 0.400 | 0.079 |
| Group 3 2.0 mg/kg AD09725 | 0.748 | 0.134 | 0.853 | 0.059 | 0.871 | 0.129 |
| Group 4 2.0 mg/kg AD09598 | 0.729 | 0.070 | 0.935 | 0.235 | 1.073 | 0.092 |
| Group 5 2.0 mg/kg AD09726 | 0.651 | 0.104 | 0.747 | 0.154 | 0.806 | 0.161 |
| Group 6 2.0 mg/kg AD09727 | 0.885 | 0.051 | 0.927 | 0.127 | 0.929 | 0.140 |
| Group 7 2.0 mg/kg AD09741 | 0.616 | 0.090 | 0.693 | 0.064 | 0.708 | 0.110 |
| Group 8 2.0 mg/kg AD09742 | 0.724 | 0.101 | 0.896 | 0.143 | 0.863 | 0.139 |
| Group 9 2.0 mg/kg AD09743 | 0.803 | 0.060 | 0.907 | 0.107 | 0.841 | 0.130 |

TABLE 59-continued

Average XDH Normalized to Pre-Treatment & Control in XDH-GLUC AAV Mice from Example 26

| | Day 8 | | Day 15 | | Day 22 | |
|---|---|---|---|---|---|---|
| Group ID | Avg XDH | Std Dev (+/−) | Avg XDH | Std Dev (+/−) | Avg XDH | Std Dev (+/−) |
| Group 10 2.0 mg/kg AD09744 | 0.477 | 0.051 | 0.576 | 0.170 | 0.558 | 0.132 |
| Group 11 2.0 mg/kg AD09745 | 0.568 | 0.045 | 0.626 | 0.062 | 0.719 | 0.045 |

Example 27. In Vivo Testing of XDH RNAi Agents in XDH-GLuc AAV Mice

The XDH-GLUC AAV mouse model described in Example 2, above, using the XDH-GLuc AAV containing the 80-2899 region of the human XDH cDNA sequence was used. At day 1, each mouse was given a single subcutaneous administration of 250 μl/25 g animal weight containing either 2.0 mg/kg (mpk) or 4.0 mg/kg (mpk) of an XDH RNAi agent formulated in isotonic saline, or vehicle control (isotonic saline with no RNAi agent), according to the following Table 60.

Each of the XDH RNAi agents included modified nucleotides that were conjugated at the 5' terminal end of the sense strand to a targeting ligand that included three N-acetylgalactosamine groups (tridentate ligand) having the modified sequences as set forth in the duplex structures herein. (See Tables 3, 4, 5A, 5B, 5C, and 6 for specific modifications and structure information related to the XDH RNAi agents, including (NAG37)s ligand). The XDH RNAi agents of Groups 2-9 all included nucleotide sequences that were designed to inhibit expression of an XDH gene at positions 2696 and 2701 of the gene. (See, e.g., SEQ ID NO:1 and Table 2 for the XDH gene referenced).

The injections were performed between the skin and muscle (i.e. subcutaneous injections) into the loose skin over the neck and shoulder area. Four (4) mice in each group were tested (n=4). Serum was collected on day 1 (pre-treatment), day 8, day 15 and day 22, and XDH expression levels were determined pursuant to the procedure set forth in Example 2, above. Data from the experiment through day 22 are shown in the following Table 60.

TABLE 60

Average XDH Normalized to Pre-Treatment & Control in XDH-GLUC AAV Mice from Example 27

| | Day 8 | | Day 15 | | Day 22 | |
|---|---|---|---|---|---|---|
| Group ID | Avg XDH | Std Dev (+/−) | Avg XDH | Std Dev (+/−) | Avg XDH | Std Dev (+/−) |
| Group 1 Saline (no RNAi agent) | 1.000 | 0.064 | 1.000 | 0.152 | 1.000 | 0.247 |
| Group 2 2.0 mg/kg AD10621 | 0.449 | 0.072 | 0.317 | 0.108 | 0.410 | 0.095 |
| Group 3 4.0 mg/kg AD10621 | 0.317 | 0.040 | 0.184 | 0.038 | 0.232 | 0.059 |
| Group 4 2.0 mg/kg AD09745 | 0.809 | 0.214 | .0567 | 0.196 | 0.690 | 0.281 |
| Group 5 4.0 mg/kg AD09745 | 0.590 | 0.090 | 0.347 | 0.047 | 0.408 | 0.026 |
| Group 6 2.0 mg/kg AD12167 | 0.712 | 0.072 | 0.546 | 0.124 | 0.650 | 0.211 |
| Group 7 4.0 mg/kg AD12167 | 0.522 | 0.087 | 0.297 | 0.093 | 0.385 | 0.092 |
| Group 8 2.0 mg/kg AD12168 | 0.881 | 0.126 | 0.497 | 0.029 | 0.631 | 0.120 |
| Group 9 4.0 mg/kg AD12168 | 0.500 | 0.019 | 0.327 | 0.028 | 0.359 | 0.060 |

TABLE 60

Targeted Positions and Dosing Groups of Example 27

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 2696 | 2.0 mg/kg AD10621 | Single injection on day 1 |
| 3 | 2696 | 4.0 mg/kg AD10621 | Single injection on day 1 |
| 4 | 2701 | 2.0 mg/kg AD09745 | Single injection on day 1 |
| 5 | 2701 | 4.0 mg/kg AD09745 | Single injection on day 1 |
| 6 | 2701 | 2.0 mg/kg AD12167 | Single injection on day 1 |
| 7 | 2701 | 4.0 mg/kg AD12167 | Single injection on day 1 |
| 8 | 2696 | 2.0 mg/kg AD12168 | Single injection on day 1 |
| 9 | 2696 | 4.0 mg/kg AD12168 | Single injection on day 1 |

As shown in Table 60, the XDH RNAi agent of Group 2 and 3 (AD010621) showed superior XHD inhibition compared to each of the RNAi agents in Groups 4-9 in vivo. For example, a single dose of 2.0 mg/kg of AD10621 reported approximately 59% inhibition of XDH (0.410) and a single 4.0 mg/kg dose reported approximately 77% inhibition (0.232) on day 22.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A pharmaceutical composition for inhibiting expression of an XDH gene, comprising an RNAi agent comprising a sense strand and an antisense strand, wherein the sense strand comprises a nucleic acid sequence of ccuccgcaCfAfGfauauugucau (SEQ ID NO: 1664) and the antisense strand comprises a nucleic acid sequence of asUfsgsAfcaauaucUfgUfgCfggagsg (SEQ ID NO: 1081), wherein lower case (n)=2'-O-Me modified nucleotide; Nf=2'-F modified nucleotide; and s=phosphorothioate backbone modification.

2. The pharmaceutical composition of claim 1, wherein the sense strand further comprises an inverted abasic residue at each of the 5' end and the 3' end.

3. The pharmaceutical composition of claim 2, wherein the inverted abasic residue is coupled to an adjacent nucleoside via a phosphorothioate backbone.

4. The pharmaceutical composition of claim 1, wherein the 5' end of the sense strand is coupled to a targeting ligand.

5. The pharmaceutical composition of claim 4, wherein the targeting ligand comprises:

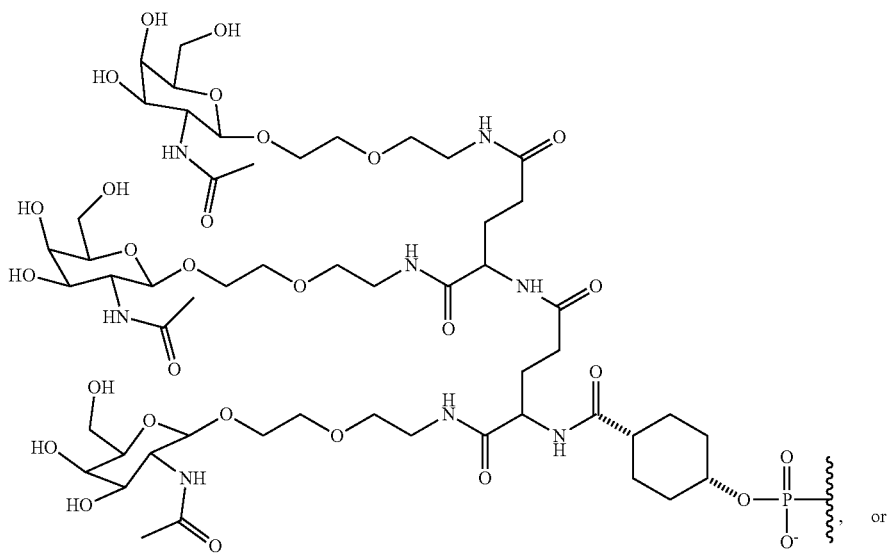

, or

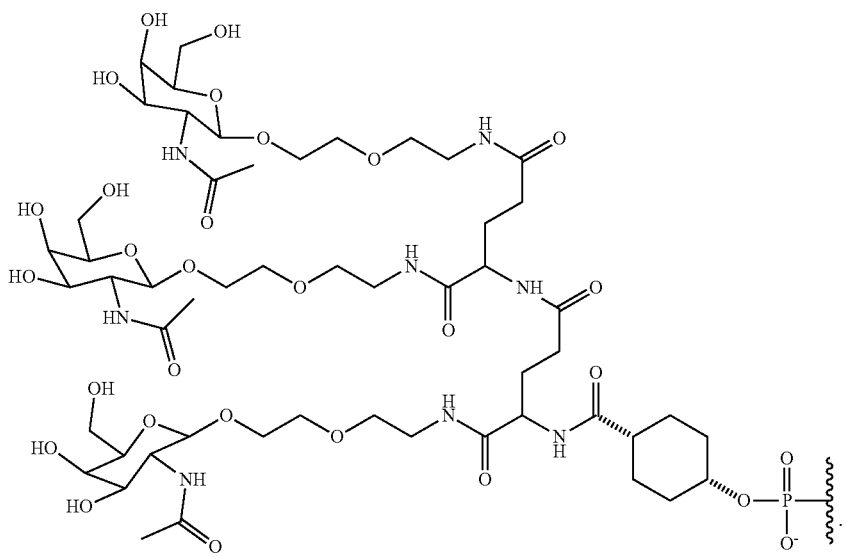

.

6. The pharmaceutical composition of claim 4, wherein the targeting ligand is

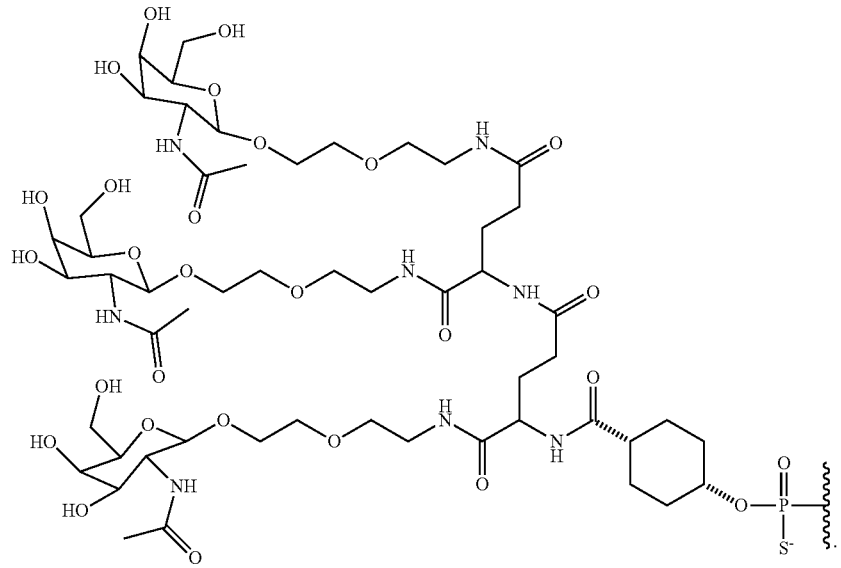

7. The pharmaceutical composition of claim 1, wherein the sense strand consists of a nucleic acid sequence of (invAb)sccuccgcaCfAfGfauauugucaus(invAb) (SEQ ID NO: 1681) and the antisense strand consists of a nucleic acid sequence of asUfsgsAfcaauaucUfgUfgCfggagsg (SEQ ID NO: 1081), wherein lower case (n)=2'-O-Me modified nucleotide; Nf=2'-F modified nucleotide; (invAb)=inverted abasic residue; and s=phosphorothioate backbone modification.

8. The pharmaceutical composition of claim 7, wherein the 5' end of the sense strand is coupled to a targeting ligand.

9. The pharmaceutical composition of claim 8, wherein the targeting ligand comprises:

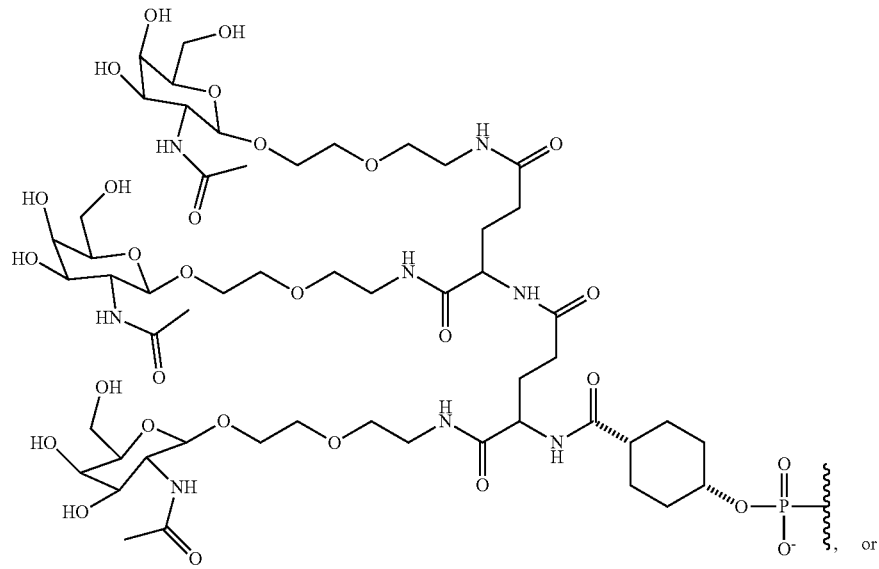

, or

-continued

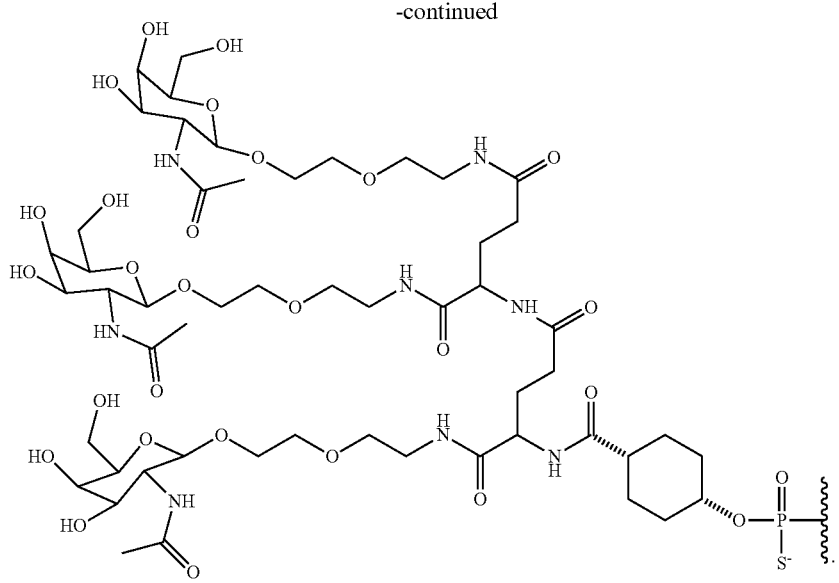

10. The pharmaceutical composition of claim 8, wherein the targeting ligand is

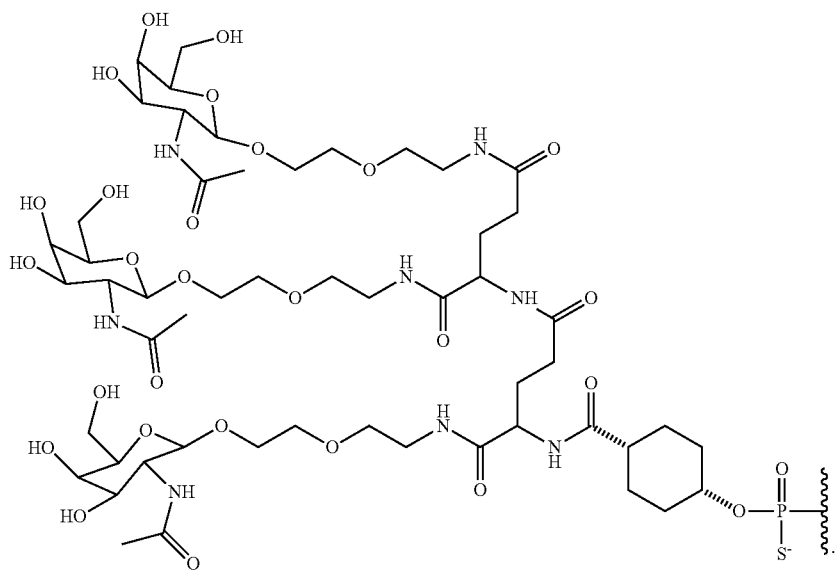

11. The pharmaceutical composition of claim 7, wherein the RNAi agent is a pharmaceutically acceptable salt.

12. The pharmaceutical composition of claim 11, wherein the pharmaceutically acceptable salt is a sodium salt.

13. The pharmaceutical composition of claim 10, wherein the RNAi agent is a pharmaceutically acceptable salt.

14. The pharmaceutical composition of claim 13, wherein the pharmaceutically acceptable salt is a sodium salt.

* * * * *